United States Patent
Thompson et al.

(10) Patent No.: US 11,690,285 B2
(45) Date of Patent: Jun. 27, 2023

(54) ELECTROLUMINESCENT DEVICES

(71) Applicant: Universal Display Corporation, Ewing, NJ (US)

(72) Inventors: Nicholas J. Thompson, New Hope, PA (US); Chun Lin, Yardley, PA (US); Hsiao-Fan Chen, Lawrence Township, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 108 days.

(21) Appl. No.: 17/328,403

(22) Filed: May 24, 2021

(65) Prior Publication Data

US 2021/0305520 A1   Sep. 30, 2021

Related U.S. Application Data

(63) Continuation-in-part of application No. 17/090,265, filed on Nov. 5, 2020, which is a continuation-in-part
(Continued)

(51) Int. Cl.
*H01L 51/00* (2006.01)
*C07F 5/02* (2006.01)
(Continued)

(52) U.S. Cl.
CPC ........ *H01L 51/0087* (2013.01); *C07D 403/14* (2013.01); *C07F 5/027* (2013.01);
(Continued)

(58) Field of Classification Search
CPC ............. H01L 51/0072; H01L 51/0067; H01L 51/5012; H01L 51/5016; H01L 2251/5384; C07D 403/14; C07D 487/04; C09K 11/02; C09K 11/06; C09K 2211/1007; C09K 2211/1018; C09K 2211/1029; C09K 2211/1044; C09K 2211/185
See application file for complete search history.

(56) References Cited

U.S. PATENT DOCUMENTS 4,769,292 A   9/1988   Tang et al.
5,061,569 A   10/1991  VanSlyke et al.
(Continued)

FOREIGN PATENT DOCUMENTS

EP   0650955   5/1995
EP   1725079   11/2006
(Continued)

OTHER PUBLICATIONS

Extended European Search Report dated Oct. 16, 2020 in corresponding European Patent Application No. 20170371.7.
(Continued)

*Primary Examiner* — Shane Fang
(74) *Attorney, Agent, or Firm* — Duane Morris LLP

(57) ABSTRACT

Disclosed is an OLED configuration that although comprises an exciplex that has an emission spectrum that is redder than the emission spectrum of the emitter, the emission from the exciplex is suppressed so that the overall OLED emission spectrum is still dominated by the emission of the emitter.

20 Claims, 6 Drawing Sheets

Related U.S. Application Data of application No. 16/841,182, filed on Apr. 6, 2020, which is a continuation-in-part of application No. 16/683,507, filed on Nov. 14, 2019.

(60) Provisional application No. 62/772,403, filed on Nov. 28, 2018.

(51) Int. Cl.

| | | |
|---|---|---|
| C09K 11/06 | (2006.01) | |
| C07D 403/14 | (2006.01) | |
| C07F 7/08 | (2006.01) | |
| C07F 15/00 | (2006.01) | |
| H01L 51/50 | (2006.01) | |

(52) U.S. Cl.

CPC ........ *C07F 7/0812* (2013.01); *C07F 15/0086* (2013.01); *C09K 11/06* (2013.01); *H01L 51/008* (2013.01); *H01L 51/0067* (2013.01); *H01L 51/0071* (2013.01); *H01L 51/0072* (2013.01); *H01L 51/0094* (2013.01); *C07B 2200/05* (2013.01); *C09K 2211/1018* (2013.01); *C09K 2211/1048* (2013.01); *C09K 2211/185* (2013.01); *H01L 51/5016* (2013.01); *H01L 2251/5384* (2013.01); *H01L 2251/552* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2015/0295197 A1 | 10/2015 | Adamovich et al. |
| 2017/0012207 A1 | 1/2017 | Seo et al. |
| 2019/0036055 A1* | 1/2019 | Lin ................... H01L 51/5024 |
| 2020/0190115 A1* | 6/2020 | Hatakeyama ......... H01L 51/008 |
| 2020/0270262 A1 | 8/2020 | Fleetham |
| 2021/0066613 A1* | 3/2021 | Cheng ................ H01L 51/0067 |
| 2021/0070791 A1* | 3/2021 | Ji ....................... C07F 15/0086 |

FOREIGN PATENT DOCUMENTS

| | | |
|---|---|---|
| EP | 2034538 | 3/2009 |
| EP | 3435438 | 1/2019 |
| EP | 3439063 | 2/2019 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |

(56) References Cited

FOREIGN PATENT DOCUMENTS

| WO | 2009018009 | 2/2009 |
|---|---|---|
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N∧C∧N—Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergard et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

(56) References Cited

OTHER PUBLICATIONS

Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ELECTROLUMINESCENT DEVICES

CROSS-REFERENCE TO RELATED APPLICATIONS

This application is a continuation-in-part of co-pending U.S. patent application Ser. No. 17/090,265, filed on Nov. 5, 2020, which is a continuation-in-part of U.S. patent application Ser. No. 16/841,182, filed on Apr. 6, 2020, which is a continuation-in-part of U.S. patent application Ser. No. 16/683,507, filed on Nov. 14, 2019, which claims priority under 35 U.S.C. § 119(e) to U.S. Provisional Application No. 62/772,403, filed on Nov. 28, 2018, the entire contents of which are incorporated herein by reference.

FIELD

The present disclosure generally relates to organometallic compounds and formulations and their various uses including as emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

An organic light emitting device (OLED) comprising an anode, a cathode, and an organic emissive layer, disposed between the anode and the cathode is disclosed where the organic emissive layer comprises a first host material having a highest occupied molecular orbital (HOMO) energy and a lowest unoccupied molecular orbital (LUMO) energy, and an emitter material having a HOMO energy and a LUMO energy. The emitter is selected from the group consisting of a phosphorescent metal complex, and a delayed fluorescent emitter. The emitter and host materials in the organic emissive layer satisfy the following conditions: $a \leq E_T - \Delta E \leq b$; where $E_T$ is triplet energy $T_1$ of the emitter, which is the lowest $T_1$ energy among all materials in the organic emissive layer; $\Delta E$ is the energy gap between the High HOMO energy and the Low LUMO energy; where a is 0.00 up to 0.15 eV, and b is 0.05 up to 0.45 eV; and where the emission spectrum of the OLED is at least 95% like the emission spectrum of an OLED whose organic emissive layer consists of the first emitter and an inert host. "High HOMO energy" is defined as the highest HOMO energy among all materials in the organic emissive layer and "Low LUMO energy" is defined as the lowest LUMO energy among all materials in the organic emissive layer.

A consumer product comprising the OLED is also disclosed.

DETAILED DESCRIPTION

A. Terminology

Figure 1:
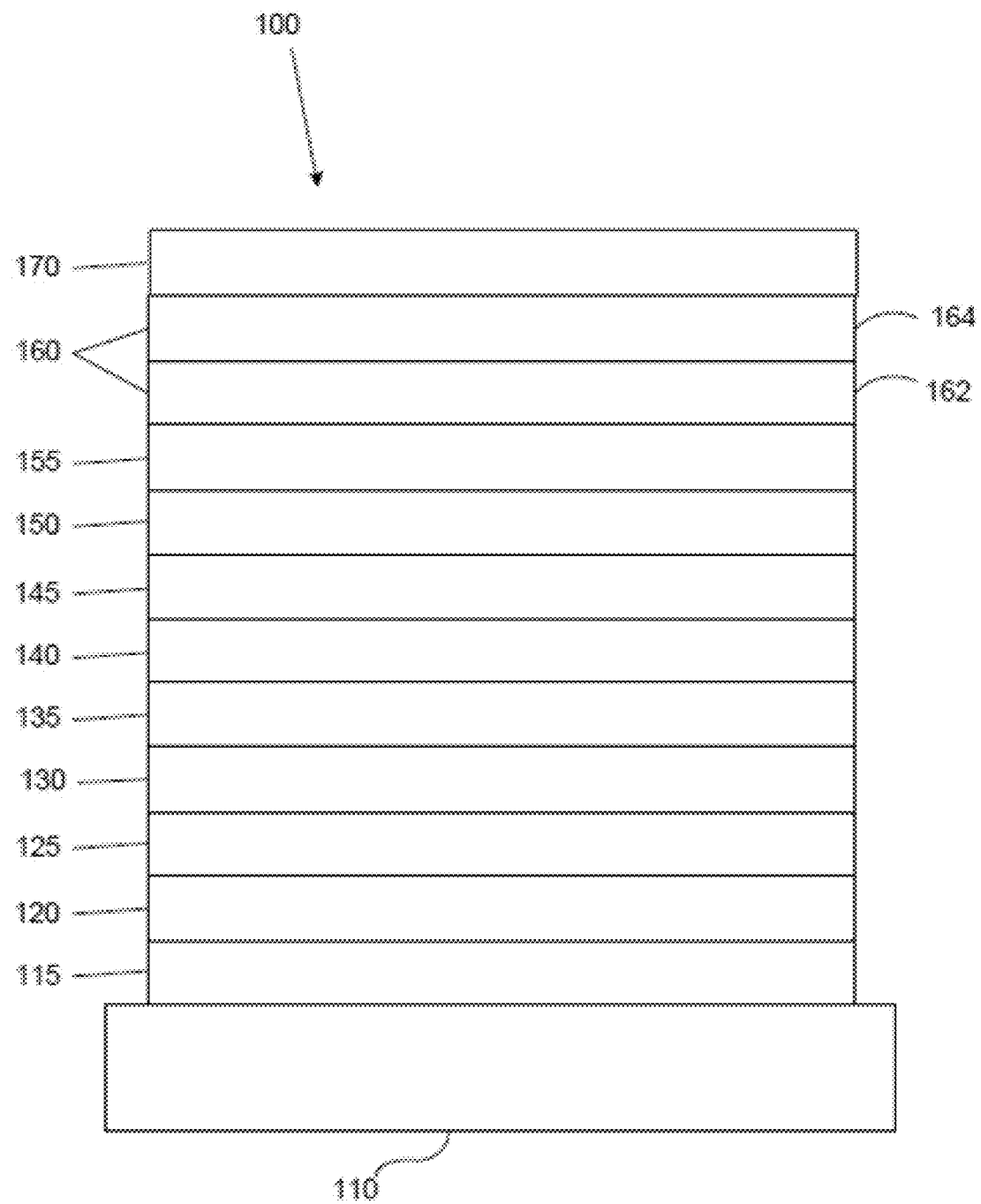
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative) Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —O$R_s$ radical.

The terms "sulfanyl" or "thio-ether" are used interchangeably and refer to a —S$R_s$ radical.

The term "selenyl" refers to a —Se$R_s$ radical.

The term "sulfinyl" refers to a —S(O)—$R_s$ radical.

The term "sulfonyl" refers to a —SO$_2$—$R_s$ radical.

The term "phosphino" refers to a —P($R_s$)$_3$ radical, wherein each $R_s$ can be same or different.

The term "silyl" refers to a —Si($R_s$)$_3$ radical, wherein each $R_s$ can be same or different.

The term "germyl" refers to a —Ge($R_s$)$_3$ radical, wherein each $R_s$ can be same or different.

The term "boryl" refers to a —B($R_s$)$_2$ radical or its Lewis adduct —B($R_s$)$_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo [3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, boryl, selenyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof.

In some instances, the preferred general substituents are selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo quinoxaline and dibenzo[fh]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed. (Reviews)* 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The OLED of the Present Disclosure

Exciplex emission spectrum is known to be broad. However, for many OLED applications, it is desirable for the OLED device to have a narrow emission spectrum. For example, to render the most saturated color with the highest efficiency for blue micro-cavity, OLEDs require a narrow spectrum emitter. Further, stabilization of the OLED device (i.e., longer lifetime) may be achieved by using lower LUMO level materials in the device. Thus, formation of exciplex in OLEDs is generally something to be avoided. However, in many cases, an exciplex can be formed between the shallowest (i.e. the highest) HOMO level material in the OLED emissive layer and the deepest (i.e. the lowest) LUMO level material. The overall emission of the OLED device can then be contaminated by the emission from the exciplex. In some cases, the emission can be a mixture of that of the exciplex and that of the emitter and in other cases the emission can be entirely dominated by the exciplex.

Disclosed is an OLED configuration that although comprises an exciplex that has an emission spectrum that is redder than the emission spectrum of the emitter, the emission from the exciplex is suppressed so that the overall OLED emission spectrum is still dominated by the emission of the emitter. This is accomplished by many different avenues. One embodiment is to design the emitter so that exciplex formation between the host material(s) and the emitter is not part of the OLED's emission spectrum even though the energy of the exciplex as dictated by the HOMO and LUMO levels is lower than that of the triplet energy $T_1$ of the emitter.

Previous to the present disclosure, it was not known that exciplex contribution to the emission of an OLED can be suppressed even when the exciplex is the lowest energy state in the OLED.

To help mathematically determine the differences between cases where exciplex formation occurs and where it does not, we utilize the root mean squared (RMSD) function, equation (1) shown below. This function returns a single value that is the average difference between two spectrums at all wavelengths.

$$RMSD = \sqrt{\frac{1}{n}\sum_{1}^{n}(I_1(\lambda) - I_2(\lambda))^2} \quad (1)$$

Figure 3:
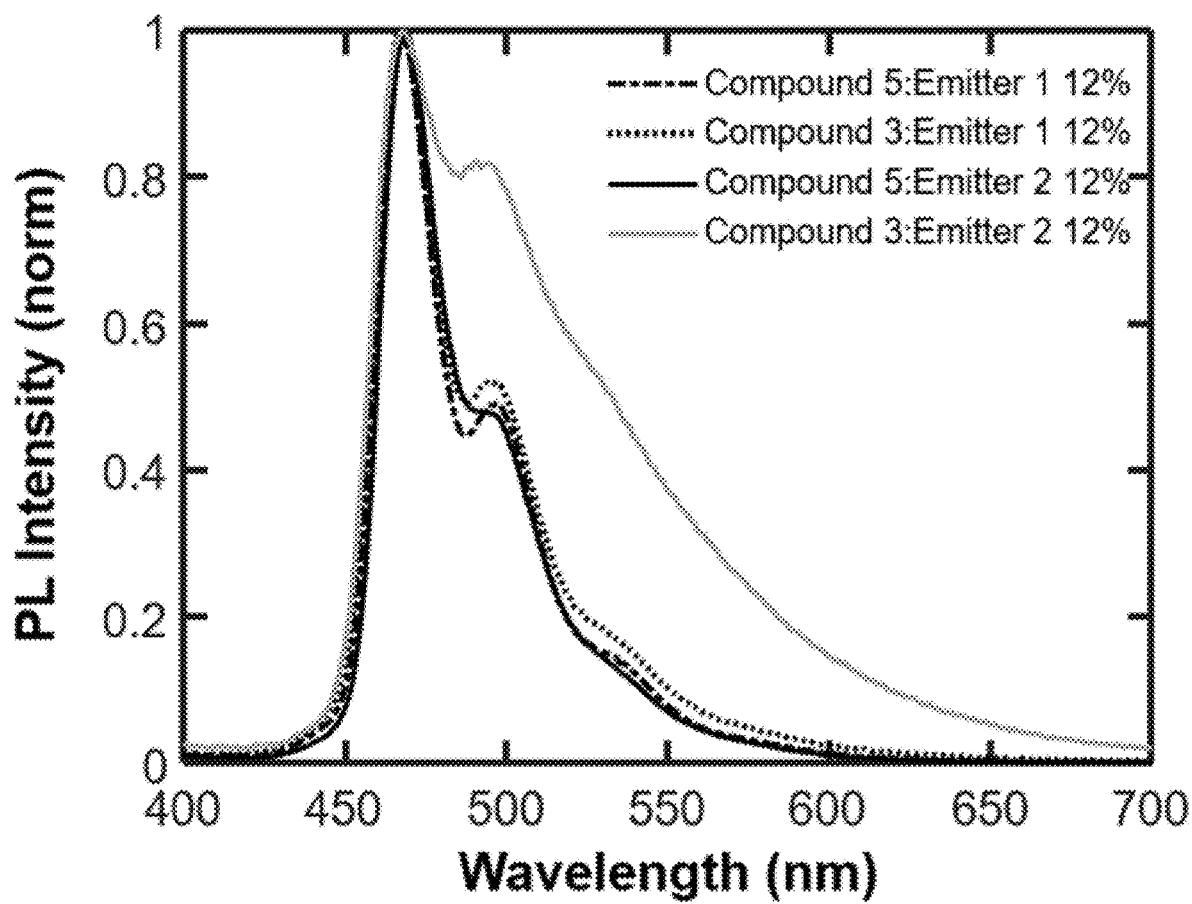
FIG. 3 shows a plot of the measured photoluminescent intensity (PL) of Emitter 1 compound and Emitter 2 compound doped in host compounds 5 and 3 individually where both spectrums are normalized to 1 and shifted to a peak wavelength of 468 nm.

In equation (1), n is the total number of points and $I_1$ and $I_2$ are the normalized intensity spectrums (electroluminescence (EL) or photoluminescence (PL)) as a function of wavelength, $\lambda$. Importantly, the spectrums that are being compared are shifted to the same peak wavelength and normalized which eliminates some of the spectral differences which can originate from putting the material into different dielectric constant materials. Functions $I_1$ and $I_2$ must have exactly the same number of points which can be achieved by interpolating existing data to a fixed number of wavelengths and must cover the same wavelength range, again achievable through interpolation. To demonstrate the versatility of this functional, we first plot the measured photoluminescent intensity (PL) of Emitter 1 and Emitter 2 doped at 12 percent by volume in host compounds 5 and 3 where both spectrums are normalized to a value of one and shifted to peak at the wavelength of 468 nm. This plot is shown in FIG. 3. Based on the energy levels of Compound 5, there is zero possibility of exciplex formation with either emitter. The PL spectrum of each emitter in Compound 5 represents the reference to which one can compare for cases where the energetics of the molecules predict formation of an exciplex. When emitters 1 and 2 are doped into Compound 3, the energy levels of the materials can predict what will happen. For both emitters in Compound 3, the emitter has the highest HOMO and Compound 3 has the lowest LUMO. We can then calculate the energy difference ($\Delta E$) for the exciplex that will occur based on the highest energy HOMO and lowest energy LUMO for each case: $\Delta E_{Emitter1}=|-5.33--2.78|=2.55$ eV and $\Delta E_{Emitter2}=|-5.35--2.78|=2.57$ eV, for these emitters doped into Compound 3. For both Emitter 1 and Emitter 2, $\Delta E$ is smaller than the triplet energy $E_T$ of 2.73 and 2.81 eV, respectively, indicating that an exciplex should form between each emitter and Compound 3. Indeed, for Emitter 2 in Compound 3 and as can be seen in FIG. 3, additional broad and red-shifted emission was observed. We attribute the distortion of the PL spectrum of Emitter 2 in Compound 3 to be indicative of the formation of an exciplex between the two materials. Conversely, there is very little change in the spectrum of Emitter 2 when it is doped into Compound 5 even though it also meets the energy criteria of exciplex formation which is that the triplet energy of the phosphorescent emitter is larger than the energy of the exciplex, $\Delta E$, which can be represented mathematically as $E_T - \Delta E_{Emitter2} > 0$.

As a stepping stone to calculating a single number to represent the differences in PL spectrum between 2 different films and provide a quantitative method for determining exciplex formation, we plot the difference as a function of wavelength for the PL spectrums of Emitter 1 and Emitter 2 in host Compounds 3 and 5, respectively. For each emitter, the absolute value of the difference between the normalize and shifted spectrum of the emitter in Compound 3 and Compound 5 is plotted in FIG. 4.

Figure 4:
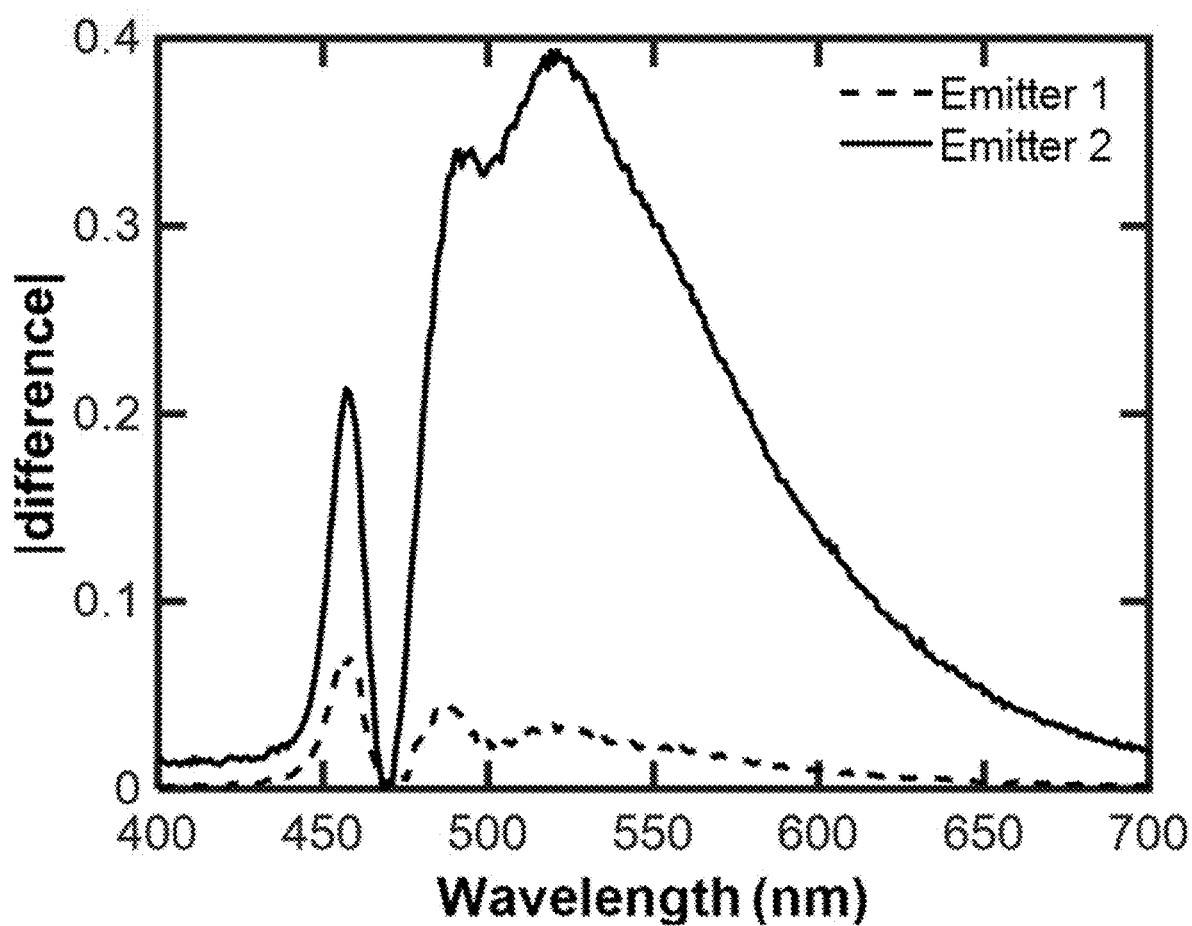
FIG. 4 shows a plot of the absolute value of the differences in PL spectrum, where the spectrums were normalized to 1 and shifted to a peak wavelength of 468 nm, between 2 films: one a film of an emitter doped in host Compound 3 at 12 vol. %; and a second film of the same emitter doped in host Compound 5 doped at 12 vol. %. The difference between the two films is plotted for Emitter 1 and Emitter 2.

The plot in FIG. 4 shows that Emitter 1 and Emitter 2 behave differently when doped into host Compounds 3 and 5. Emitter 1 exhibited very little difference when doped in the two host compounds. However, at many wavelengths Emitter 2 exhibited significant differences in PL spectrum compared for Compound 5 compared to Compound 3. Importantly, the values of the maximum difference occurred over the wavelength range from ~500 nm to >650 nm, which is the same region in the PL spectrum for Emitter 2 in Compound 3 (FIG. 3) that changed compared to the PL in Compound 5. The sharp features from ~430 nm to ~480 nm in both emitters originates from the fact that the shape of the PL intensity around the maximum is slightly different leading to large differences. This difference is to be expected as each material has a different dielectric constant leading to slight differences in the measured PL spectrum around areas of high slope or could originate from differences in the original sampling of data and then the interpolation around those area of high slope.

Given the plot shown in FIG. 4, we can now calculate the RMSD value for each spectrum. We find that the RMSD for Emitter 1 (from comparing the PL spectrum of Emitter 1 doped into host Compounds 3 and 5 at 12 percent by volume) is 0.021 while the RMSD for Emitter 2 (from comparing the PL spectrum of Emitter 2 doped into host Compounds 3 and 5 at 12 percent by volume) is 0.198. The RMSD function is nearly 10× for the host and emitter combination that generates an exciplex (based on experimentally observed exciplex formation seen in FIG. 3), thus demonstrating the validity of using RMSD to determine if a material combination generates an exciplex and generate a quantative number.

Figure 5:
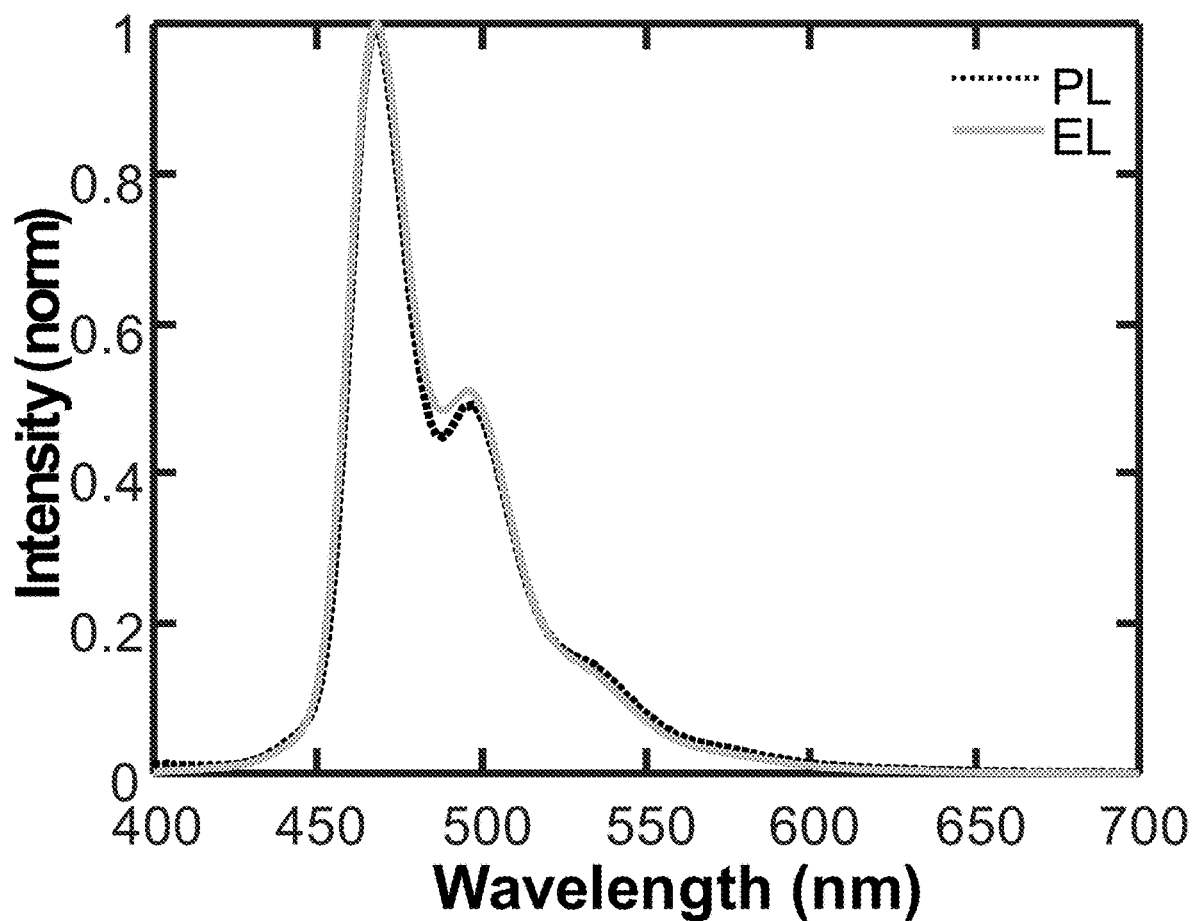
FIG. 5 shows a plot of the normalized and shifted PL spectrum of Emitter 1 doped in host Compound 5 (at 12 vol. %) and the normalized and shifted EL spectrum of Emitter 1 doped in a host (at 12 vol. %) where the host is a mixture of Compound 5 and Compound 4 (60 vol. % of Compound 4).

Next, a baseline level of RMSD that occurs when comparing different spectrums was determined. First, the RMSD value for different types of spectral measurements was calculated. FIG. 5 shows a plot of the normalized and shifted PL spectrum of Emitter 1 in host Compound 5 (12 vol. %) and the EL spectrums of Emitter 1 in a host that is a mixture of Compound 5 and Compound 4 (60 vol. % of Compound 4 and 12 vol. % Emitter 1). The RMSD was 0.012 which is quite low. The RMSD in EL was also calculated where the emissive layer (EML) composition is Compound 5 doped with 40 vol. % Compound 3, and 10 or 15 vol. % Emitter 1. The RMSD was 0.0073. The RMSD in EL was also calculated where the EML composition is Compound 5 doped with 20 vol. % Compound 3 and 15 vol. % Emitter 1 to Compound 5 doped with 60 vol. % Compound 3 and 15 vol. % Emitter 1. The RMSD was 0.0147. Given that the RMSD for comparing spectrum generated from different methods of generating the spectrum (EL vs. PL), varying the percentage of emitter doping, and varying the ratio of hosts in the EML are all low values indicates that RMSD is a robust method for comparing spectrums. We further reviewed many different spectra where there were NO expected exciplex, we found that a RMSD difference of greater than 0.05 is meaningful and a good value at which exciplex formation can be considered significant.

At times, the conversion of a purely mathematical expression to a verbal description is useful. The RMSD can be recast into a description of likeness. For example, if the 2 spectrums compared are identical, then the RMSD is 0. Such two spectrums are exactly alike or 100% alike. Thus, one can define and quantify the likeness between two spectrums as a percentage using the following relation: (1−RMSD)*100. Thus, in the present context, all spectrums that are ≥95% alike will be considered to be the same due to the fact that values of RDMS less than 0.05 are not meaningfully different.

Table 1 below lists the HOMO, LUMO, triplet energy $T_1$, and predicted excimer energy levels for Compounds 1 through 5, and Emitters 1 and 2. For both Emitters 1 and 2, Compounds 1, 2, and 3 should form exciplexes based on the energy levels while Compounds 4 and 5 should not. The HOMO energy is estimated from the first oxidation potential derived from cyclic voltammetry. The LUMO energy is estimated from the first reduction potential derived from cyclic voltammetry. The triplet energy $T_1$ of the emitter compounds is measured using the peak wavelength from the photoluminescence at 77 K. In choosing the emitter-host combination, if the condition a≤$E_T$−ΔE≤b is met, exciplex should form. In a≤$E_T$−ΔE≤b, $E_T$ is triplet energy $T_1$ of the emitter, which is the lowest $T_1$ energy among all materials in the organic emissive layer, ΔE is the energy gap between the HOMO energy of the material having the highest HOMO energy in the organic emissive layer and the LUMO energy of the material having the lowest LUMO energy in the organic emissive layer, a has a value of 0.00 up to 0.15 eV, and b has a value of 0.05 up to 0.45 eV. Although, the above condition is met, by designing an appropriate emitter, the OLED will have an emission spectrum that is at least 95% like the emission spectrum of an OLED whose organic emissive layer consists of the emitter and an inert host.

Figure 6:
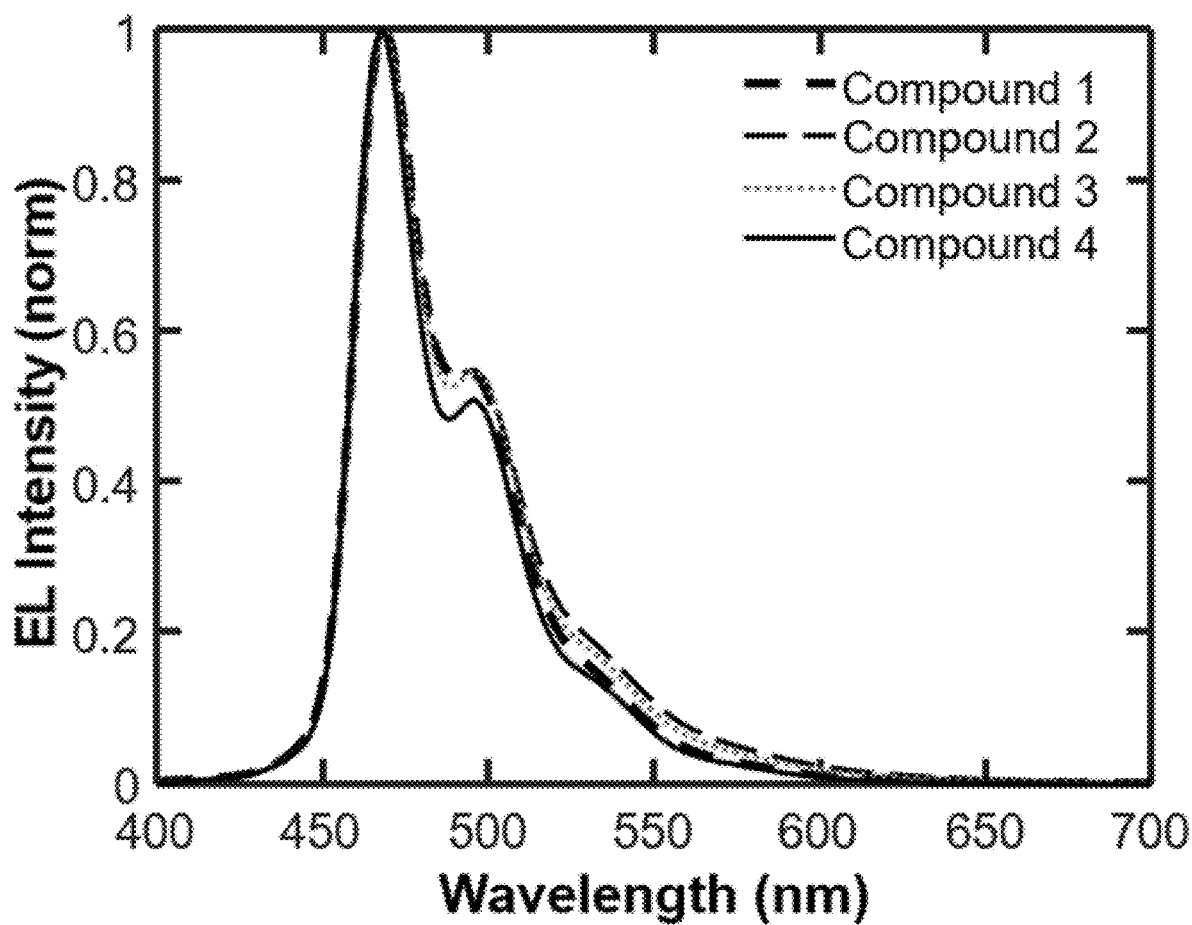
FIG. 6 shows the normalized and shifted EL spectra of Emitter 1 doped in four different mixtures of Compound 5 and Compounds 1, 2, 3, and 4.

Shown in FIG. 6 is the EL spectra of Emitter 1 doped in four different mixtures of Compound 5 and Compounds 1, 2, 3, and 4. For each host Compound 1-4 the mixtures prepared according to the following the formula: Compound 5 doped with 40 vol. % of Compound 1 and 12 vol. % of Emitter 1; Compound 5 doped with 40 vol. % of Compound 2 and 12 vol. % of Emitter 1; Compound 5 doped with 40 vol. % of Compound 3 and 12 vol. % of Emitter 1; Compound 5 doped with 40 vol. % of Compound 4 and 12 vol. % of Emitter 1. We find that the RMSD of comparing mixtures with Compound 5 and 1, 2 or 3 to Compound 5 doped with Compound 4 where exciplex formation is not energetically predicted are 0.0201, 0.0306, and 0.0239 respectively. Or in plain language, EMLs of the same composition as but varying the host from Compound 4 to Compounds 1, 2, or 3 all within 3% like each other and thus are effectively the same. Thus, there is NO excimer formation between Emitter 1 and these hosts even though the energetics of the HOMO level of the emitter and the LUMO level of the host predict that there should be excimer formation. This result is completely unexpected. Without being bound by any theories, this unexpected result may be due to the steric effect from the emitter. The energy of an exciton has a spatial component and increases as the distances between the hole and electron parts of the wavefunction increases. If the steric component of the emitter increases the distance over which the exciplex between the emitter and E-type host is formed, that would lead to a higher exciplex energy and push the energy of the exciplex to be greater than the triplet energy $T_1$ of the emitter. Thus, emitter molecules with greater steric protection enables the use of E-type hosts with lower LUMO levels which in turn leads to stabilization of the overall device. The advantage of expanding the energy level range that can be used in the devices is especially beneficial for blue emitters. Thus, the OLED configuration disclosed herein provides a roadmap for designing emitter molecules and choosing proper host system, especially an e-host, to achieve a stable OLED, especially, a stable blue phosphorescent OLED.

TABLE 1

Energy levels and predictions of excimer formation based on the energy levels for the emitters and host compounds.

| Material | Triplet energy $T_1$ [eV] | HOMO [eV] | LUMO [eV] | $\Delta E_{Emitter1}$; $E_{TEmitter1}-\Delta E_{Emitter1}$ (Possible exciplex); (reality) | $\Delta E_{Emitter2}$; $E_{TEmitter2}-\Delta E_{Emitter2}$ (Possible exciplex); (reality) |
|---|---|---|---|---|---|
| Host Compound 1 | 3.00 | −5.76 | −2.65 | 2.68; 0.05 (Yes); (No) | 2.70; 0.11 (Yes); (Yes) |
| Host Compound 2 | 2.97 | −5.74 | −2.75 | 2.58; 0.15 (Yes); (No) | 2.60; 0.21 (Yes); (Yes) |
| Host Compound 3 | 2.98 | <−5.8 | −2.78 | 2.55; 0.18 (Yes); (No) | 2.57; 0.24 (Yes); (Yes) |
| Host Compound 4 | 2.95 | −5.7 | −2.46 | 2.87; −0.14 (No); (No) | 2.89; −0.08 (No); (No) |
| Host Compound 5 | 2.99 | −5.46 | −1.96 | 3.26; −0.53 (No); (No) | 3.18; −0.37 (No); (No) |
| Emitter 1 | 2.73 | −5.33 | −2.07 | — | — |
| Emitter 2 | 2.81 | −5.35 | −2.17 | — | — |

In Table 1, ΔE for each EML mixture is calculated by first determining which compound in the mixture has the High HOMO energy (the highest HOMO energy among all materials in the EML mixture) and which compound in the mixture has the Low LUMO energy (the lowest LUMO energy among all materials in the EML mixture). Then, ΔE is the energy gap between the High HOMO energy and the Low LUMO energy. Then, one determines $E_T-\Delta E$ and whether the following condition, $a \leq E_T-\Delta E \leq b$, is satisfied, where $E_T$ is the triplet energy $T_1$ of the first emitter, which is the lowest $T_1$ energy among all materials in the organic emissive layer, and wherein a is 0.00 up to 0.15 eV, and b is 0.05 up to 0.45 eV.

The compounds referenced in the data shown in Table 1 are shown below:

Compound 1

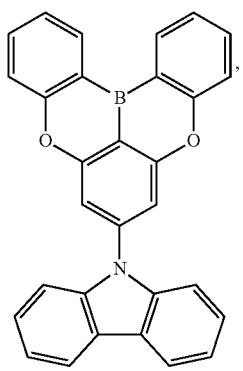

Compound 2

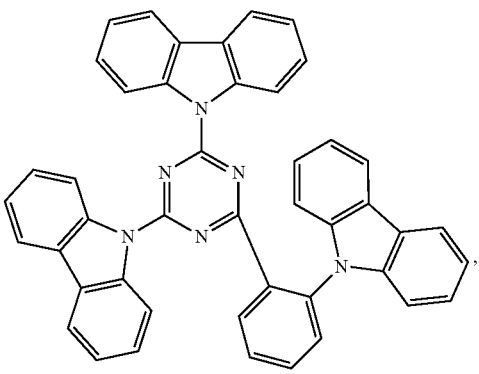

Compound 3

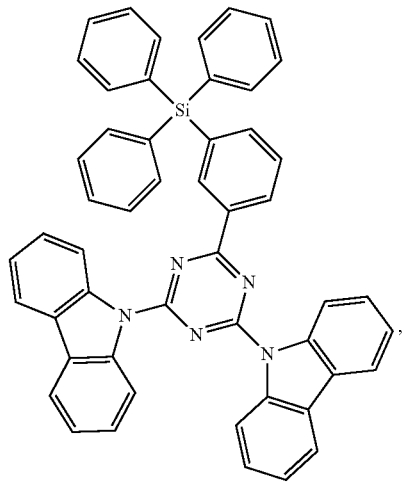

Compound 4

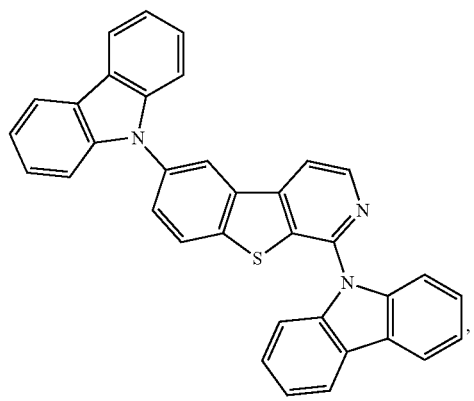

Compound 5

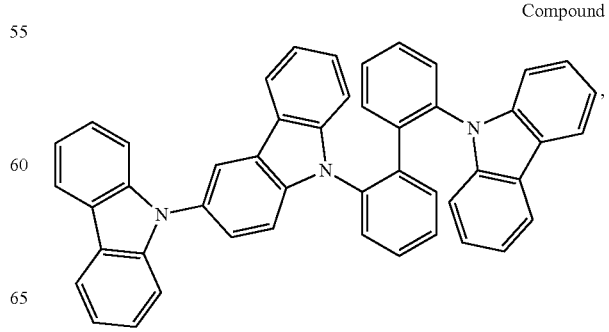

-continued

Emitter 1

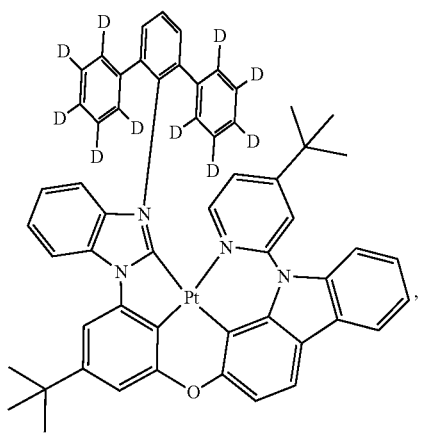

Emitter 2

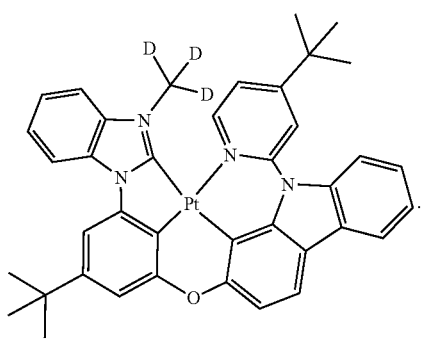

Solution cyclic voltammetry and differential pulsed voltammetry were performed using a CH Instruments model 6201B potentiostat using anhydrous dimethylformamide solvent and tetrabutylammonium hexafluorophosphate as the supporting electrolyte. Glassy carbon, and platinum and silver wires were used as the working, counter and reference electrodes, respectively. Electrochemical potentials were referenced to an internal ferrocene-ferroconium redox couple (Fc$^+$/Fc) by measuring the peak potential differences from differential pulsed voltammetry. The $E_{HOMO}=-[(E_{ox1}$ vs Fc$^+$/Fc)+4.8]$, and the $E_{LUMO}=-[(E_{red1}$ vs Fc$^+$/Fc)+4.8]$, wherein $E_{ox1}$ is the first oxidation potential, and the $E_{red1}$ is the first reduction potential.

Disclosed herein is an organic light emitting device (OLED) comprising an anode, a cathode, and an organic emissive layer, disposed between the anode and the cathode. The organic emissive layer comprises a first host material having a highest occupied molecular orbital (HOMO) energy and a lowest unoccupied molecular orbital (LUMO) energy, and an emitter material having a HOMO energy and a LUMO energy. The emitter is selected from the group consisting of a phosphorescent metal complex, and a delayed fluorescent emitter. The emitter and host materials in the organic emissive layer satisfy the following conditions: $a \leq E_T - \Delta E \leq b$; where $E_T$ is triplet energy $T_1$ of the emitter, which is the lowest $T_1$ energy among all materials in the organic emissive layer; $\Delta E$ is the energy gap between the High HOMO energy and the Low LUMO energy; where a is 0.00 up to 0.15 eV, and b is 0.05 up to 0.45 eV; and where the emission spectrum of the OLED is at least 95% like the emission spectrum of an OLED whose organic emissive layer consists of the first emitter and an inert host. "High HOMO energy" is defined as the highest HOMO energy among all materials in the organic emissive layer and "Low LUMO energy" is defined as the lowest LUMO energy among all materials in the organic emissive layer.

In some embodiments, all materials in the organic emissive layer can be in a mixture. The mixture can be a homogeneous mixture or the components of the organic emissive layer can be in graded concentrations through the thickness of the emissive layer. The concentration grading can be linear, non-linear, sinusoidal, etc.

The emitter can be a phosphorescent metal complex or a delayed fluorescent emitter.

In some embodiments of the OLED, a is 0.15 eV. In some embodiments, a is 0.10 eV. In some embodiments a is preferably 0.05 eV. In some embodiments, b is 0.05 eV. In some embodiments, b is 0.15 eV. In some embodiments, b is 0.25 eV. In some embodiments, b is preferably 0.35 eV. In some embodiments, $E_T$ is at least 2.60 eV. In some embodiments, $E_T$ is at least 2.65 eV. In some embodiments $E_T$ is at least 2.70 eV. In some embodiments $E_T$ is preferably at least 2.75 eV.

In some embodiments of the OLED, the High HOMO energy is the HOMO energy of the emitter, and the Low LUMO energy is the LUMO energy of the first host. In some embodiments, the High HOMO energy is the HOMO energy of the first host, and the Low LUMO energy is the LUMO energy of the emitter.

In some embodiments, the OLED further comprises a second host, where the High HOMO energy is the HOMO energy of the first host, and the Low LUMO energy is the LUMO energy of the second host. In some embodiments, the High HOMO energy is the HOMO energy of the second host, and the Low LUMO energy is the LUMO energy of the first host.

In some embodiments of the OLED that comprises a second host, the first host, the second host, and the emitter are the only components in the emissive layer. In some embodiments, the first host, the second host, and the emitter are the only components in the emissive layer.

In some embodiments, the OLED has an operation voltage less than 6.0 V at 10 mA/cm$^2$. In some embodiments, the OLED has an operation voltage less than 5.0 V at 10 mA/cm$^2$. In some embodiments, the OLED has an operation voltage less than 4.0 V at 10 mA/cm$^2$.

In some embodiments of the OLED, the first host comprises at least one chemical moiety selected from the group consisting of triphenylene, carbazole, indolocarbazole, benzothiophene, benzofuran, dibenzothiophene, dibenzofuran, pyridine, pyridazine, pyrimidine, pyrazine, triazine, imidazole, boryl, 5,9-dioxa-13b-boranaphtho[3,2,1-de]anthracene, and aza-variants thereof.

In some embodiments of the OLED, the emitter is a phosphorescent blue emitter. Blue emitter here refers to a phosphorescent emitter whose emission λmax is less than 490 nm, less than 480 nm, less then 470 nm, or preferably less than 460 nm, or whose emission in CIE coordinate is: X<0.3, <0.25, <0.2, or preferably <0.18, and Y<0.5, <0.4, <0.3, or preferably <0.2.

In some embodiments of the OLED, the emitter has the formula of $M(L^1)_x(L^2)_y(L^3)_z$; where, $L^1$, $L^2$ and $L^3$ can be the same or different; x is 1, 2, or 3; y is 0, 1, or 2; z is 0, 1, or 2; x+y+z is the oxidation state of the metal M; $L^1$, $L^2$, and $L^3$ are each independently selected from the group consisting of:
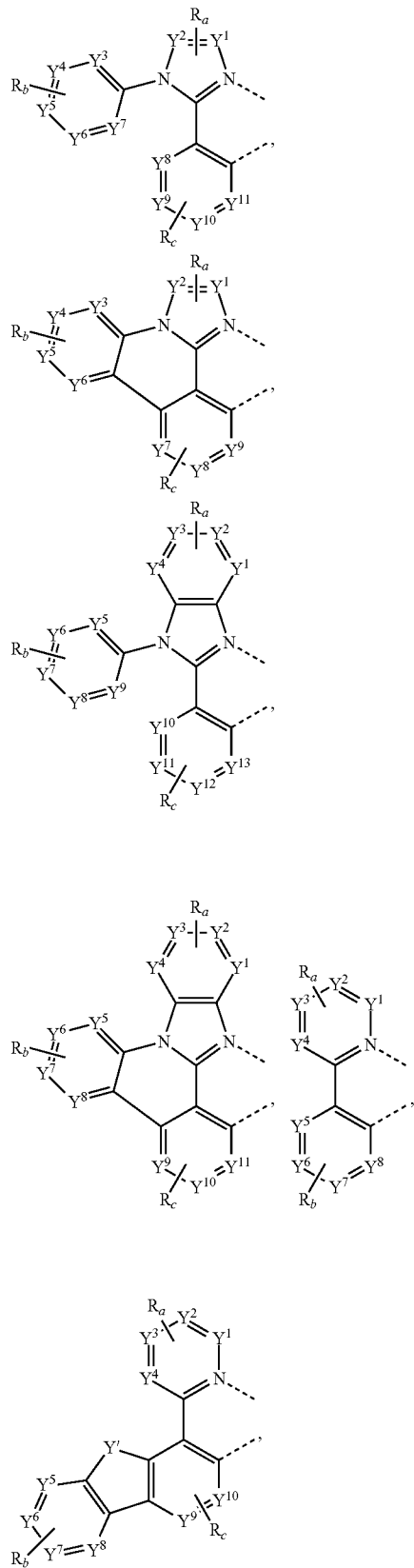
-continued
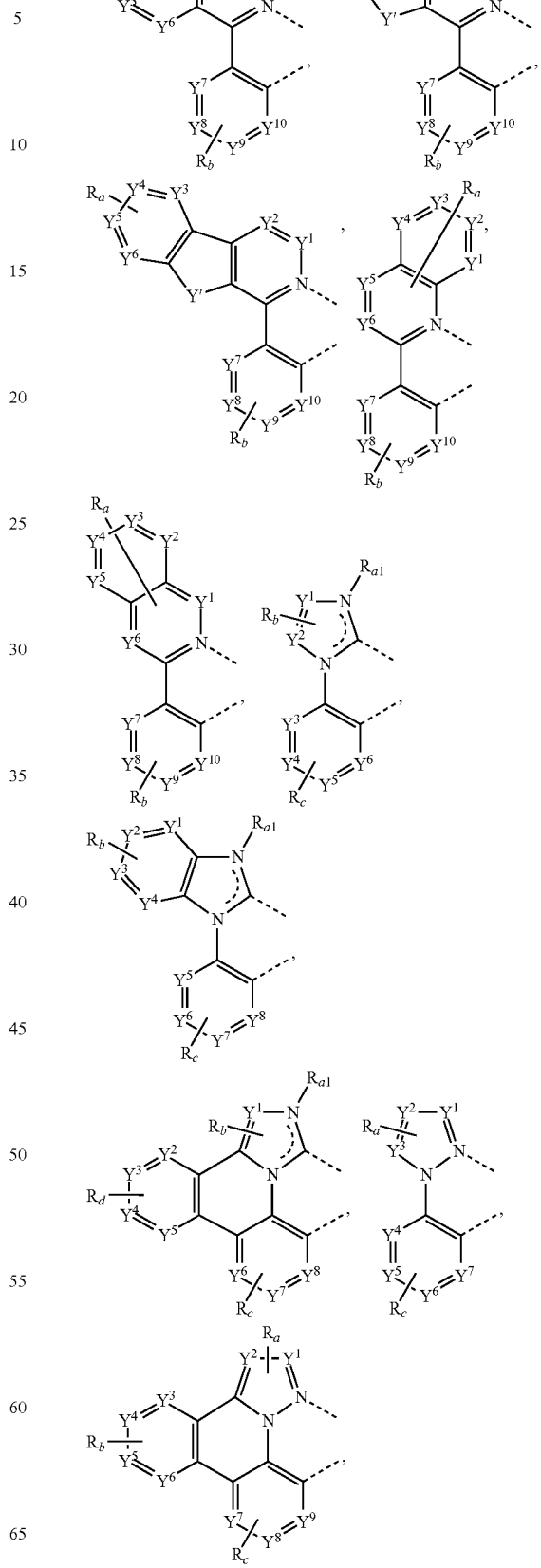

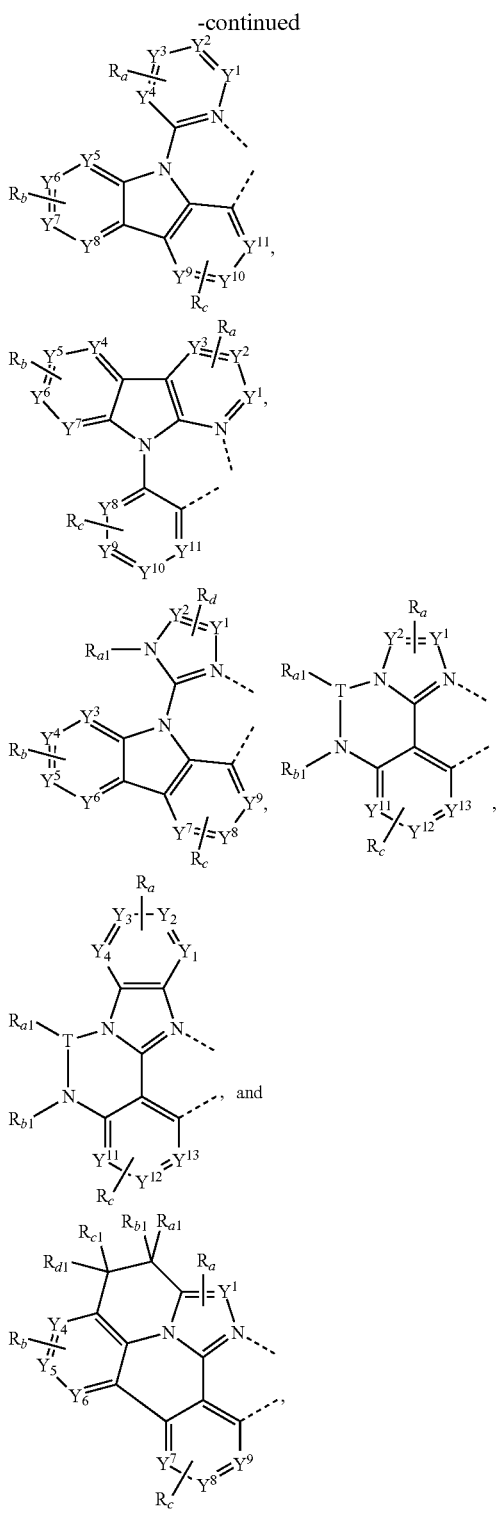

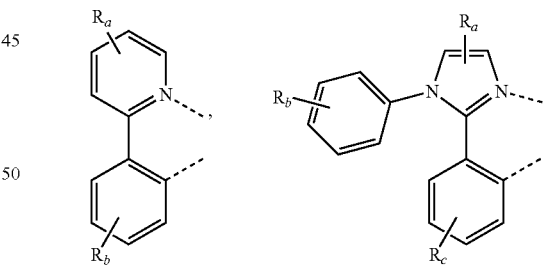

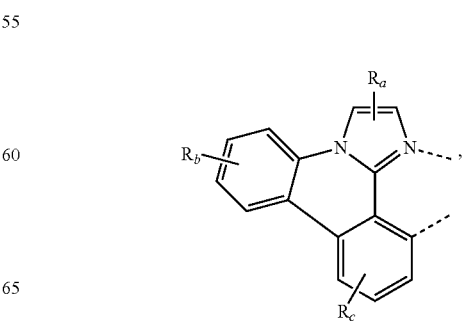

wherein T is selected from the group consisting of B, Al, Ga, and In; each of $Y^1$ to $Y^{13}$ is independently selected from the group consisting of C and N; Y' is selected from the group consisting of $BR_e$, $NR_e$, $PR_e$, O, S, Se, C=O, S=O, $SO_2$, $CR_eR_f$, $SiR_eR_f$, and $GeR_eR_f$; $R_e$ and $R_f$ can be fused or joined to form a ring; each $R_a$, $R_b$, $R_c$, and $R_d$ independently represents zero, mono, or up to a maximum allowed number of substitutions to its associated ring; each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of the general substituents defined herein; and and any two adjacent substituents of $R_{a1}$, $R_{b1}$, $R_{c1}$, $R_{d1}$, $R_a$, $R_b$, $R_c$, $R_d$, $R_e$ and $R_f$ can be fused or joined to form a ring or form a multidentate ligand.

In some embodiments, at least one of $R_{a1}$, $R_{b1}$, $R_{c1}$, $R_{d1}$, $R_a$, $R_b$, $R_c$, $R_d$, $R_e$ and $R_f$ comprises a chemical group containing at least three 6-membered aromatic rings that are not fused next to each other. In some embodiments, at least one of $R_{a1}$, $R_{b1}$, $R_{c1}$, $R_{d1}$, $R_a$, $R_b$, $R_c$, $R_d$, $R_e$ and $R_f$ comprises a chemical group containing at least four 6-membered aromatic rings that are not fused next to each other. In some embodiments, at least one of $R_{a1}$, $R_{b1}$, $R_{c1}$, $R_{d1}$, $R_a$, $R_b$, $R_c$, $R_d$, $R_e$ and $R_f$ comprises a chemical group containing at least five 6-membered aromatic rings that are not fused next to each other. In some embodiments, at least one of $R_{a1}$, $R_{b1}$, $R_{c1}$, $R_{d1}$, $R_a$, $R_b$, $R_c$, $R_d$, $R_e$ and $R_f$ comprises a chemical group containing at least six 6-membered aromatic rings that are not fused next to each other. In some embodiments, at least one of $R_{a1}$, $R_{b1}$, $R_{c1}$, $R_{d1}$, $R_a$, $R_b$, $R_c$, $R_d$, $R_e$ and $R_f$ comprises a chemical group containing terphenyl (more preferably meta-terphenyl) or N-phenyl carbazole. In some embodiments, $R_{a1}$ comprises a chemical group as described herein. The more detailed descriptions of adding bulky group to the ligand periphery of the emitter complex has been disclosed in detail elsewhere, such as in U.S. application Ser. No. 16/807,877, the entire contents of which are incorporated herein by reference. In some embodiments of the OLED where the emitter comprises at least one metal-carbene bond. In some embodiments of the OLED where the minimum amount of the the hydrogen of the emitter being deuterated is selected from the group consisting of 25%, 30%, 35%, 40%, 50%, 60%, 70%, 80%, 90%, and 100%.

In some embodiments of the OLED where the emitter has the formula of $M(L^1)_x(L^2)_y(L^3)_z$, the emitter can have the formula selected from the group consisting of $Ir(L^1)(L^2)(L^3)$, $Ir(L^1)_2(L^2)$, and $Ir(L^1)_3$, where $L^1$, $L^2$, and $L^3$ are different and each is independently selected from the group consisting of:

-continued

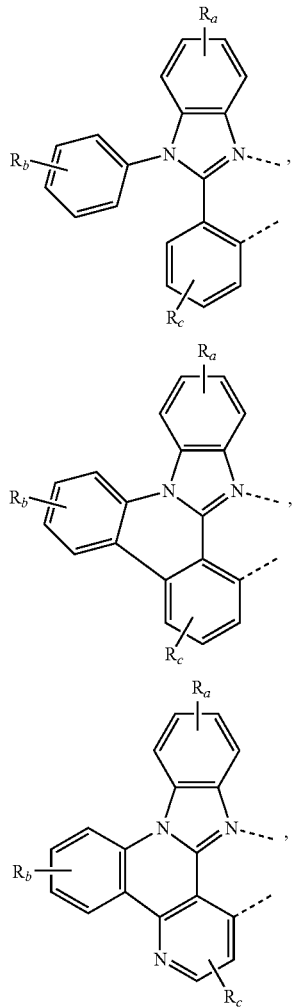

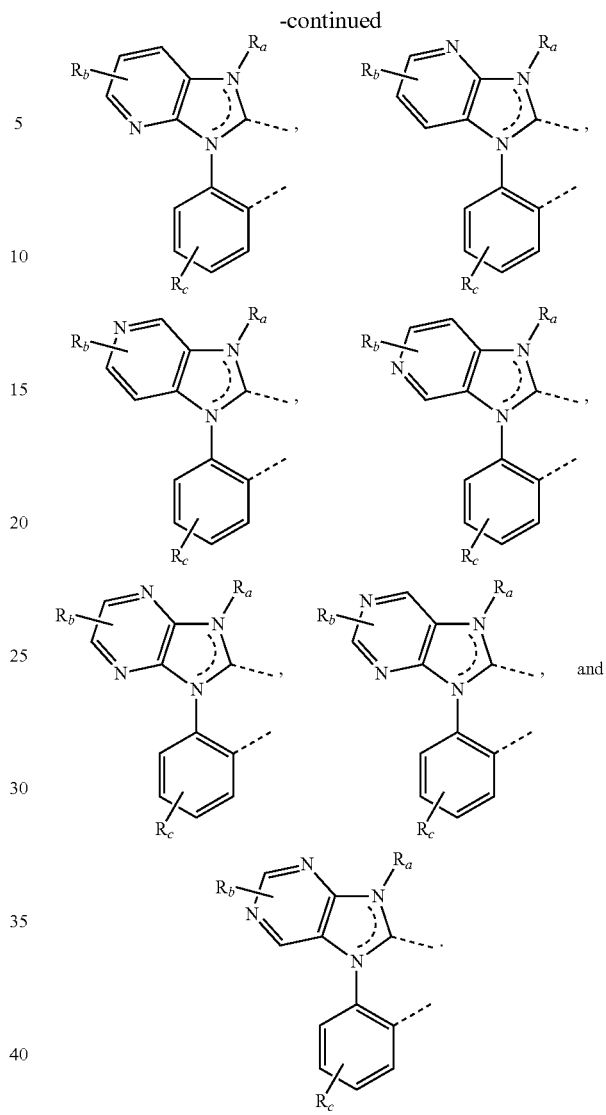

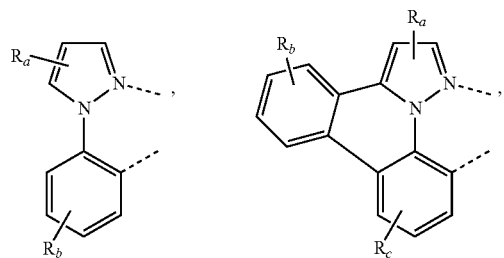

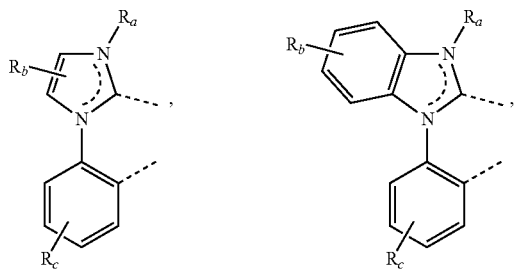

In some embodiments of the compound where the emitter has the formula of $M(L^1)_x(L^2)_y(L^3)_z$, the emitter can have the formula of $Pt(L^1)_2$, $Pt(L^1)(L^2)$, $Pd(L^1)_2$ or $Pd(L^1)(L^2)$, and $L^1$ and $L^2$ are each a different bidentate ligand. In some embodiments, $L^1$ is connected to the other $L^1$ or $L^2$ to form a tetradentate ligand. In some embodiments, the emitter has the formula of $M(L^1)_2$ or $M(L^1)(L^2)$, where M is Ir, Rh, Re, Ru, or Os, and $L^1$ and $L^2$ are each a different tridentate ligand. In some embodiments, $L^1$ is selected from the group consisting of:

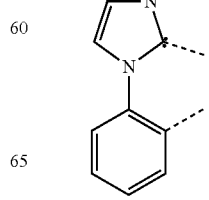

$L_{B1}$

-continued
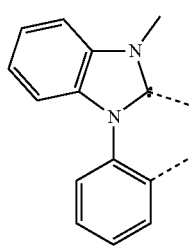
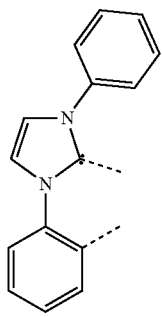
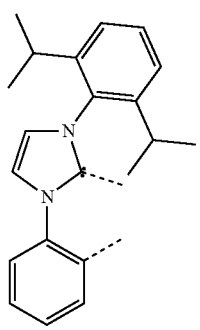
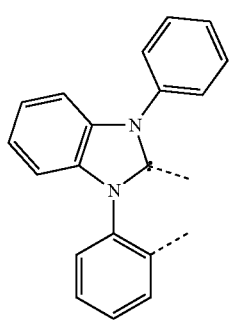
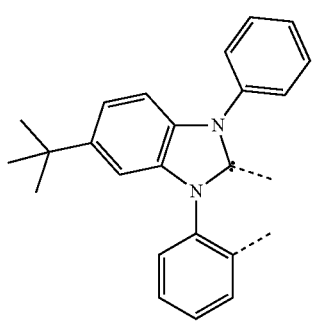
-continued
L$_{B2}$ 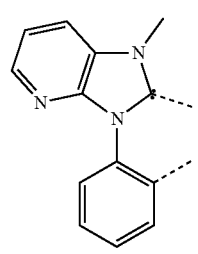 L$_{B7}$
L$_{B3}$ 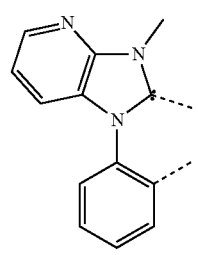 L$_{B8}$
L$_{B4}$ 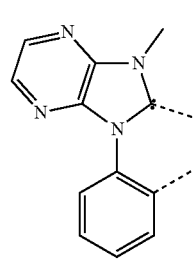 L$_{B9}$
L$_{B5}$ 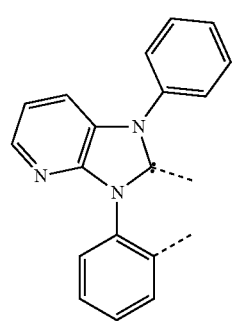 L$_{B10}$
L$_{B6}$ 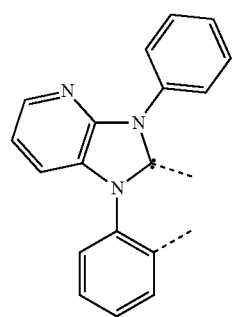 L$_{B11}$ L_{B12}
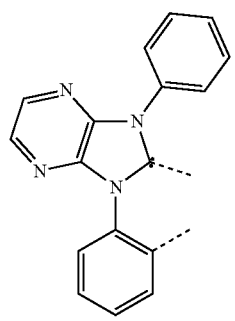
L_{B13}
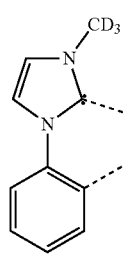
L_{B14}
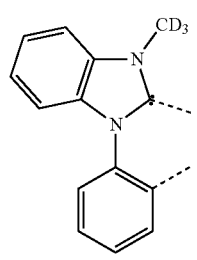
L_{B15}
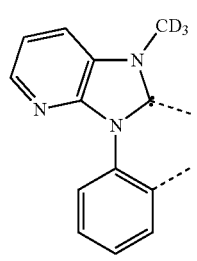
L_{B16}
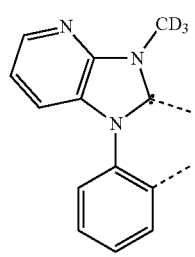
L_{B17}
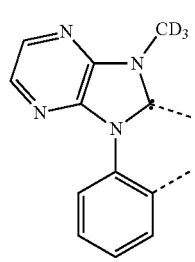
L_{B18}
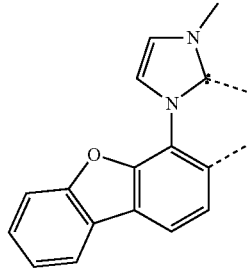
L_{B19}
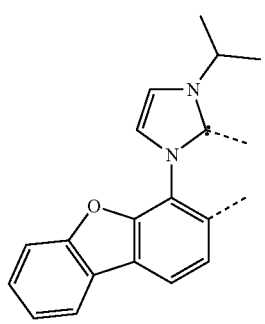
L_{B20}
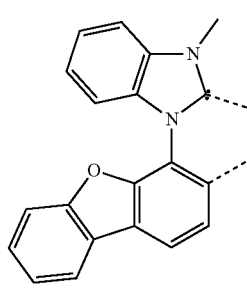
L_{B21}
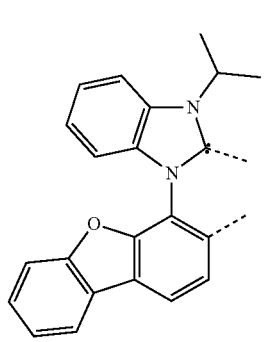
L_{B22}
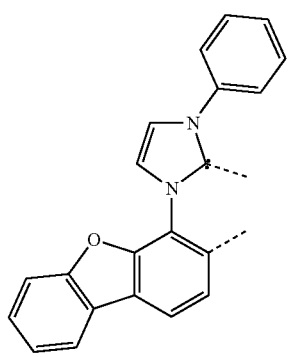

L_{B23}
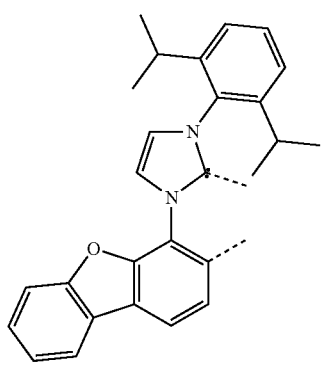
L_{B24}
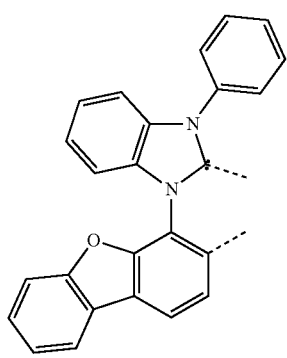
L_{B25}
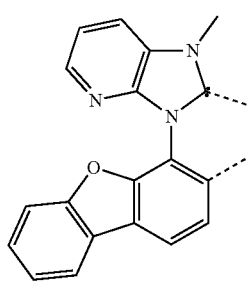
L_{B26}
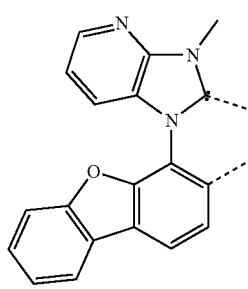
L_{B27}
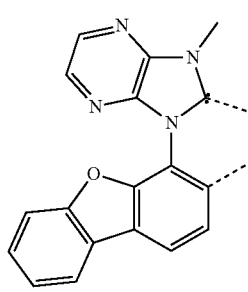
L_{B28}
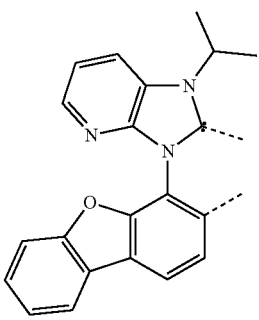
L_{B29}
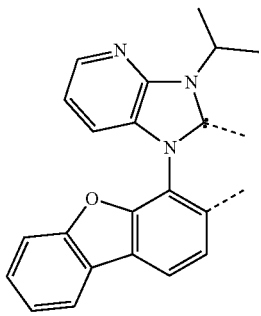
L_{B30}
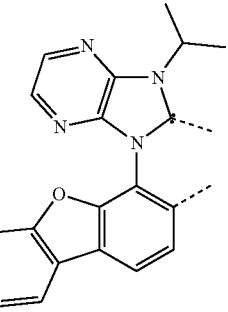
L_{B31}
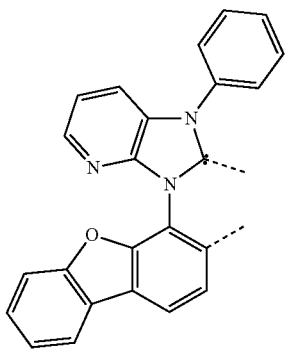

L<sub>B32</sub> 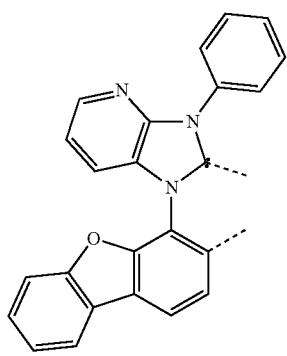
L<sub>B33</sub> 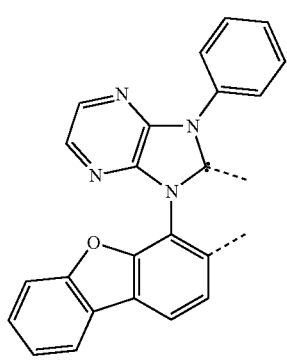
L<sub>B34</sub> 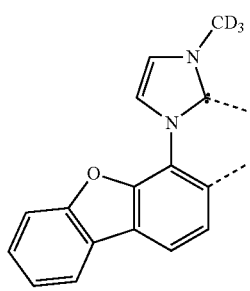
L<sub>B35</sub> 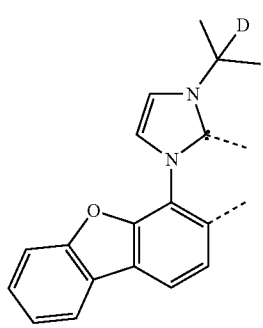
L<sub>B36</sub> 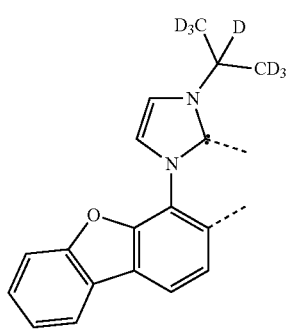
L<sub>B37</sub> 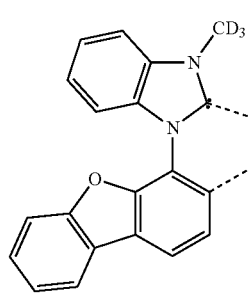
L<sub>B38</sub> 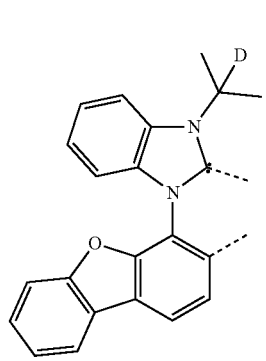
L<sub>B39</sub> 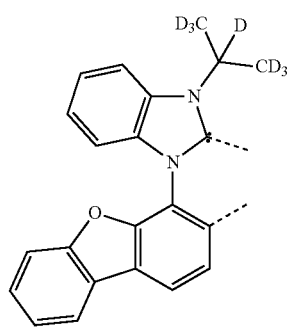
L<sub>B40</sub> 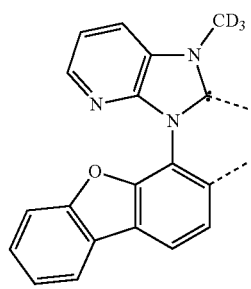
L<sub>B41</sub> 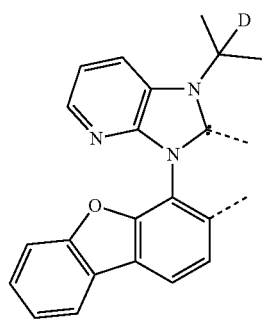

| | |
|---|---|
| 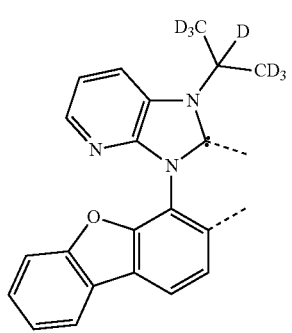 | L_{B42} 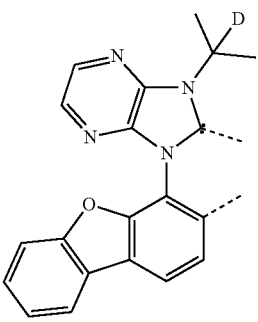 L_{B47} |
| 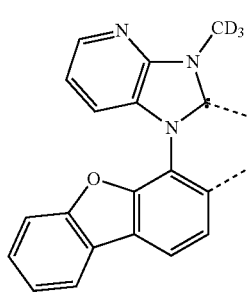 L_{B43} | L_{B48} 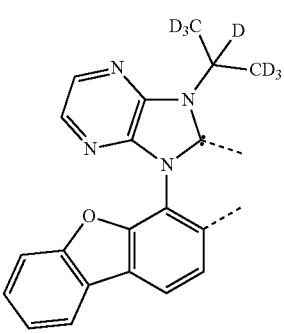 |
| 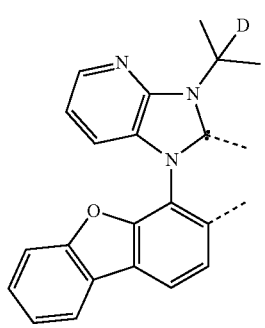 L_{B44} | L_{B49} 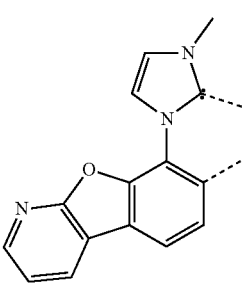 |
| 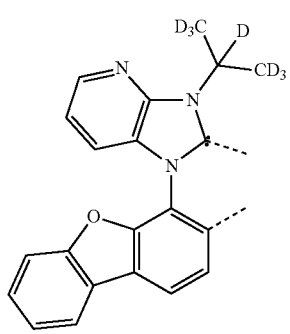 L_{B45} | L_{B50} 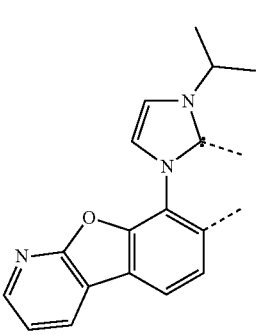 |
| 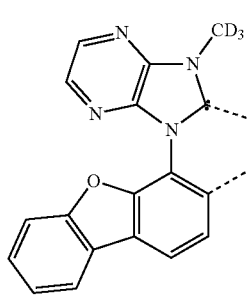 L_{B46} | L_{B51} 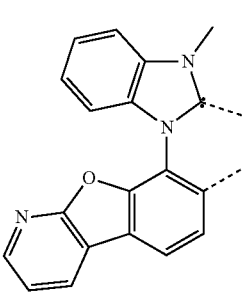 |

L<sub>B52</sub> 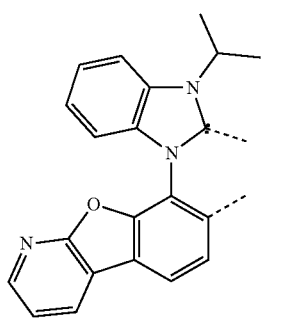
L<sub>B53</sub> 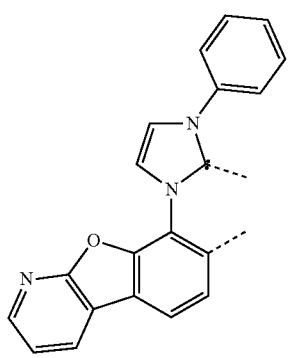
L<sub>B54</sub> 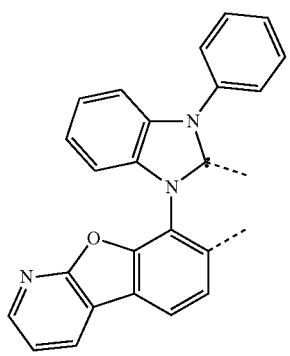
L<sub>B55</sub> 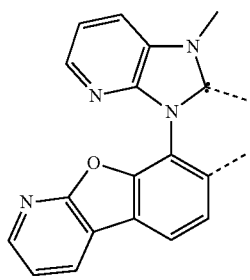
L<sub>B56</sub> 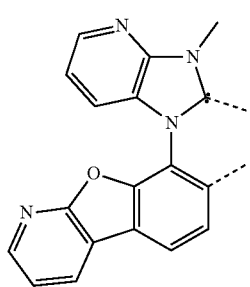
L<sub>B57</sub> 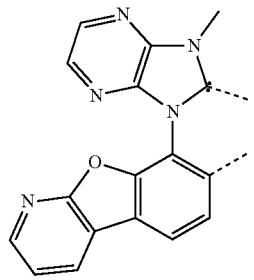
L<sub>B58</sub> 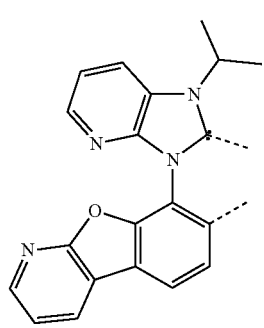
L<sub>B59</sub> 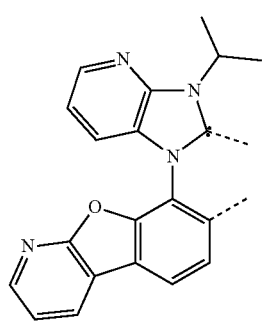
L<sub>B60</sub> 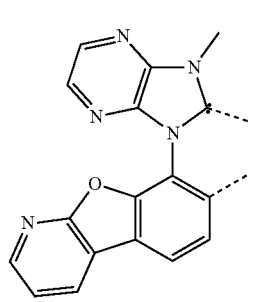
L<sub>B61</sub> 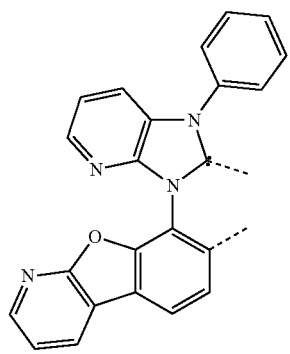

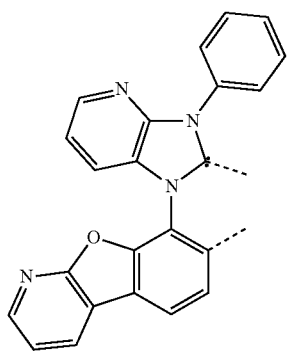
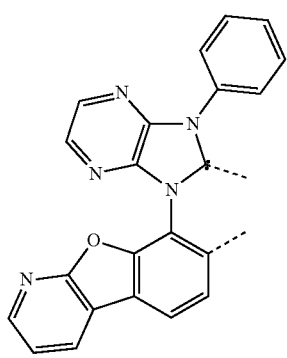
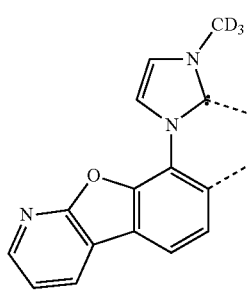
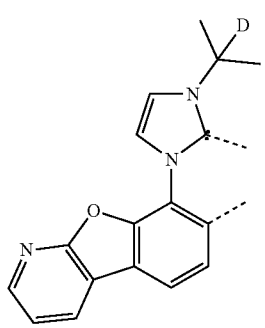
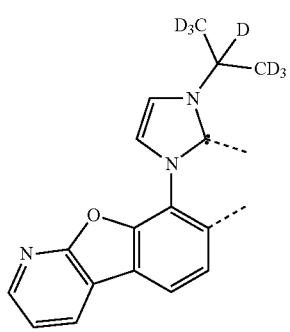
$L_{B62}$
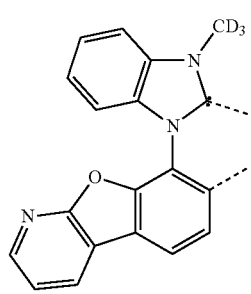
$L_{B63}$
$L_{B64}$
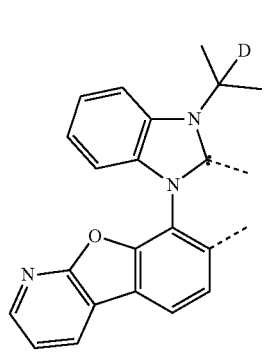
$L_{B65}$
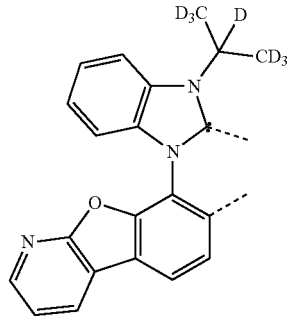
$L_{B66}$
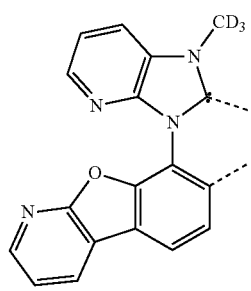
$L_{B67}$
$L_{B68}$
$L_{B69}$
$L_{B70}$
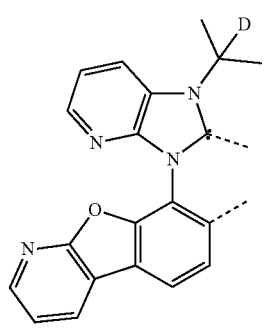
$L_{B71}$

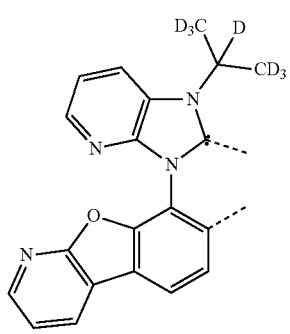
L<sub>B72</sub>
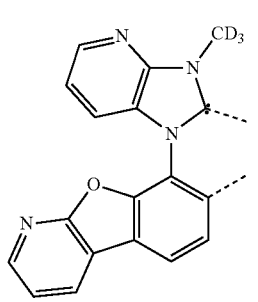
L<sub>B73</sub>
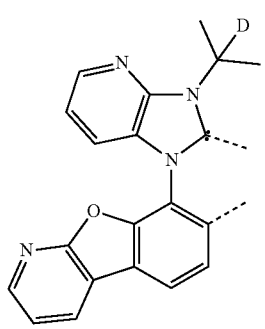
L<sub>B74</sub>
L<sub>B75</sub>
L<sub>B76</sub>
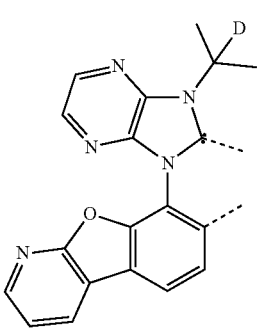
L<sub>B77</sub>
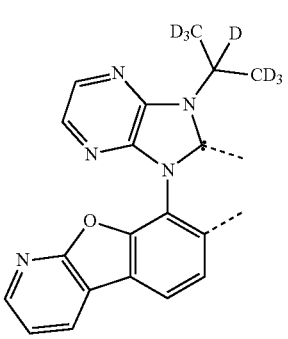
L<sub>B78</sub>
L<sub>B79</sub>
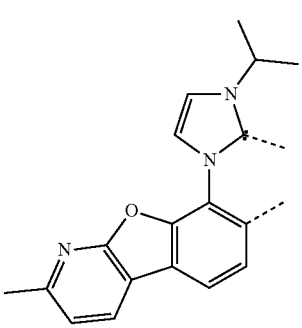
L<sub>B80</sub>
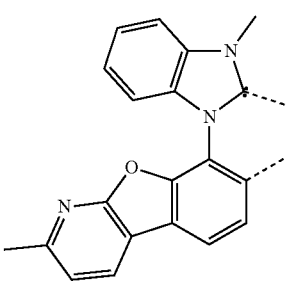
L<sub>B81</sub>
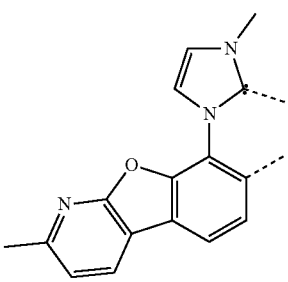

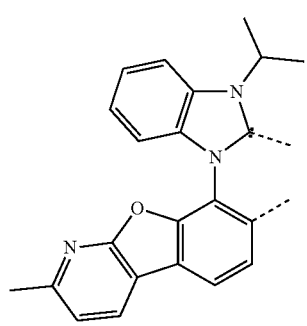
L_{B82}
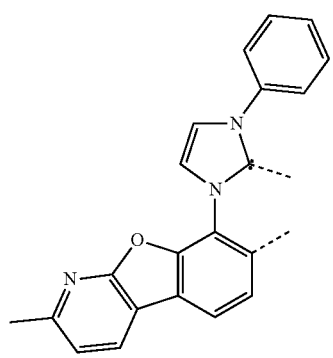
L_{B83}
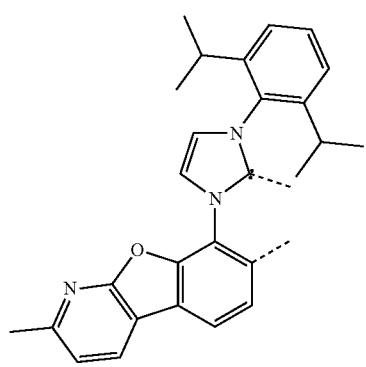
L_{B84}
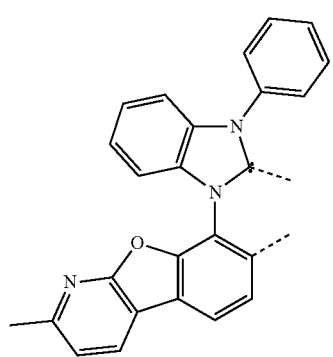
L_{B85}
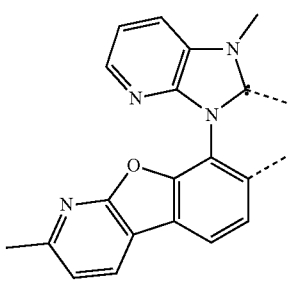
L_{B86}
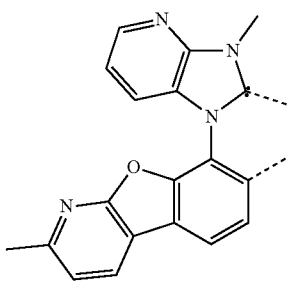
L_{B87}
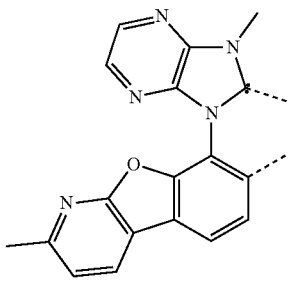
L_{B88}
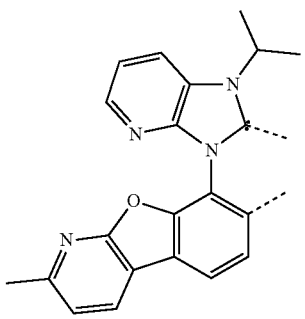
L_{B89}
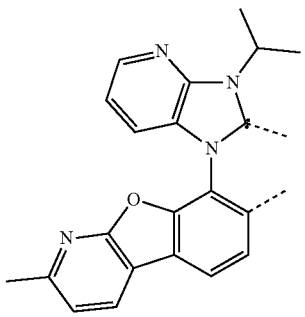
L_{B90}

L<sub>B91</sub> 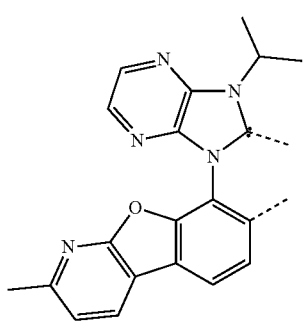
L<sub>B92</sub> 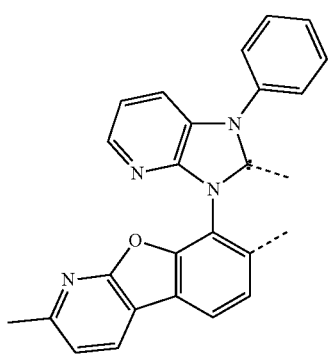
L<sub>B93</sub> 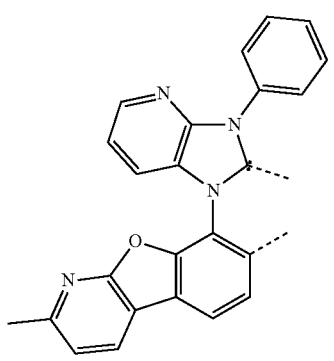
L<sub>B94</sub> 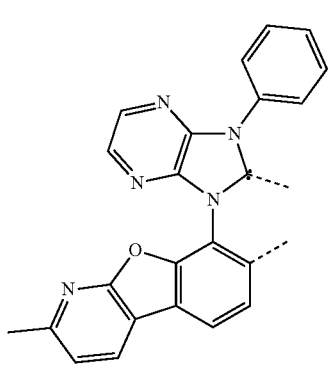
L<sub>B95</sub> 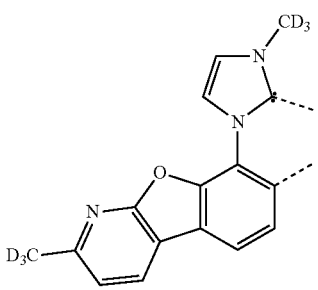
L<sub>B96</sub> 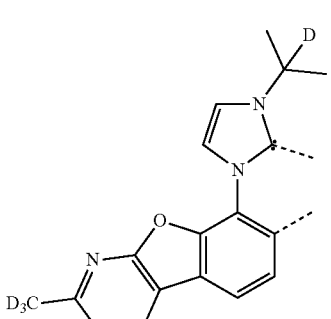
L<sub>B97</sub> 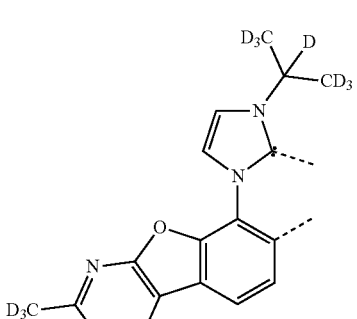
L<sub>B98</sub> 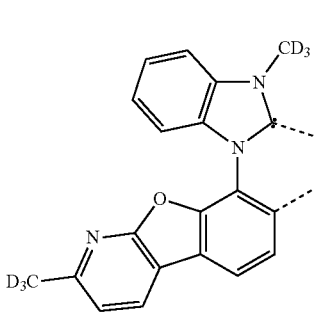
L<sub>B99</sub> 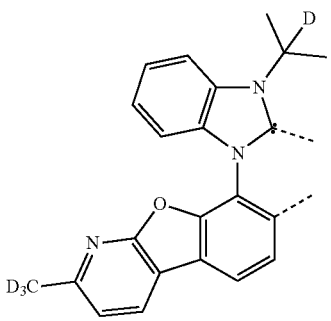

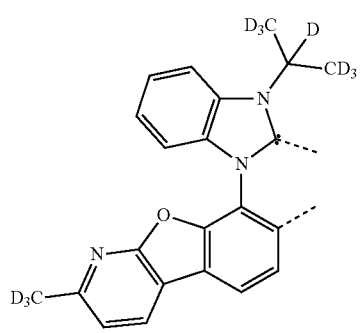
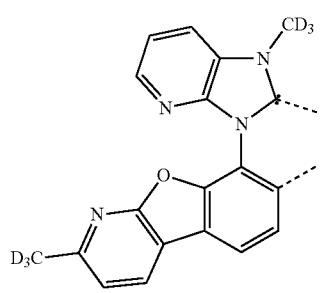
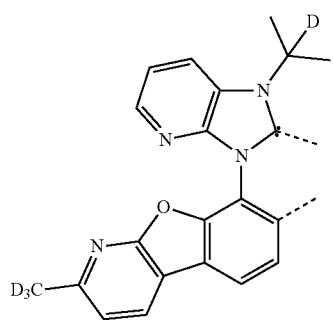
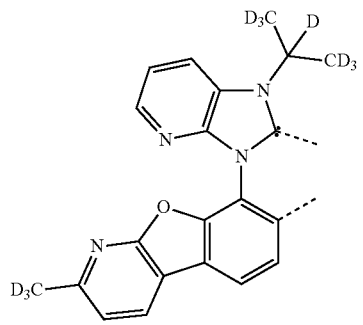
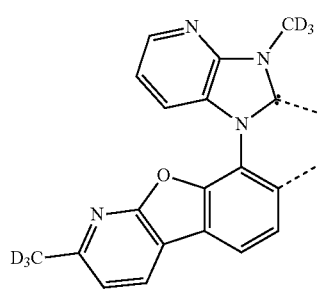
L$_{B100}$
L$_{B101}$
L$_{B102}$
L$_{B103}$
L$_{B104}$
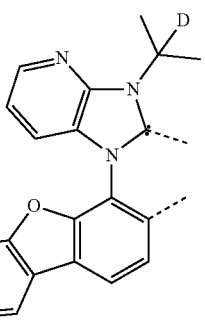
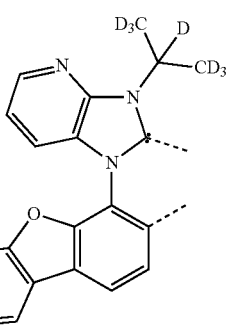
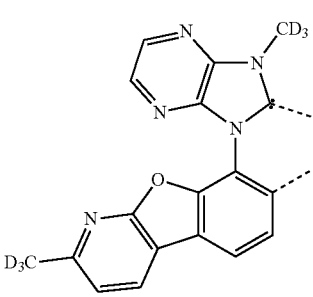
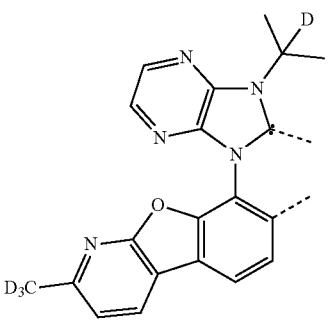
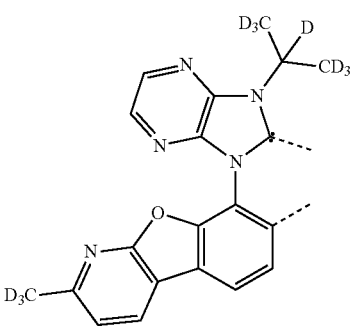
L$_{B105}$
L$_{B106}$
L$_{B107}$
L$_{B108}$
L$_{B109}$ L<sub>B110</sub>
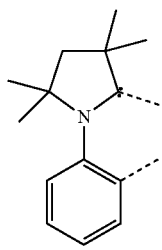
L<sub>B111</sub>
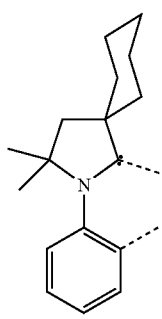
L<sub>B112</sub>
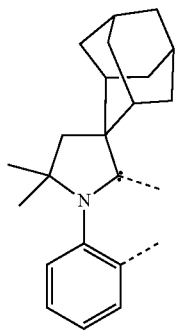
L<sub>B113</sub>
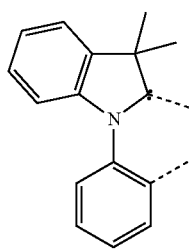
L<sub>B114</sub>
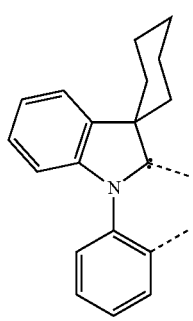
L<sub>B115</sub>
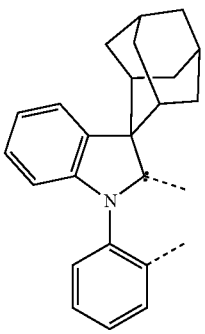
L<sub>B116</sub>
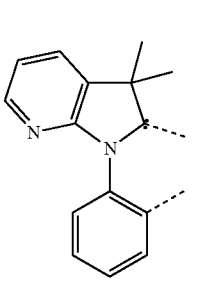
L<sub>B117</sub>
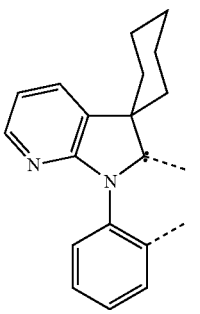
L<sub>B118</sub>
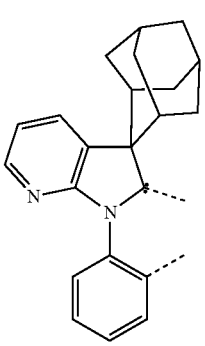
L<sub>B119</sub>
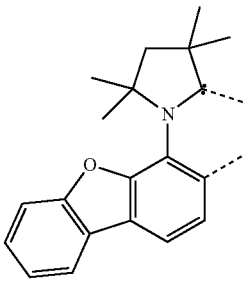

L<sub>B120</sub>
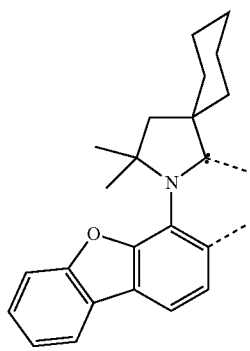
L<sub>B121</sub>
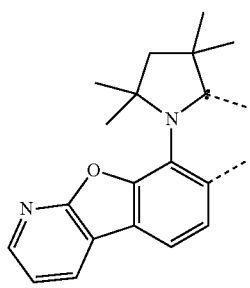
L<sub>B122</sub>
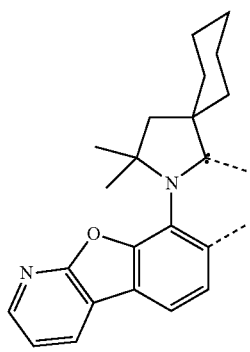
L<sub>B123</sub>
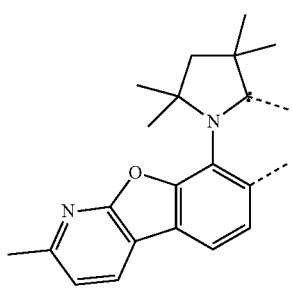
L<sub>B124</sub>
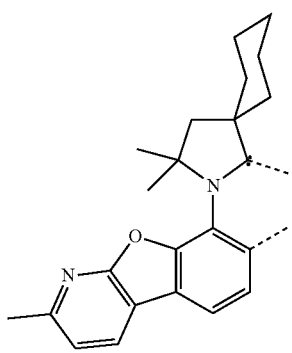
L<sub>B125</sub>
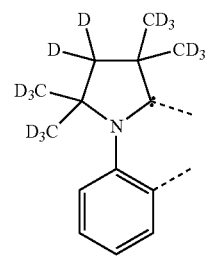
L<sub>B126</sub>
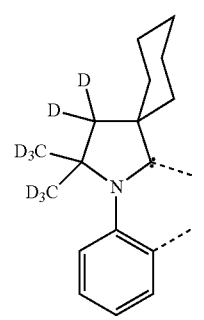
L<sub>B127</sub>
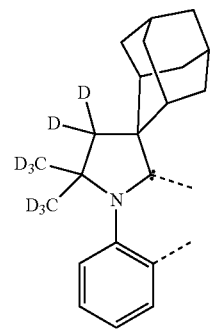
L<sub>B128</sub>
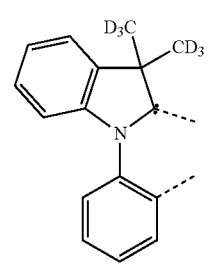
L<sub>B129</sub>
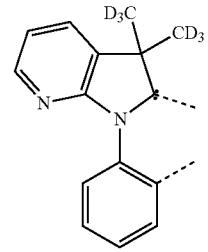

-continued
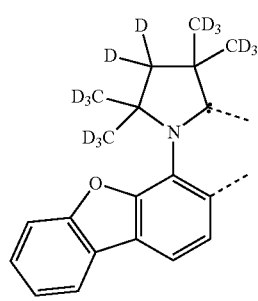
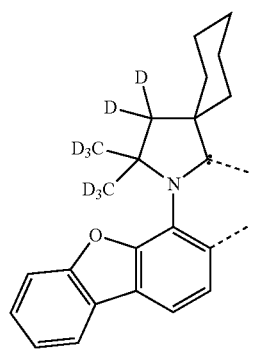
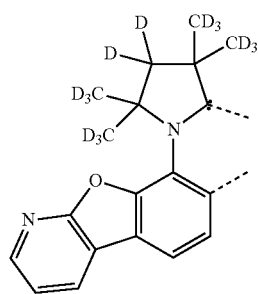
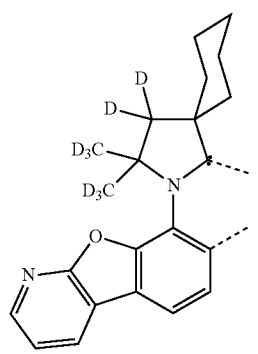
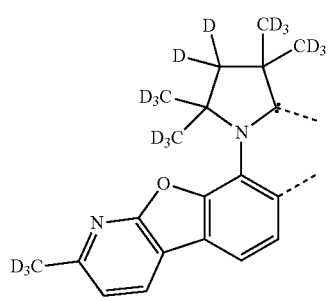
-continued
L$_{B130}$
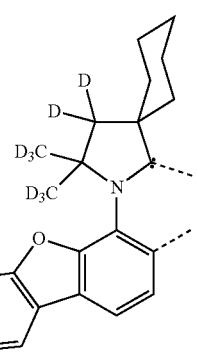
L$_{B135}$
L$_{B131}$
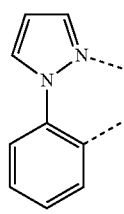
L$_{B136}$
L$_{B132}$
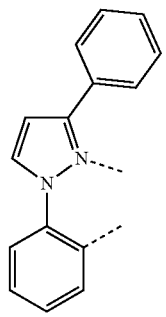
L$_{B137}$
L$_{B133}$
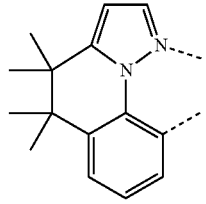
L$_{B138}$
L$_{B134}$
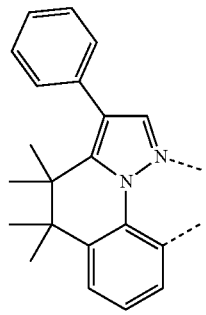
L$_{B139}$ L<sub>B140</sub>
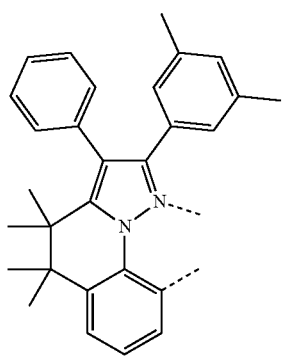
L<sub>B145</sub>
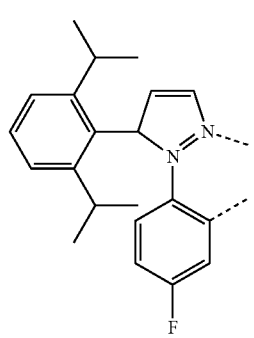
L<sub>B141</sub>
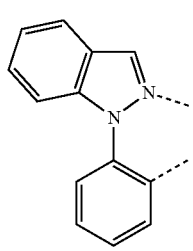
L<sub>B146</sub>
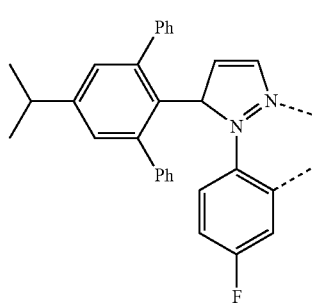
L<sub>B142</sub>
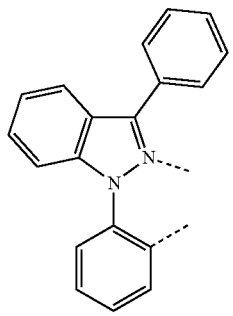
L<sub>B147</sub>
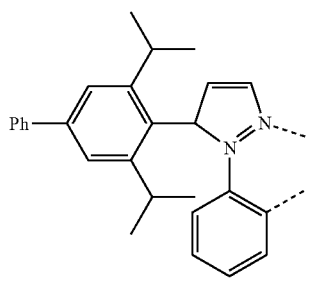
L<sub>B143</sub>
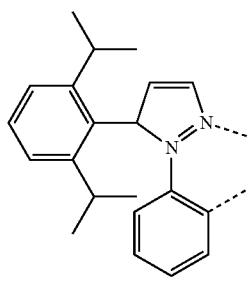
L<sub>B148</sub>
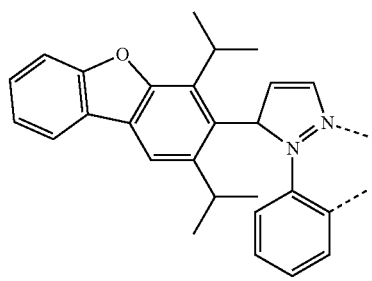
L<sub>B144</sub>
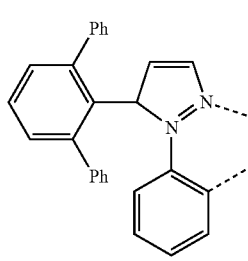
L<sub>B149</sub>
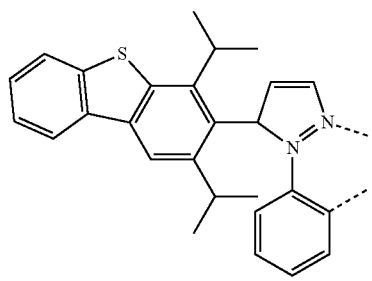

-continued
L$_{B150}$
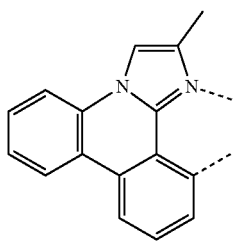
L$_{B151}$
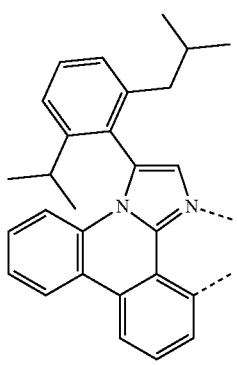
L$_{B152}$
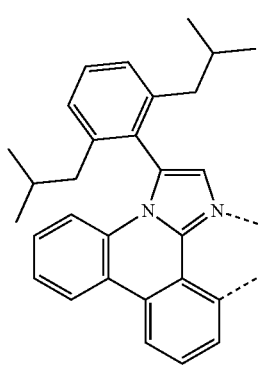
L$_{B153}$
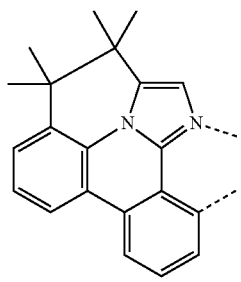
L$_{B154}$
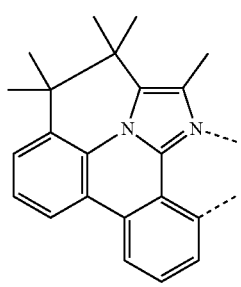
-continued
L$_{B155}$
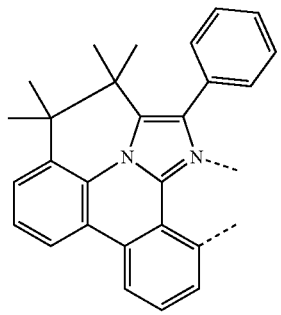
L$_{B156}$
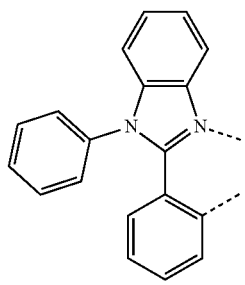
L$_{B157}$
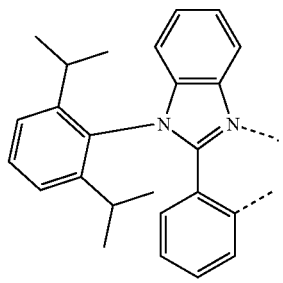
In some embodiments of the OLED where the emitter has the formula of $M(L^1)_2$ or $M(L^1)(L^2)$, where M is Pt or Pd, the emitter is selected from the following Group 1 consisting of:
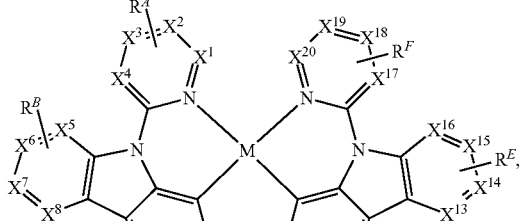
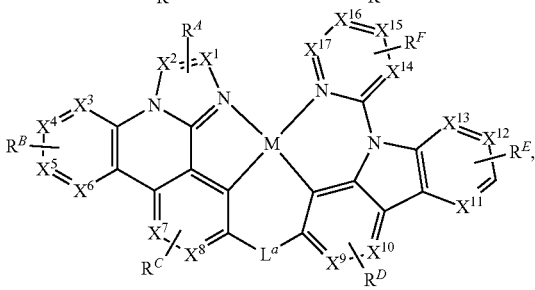

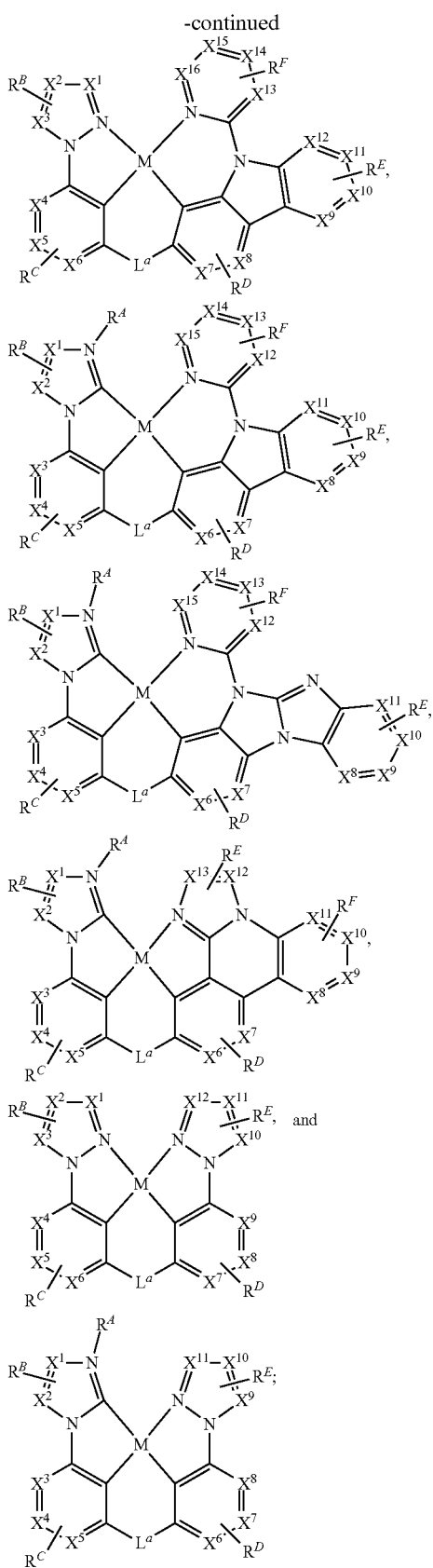

where $X^1$ to $X^{20}$ is C or N, $L^a$ is selected from the group consisting of O, S, Se, NR, PR, BR, BRR', CRR', SiRR', GeRR, and C=X, wherein X is O, S, NR", or CR'R"; each $R^A$ to $R^F$ may represent from mono substitution to the possible maximum number of substitution, or no substitution; each R, R', R", $R^A$ to $R^F$ is independently a hydrogen or a substitution selected from the group consisting of the general substituents defined herein; and any two R, R', R", $R^A$ to $R^F$ are optionally fused or joined to form a ring or form a multidentate ligand. In some embodiments, the maximum number of nitrogen atoms that can connect to each other within a ring is two. In some embodiments, each 6-membered ring can contain up to one nitrogen atom. In some embodiments, at least one of $R^A$ to $R^F$ comprises a chemical group containing at least three, four, five, or six 6-membered aromatic rings that are not fused next to each other.

In some embodiments of the OLED where the emitter has the formula of $M(L^1)_2$ or $M(L^1)(L^2)$ and the emitter is selected from the Group 1, $R^A$ comprises a chemical group containing at least three, four, five, or six 6-membered aromatic rings that are not fused next to each other.

In some embodiments of the OLED where the emitter is selected from the group consisting of:

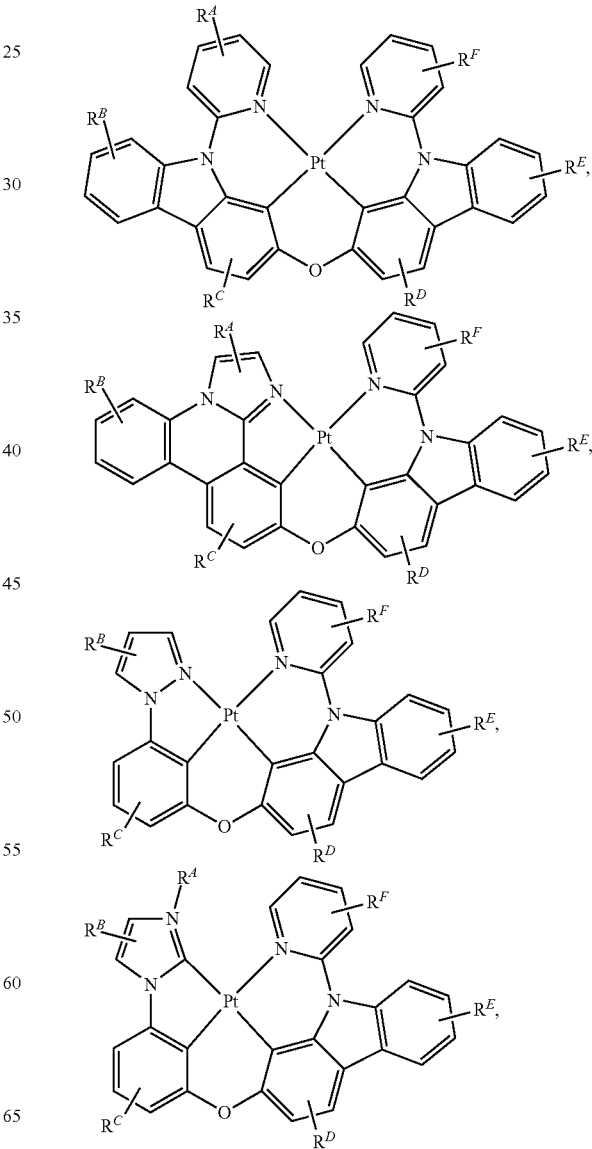

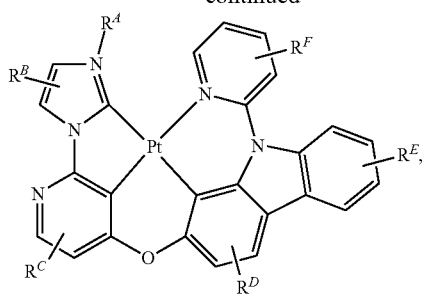
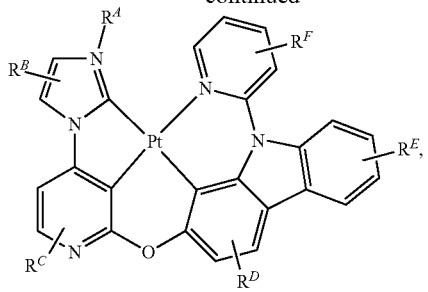
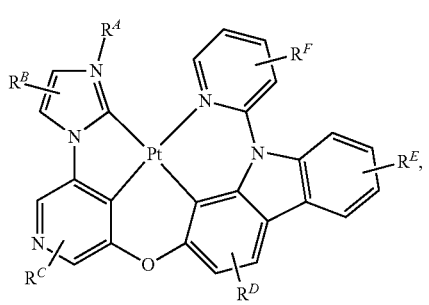
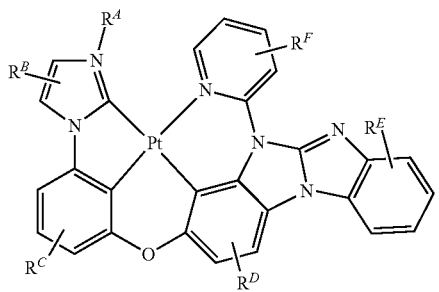
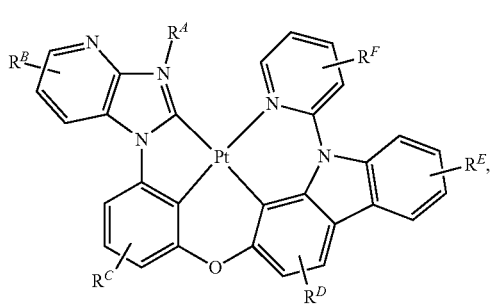
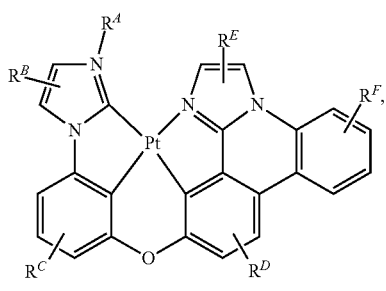
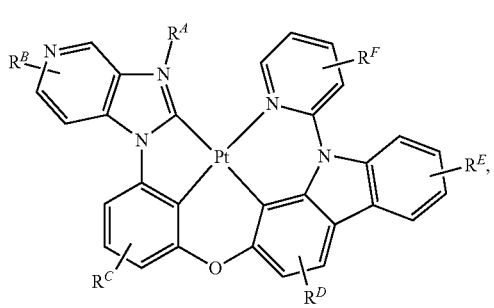
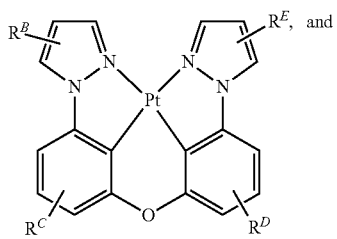
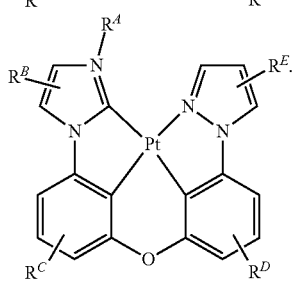
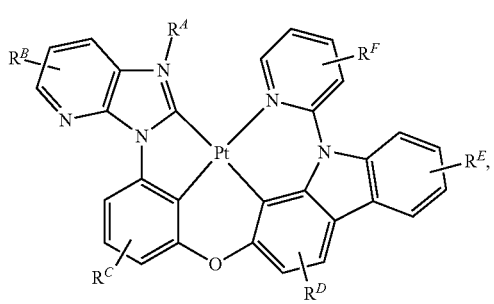
In some embodiments of the OLED, the emitter is selected from the group consisting of the structures defined by β-(Ri)(Rj)(Rk)(Rl)(Rm)(Rn), where β is an integer from 1 to 15, and β'-(Ri)(Rj)(Rk)(Rl)(Rm)(Rn)(Xo), where β' is an integer from 16 to 27, where i is an integer from 1 to 292, j, k, l, m, and n are integers independently from 1 to 307, and o is an integer from 1 to 21:

| Emitter | Structure of emitter |
|---|---|
| wherein when β is 1, 1-(R1)(R1)(R1)(R1)(R1)(R1) to 1-(R292)(R307)(R307)(R307)(R307)(R307), having the structure | 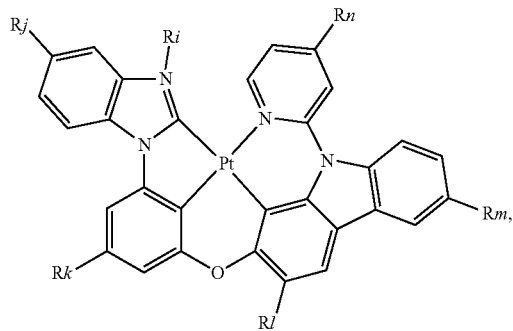 |
| wherein when β is 2, 2-(R1)(R1)(R1)(R1)(R1)(R1) to 2-(R292)(R307)(R307)(R307)(R307)(R307), having the structure | 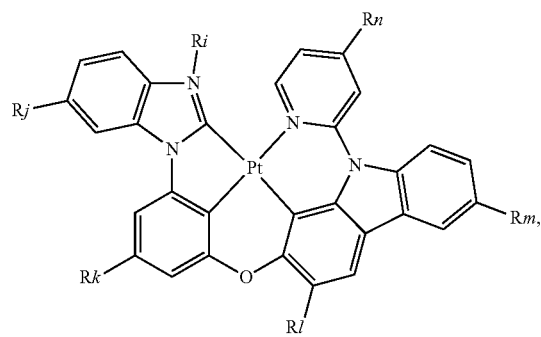 |
| wherein when β is 3, 3-(R1)(R1)(R1)(R1)(R1)(R1) to 3-(R292)(R307)(R307)(R307)(R307)(R307), having the structure | 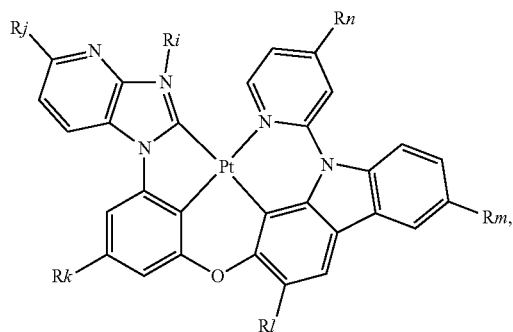 |
| wherein when β is 4, 4-(R1)(R1)(R1)(R1)(R1)(R1) to 4-(R292)(R307)(R307)(R307)(R307)(R307), having the structure | 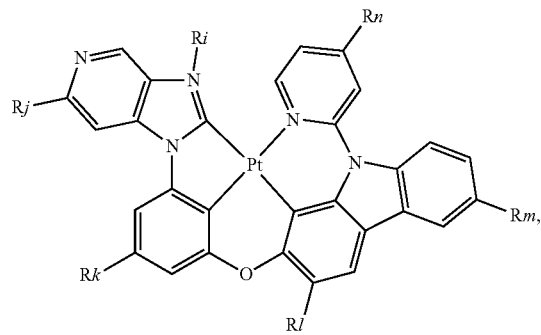 |

| Emitter | Structure of emitter |
|---|---|
| wherein when β is 5,<br>5-(R1)(R1)(R1)(R1)(R1)(R1) to<br>5-(R292)(R307)(R307)(R307)(R307)(R307), having the structure | 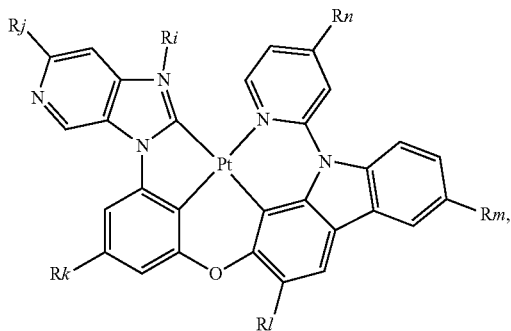 |
| wherein when β is 6,<br>6-(R1)(R1)(R1)(R1)(R1)(R1) to<br>6-(R292)(R307)(R307)(R307)(R307)(R307), having the structure | 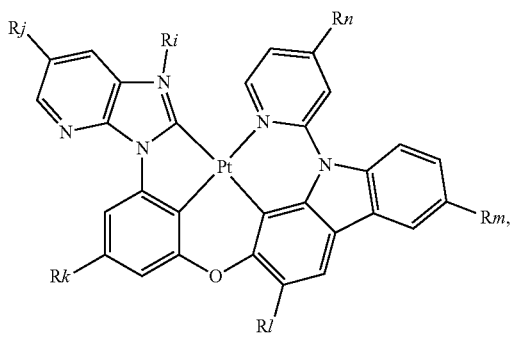 |
| wherein when β is 7,<br>7-(R1)(R1)(R1)(R1)(R1)(R1) to<br>7-(R292)(R307)(R307)(R307)(R307)(R307), having the structure | 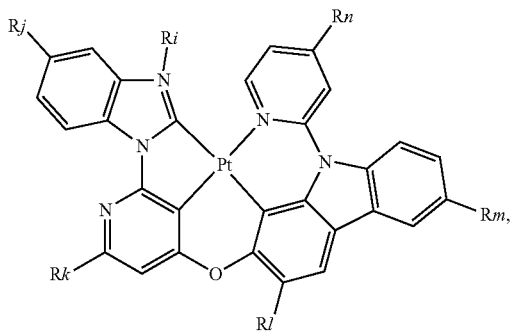 |
| wherein when β is 8,<br>8-(R1)(R1)(R1)(R1)(R1)(R1) to<br>8-(R292)(R307)(R307)(R307)(R307)(R307), having the structure | 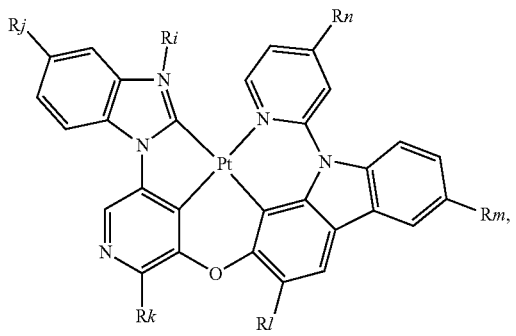 |

| Emitter | Structure of emitter |
|---|---|
| wherein when β is 9, 9-(R1)(R1)(R1)(R1)(R1) to 9-(R292)(R307)(R307)(R307)(R307)(R307), having the structure | 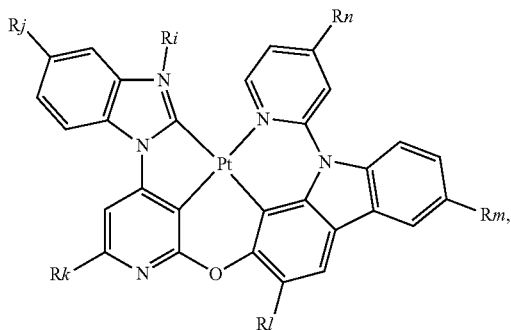 |
| wherein when β is 10, 10-(R1)(R1)(R1)(R1)(R1)(R1) to 10-(R292)(R307)(R307)(R307)(R307)(R307), having the structure | 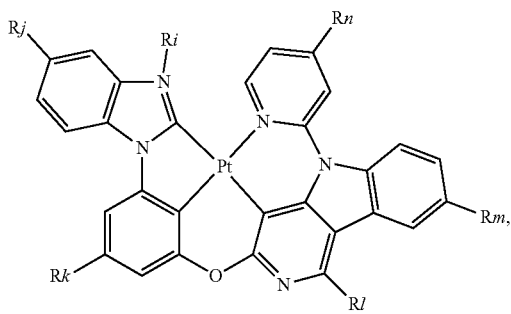 |
| wherein when β is 11, 11-(R1)(R1)(R1)(R1)(R1)(R1) to 11-(R292)(R307)(R307)(R307)(R307)(R307), having the structure | 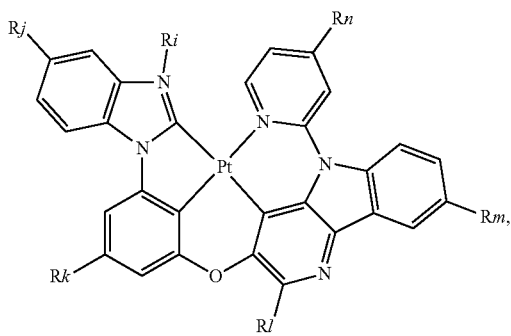 |
| wherein when β is 12, 12-(R1)(R1)(R1)(R1)(R1)(R1) to 12-(R292)(R307)(R307)(R307)(R307)(R307), having the structure | 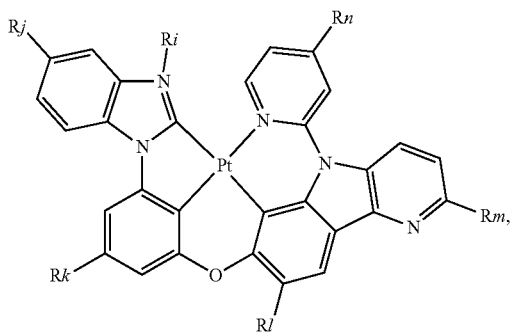 |

| Emitter | Structure of emitter |
|---|---|
| wherein when β is 13,<br>13-(R1)(R1)(R1)(R1)(R1)(R1) to<br>13-(R292)(R307)(R307)(R307)(R307)(R307), having the structure | 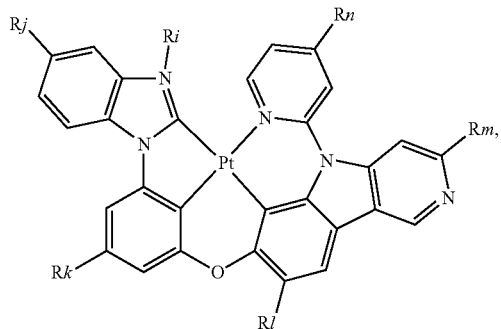 |
| wherein when β is 14,<br>14-(R1)(R1)(R1)(R1)(R1)(R1) to<br>14-(R292)(R307)(R307)(R307)(R307)(R307), having the structure | 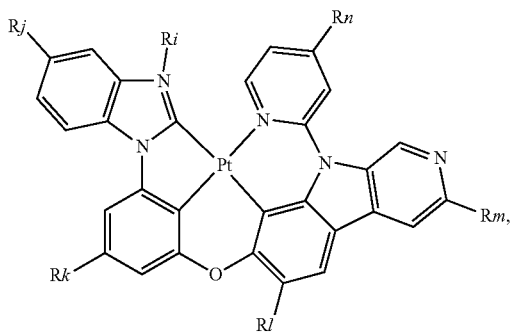 |
| wherein when β is 15,<br>15-(R1)(R1)(R1)(R1)(R1)(R1) to<br>15-(R292)(R307)(R307)(R307)(R307)(R307), having the structure | 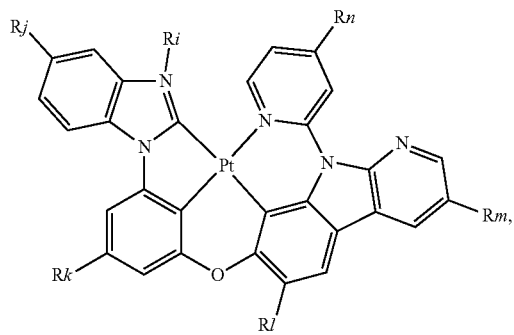 |
| wherein when β' is 16,<br>16-(R1)(R1)(R1)(R1)(R1)(R1)(X1) to<br>16-(R292)(R307)(R307)(R307)(R307)(R307)(X21), having the structure | 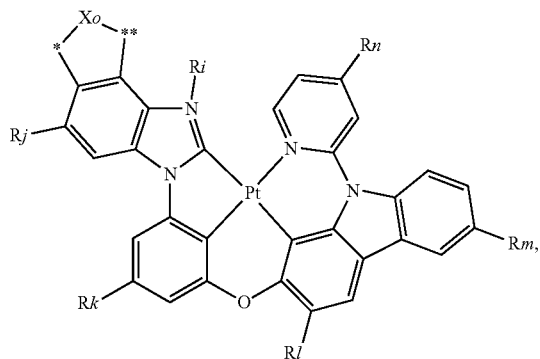 |

| Emitter | Structure of emitter |
|---|---|
| wherein when β' is 17, 17-(R1)(R1)(R1)(R1)(R1)(X1) to 17-(R292)(R307)(R307)(R307)(R307)(R307)(X21), having the structure | 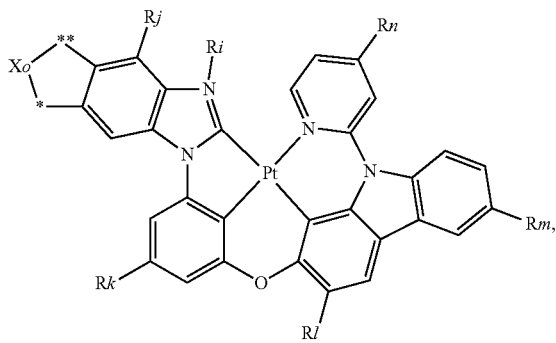 |
| wherein when β' is 18, 18-(R1)(R1)(R1)(R1)(R1)(R1)(X1) to 18-(R292)(R307)(R307)(R307)(R307)(R307)(X21), having the structure | 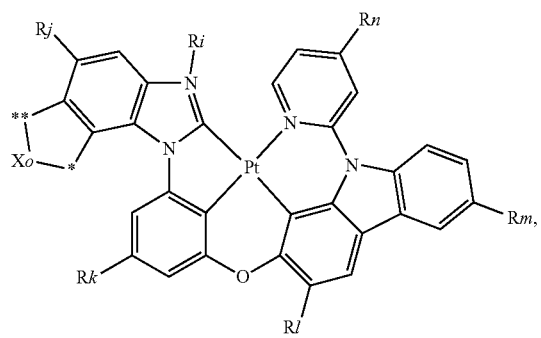 |
| wherein when β' is 16, 19-(R1)(R1)(R1)(R1)(R1)(R1)(X1) to 19-(R292)(R307)(R307)(R307)(R307)(R307)(X21), having the structure | 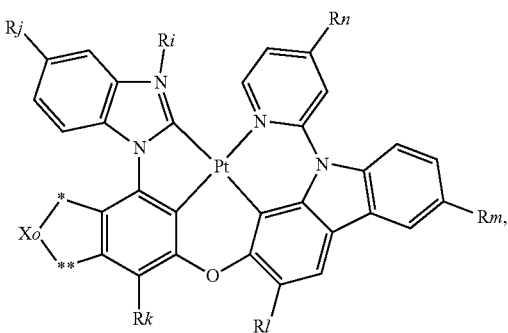 |
| wherein when β' is 20, 20-(R1)(R1)(R1)(R1)(R1)(R1)(X1) to 20-(R292)(R307)(R307)(R307)(R307)(R307)(X21), having the structure | 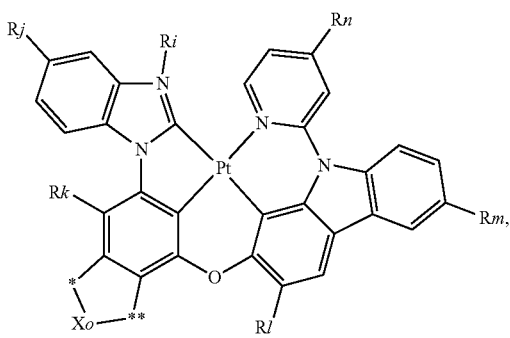 |

| Emitter | Structure of emitter |
|---|---|
| wherein when β' is 21, 21-(R1)(R1)(R1)(R1)(R1)(R1)(X1) to 21-(R292)(R307)(R307)(R307)(R307)(R307)(X21), having the structure | 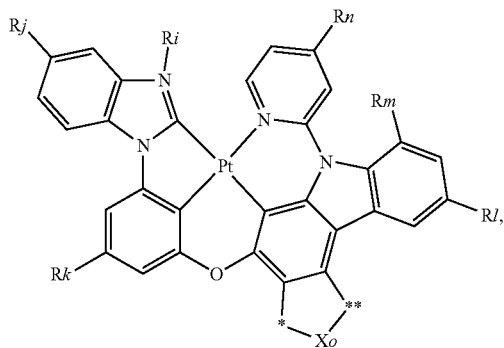 |
| wherein when β' is 22, 22-(R1)(R1)(R1)(R1)(R1)(R1)(X1) to 22-(R292)(R307)(R307)(R307)(R307)(R307)(X21), having the structure | 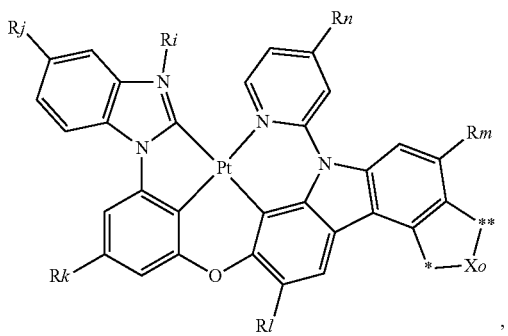 |
| wherein when β' is 23, 23-(R1)(R1)(R1)(R1)(R1)(R1)(X1) to 23-(R292)(R307)(R307)(R307)(R307)(R307)(X21), having the structure | 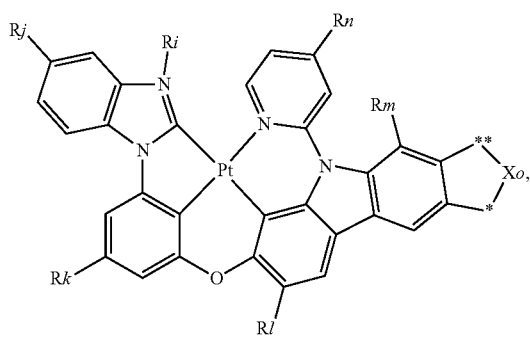 |
| wherein when β' is 24, 24-(R1)(R1)(R1)(R1)(R1)(R1)(X1) to 24-(R292)(R307)(R307)(R307)(R307)(R307)(X21), having the structure | 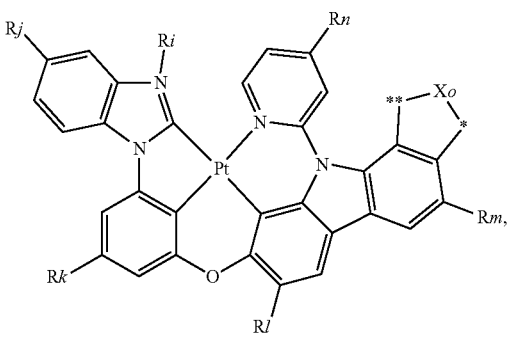 |

| Emitter | Structure of emitter |
|---|---|
| wherein when β' is 25, 25-(R1)(R1)(R1)(R1)(R1)(R1)(X1) to 25-(R292)(R307)(R307)(R307)(R307)(R307)(X21), having the structure | 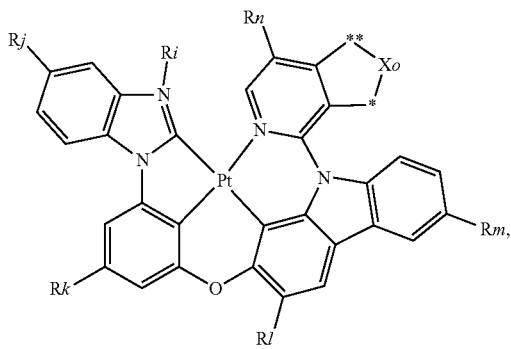 |
| wherein when β' is 26, 26-(R1)(R1)(R1)(R1)(R1)(R1)(X1) to 26-(R292)(R307)(R307)(R307)(R307)(R307)(X21), having the structure | 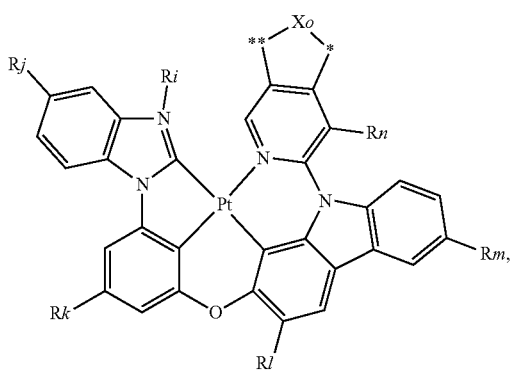 |
| wherein when β' is 27, 27-(R1)(R1)(R1)(R1)(R1)(R1)(X1) to 27-(R292)(R307)(R307)(R307)(R307)(R307)(X21), having the structure | 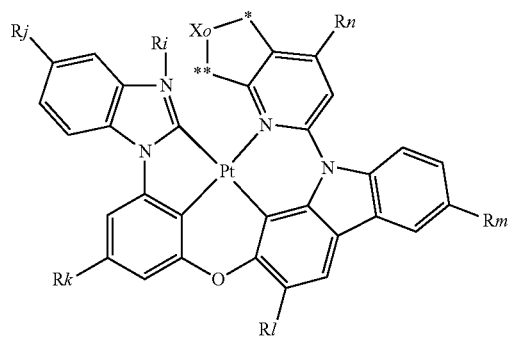 |
wherein R1 to R307 have the following structures:
Me,    R1
iPr,   R2
tBu,   R3
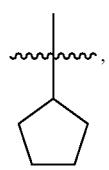   R4
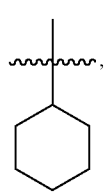   R5
-continued
R6

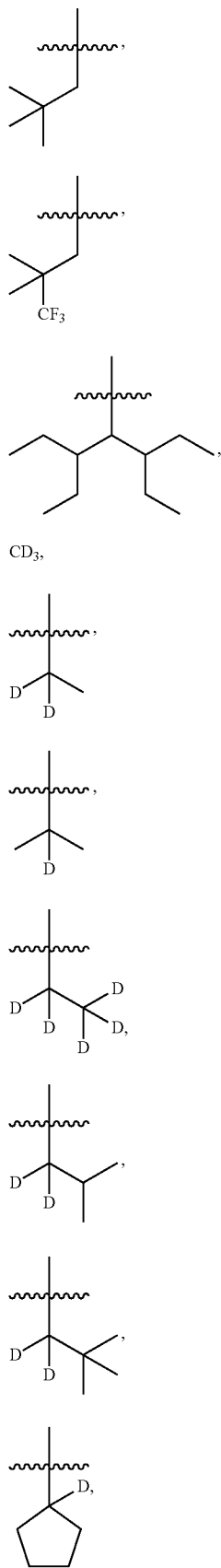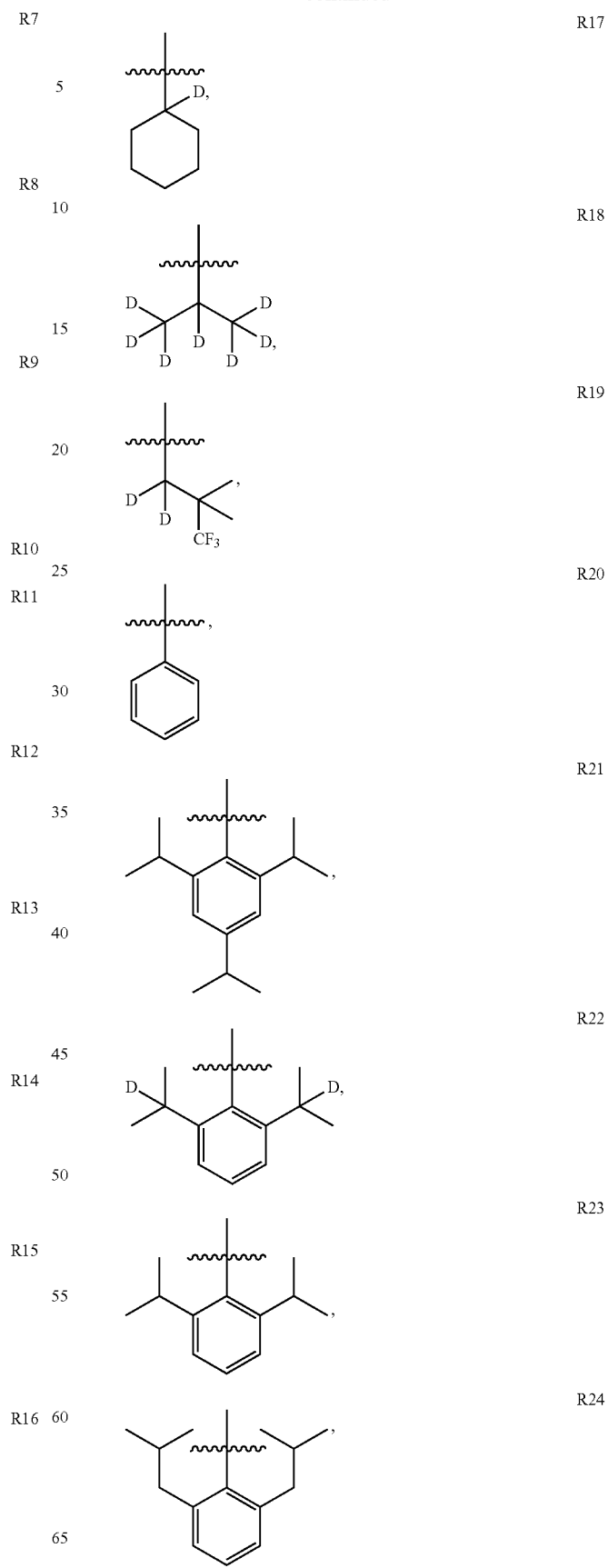

-continued
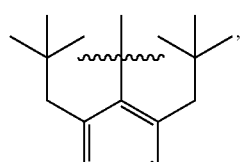 R25
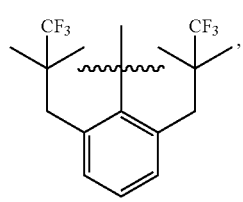 R26
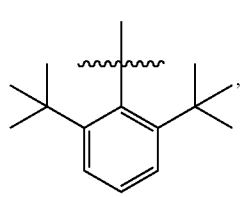 R27
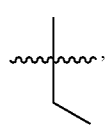 R28
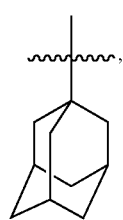 R29
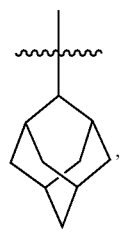 R30
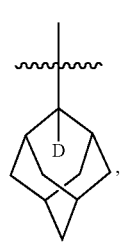 R31
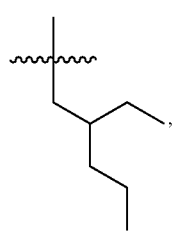 R32
-continued
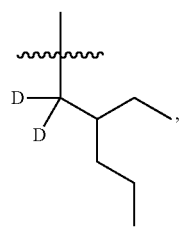 R33
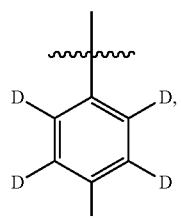 R34
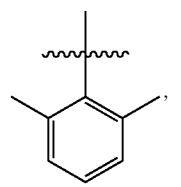 R35
 R36
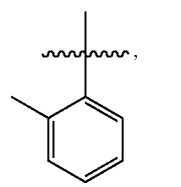 R37
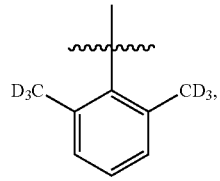 R38
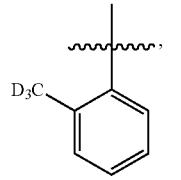 R39
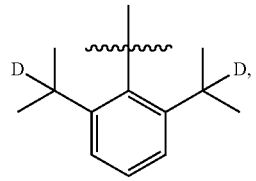 R40

75
-continued
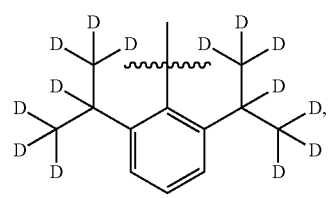
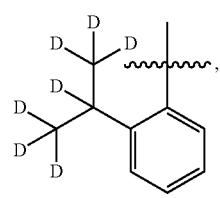
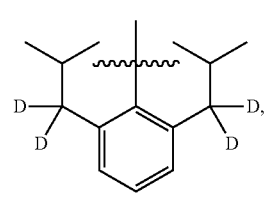
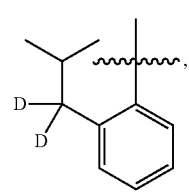
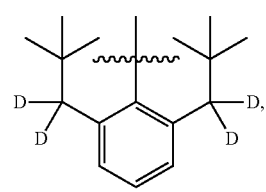
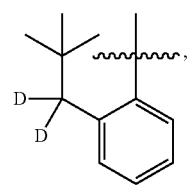
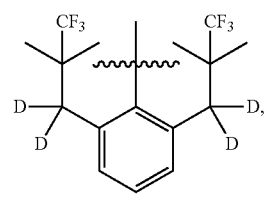
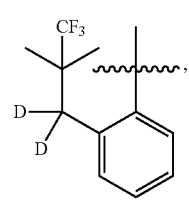
76
-continued
R41
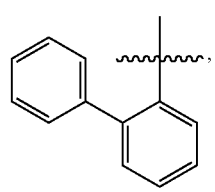
R49
R42
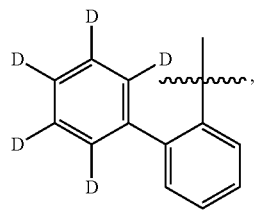
R50
R43
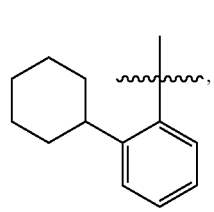
R51
R44
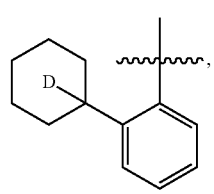
R52
R45
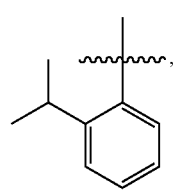
R53
R46
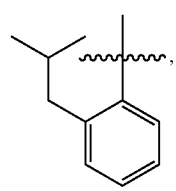
R54
R47
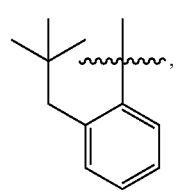
R55
R48
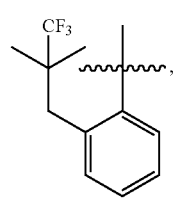
R56

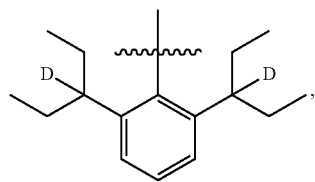
R57
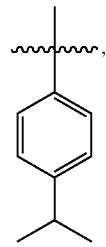
R64
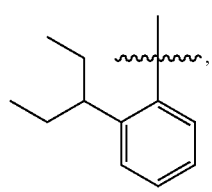
R58
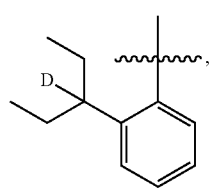
R59
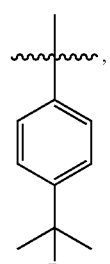
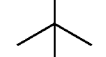
R65
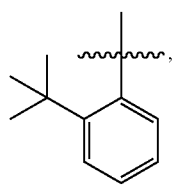
R60
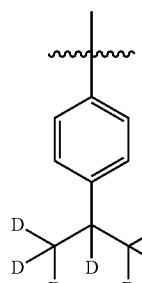
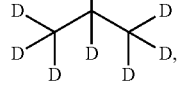
R66
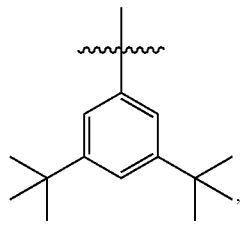
R61
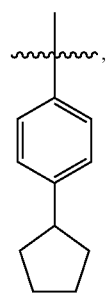
R67
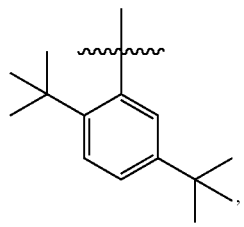
R62
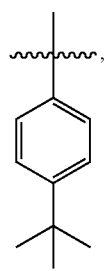
R63
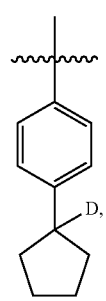
R68

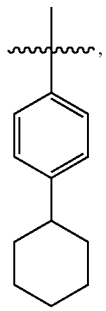
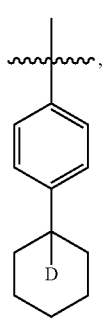
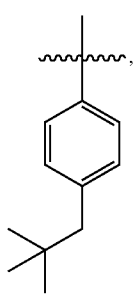
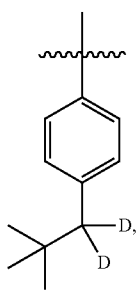
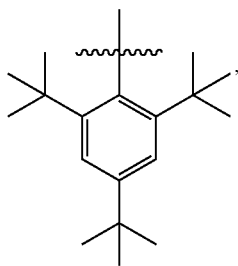
R69
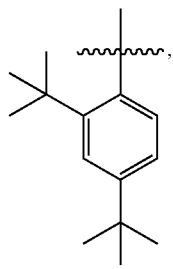
R70
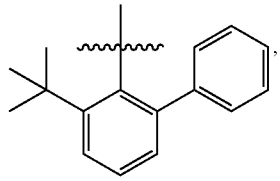
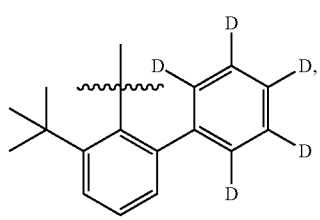
R71
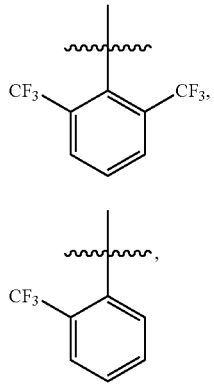
R72
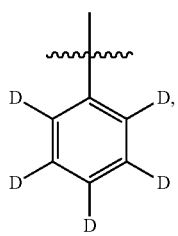
R73
R74
R75
R76
R77
R78
R79
R80

R81
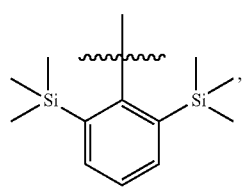
R82
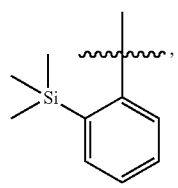
R83
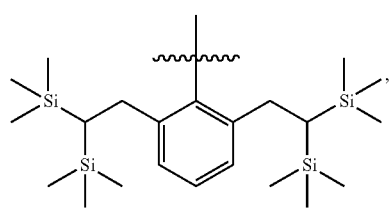
R84
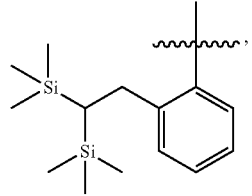
R85
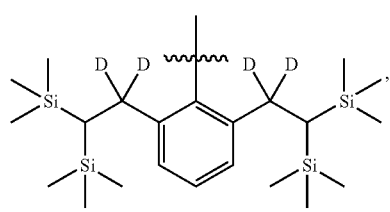
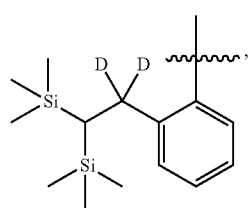
R86
R87
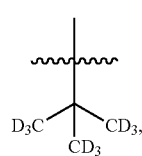
R88
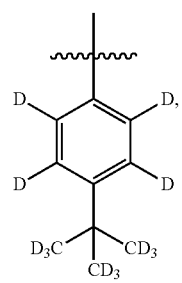
R89
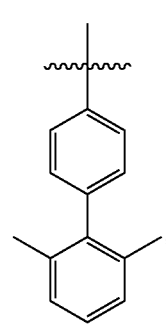
R90
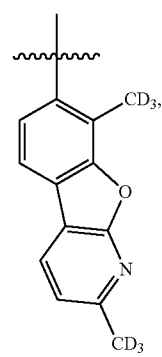
R91
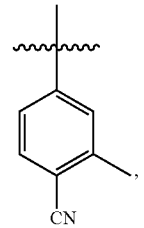
R92
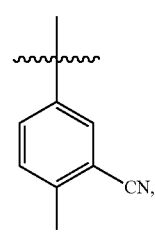

R93 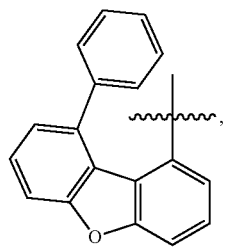
R94 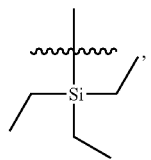
R95 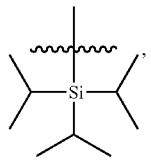
R96 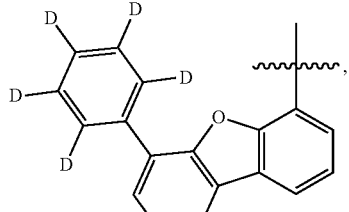
R97 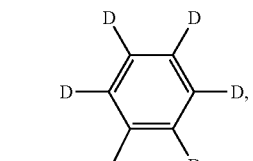
R98 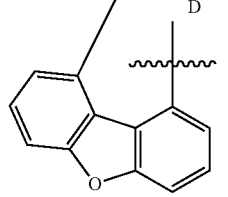
R99 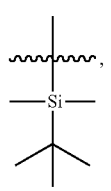
R100 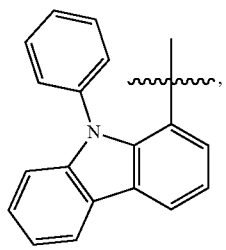
R101 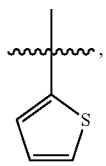
R102 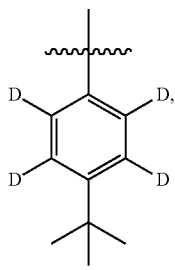
R103 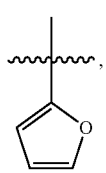
R104 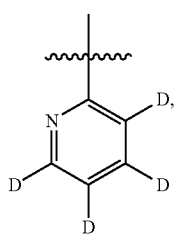
R105 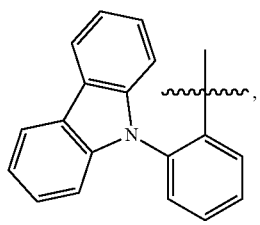
R106 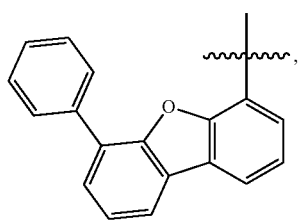

R107 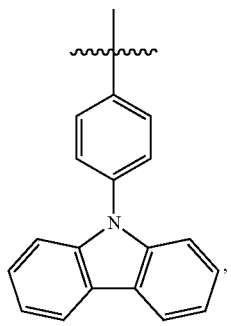
R108 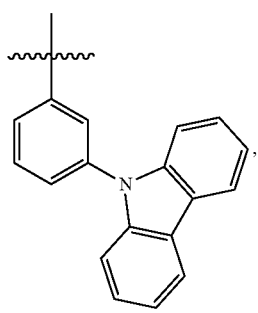
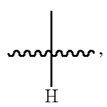 R109
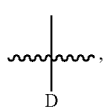 R110
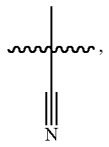 R111
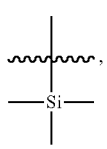 R112
R113 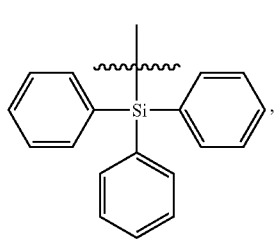
R114 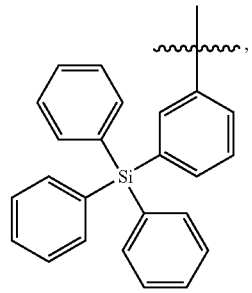
R115 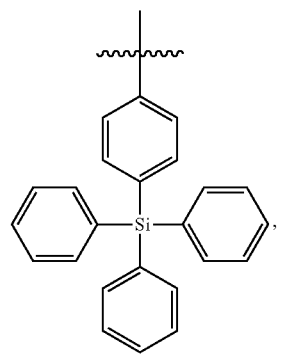
R116 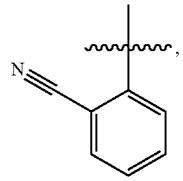
R117 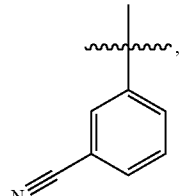
R118 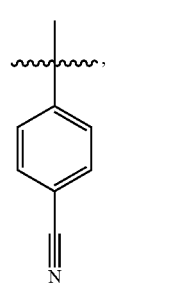
R119 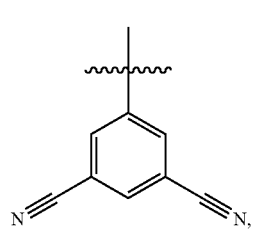

-continued
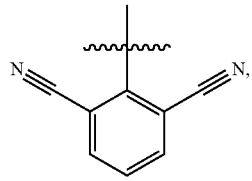
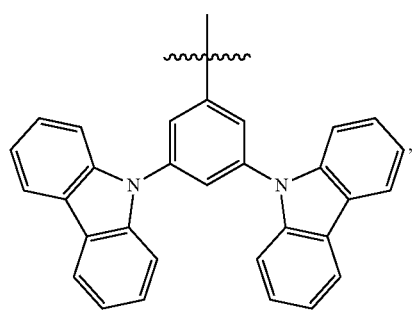
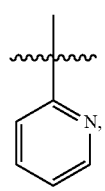
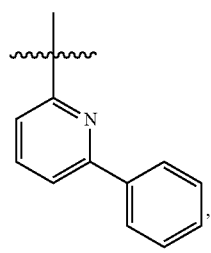
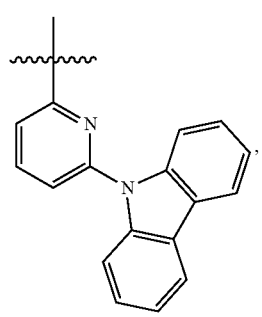
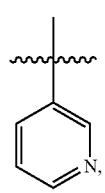
R120 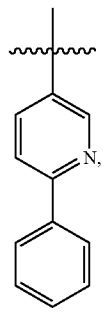
R121 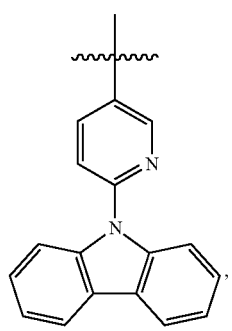
R123 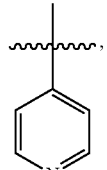
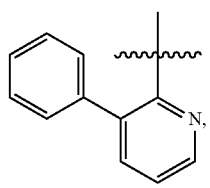
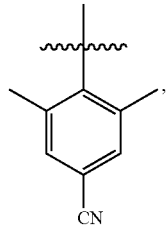
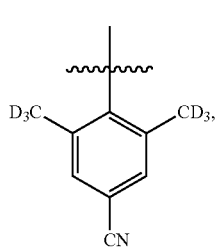
R126
R127
R128
R129
R130
R131

R132 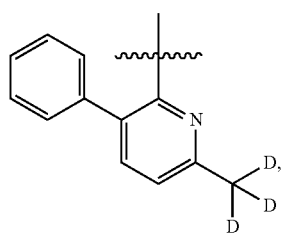
R133 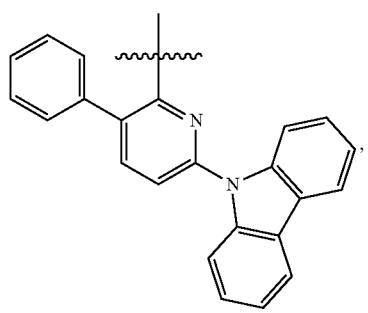
R134 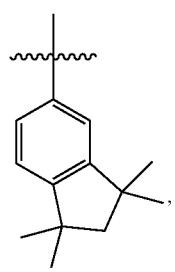
R135 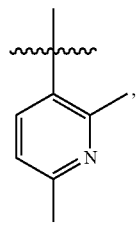
R136 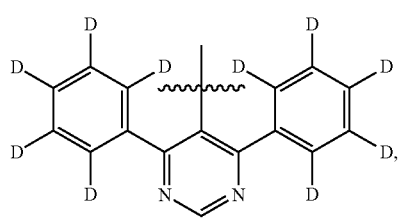
R137 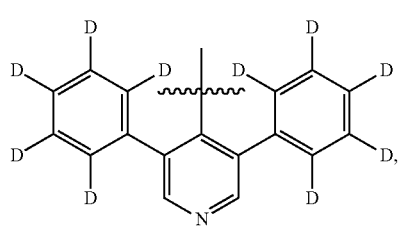
R138 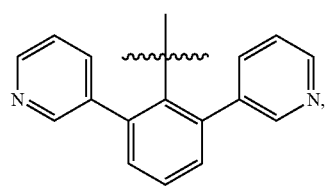
R139 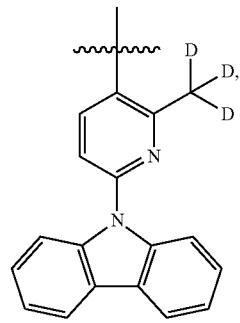
R140 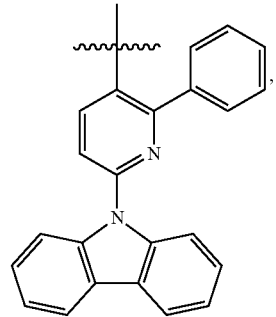
R141 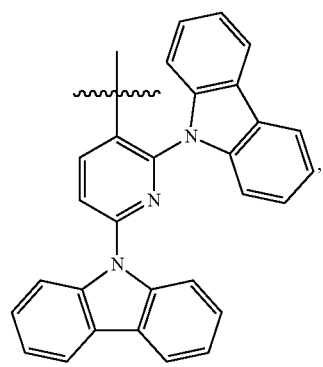
R142 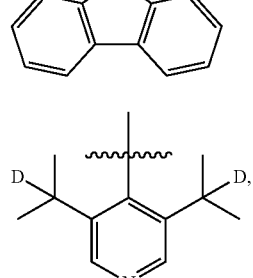
R143 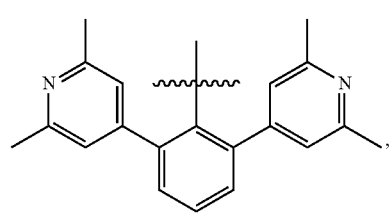

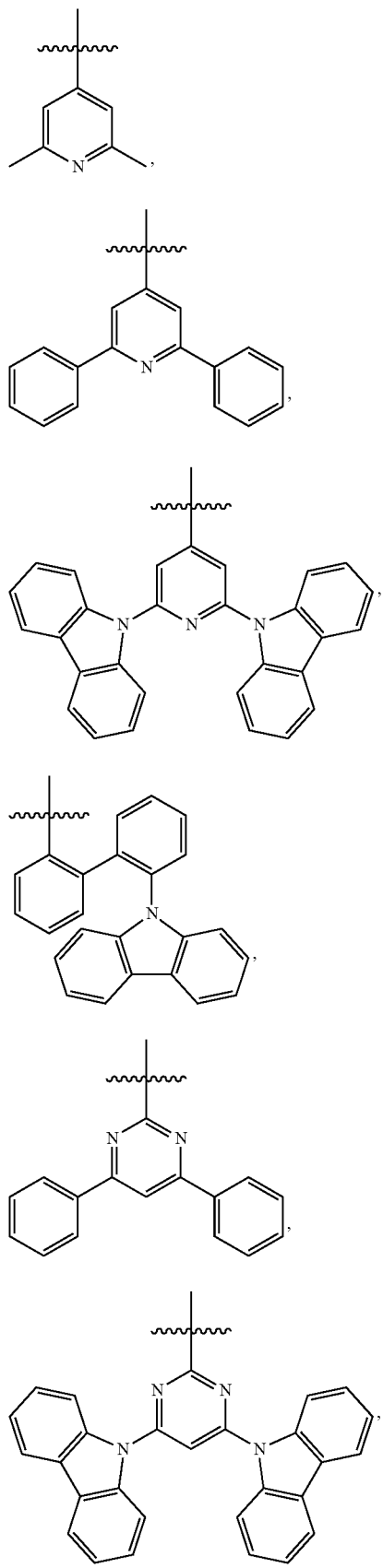
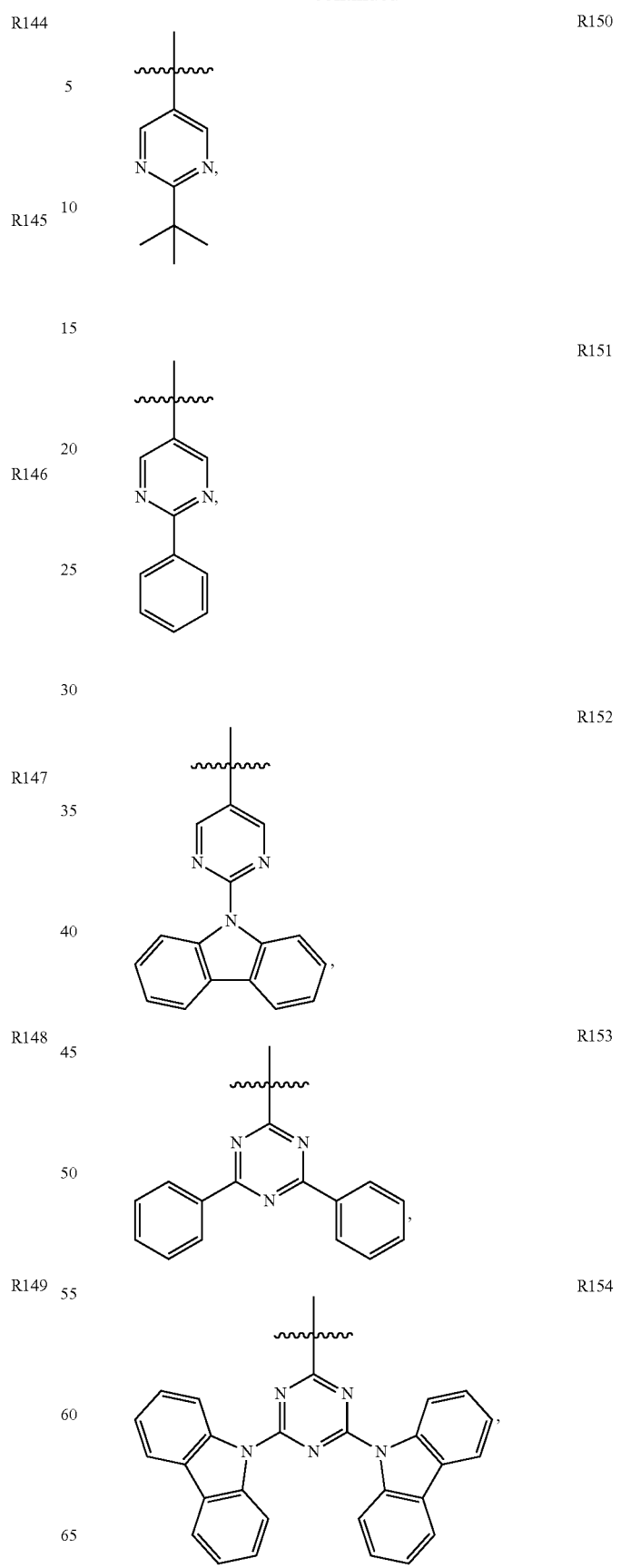

R155
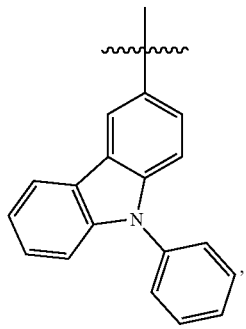
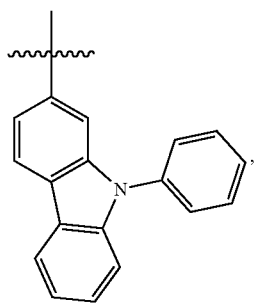
R156
R157
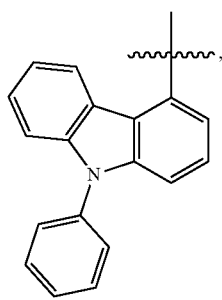
R158
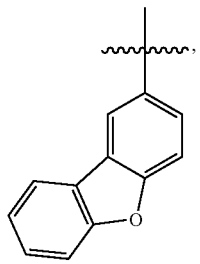
R159
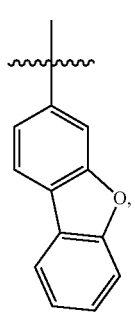
R160
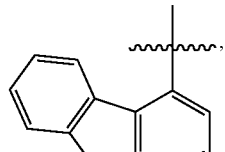
R161
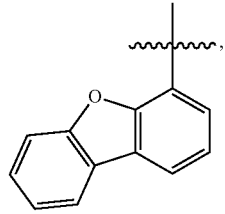
R162
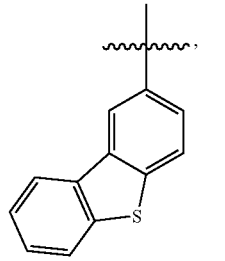
R163
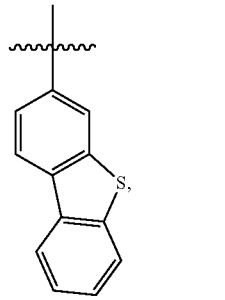
R164
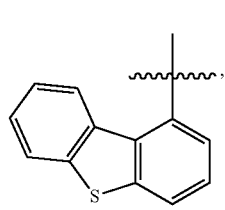
R165
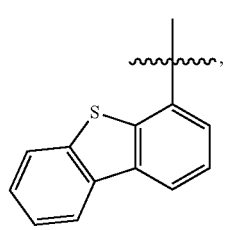

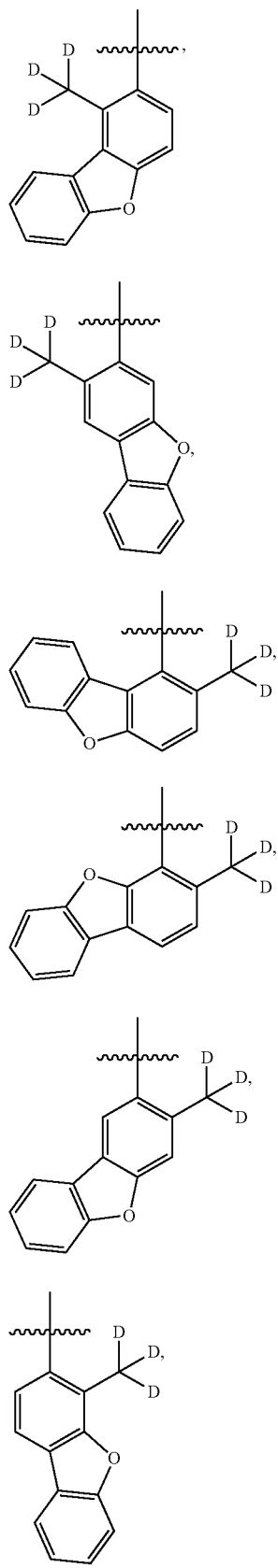

R178 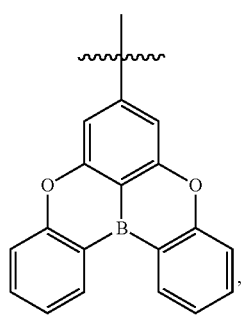
R179 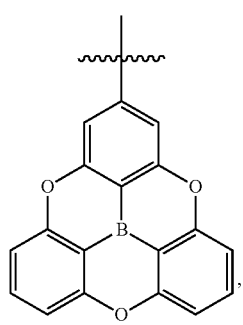
R180 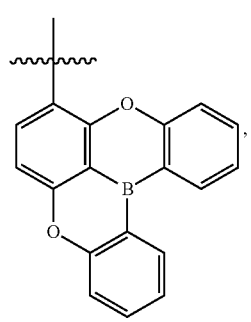
R181 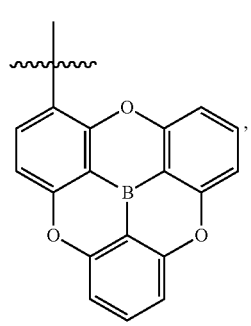
R182 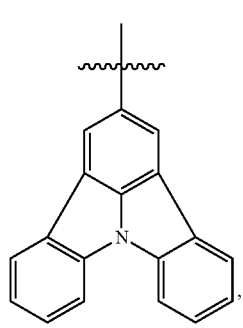
R183 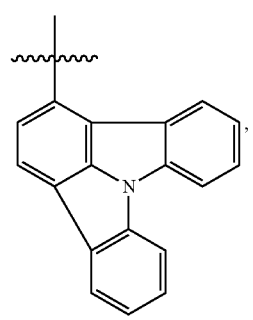
R184 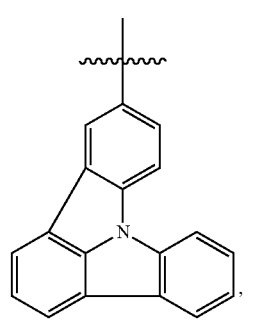
R185 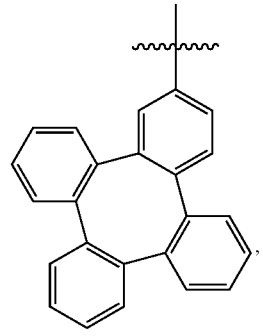
R186 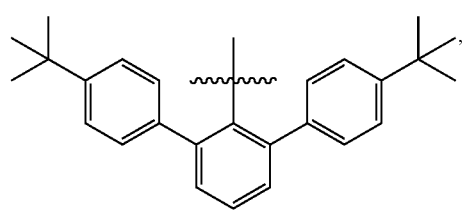
R187 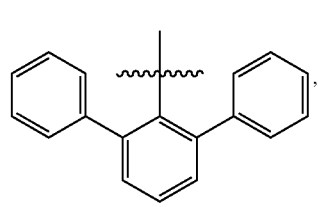
R188

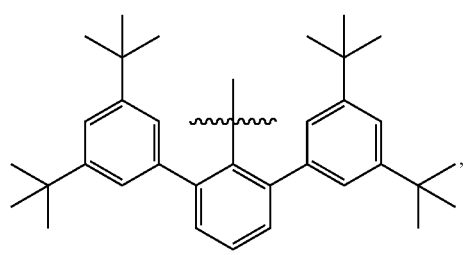 R189
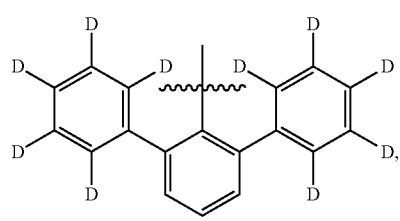 R190
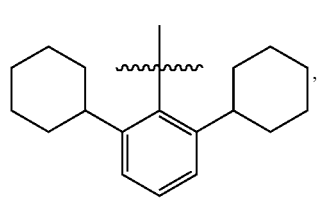 R191
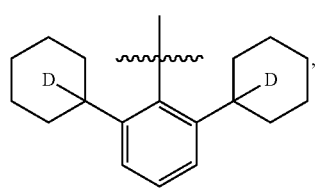 R192
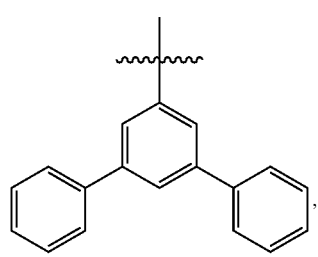 R193
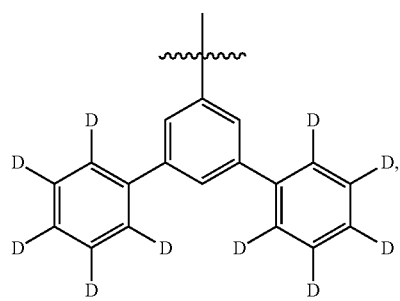 R194
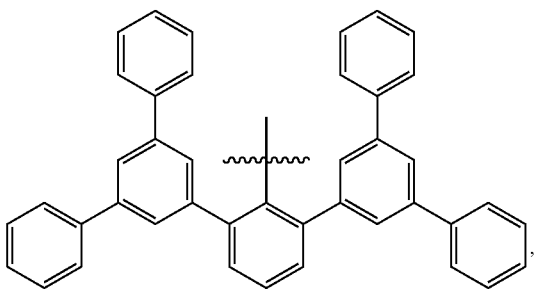 R195
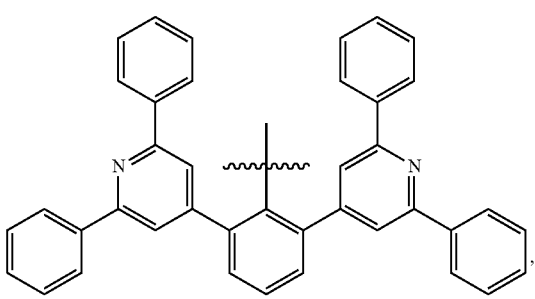 R196
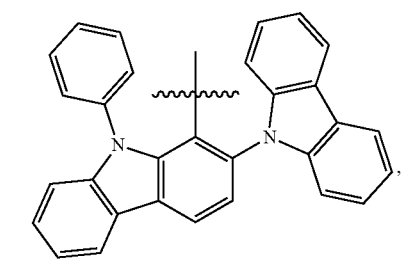 R197
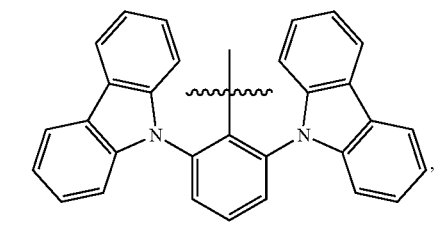 R198
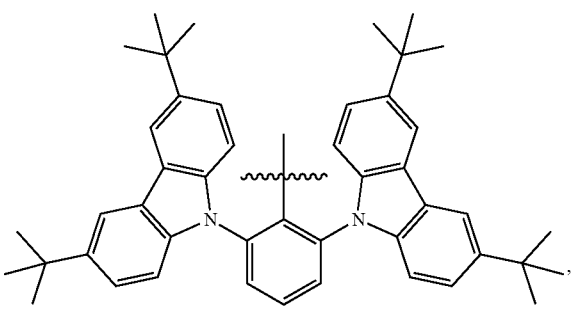 R199

101
-continued
R200
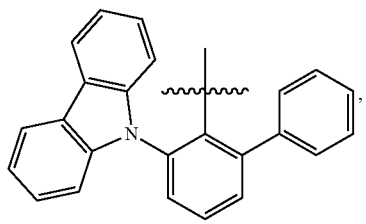
R201
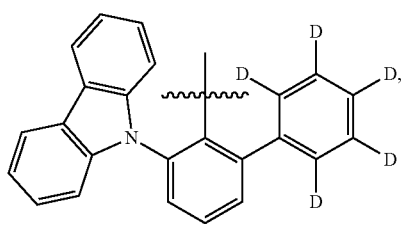
R202
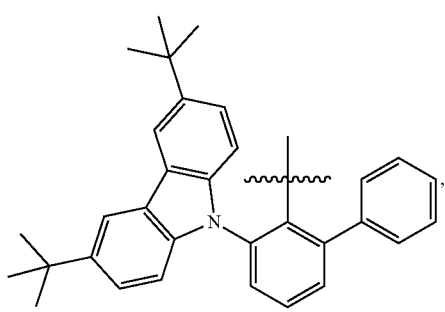
R203
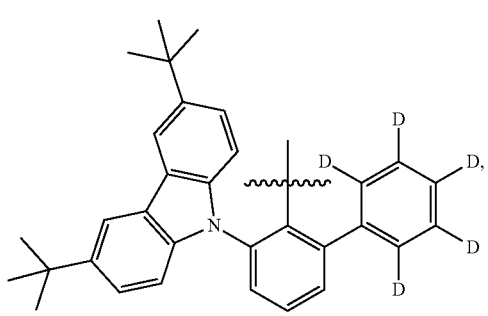
R204
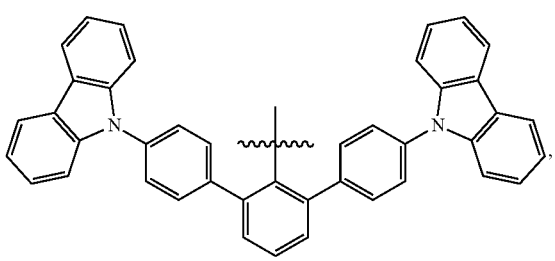
102
-continued
R205
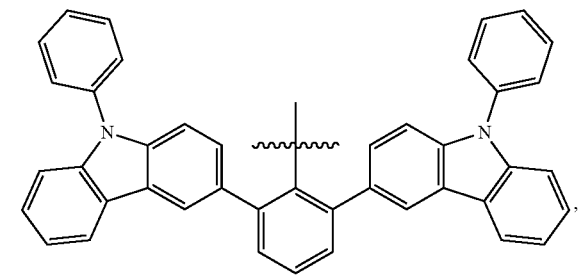
R206
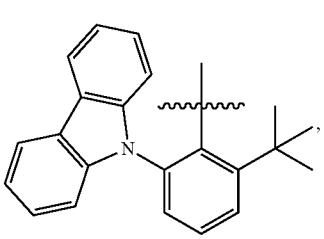
R207
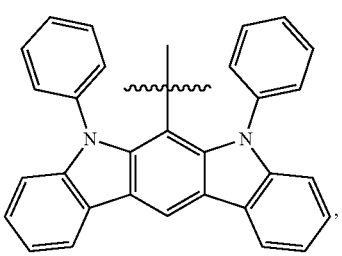
R208
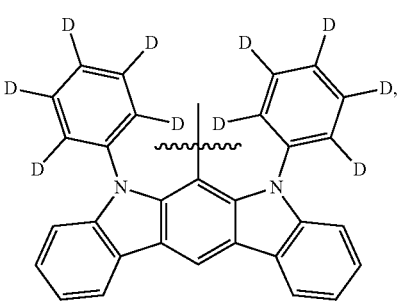
R209
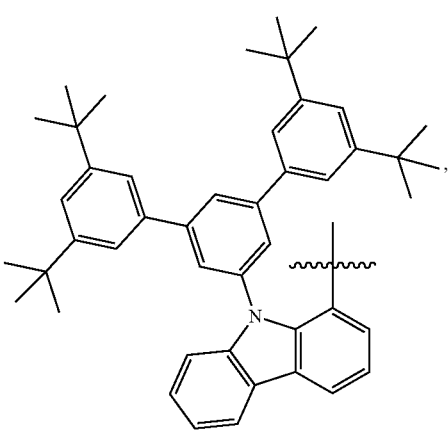

| 103 | 104 |
|---|---|
| 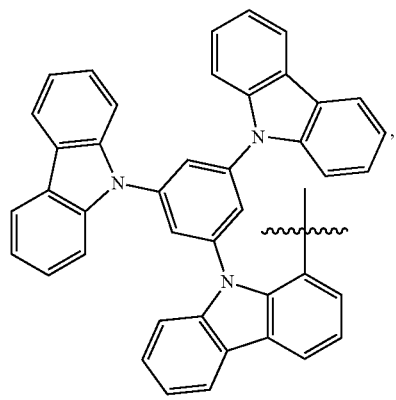 | R210 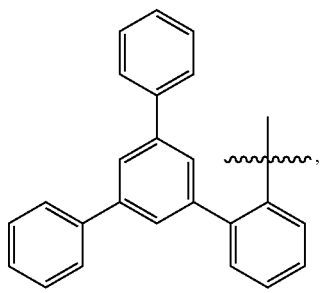 R211 |
| 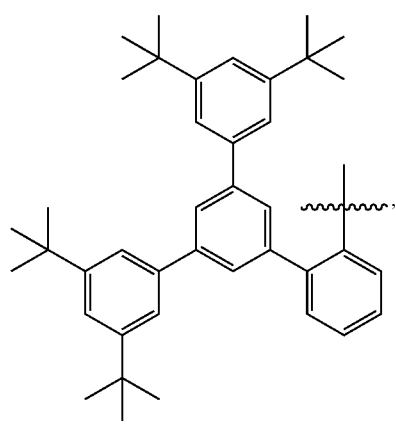 | R212 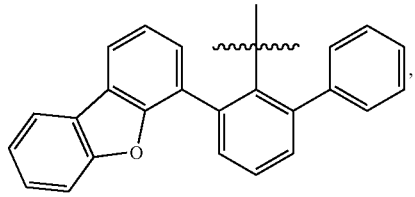 R213 |
| 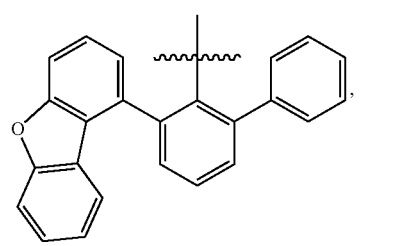 | R214 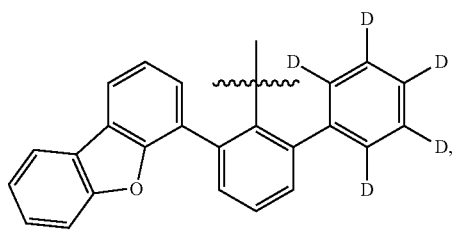 R215 |
| 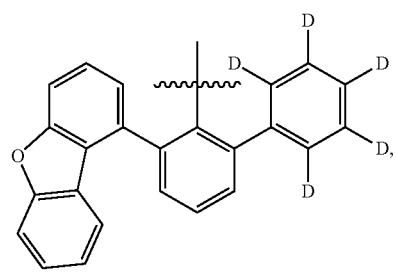 | R216 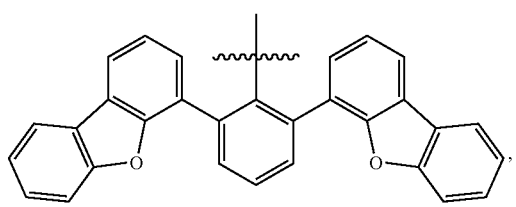 R217 |
| | R218 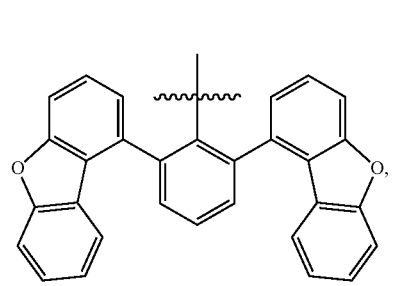 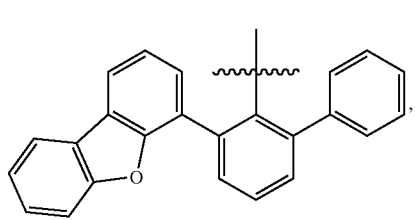 R219 |

R220 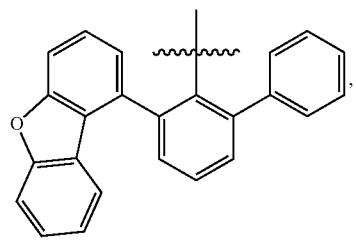 R221 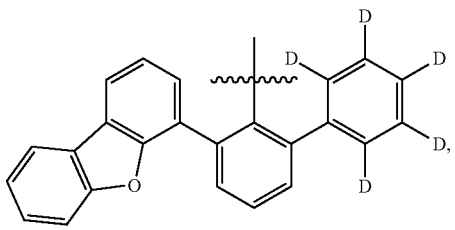
R222 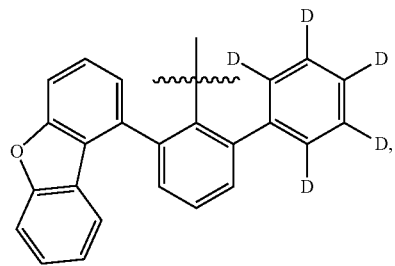 R223 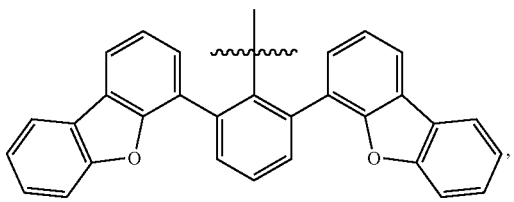
R224 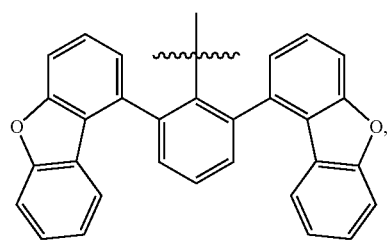 R225 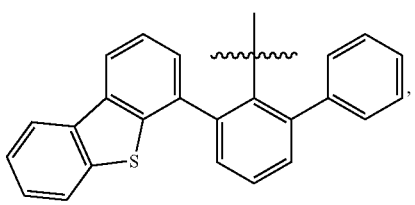
R226 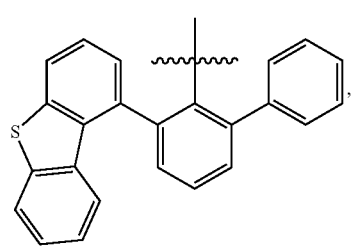 R227 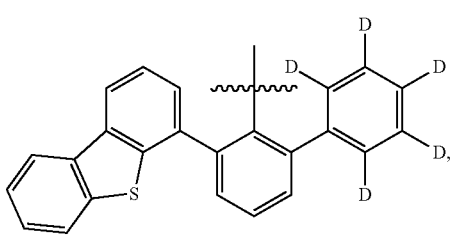
R228 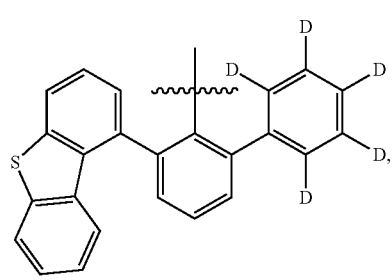 R229 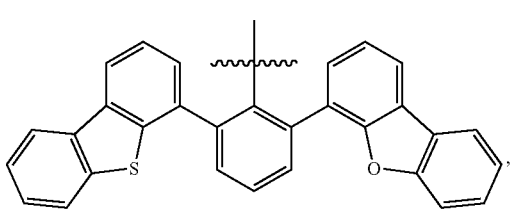
R230 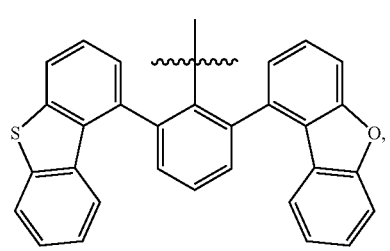 R231 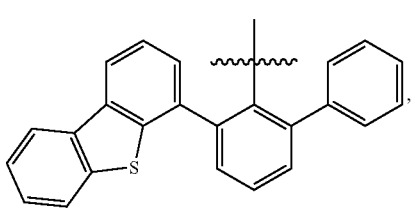

-continued
R232 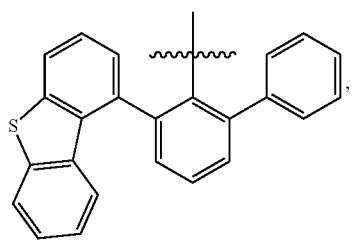
R233 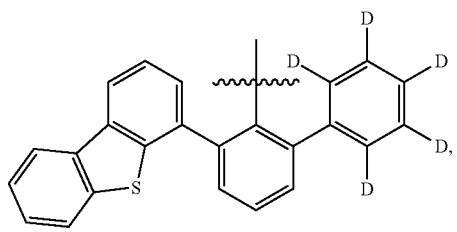
R234 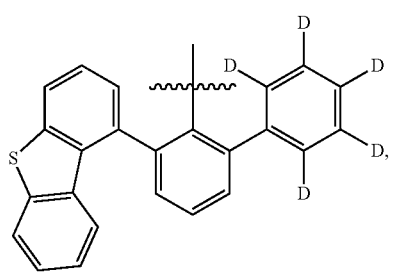
R235 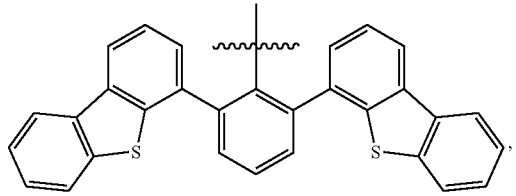
R236 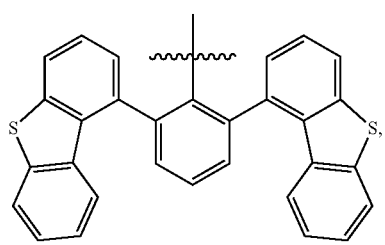
R237 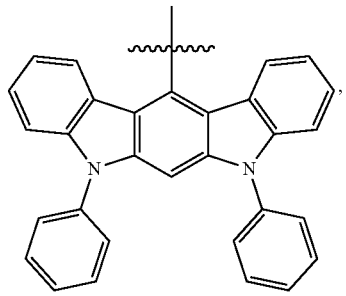
R238 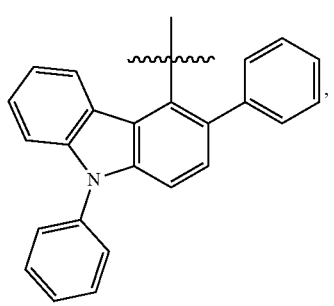
R239 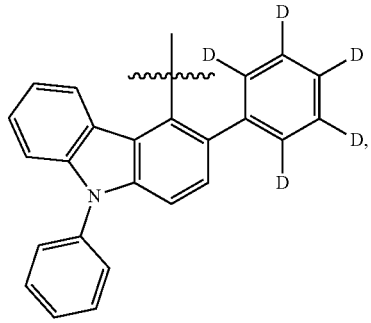
R240 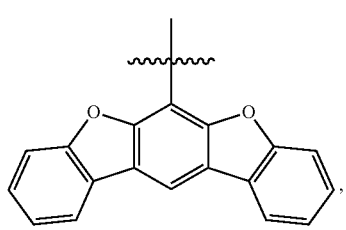
R241 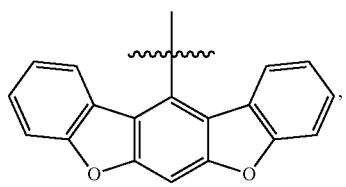
R242 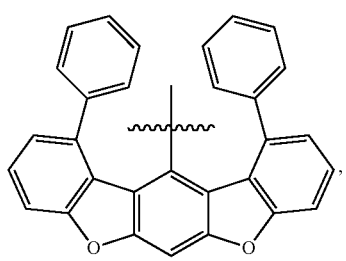
R243 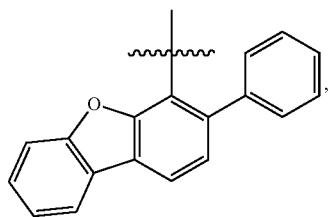

-continued
R244
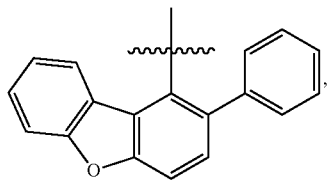
R245
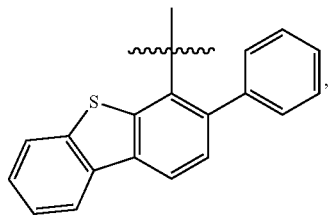
R246
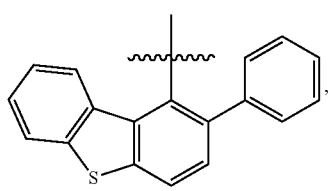
R247
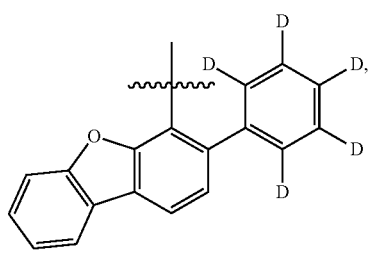
R248
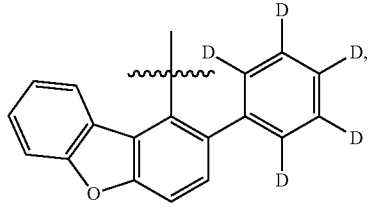
R249
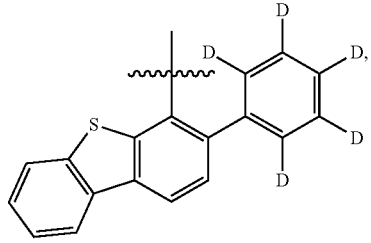
R250
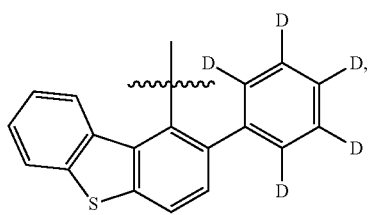
R251
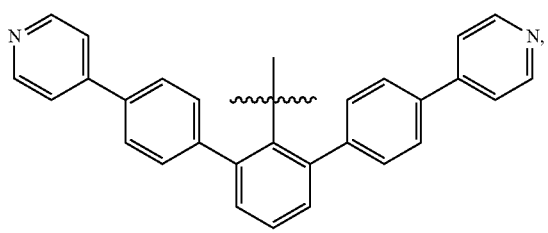
R252
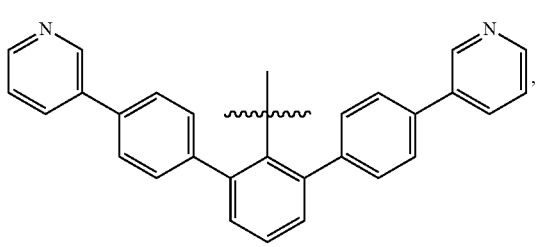
R253
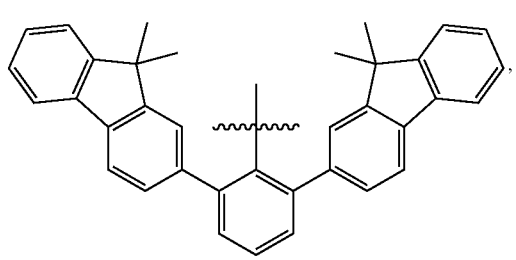
R254
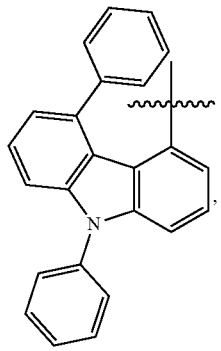
R255
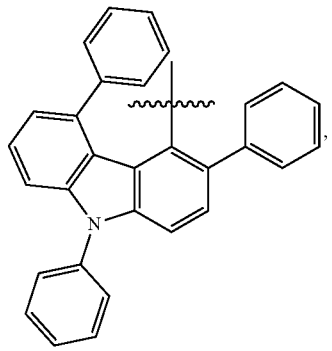

-continued
R256
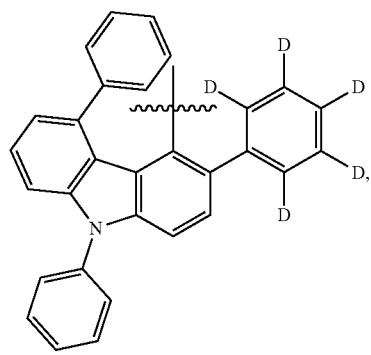
R257
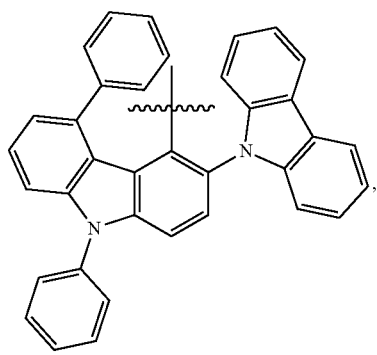
R258
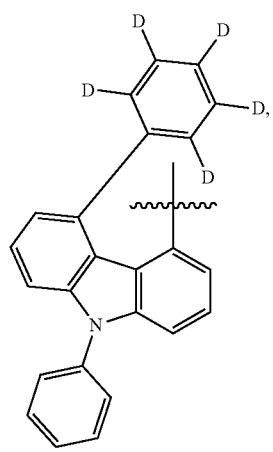
R259
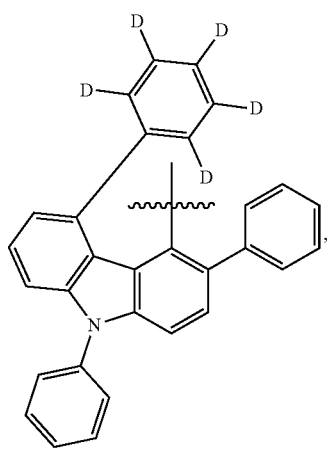
R260
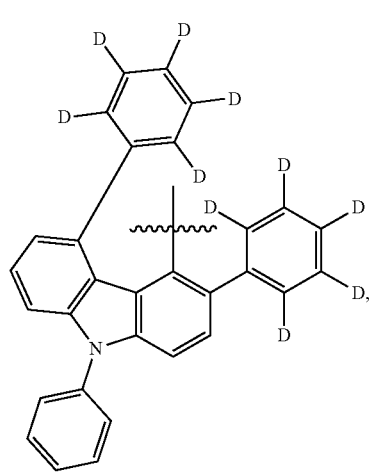
R261
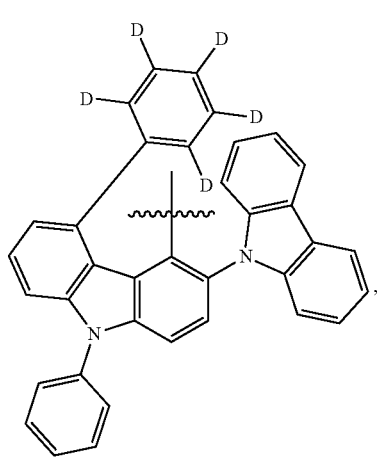
R262
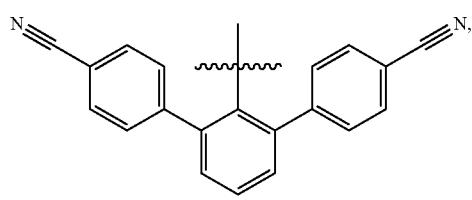
R263
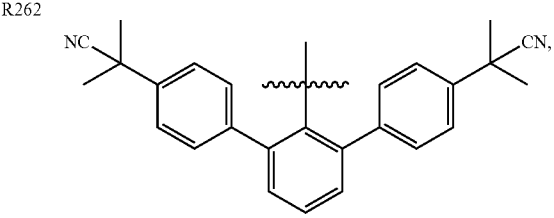

-continued
R264
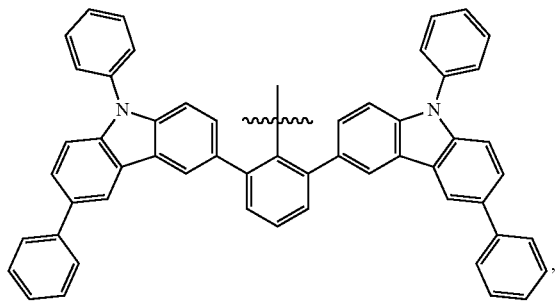
R265
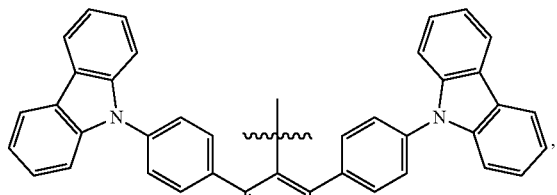
R266
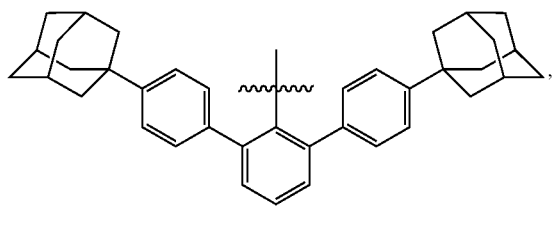
R267
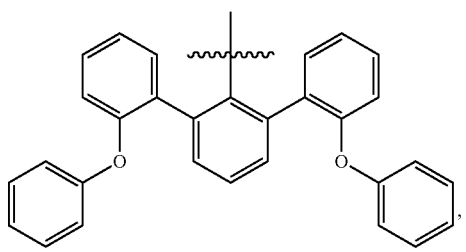
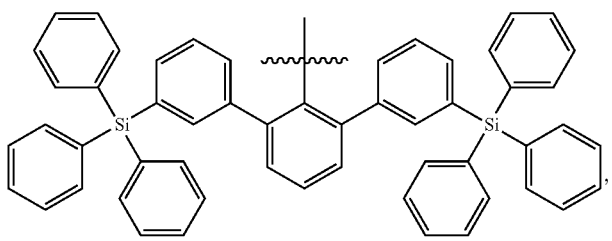
R268
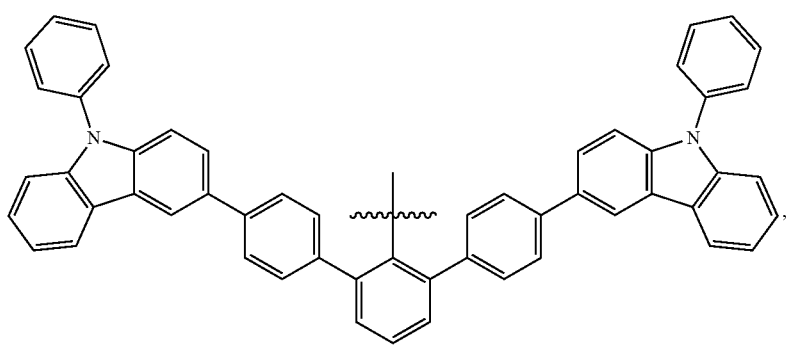
R269
R270
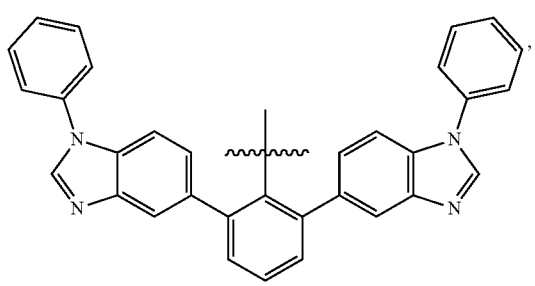
R271
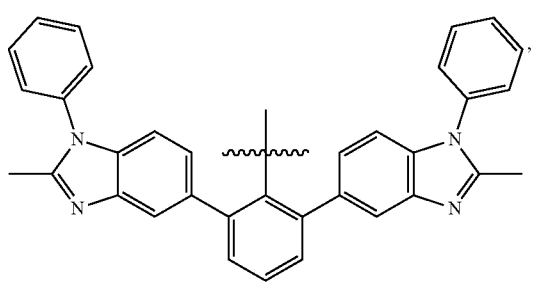

-continued
R272
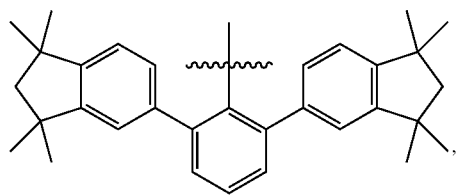
R273
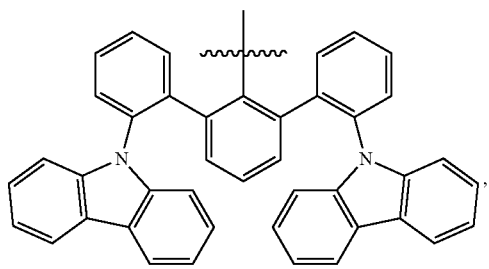
R274
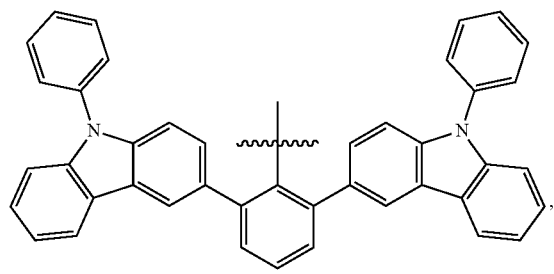
R275
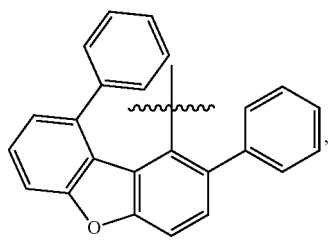
R276
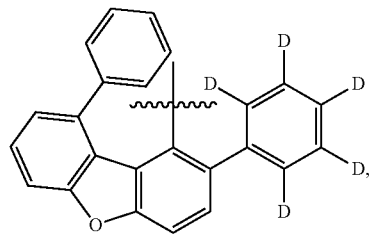
R277
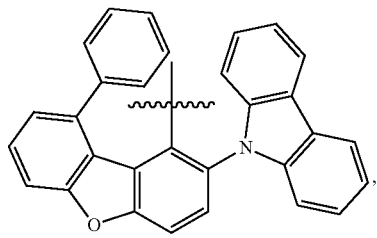
R278
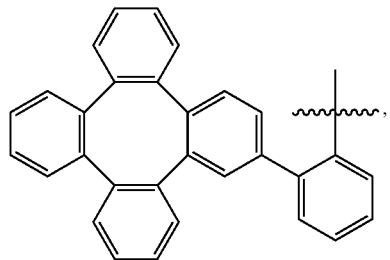
R279
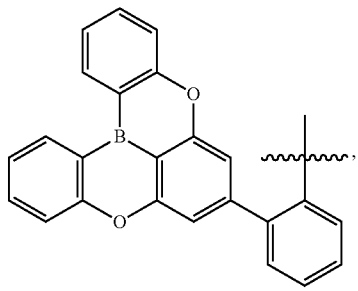
R280
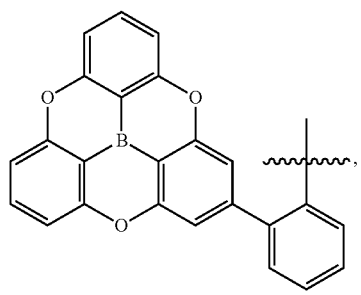
R281
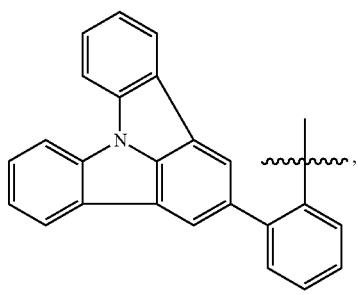

-continued
R282
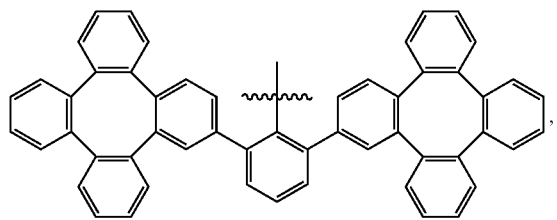
R283
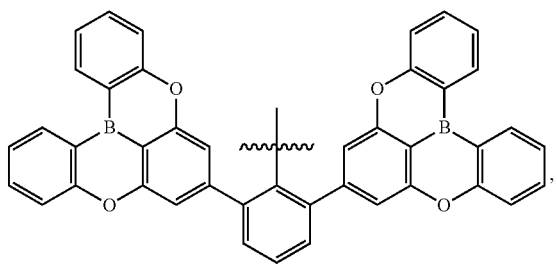
R284
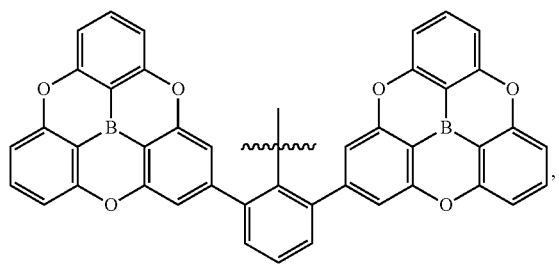
R285
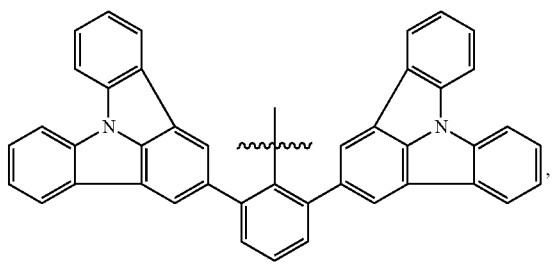
R286
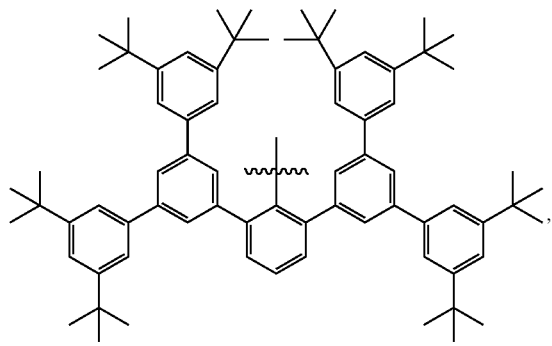
R287
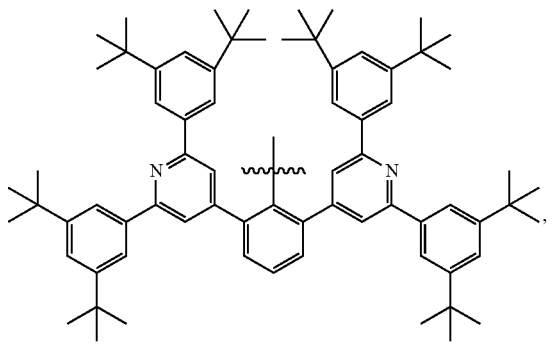
R288
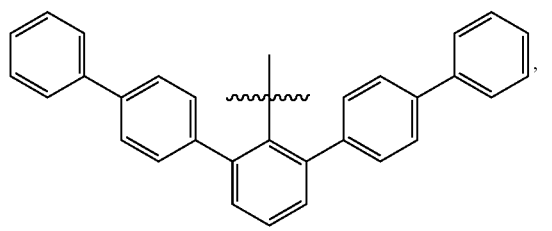
R289
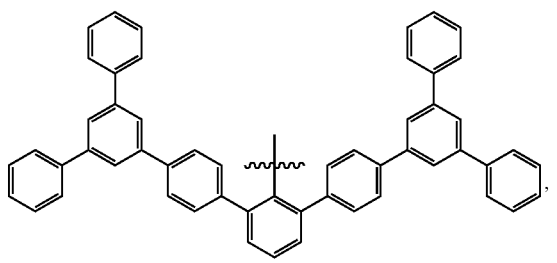
R290
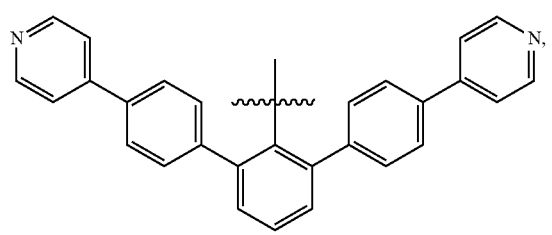
R291
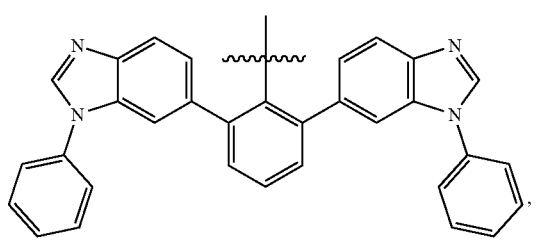

-continued
R292
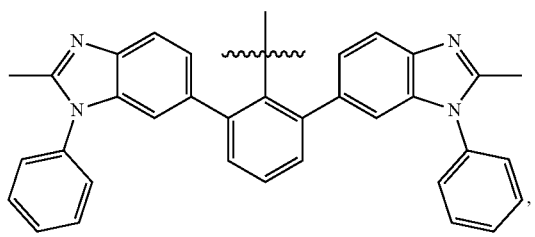
R293
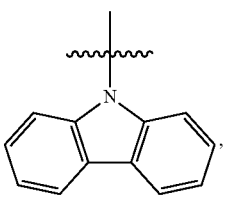
R294
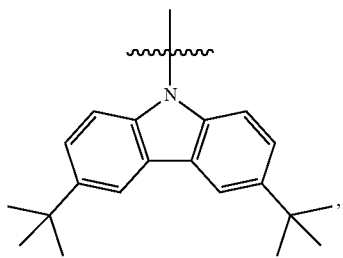
R295
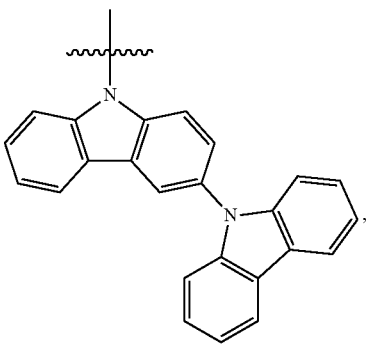
R296
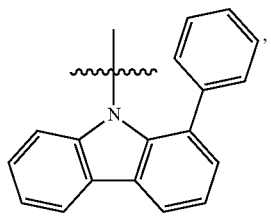
R297
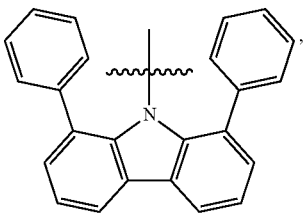
R298
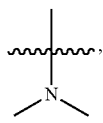
R299
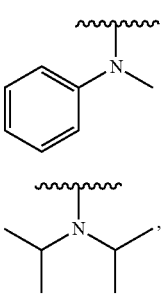
R300
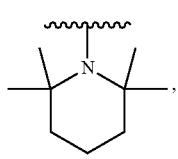
R301
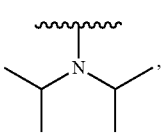
R302
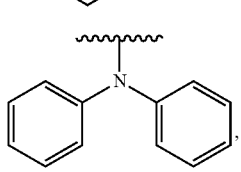
R303
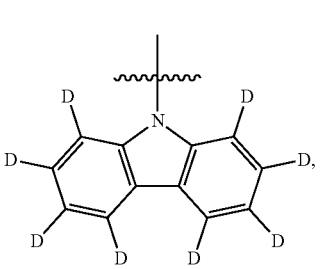
R304
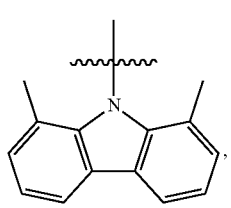
R305
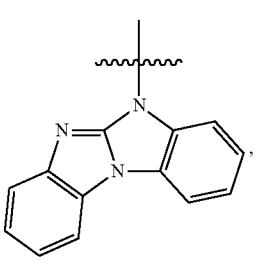

121
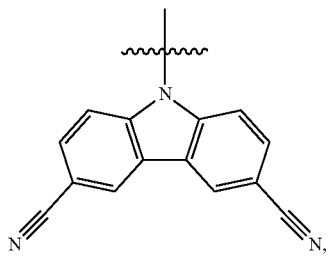
R306
122
-continued
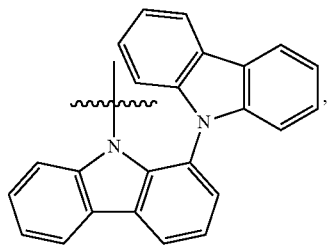
R307
wherein X1 to X21 have the following structures:
X1
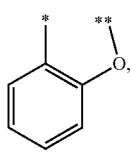
X2
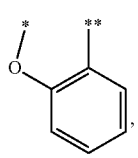
X3
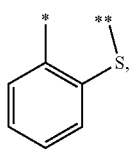
X4
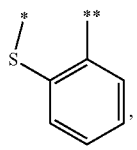
X5
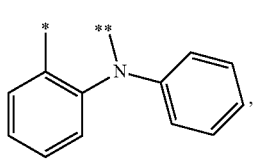
X6
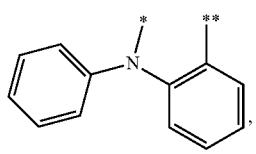
X7
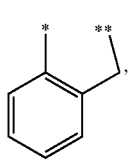
X8
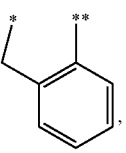
X9
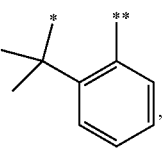
X10
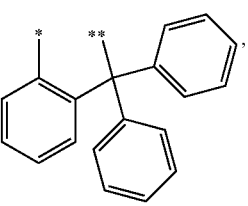
X11
(structure not shown in crops)
X12
(structure not shown in crops)
X13
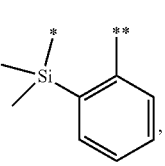
X14
(structure not shown in crops)

123
-continued
X15 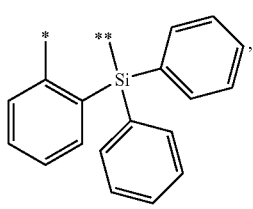
X16 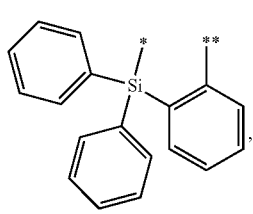
X17 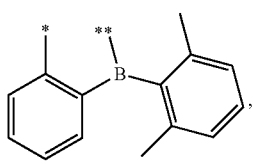
X18 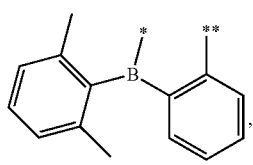
124
-continued
X19 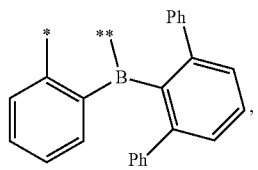
X20 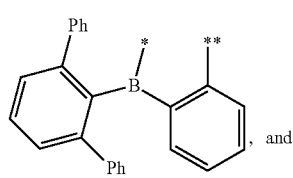, and
X21 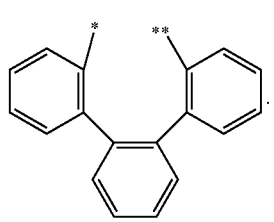
In some embodiments of the OLED, the emitter is selected from the group consisting of:
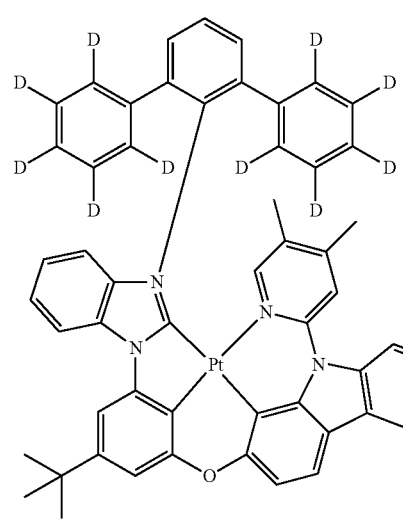
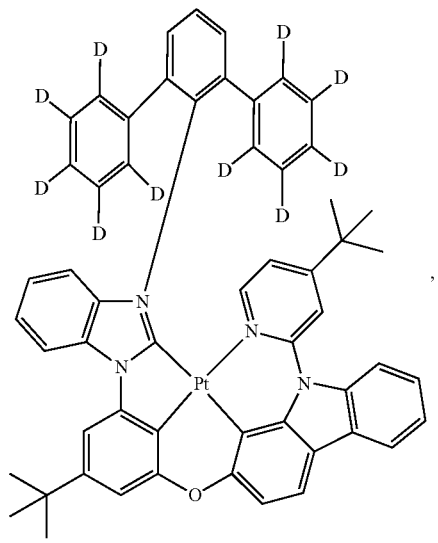

125
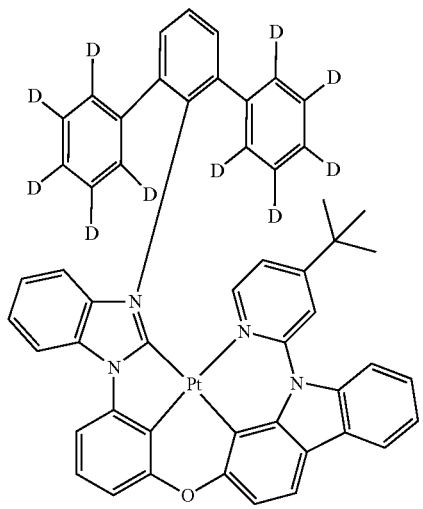
126
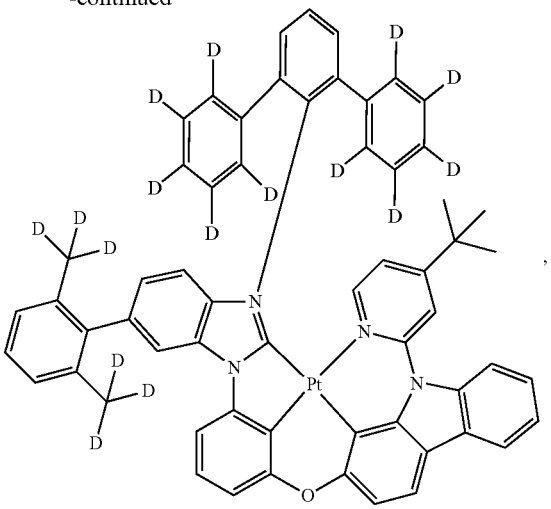
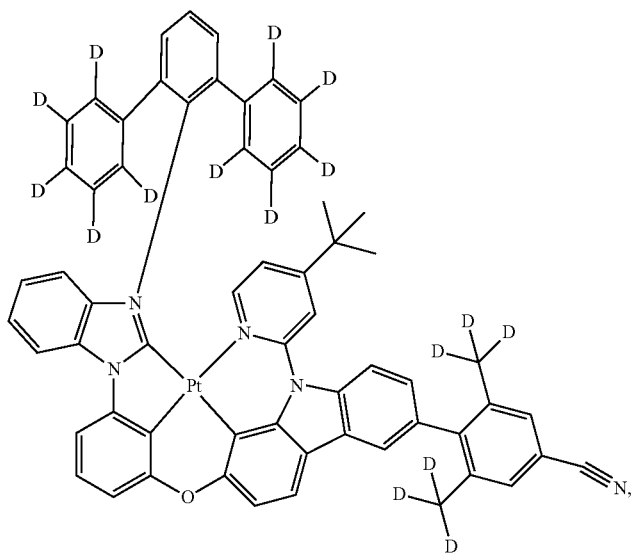
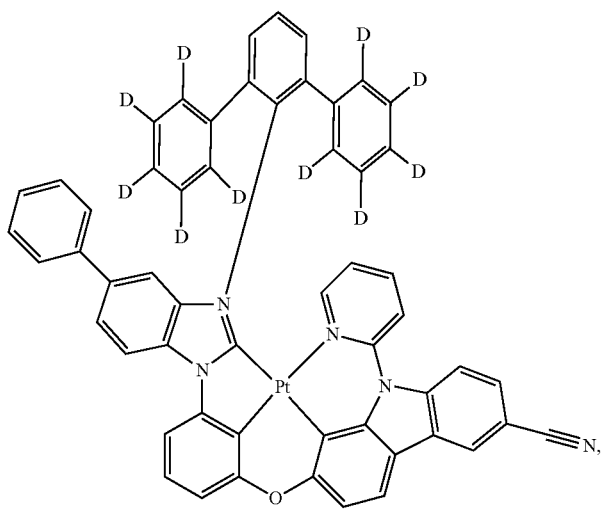

-continued
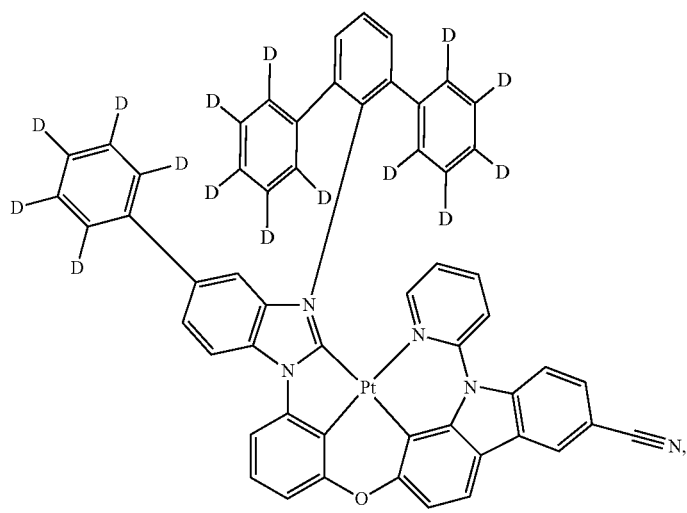
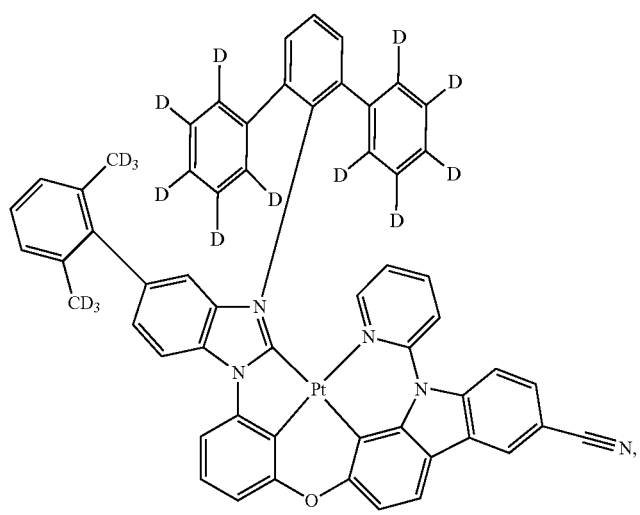
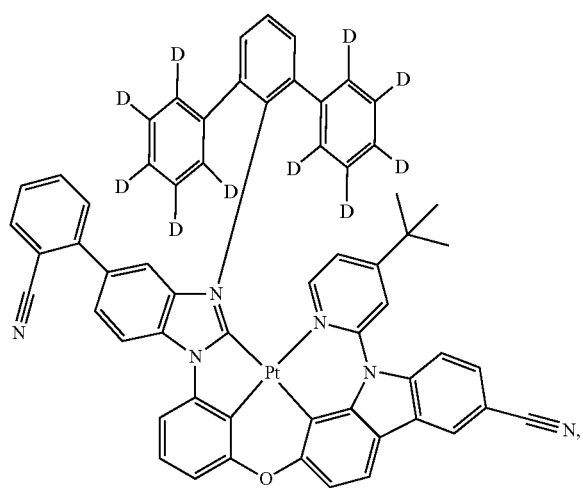

129 130
-continued
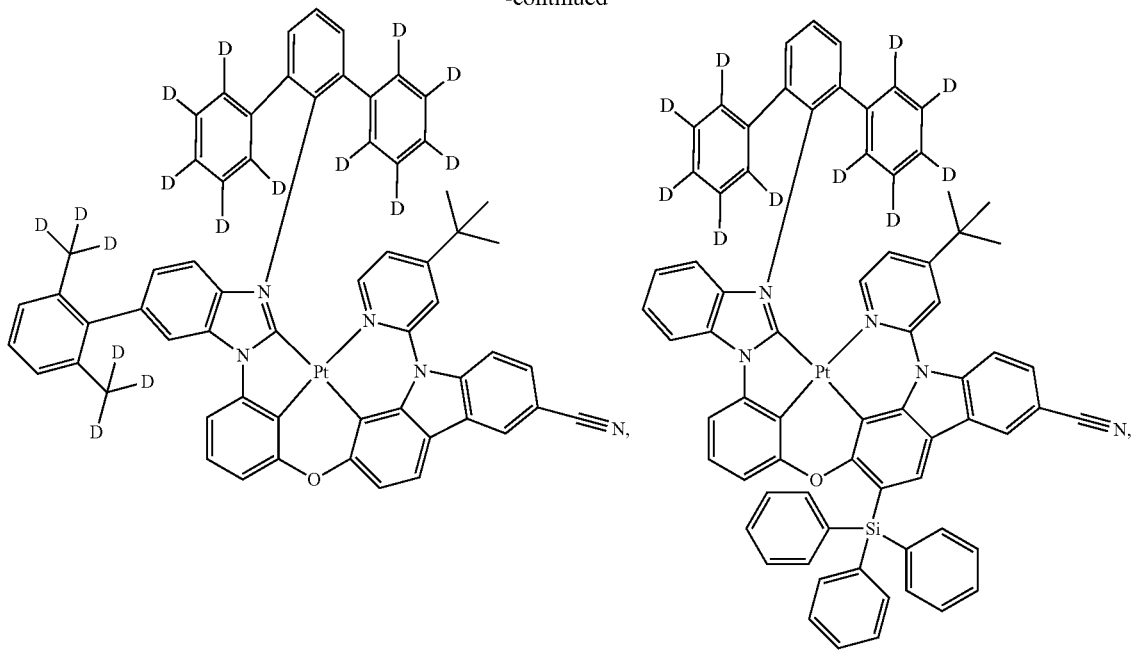
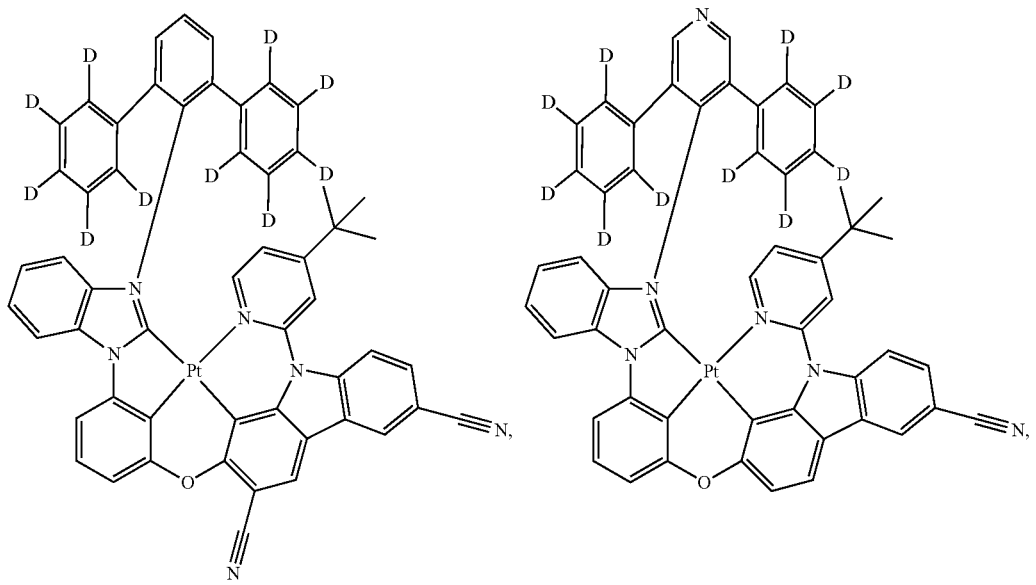

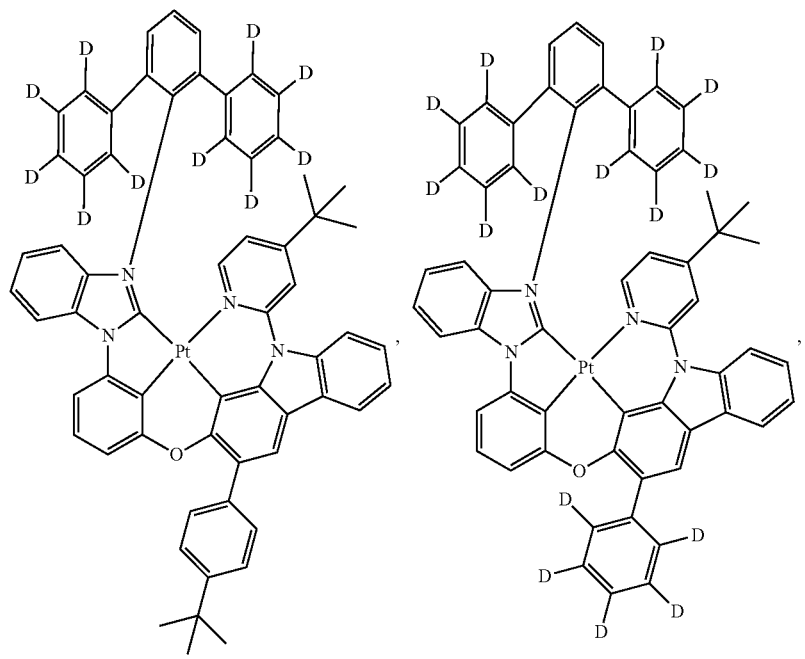
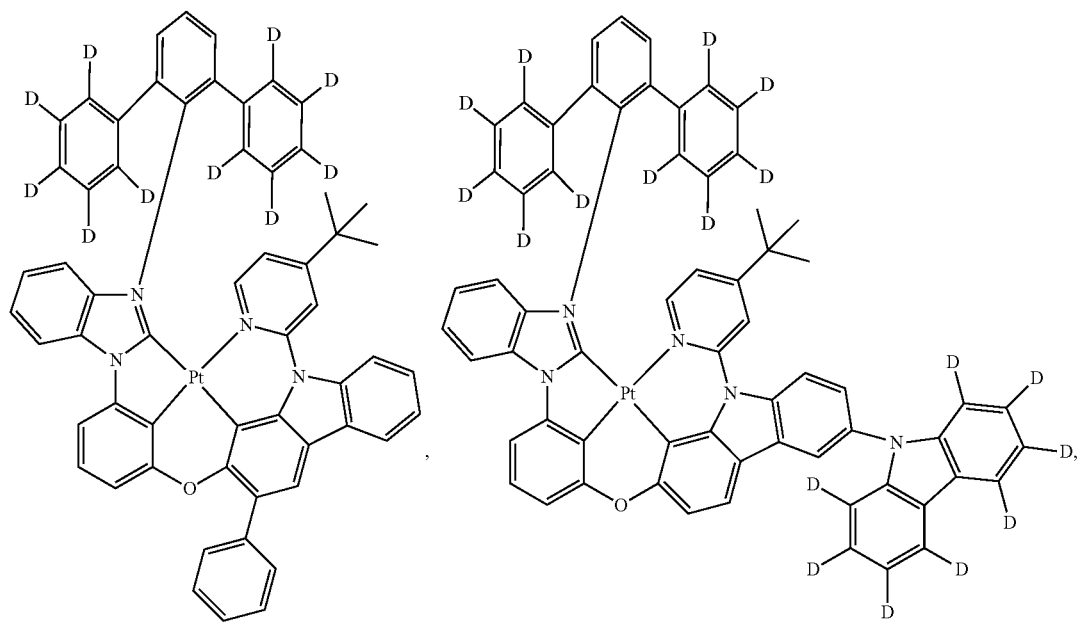

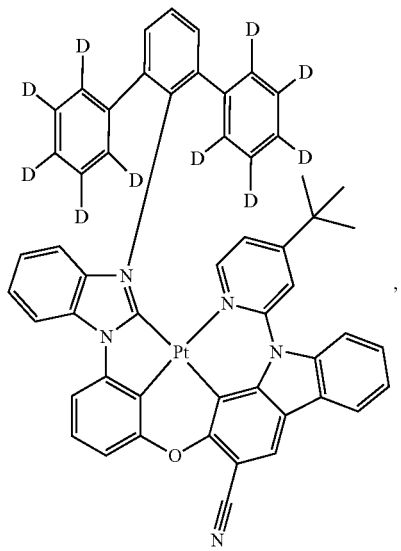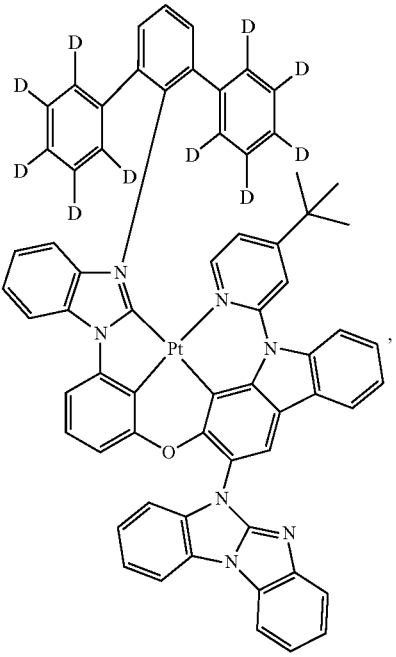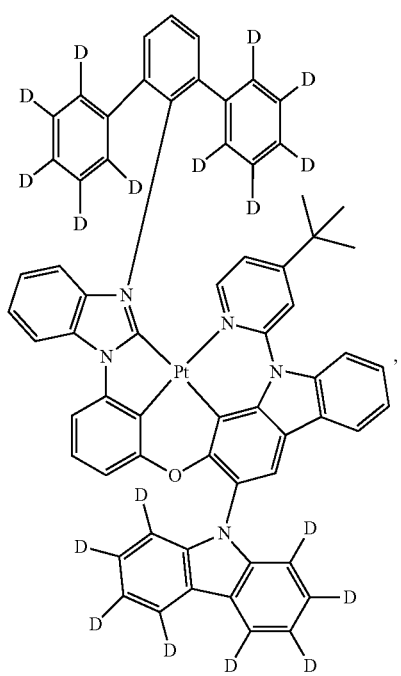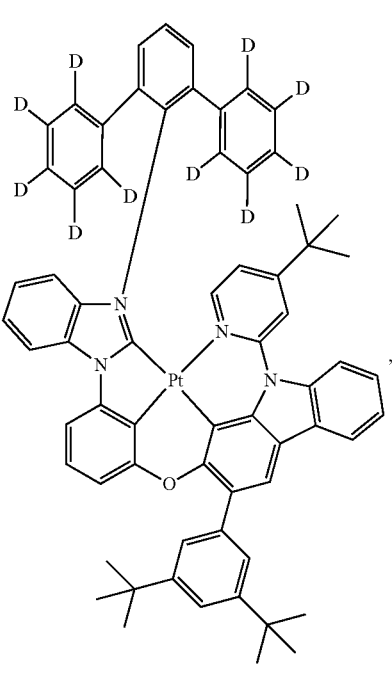

-continued
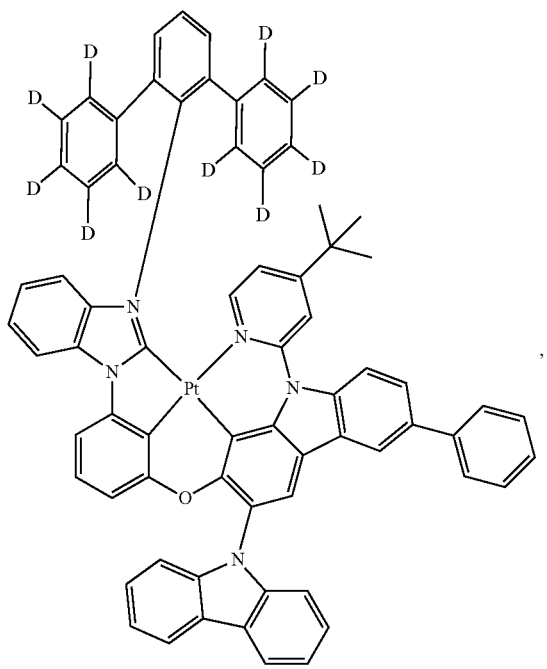
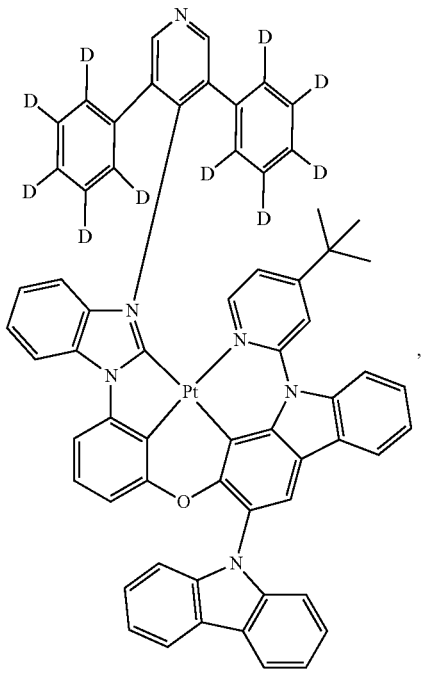
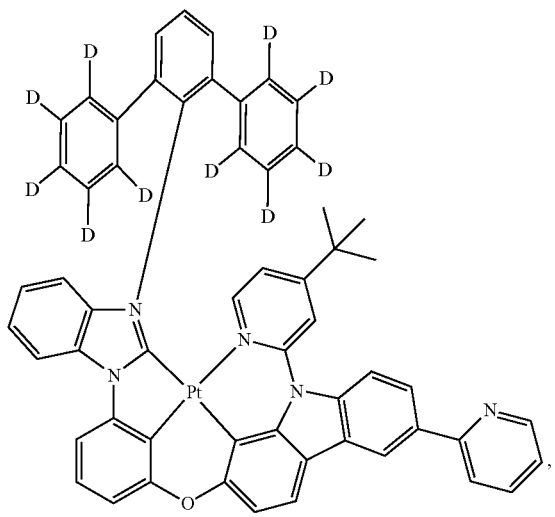
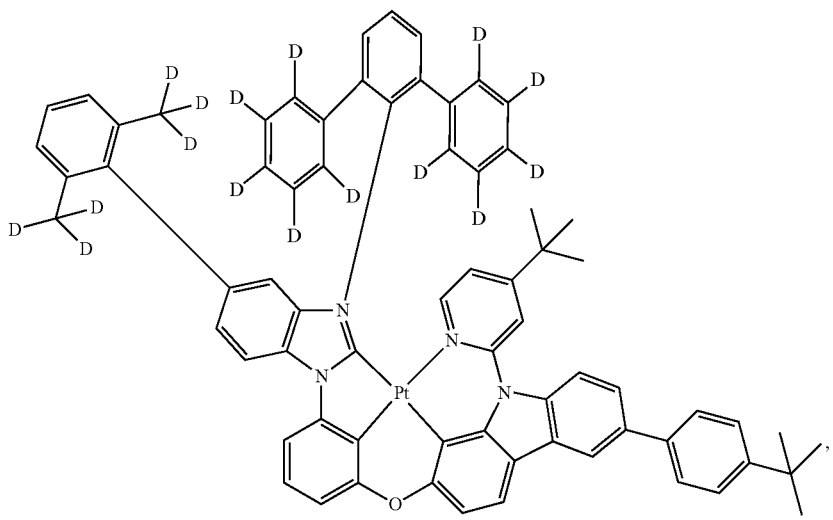

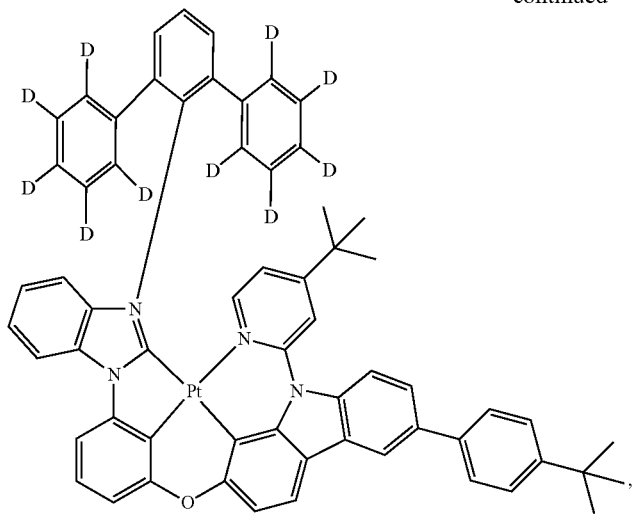
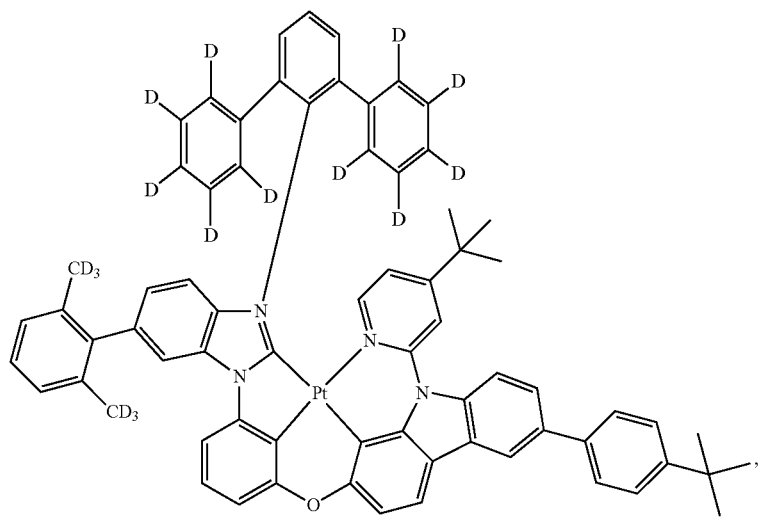
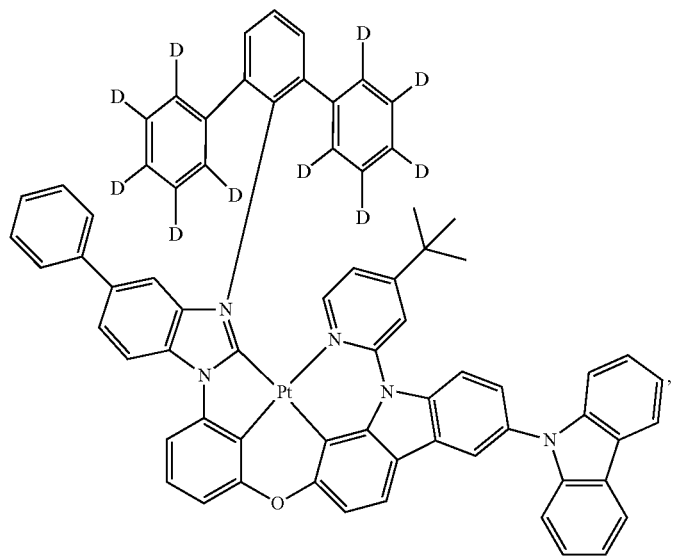

-continued
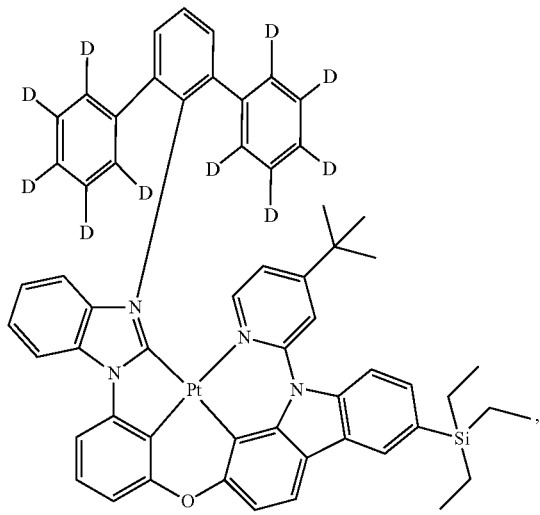
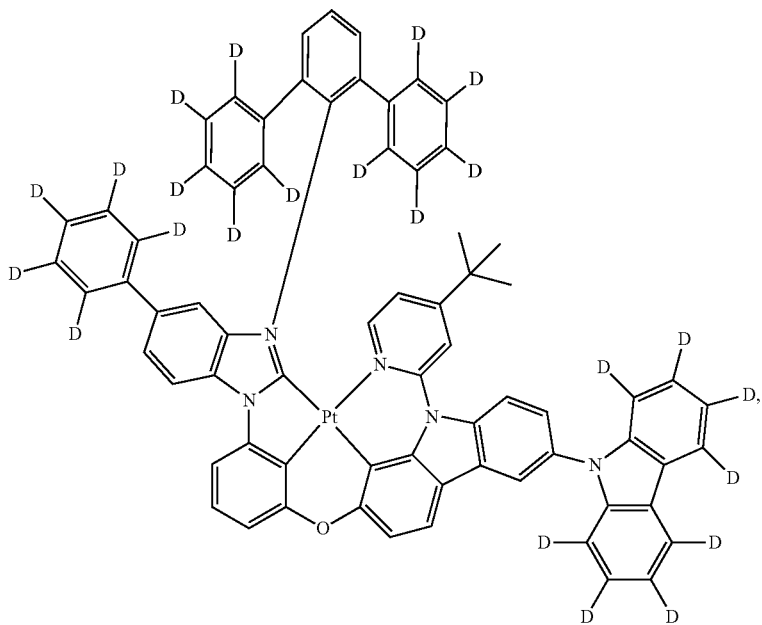
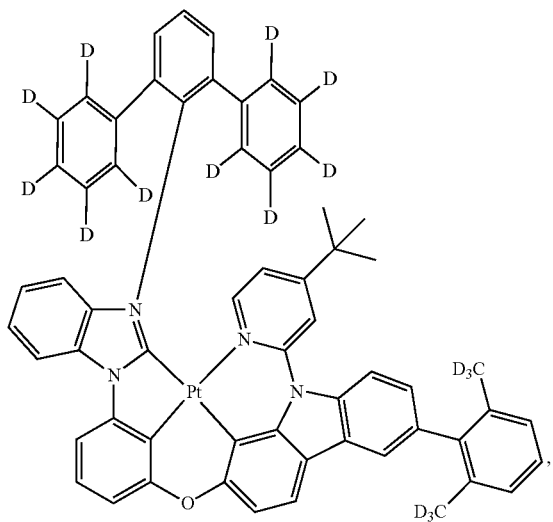

-continued
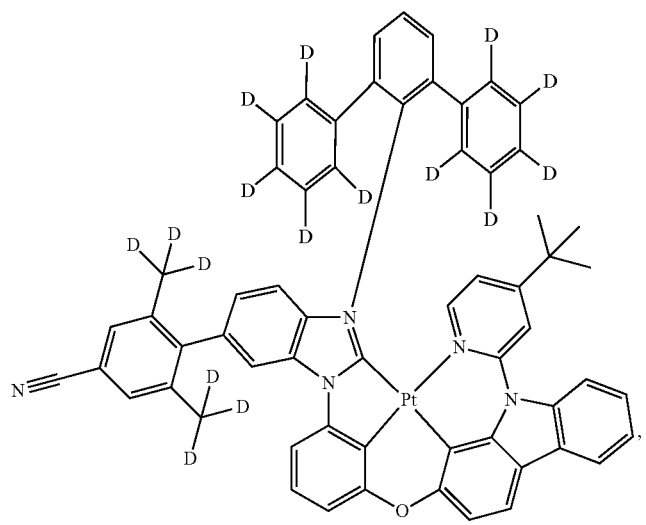
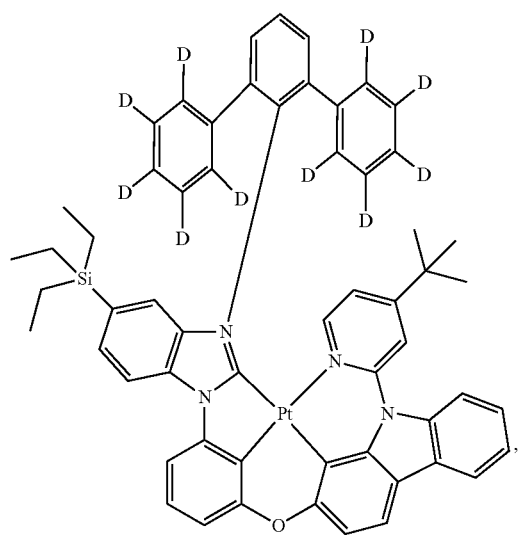
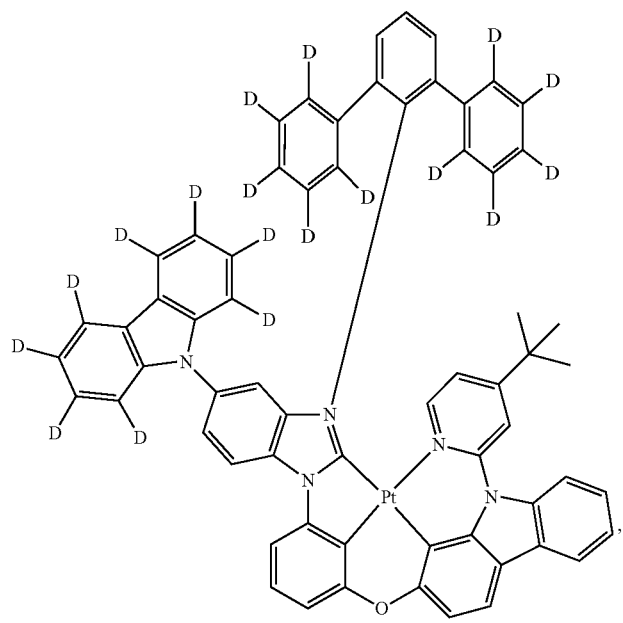

143 144
-continued
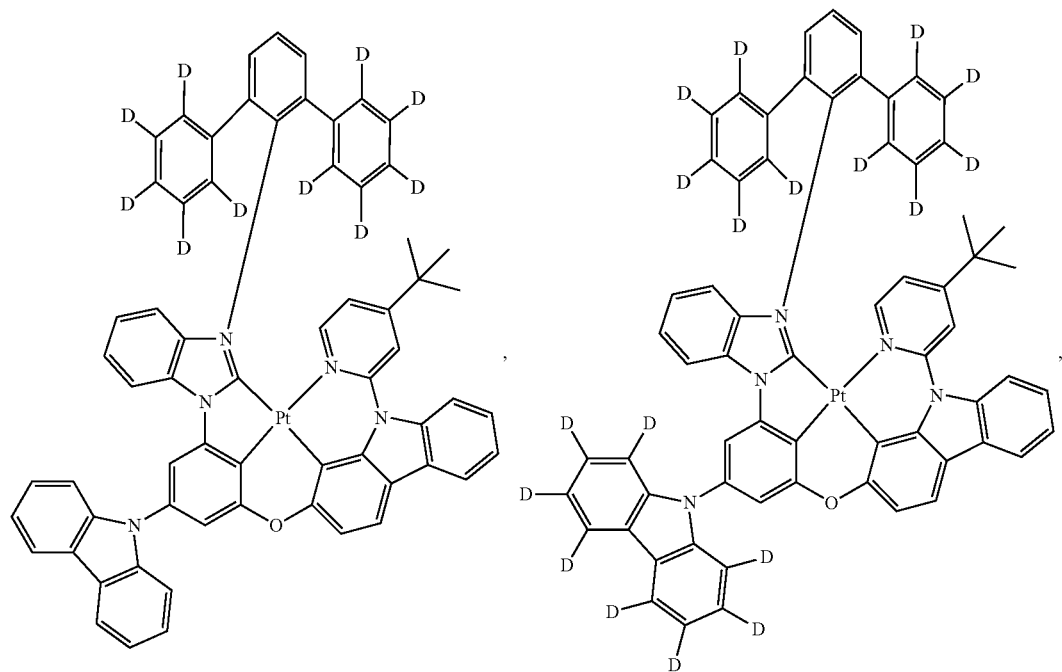
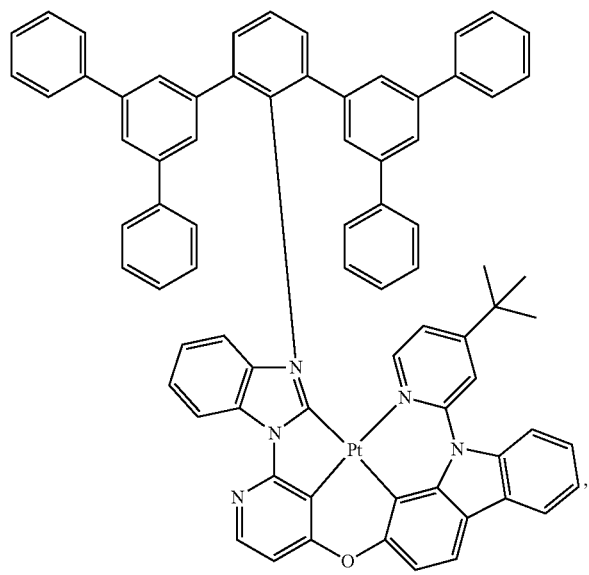

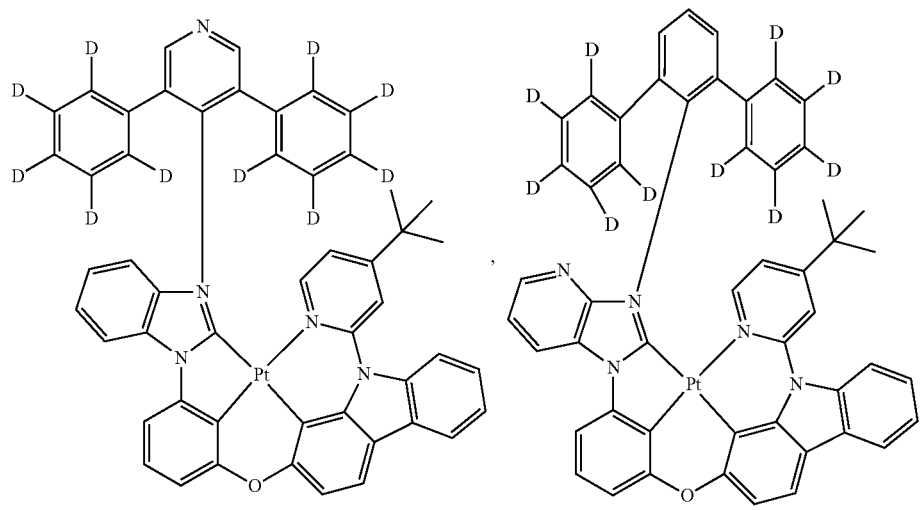
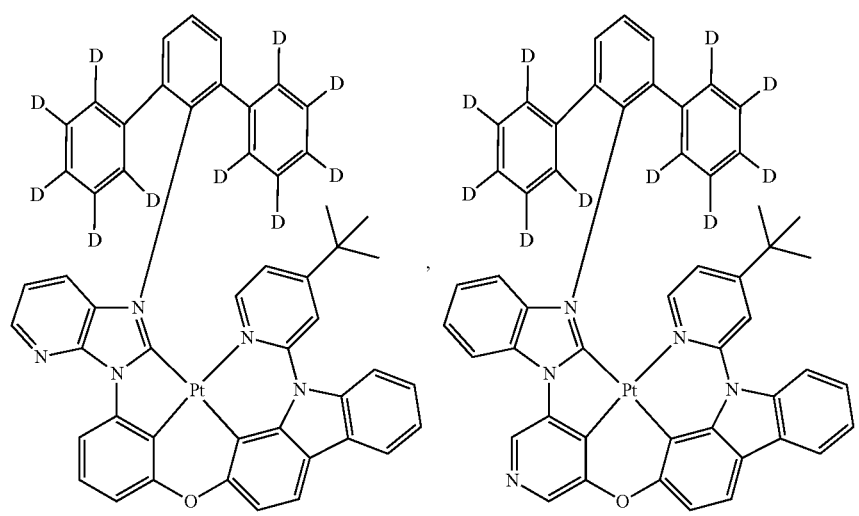
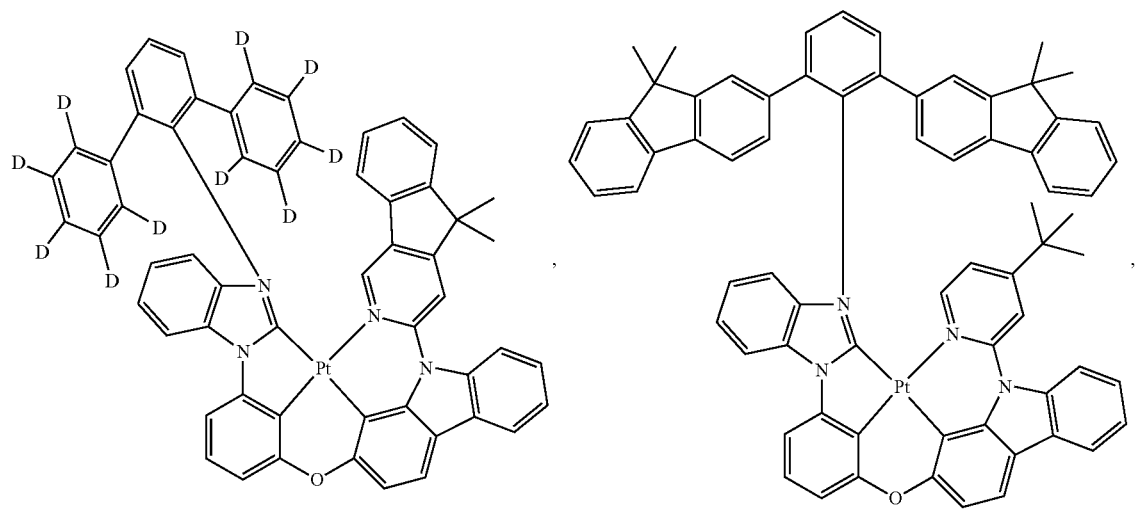

-continued
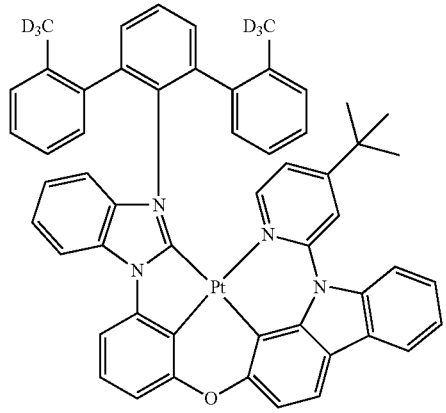
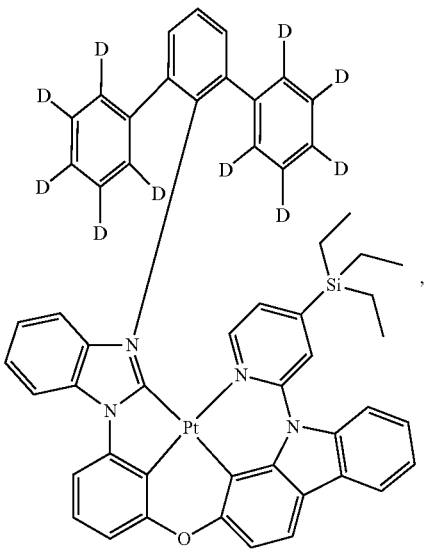
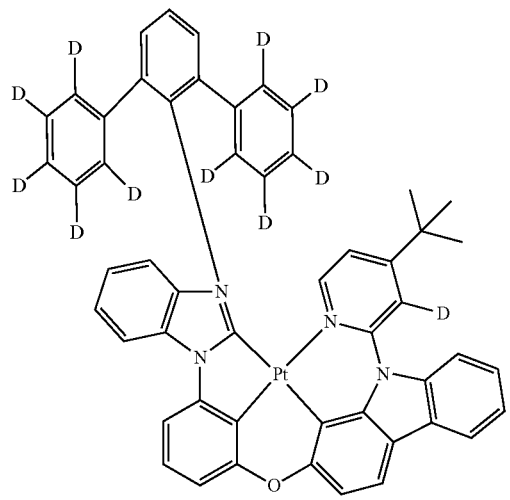
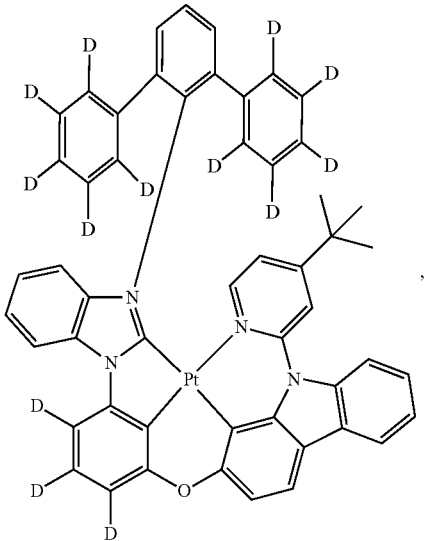
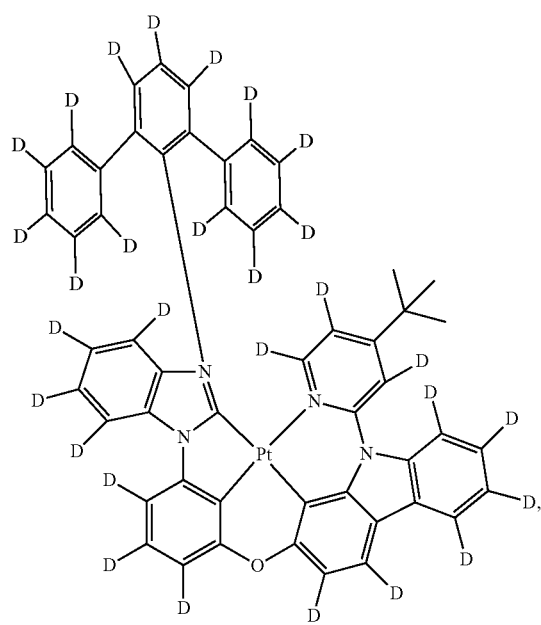
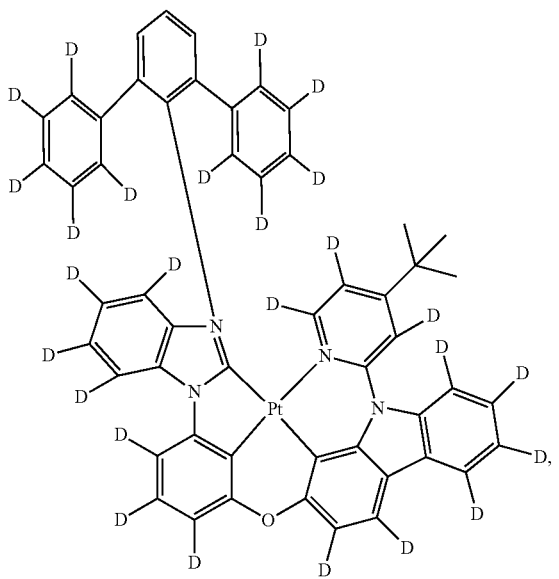

-continued
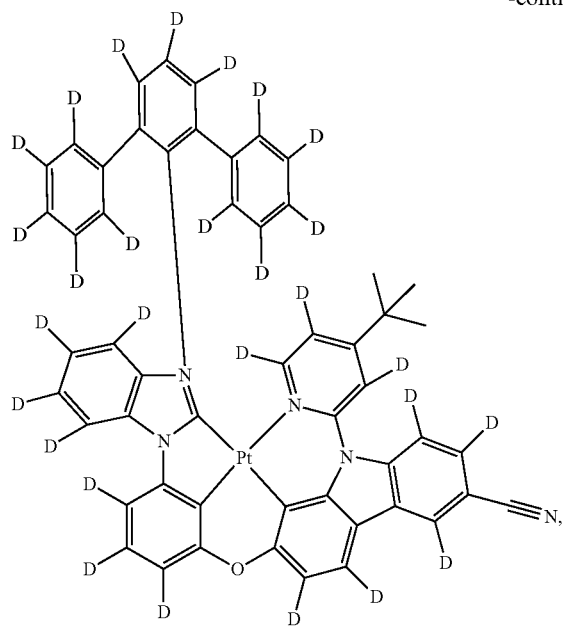
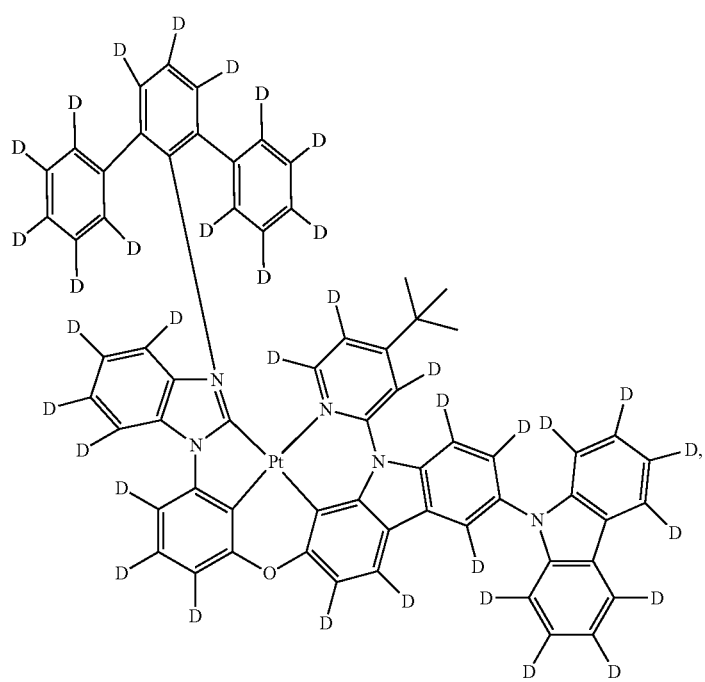

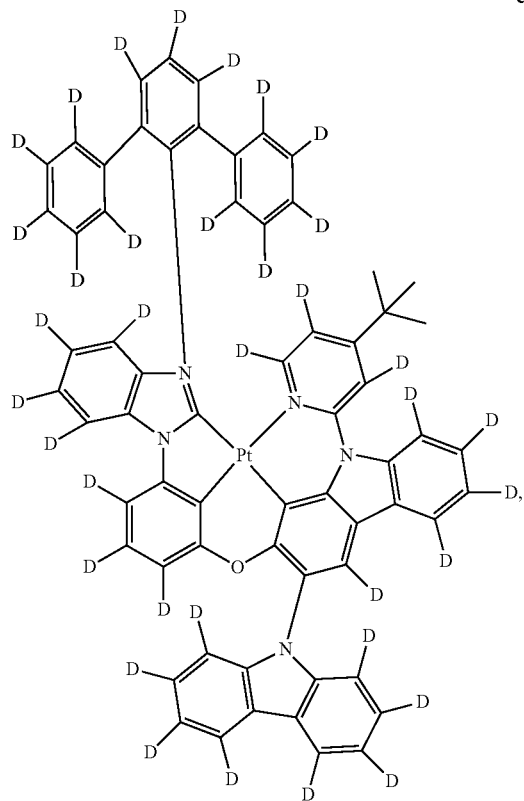
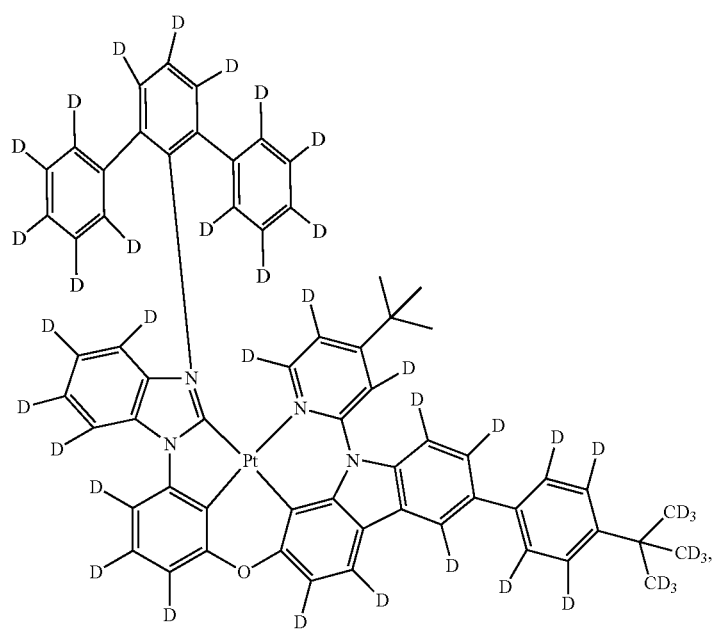

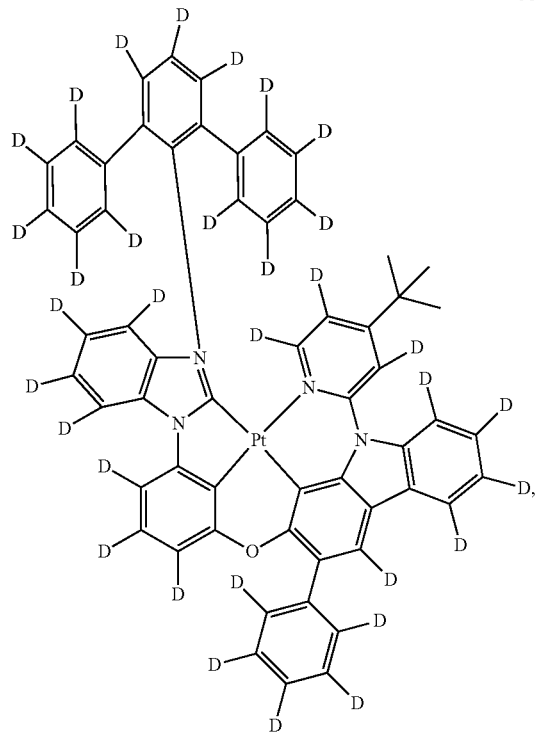
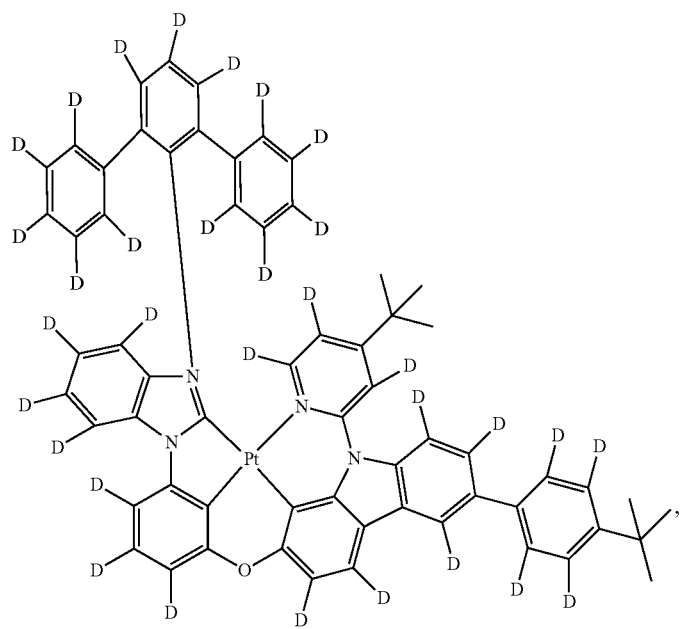

155
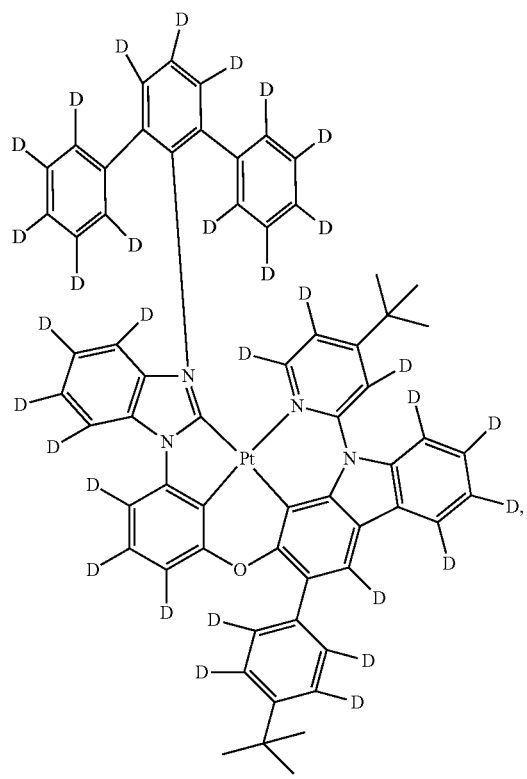
156
-continued
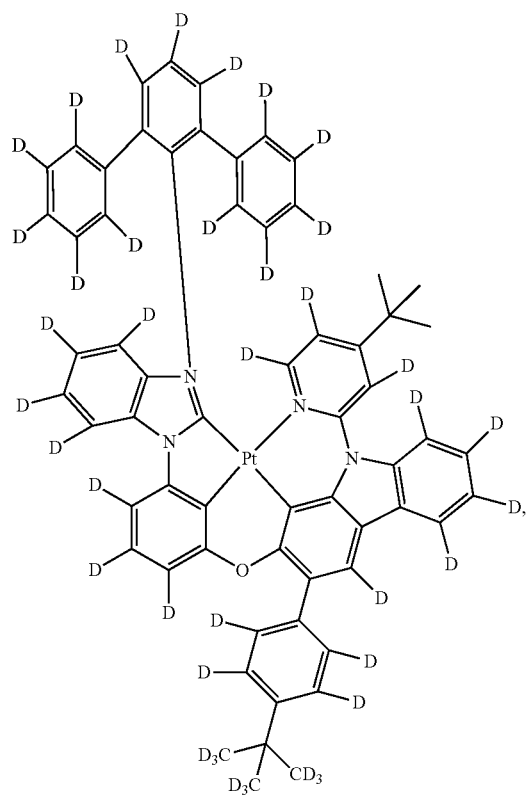
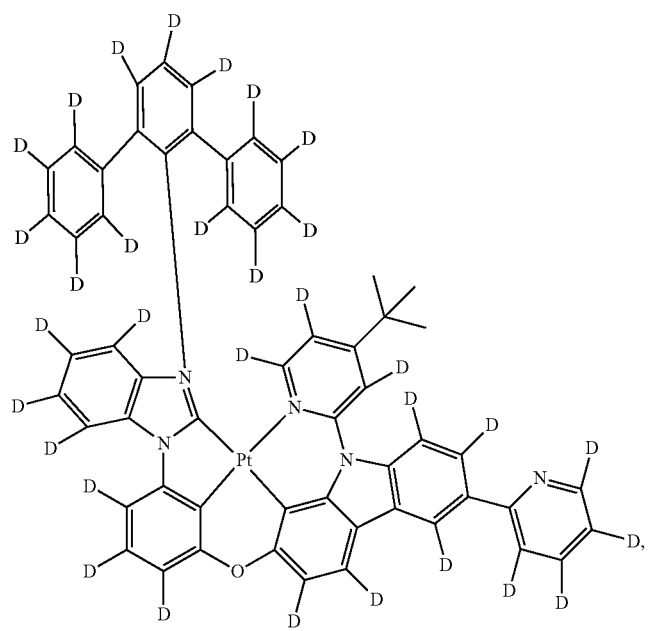

-continued
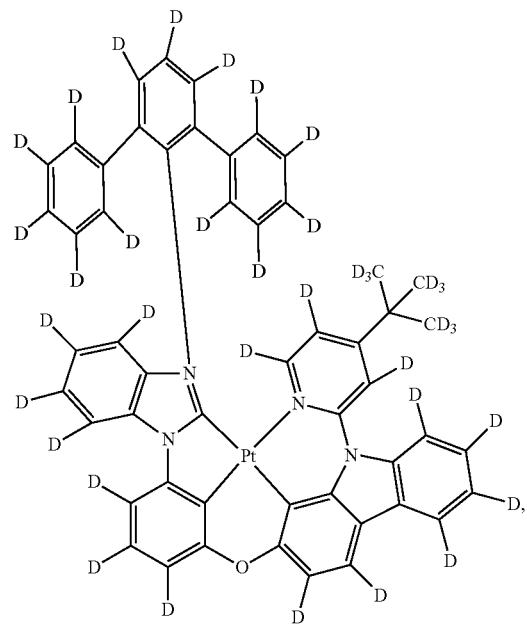
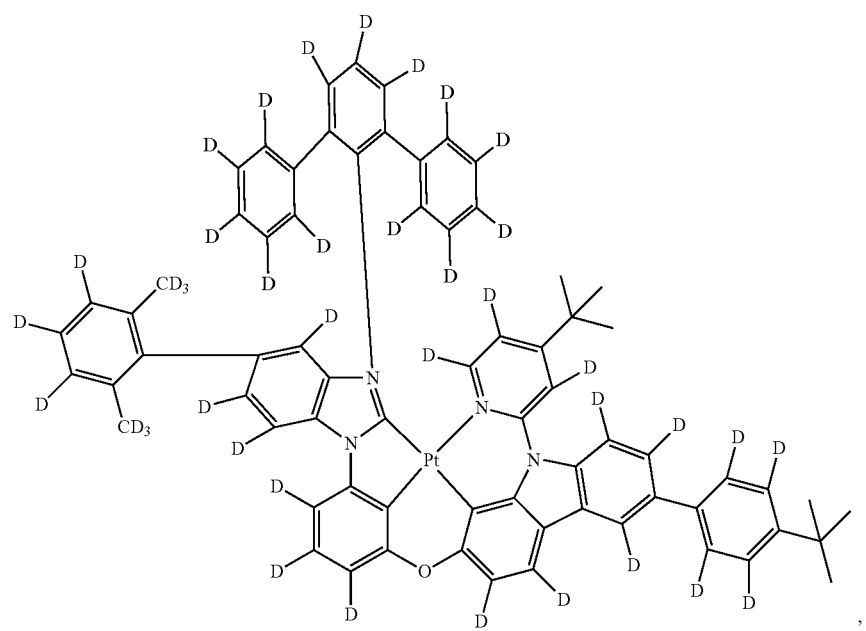

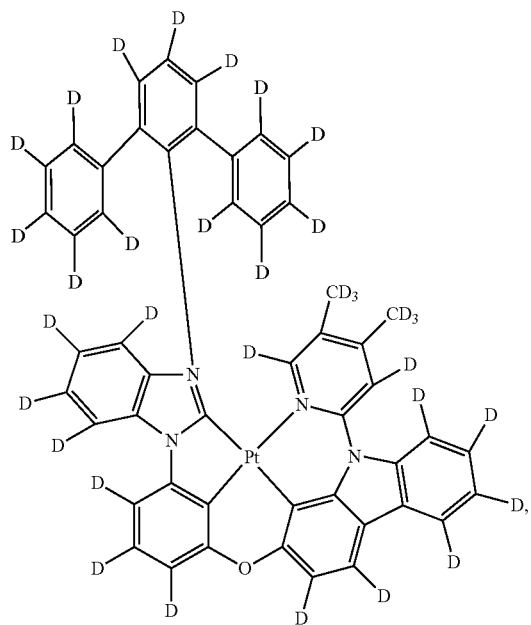
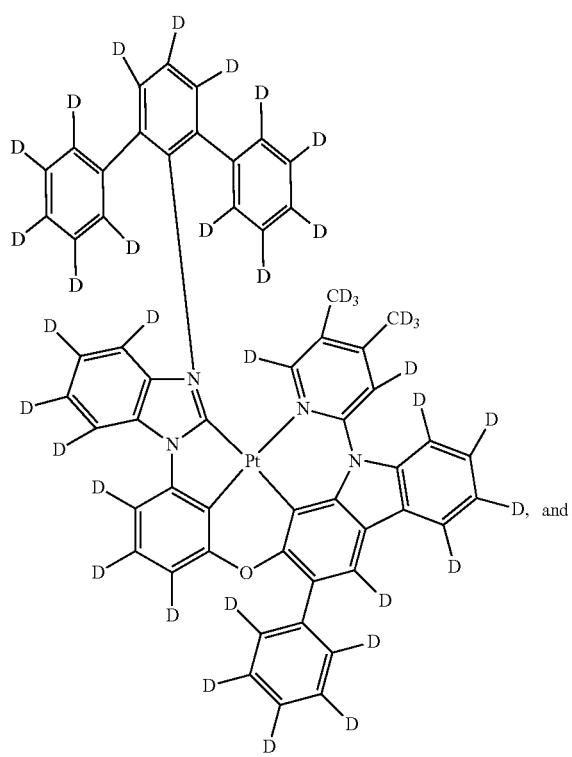

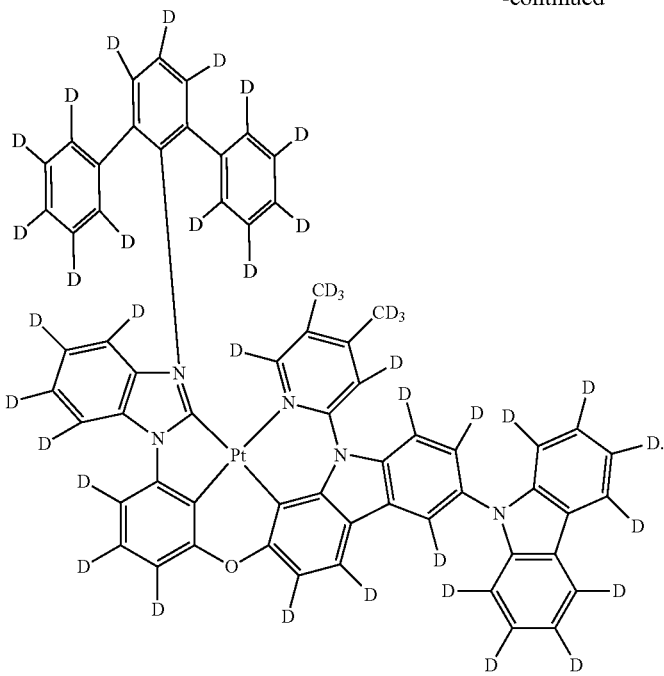

In some embodiments of the OLED, the emitter is an E-type delayed fluorescent emitter. In some embodiments, the emitter has the formula of D-L-A; and wherein D is an electron donor group, A is an electron acceptor group, and L is a direct bond or linker. In some embodiments, the electron donor group comprises at least one chemical moiety selected from the group consisting of amino, indole, carbazole, indolocarbazole, benzothiohpene, benzofuran, dibenzothiophene, dibenzofuran, and combinations thereof. In some embodiments, the electron acceptor group comprises at least one chemical moiety selected from the group consisting of pyridine, pyridazine, pyrimidine, pyrazine, triazine, nitrile, isonitrile, and boryl.

According to another aspect, a consumer product comprising the inventive OLED disclosed herein is also disclosed. The consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, any metal complexes or organic compounds may be used as host materials in the OLEDs of the present disclosure as long as the energy requirement described above is met in the EML. For example, it can be an electron transporting host (e-host) with a hole transporting emitter, or vice versa. A family of such e-hosts are disclosed in U.S. patent application Ser. No. 16/683,507, filed on Nov. 14, 2019, the contents of which are incorporated herein by reference.

In some embodiments, the organic layer may be an emissive layer and the compound as described herein may be an emissive dopant or a non-emissive dopant.

In some embodiments, the organic layer may further comprise a host, wherein the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments, the organic layer may further comprise a host, wherein host comprises at least one chemical moiety selected from the group consisting of naphthalene, fluorene, triphenylene, carbazole, indolocarbazole, dibenzothiphene, dibenzofuran, dibenzoselenophene, 5,9-dioxa-13b-boranaphtho[3,2,1-de]anthracene, aza-naphthalene, aza-fluorene, aza-triphenylene, aza-carbazole, aza-indolocarbazole, aza-dibenzothiophene, aza-dibenzofuran, aza-dibenzoselenophene, and aza-(5,9-dioxa-13b-boranaphtho[3,2,1-de]anthracene).

In some embodiments, the host may be selected from the group consisting of:

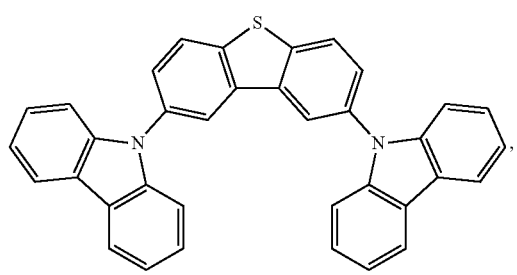

163
-continued
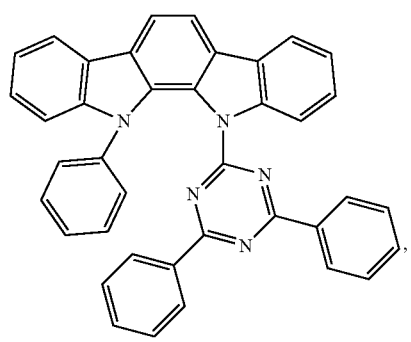
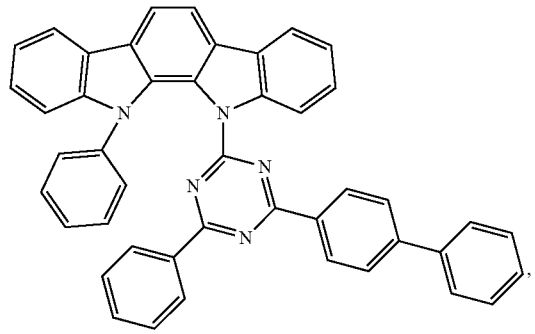
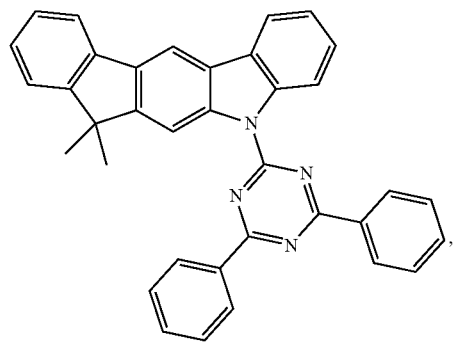
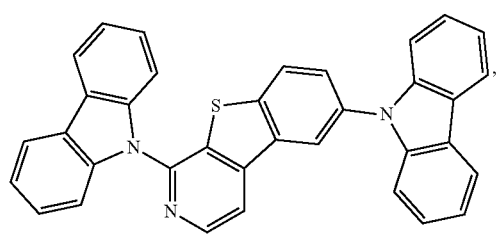
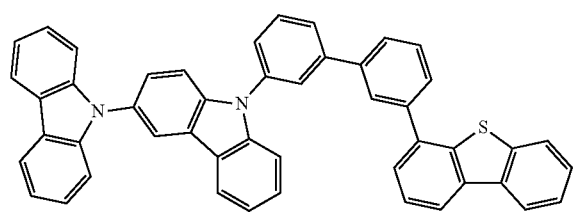
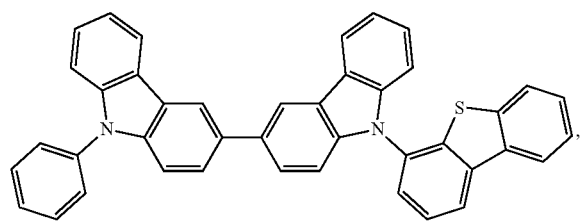
164
-continued
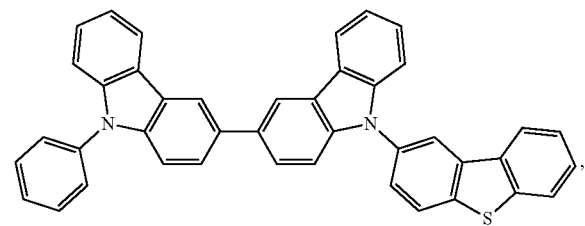
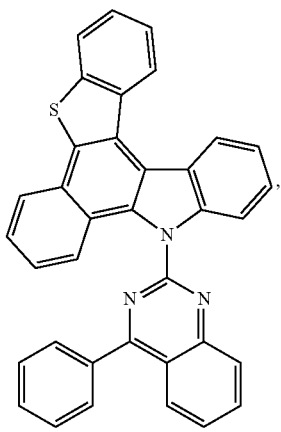
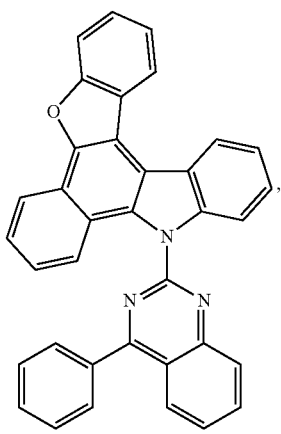
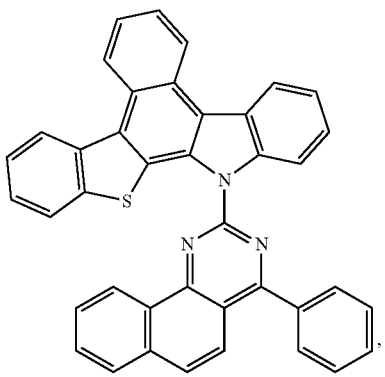 [SMILES: c1ccc(-c2nc(-n3c4ccccc4c4c5ccccc5c5c6ccccc6sc5c43)nc3c2ccc2ccccc23)cc1]

165
-continued
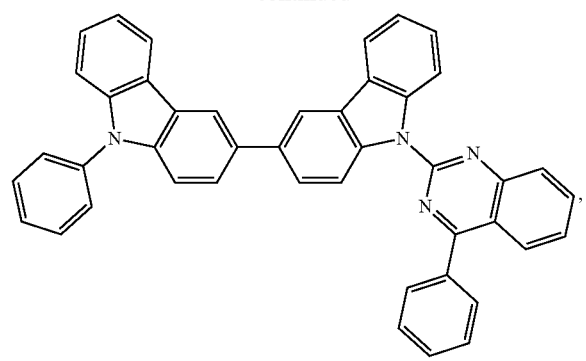
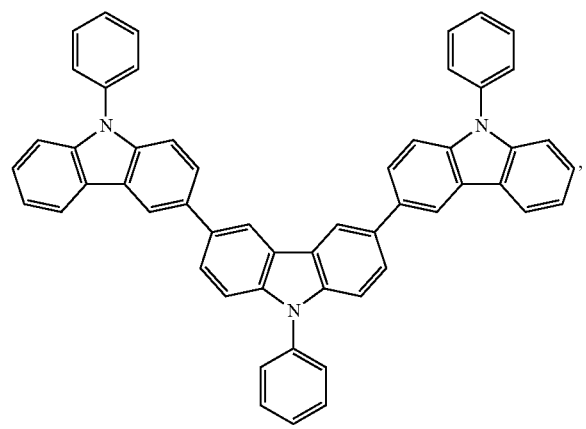
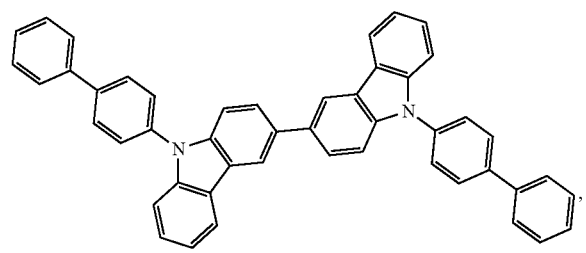
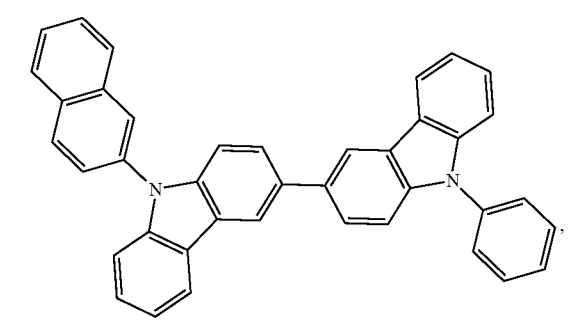
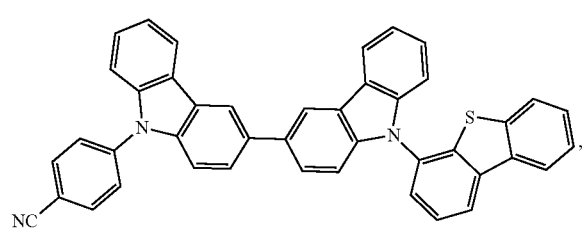
166
-continued
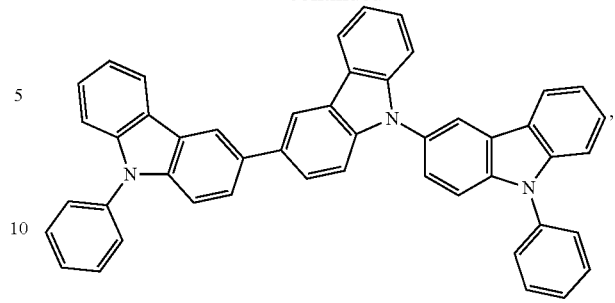
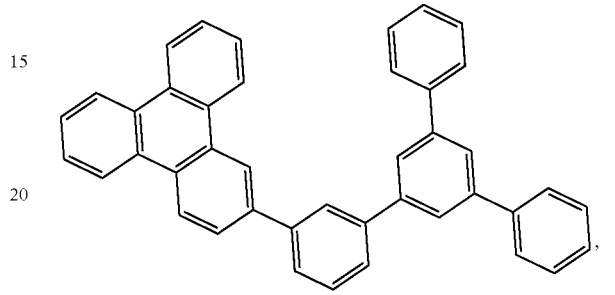
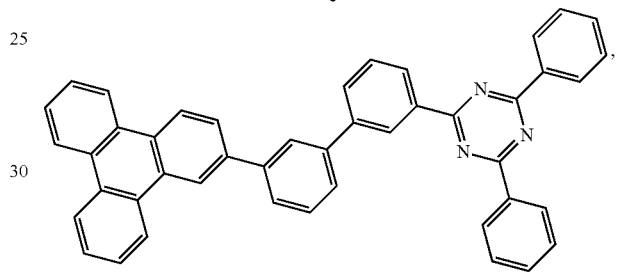

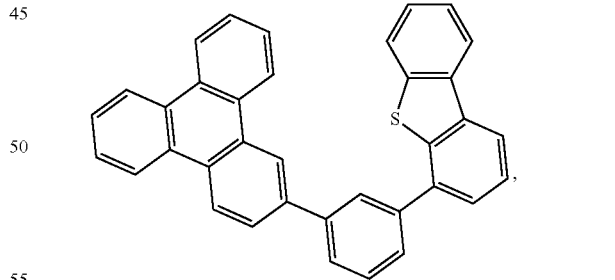
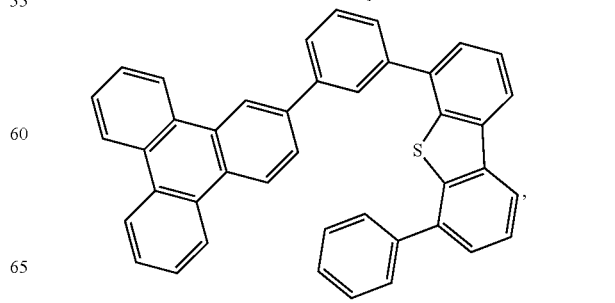

167
-continued
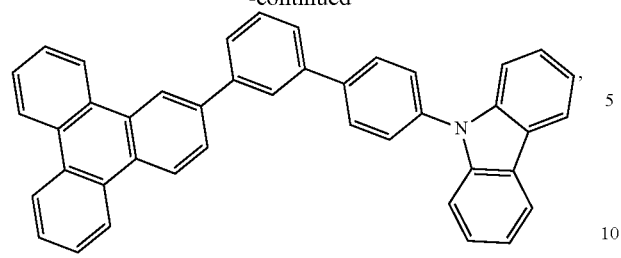
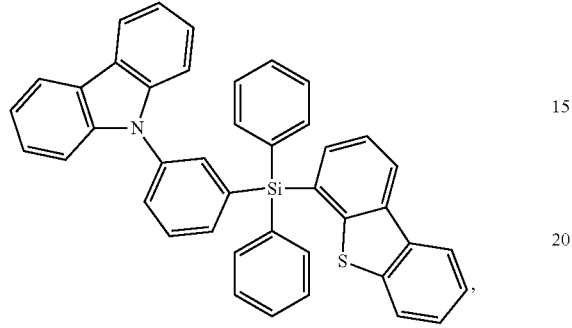
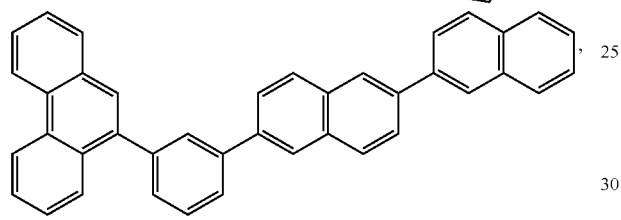
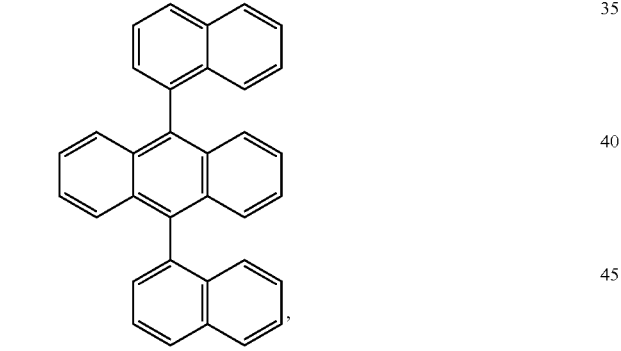
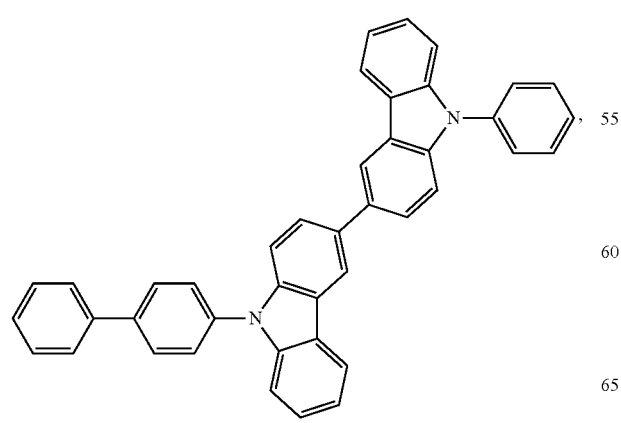
168
-continued
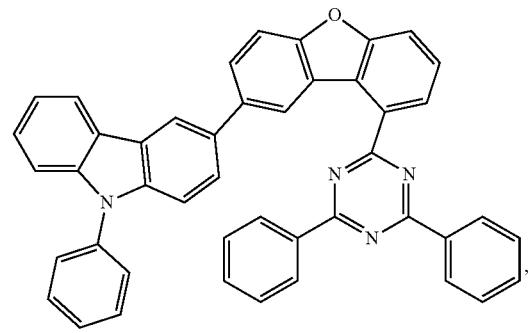
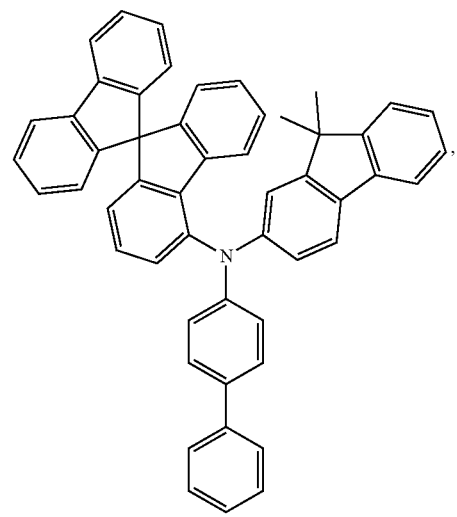
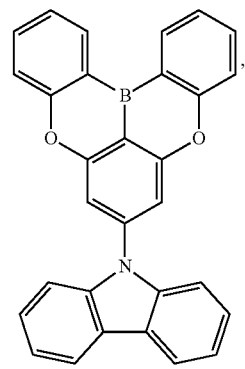
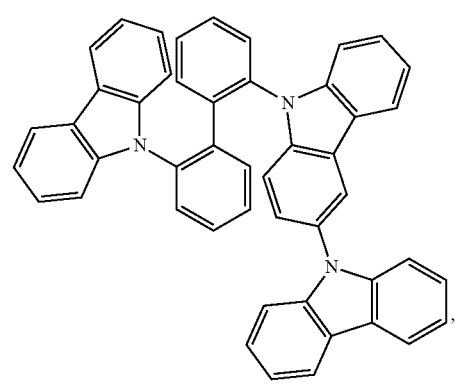

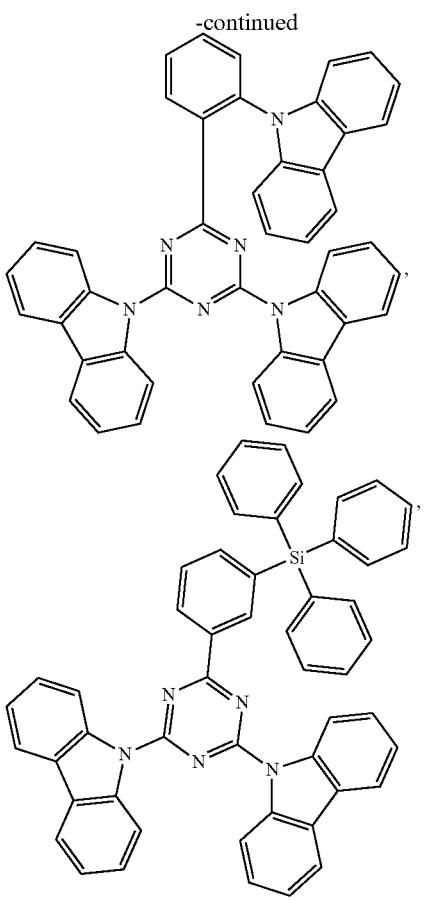

and combinations thereof.

In some embodiments, the organic layer may further comprise a host, wherein the host comprises a metal complex.

In some embodiments, the compound as described herein may be a sensitizer; wherein the device may further comprise an acceptor; and wherein the acceptor may be selected from the group consisting of fluorescent emitter, delayed fluorescence emitter, and combination thereof.

In yet another aspect, the OLED of the present disclosure may also comprise an emissive region containing a compound as disclosed in the above compounds section of the present disclosure.

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space. In some embodiments, one or more intervening layer can be disposed between the enhancement layer and the outcoupling layer. The examples for interventing layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
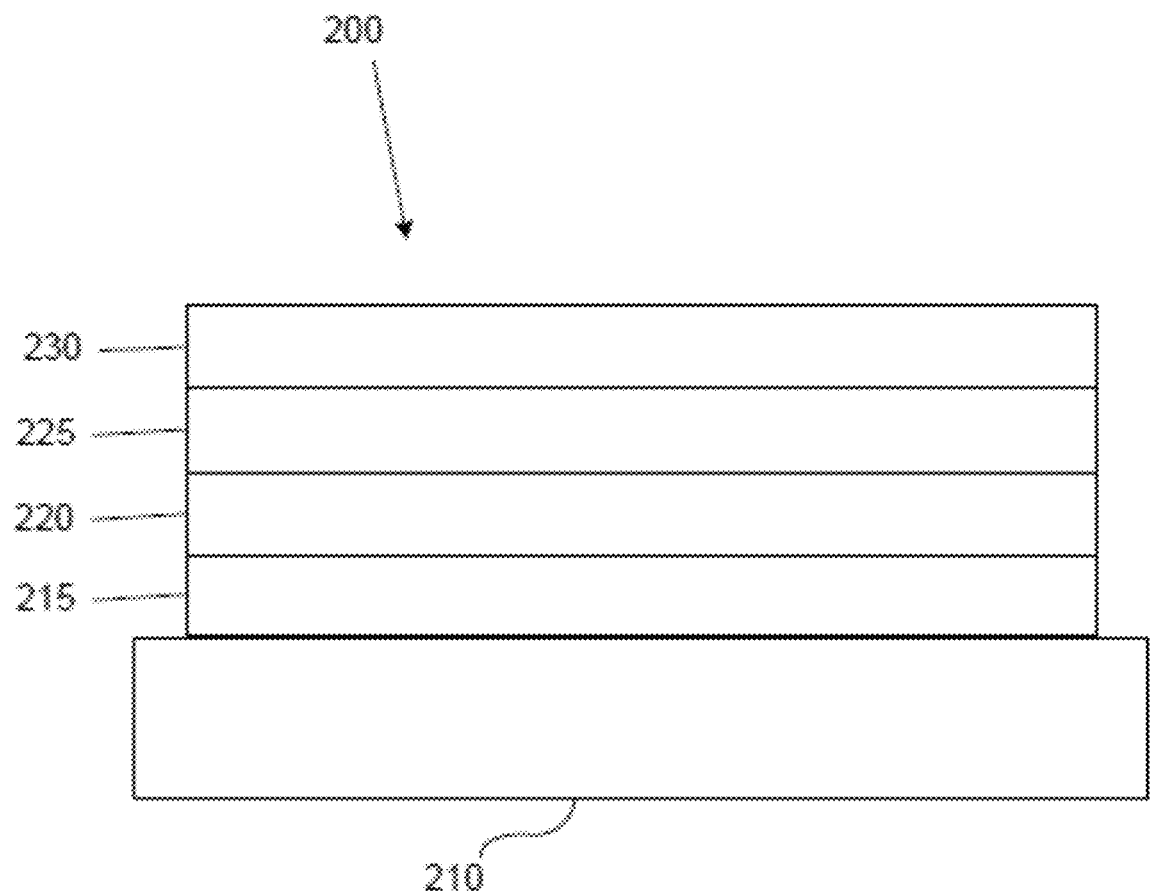
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18 degrees C. to 30 degrees C., and more preferably at room temperature (20-25° C.), but could be used outside this temperature range, for example, from −40 degree C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers.

In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.
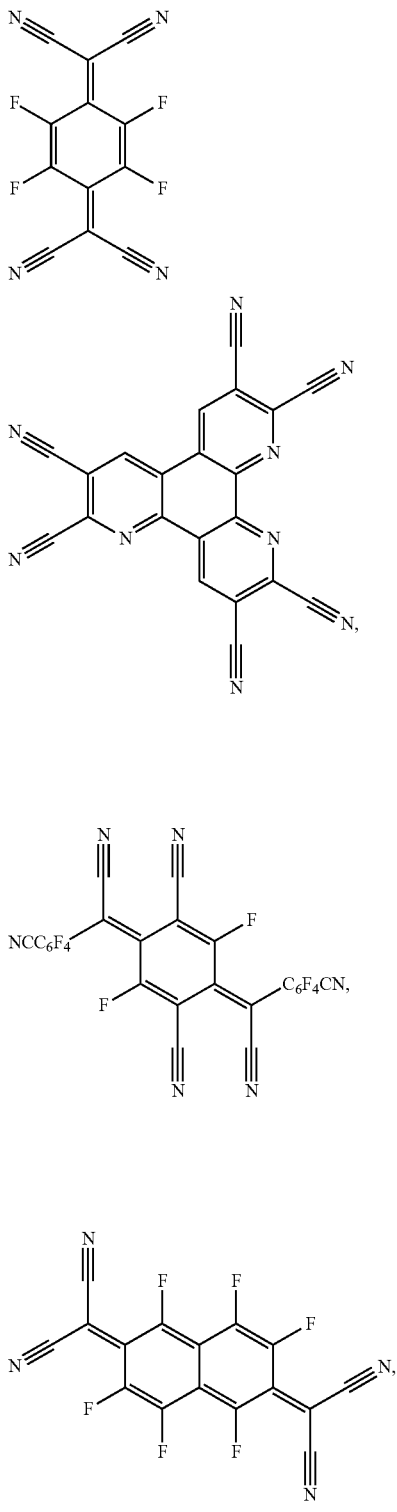
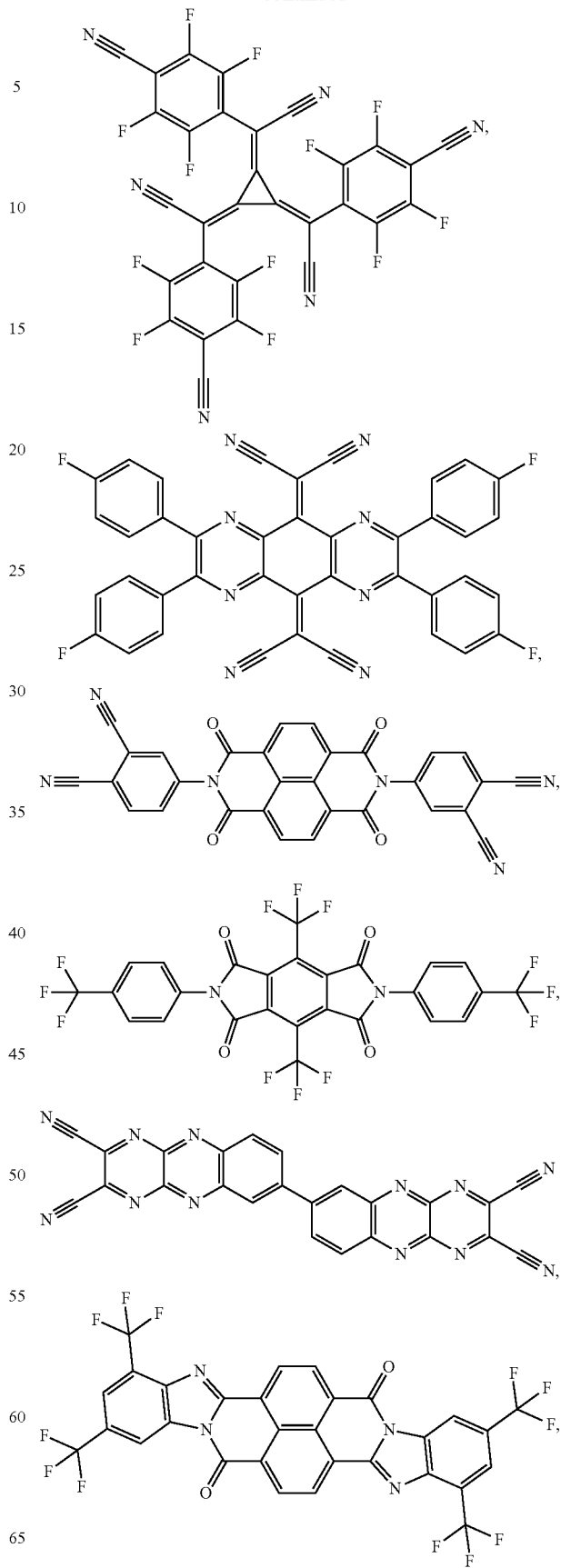

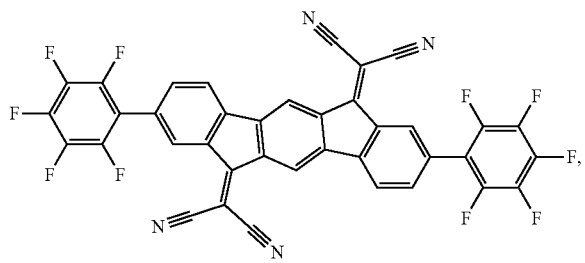

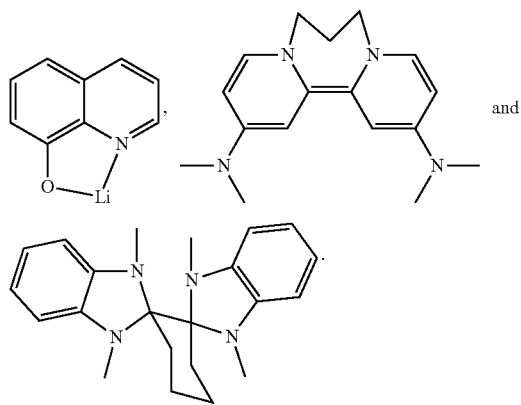

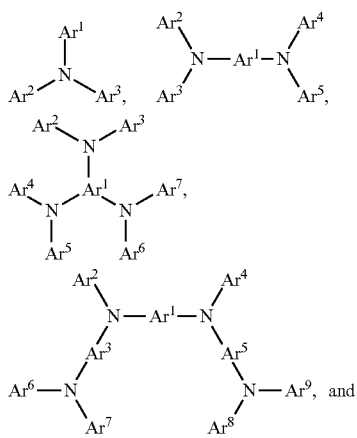

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

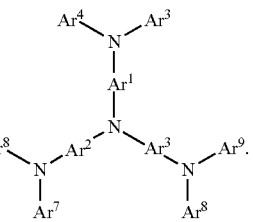

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

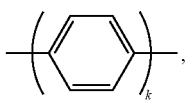

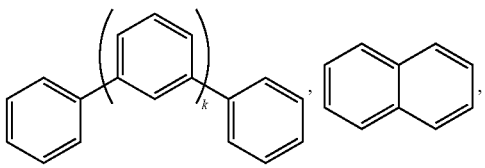

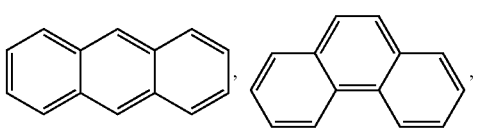

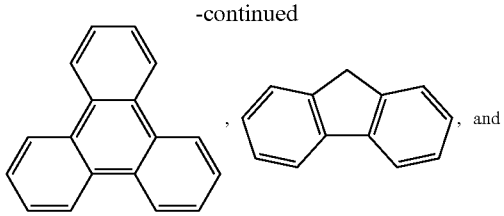, and

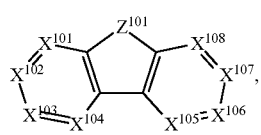

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

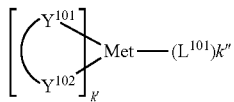

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Pat. No. 6,517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

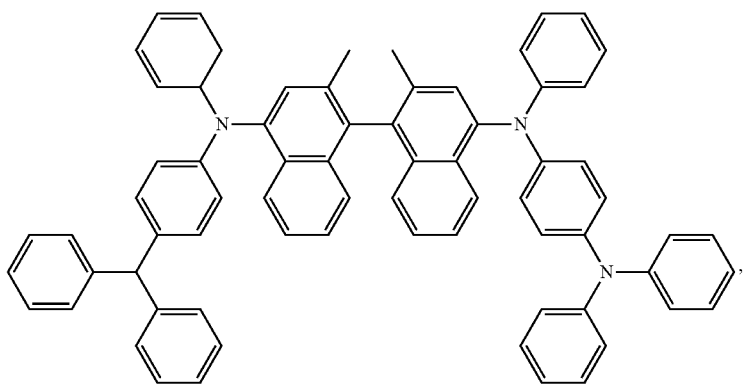

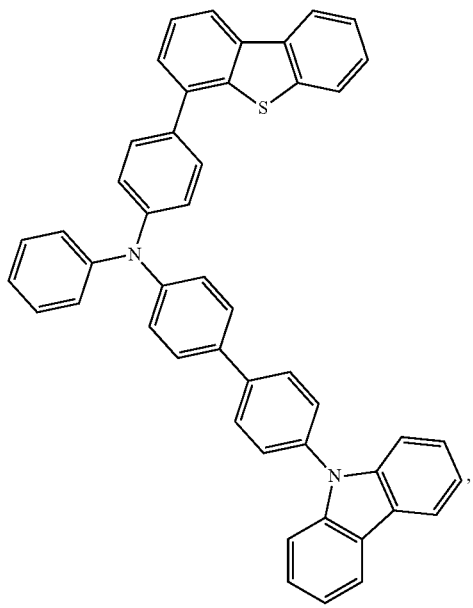
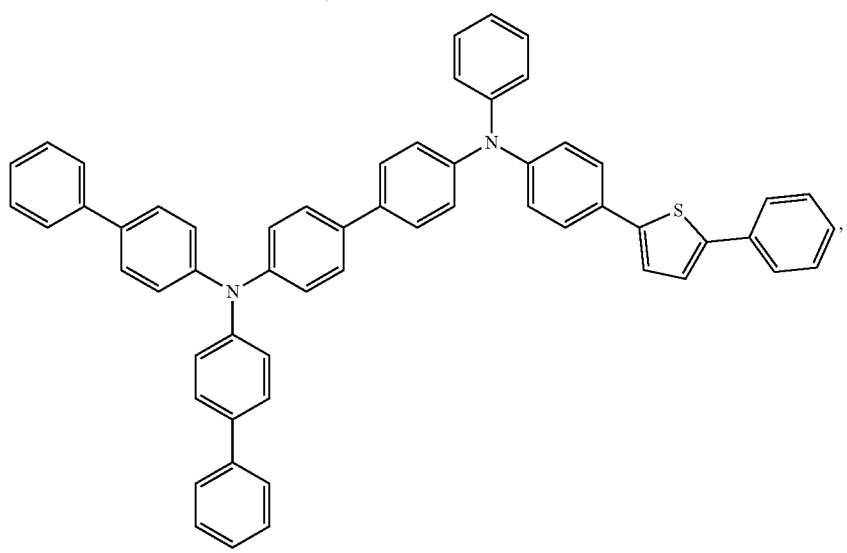
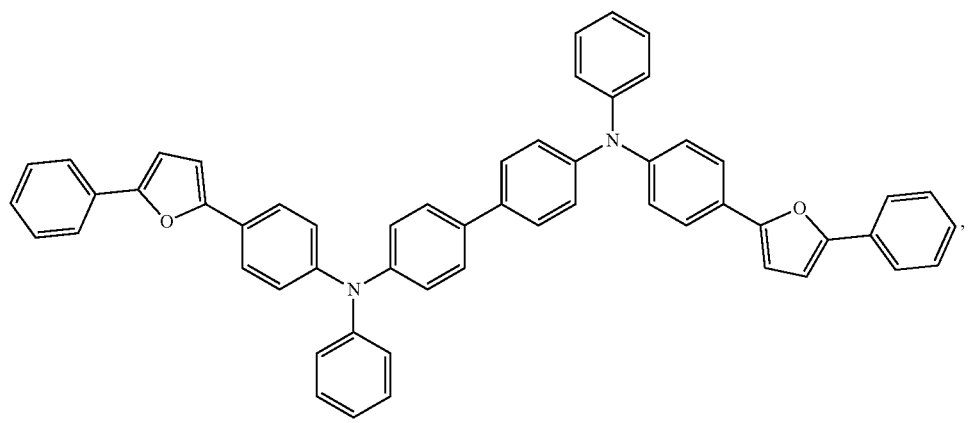

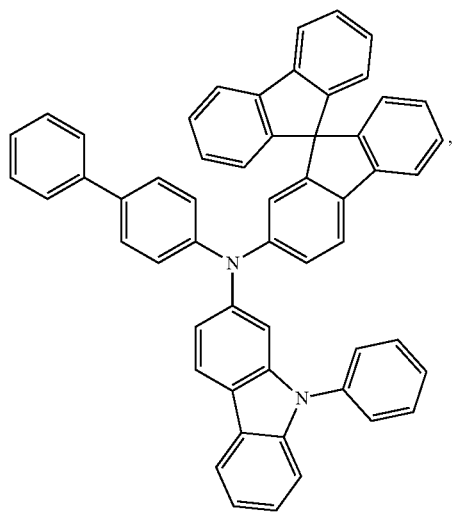
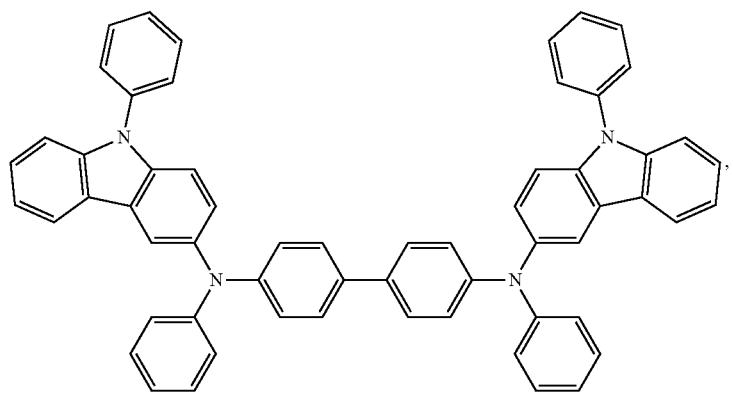
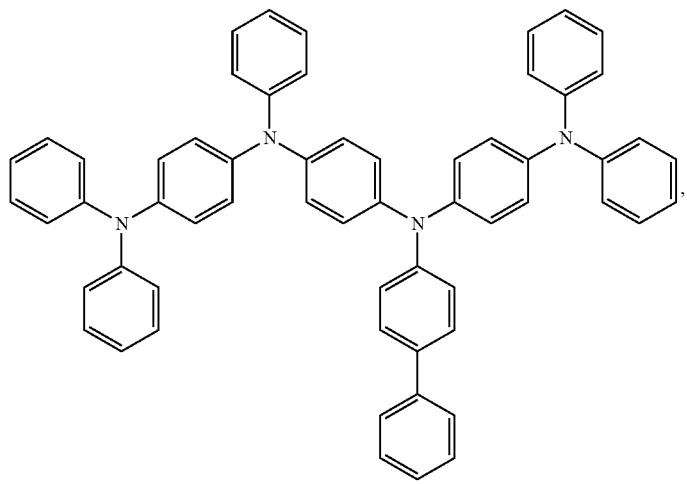 [SMILES: c1ccc(-c2ccc(N(c3ccc(N(c4ccccc4)c4ccccc4)cc3)c3ccc(N(c4ccccc4)c4ccc(N(c5ccccc5)c5ccccc5)cc4)cc3)cc2)cc1]

-continued
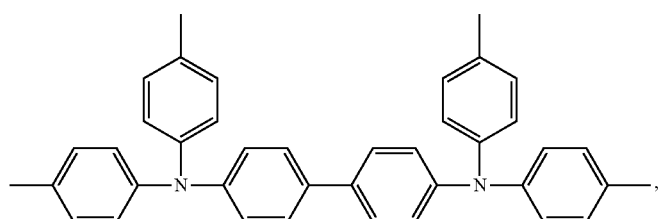
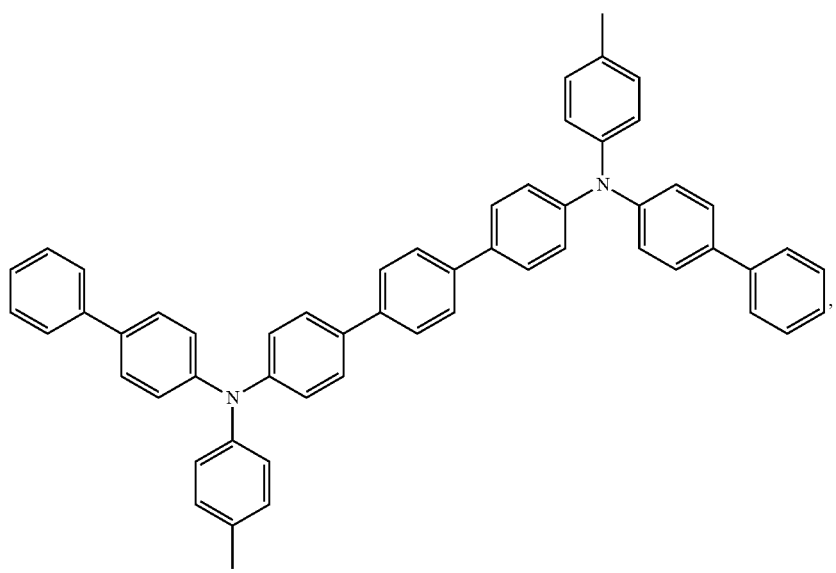

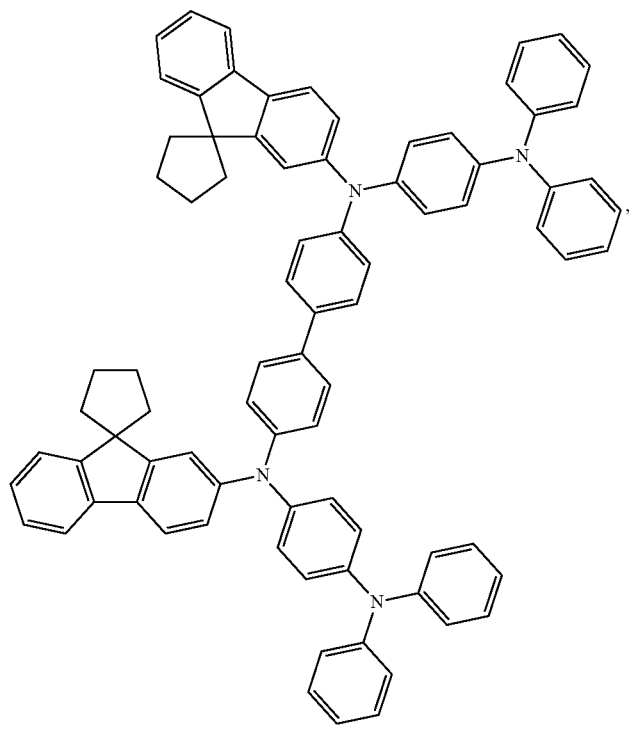
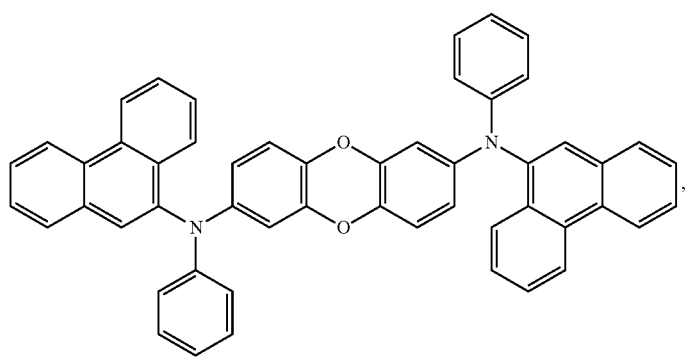
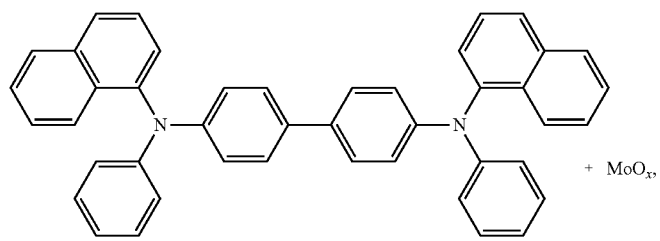
+ MoO$_x$, 191  192
-continued
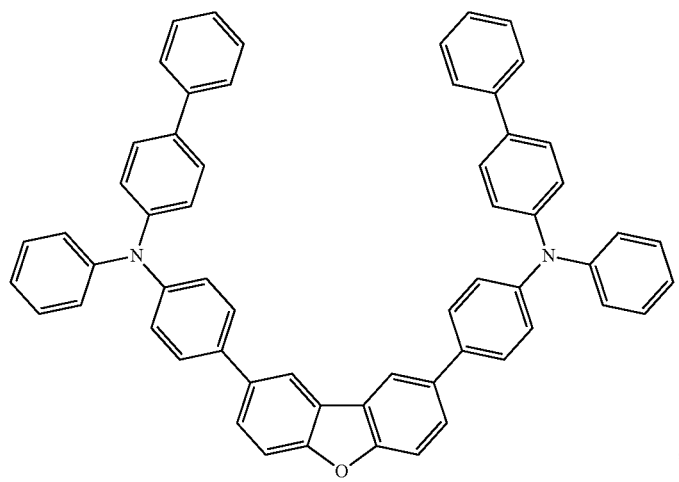
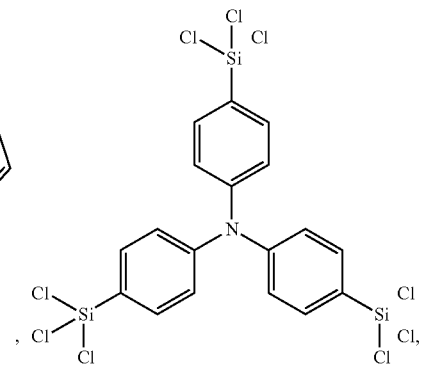
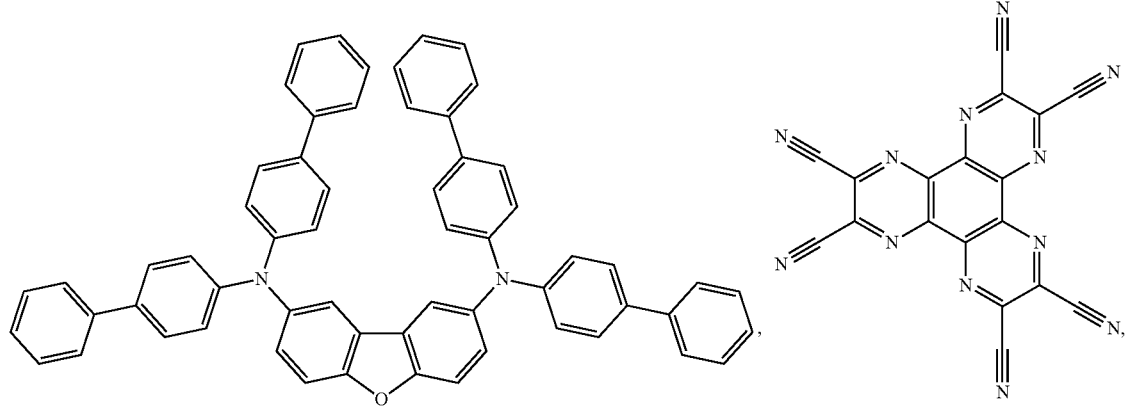
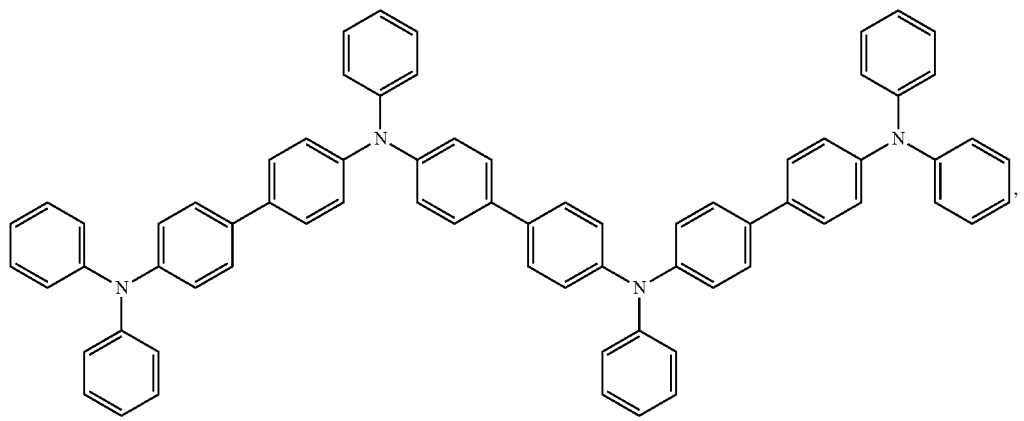

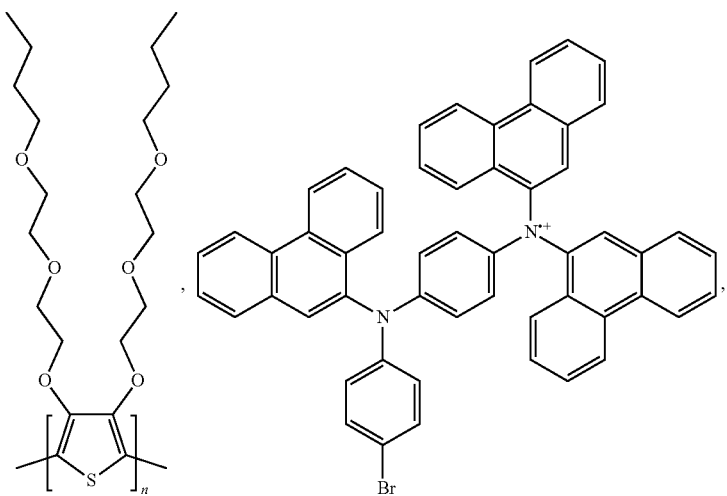
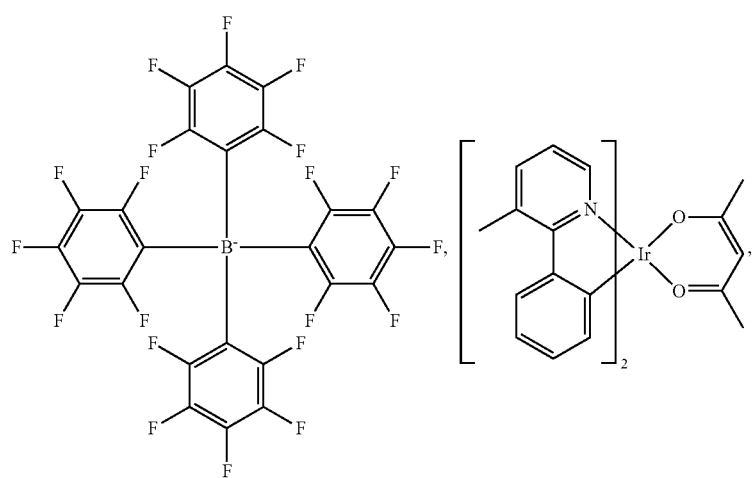
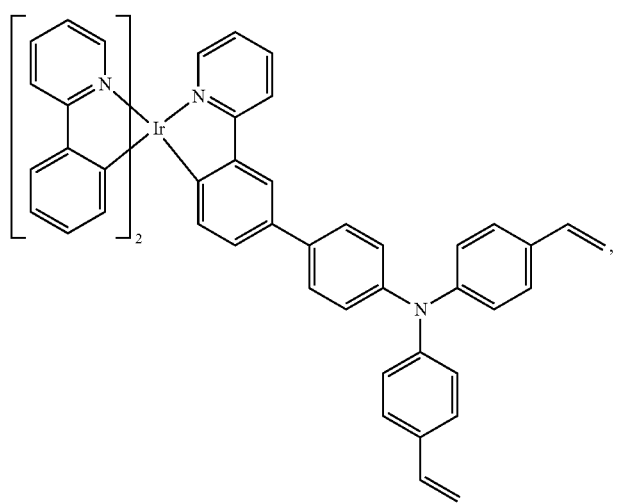

-continued
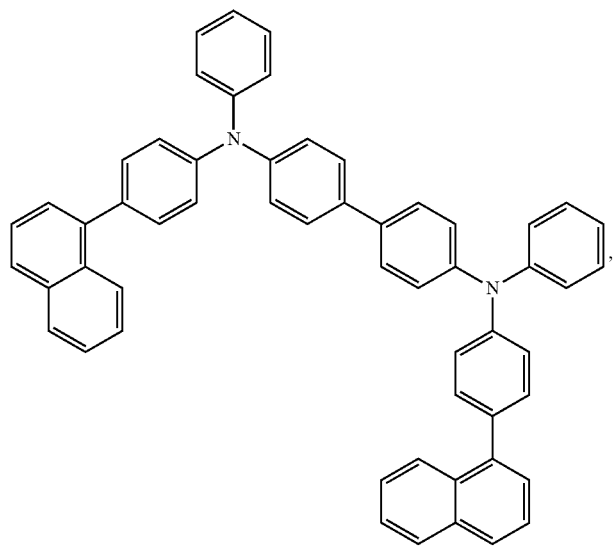
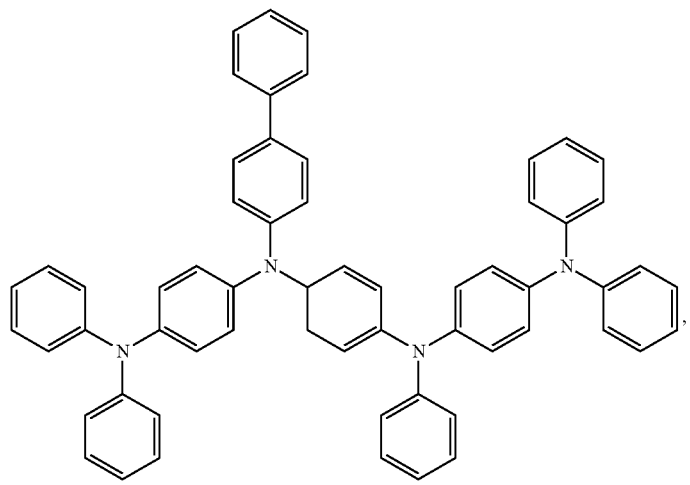
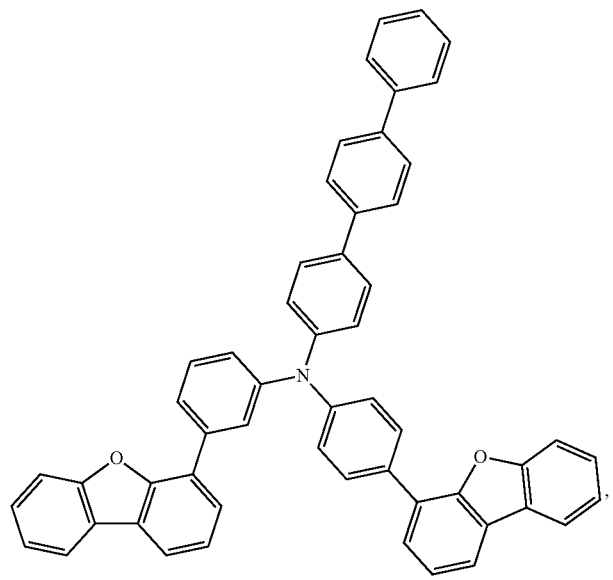

-continued
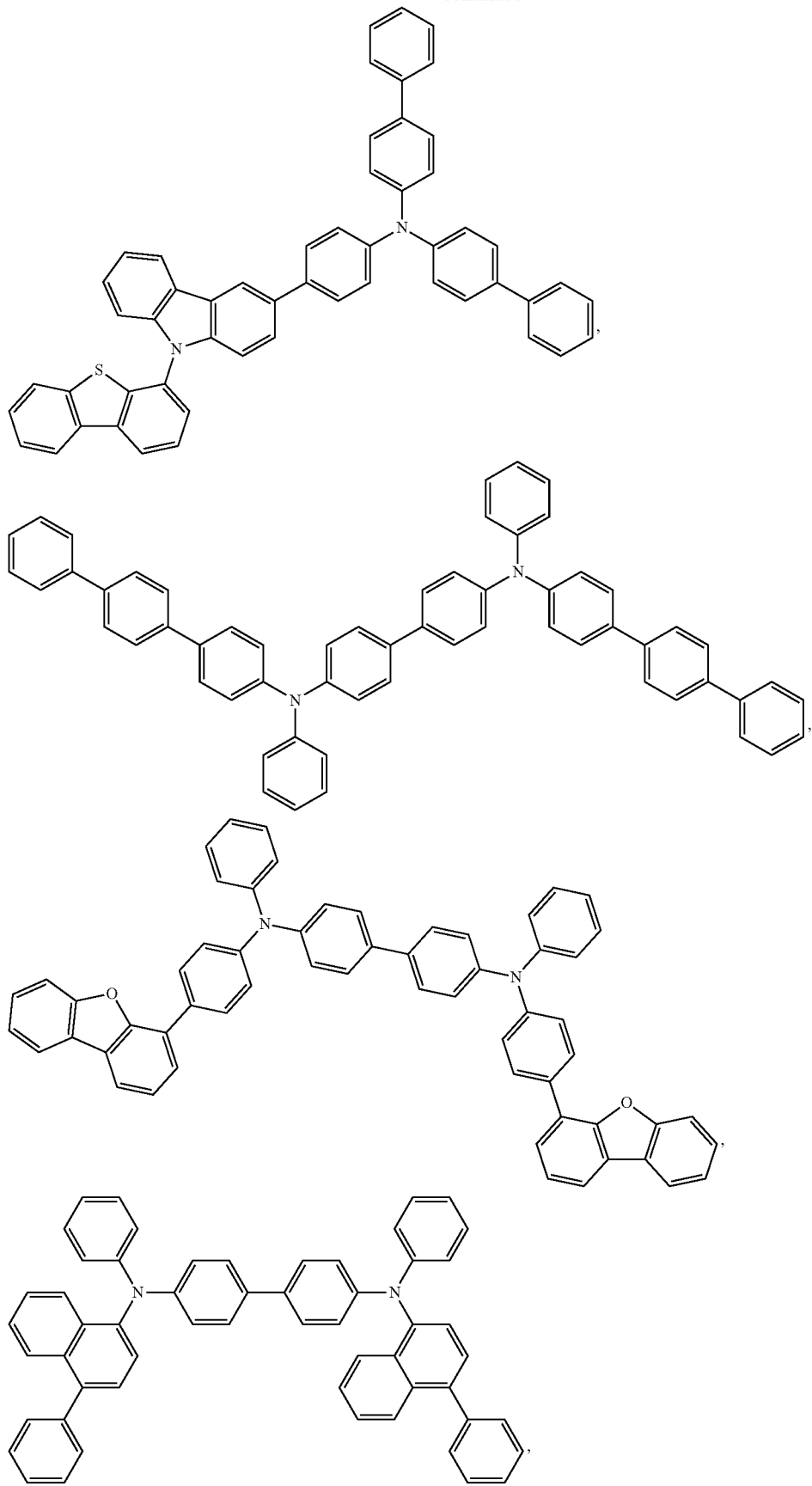

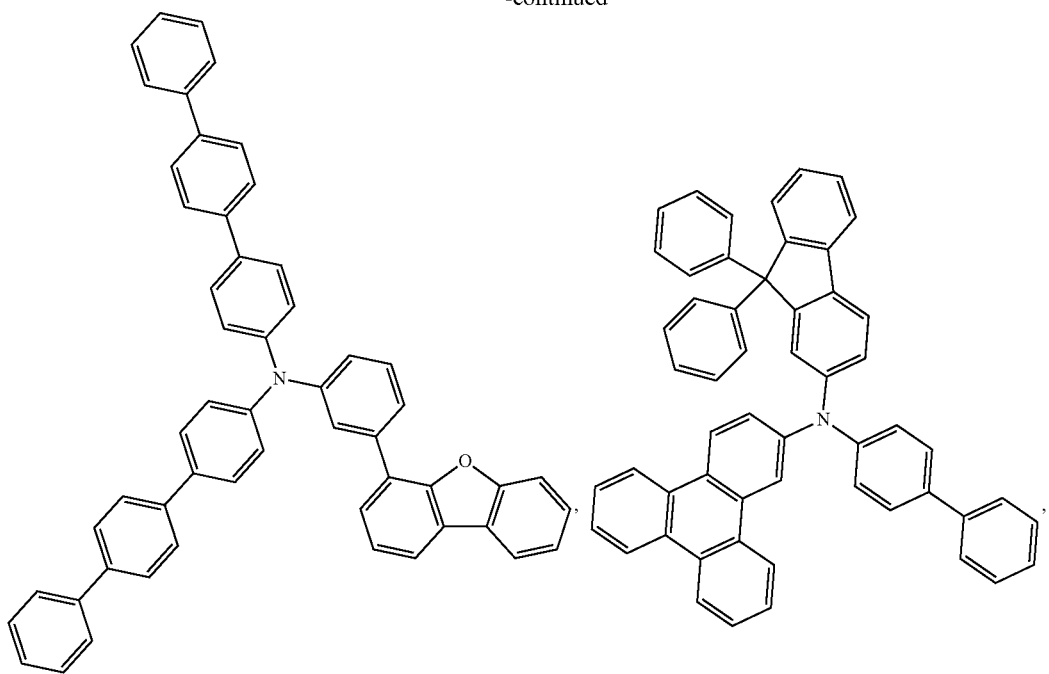
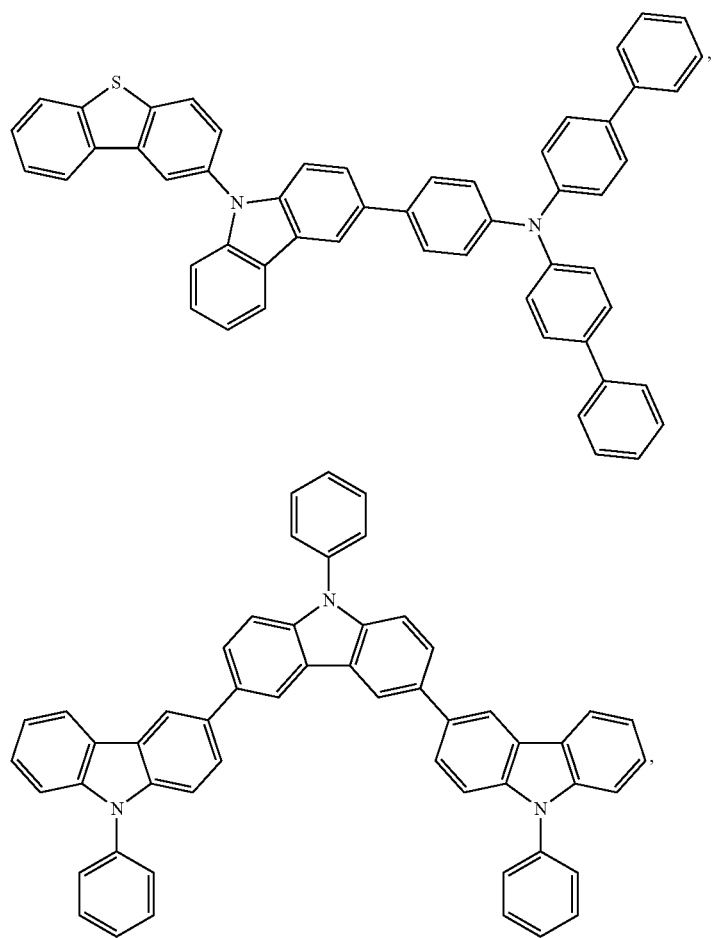

-continued
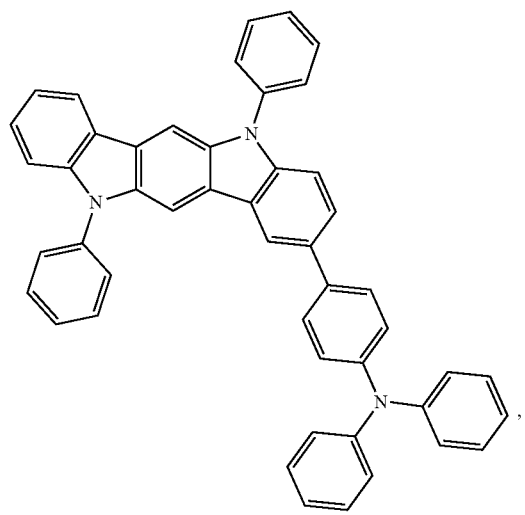
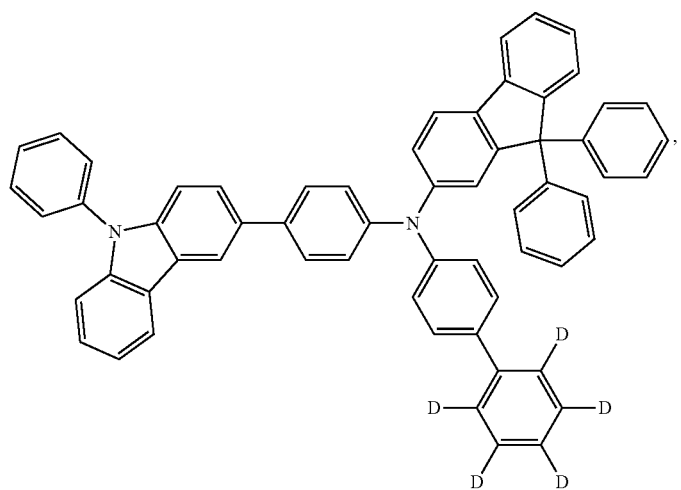
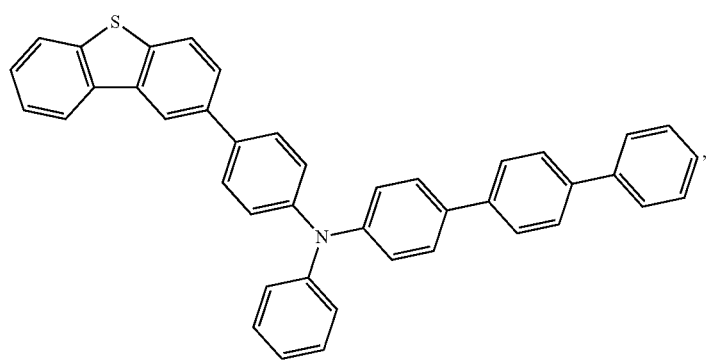

203
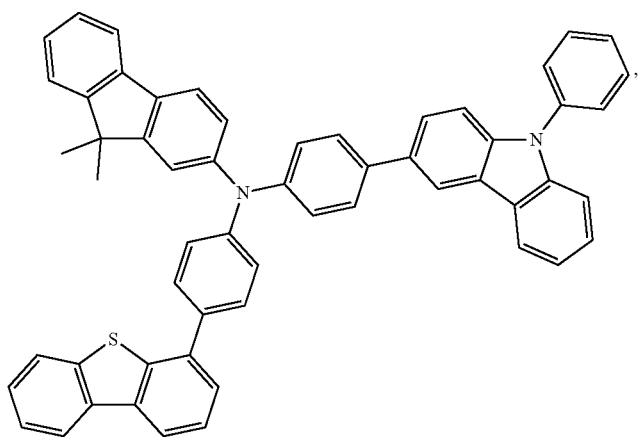
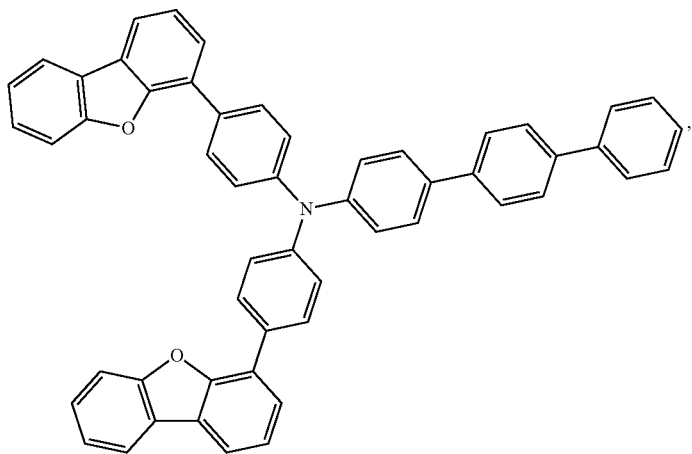
204
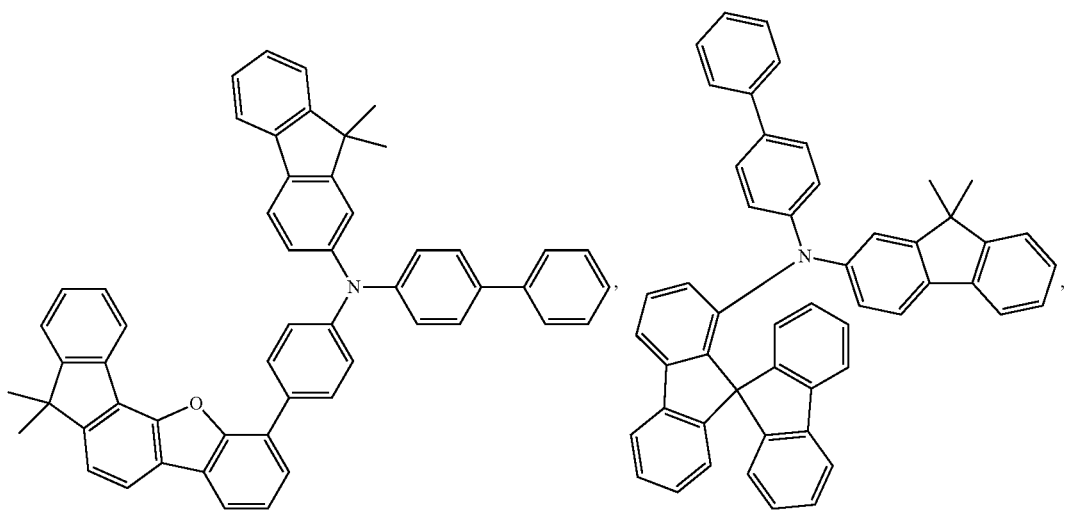

205 206
-continued
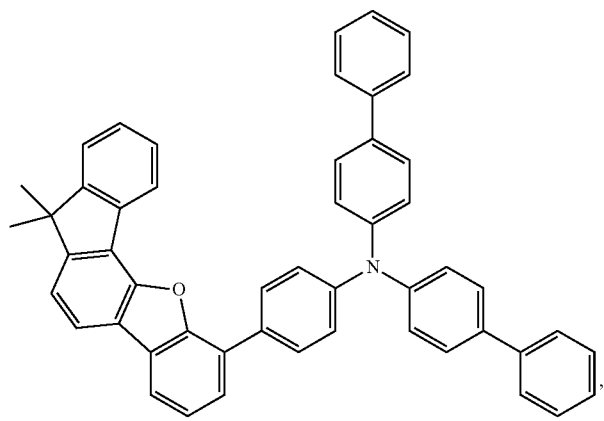
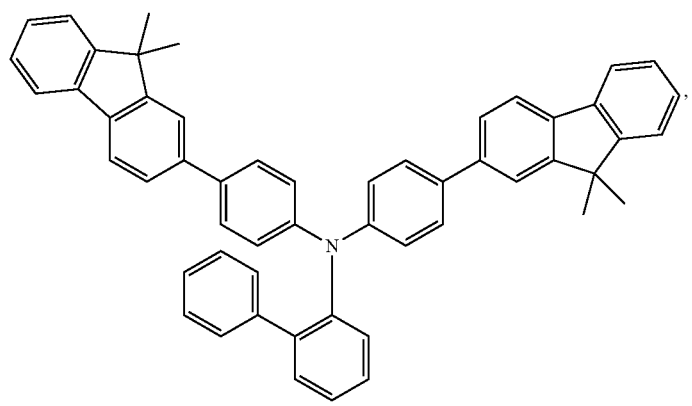
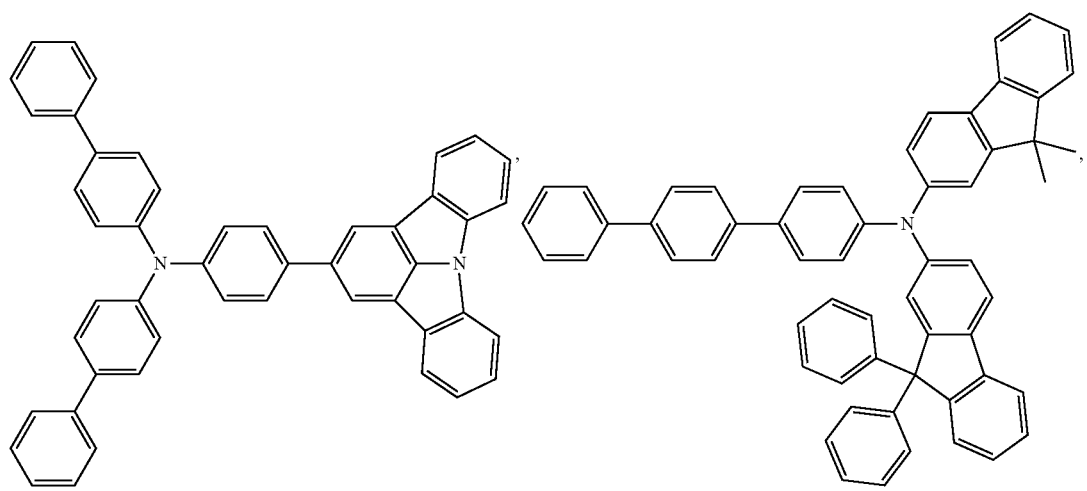

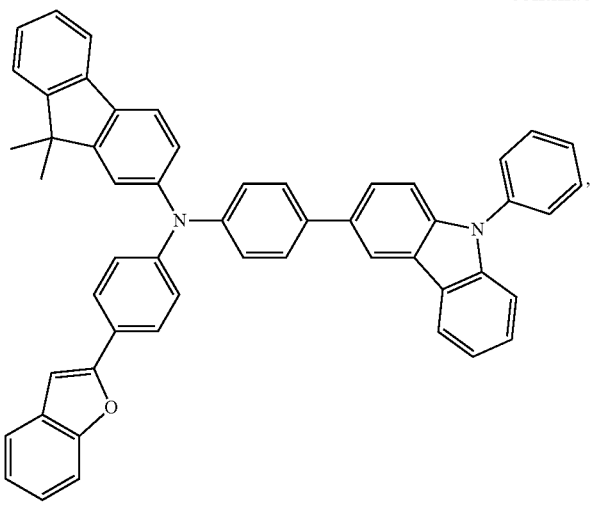
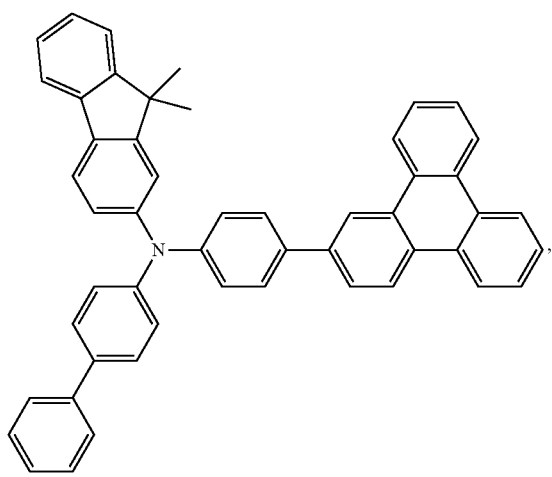
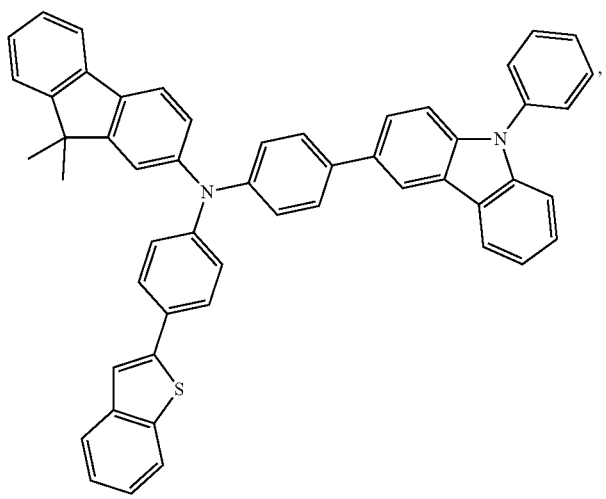

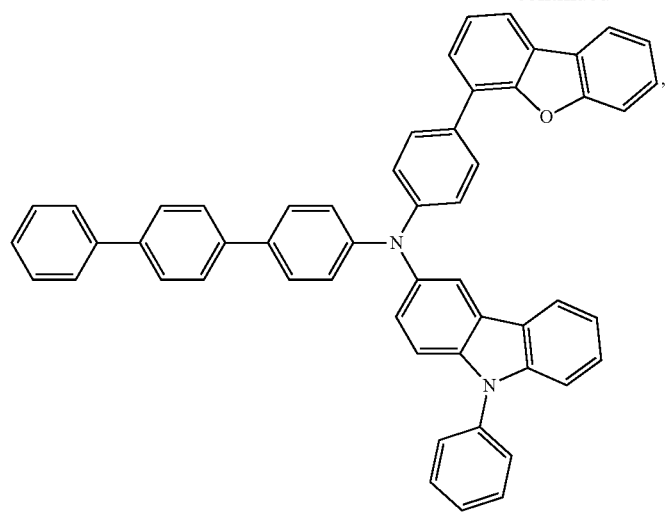 [SMILES: c1ccc(-c2ccc(-c3ccc(N(c4ccc(-c5cccc6c5oc5ccccc56)cc4)c4ccc5c(c4)c4ccccc4n5-c4ccccc4)cc3)cc2)cc1]
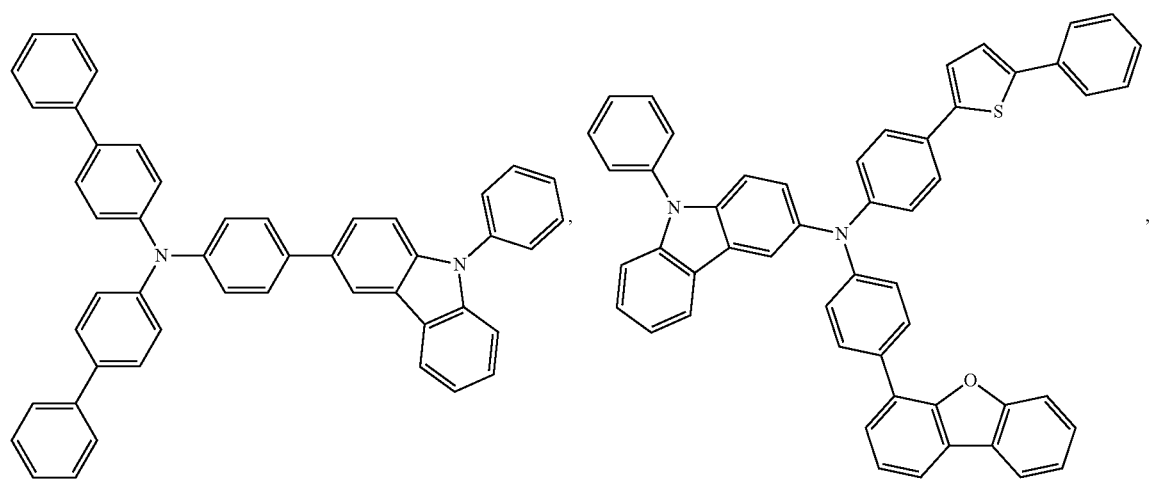
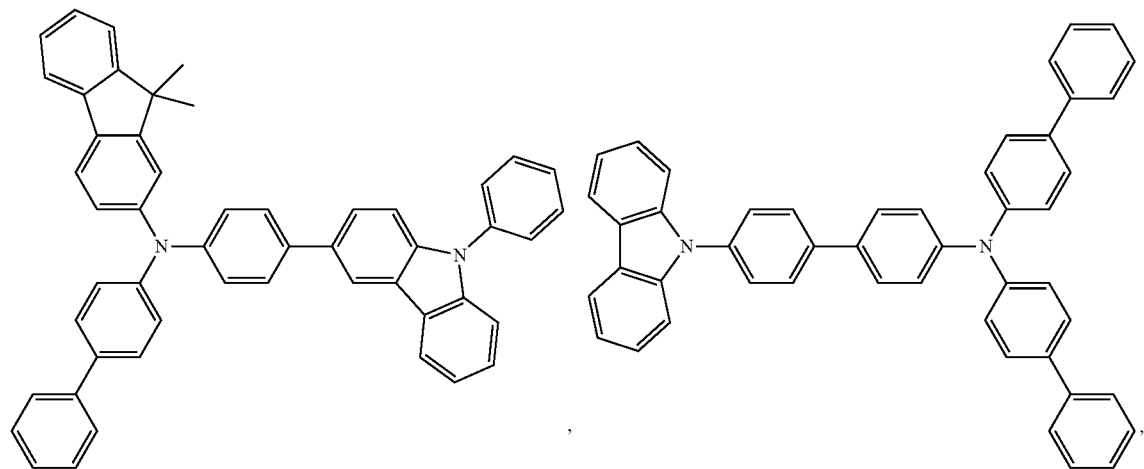

-continued
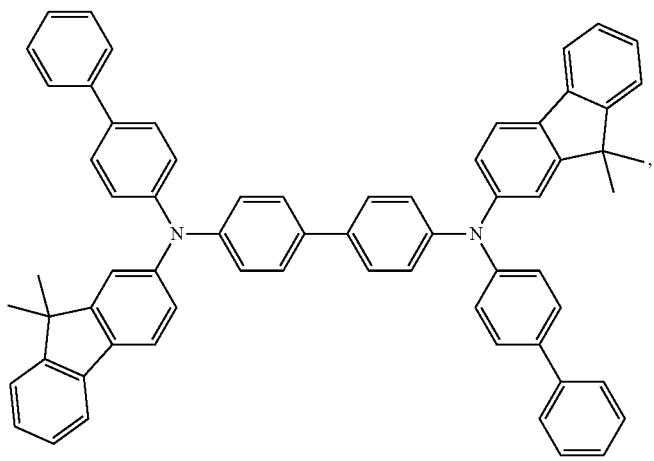
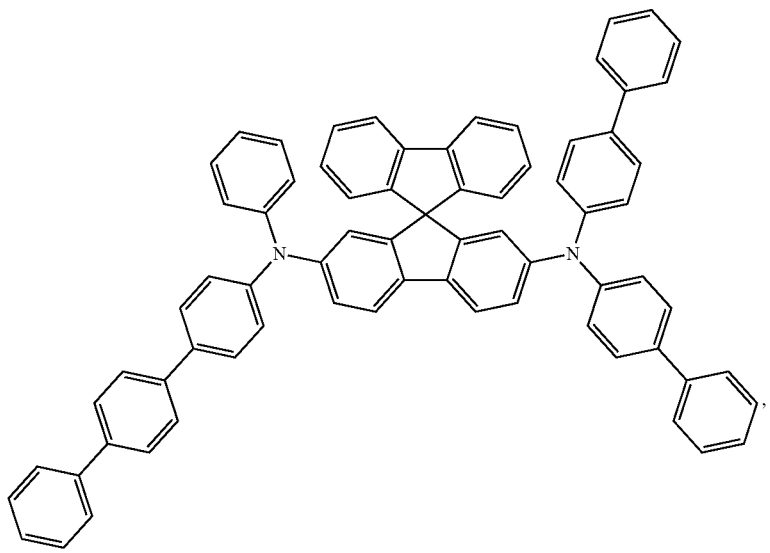
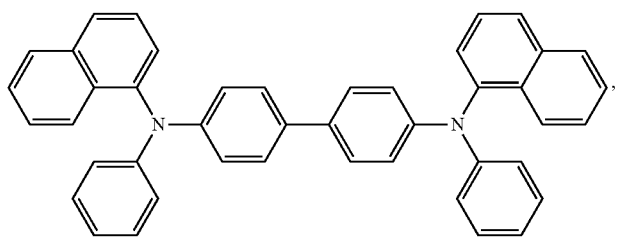
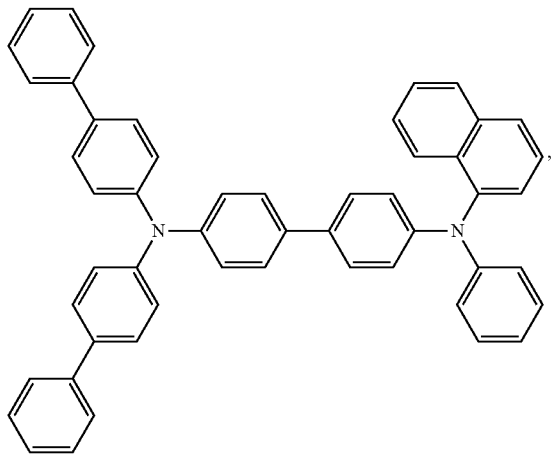

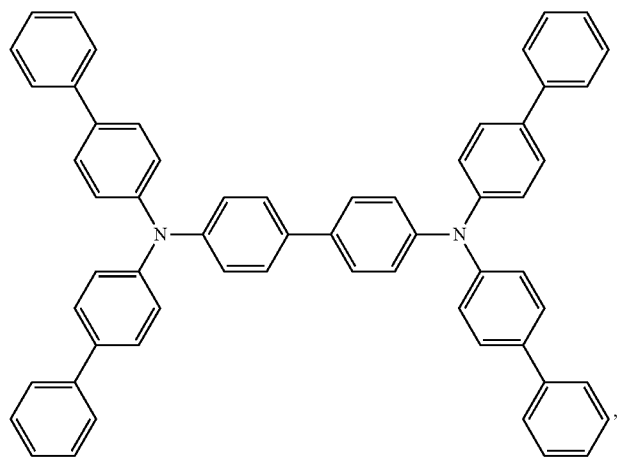 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
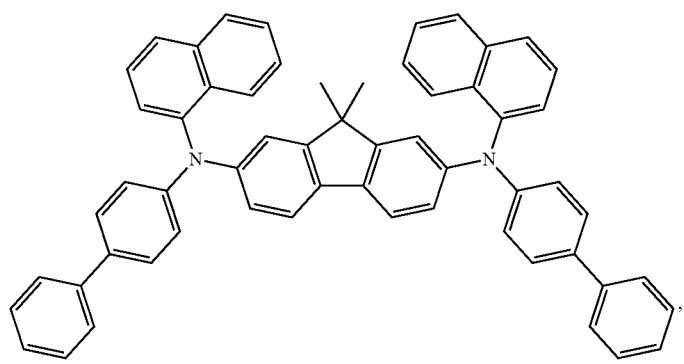
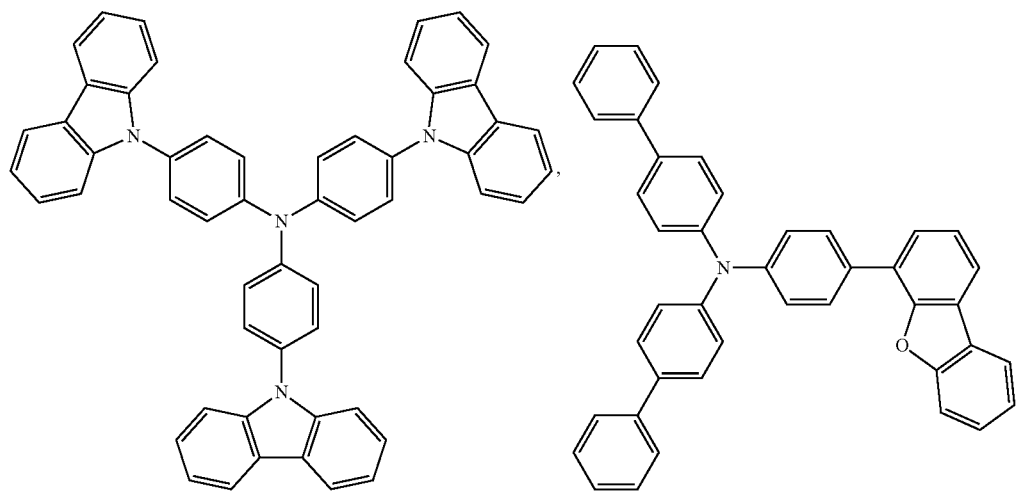

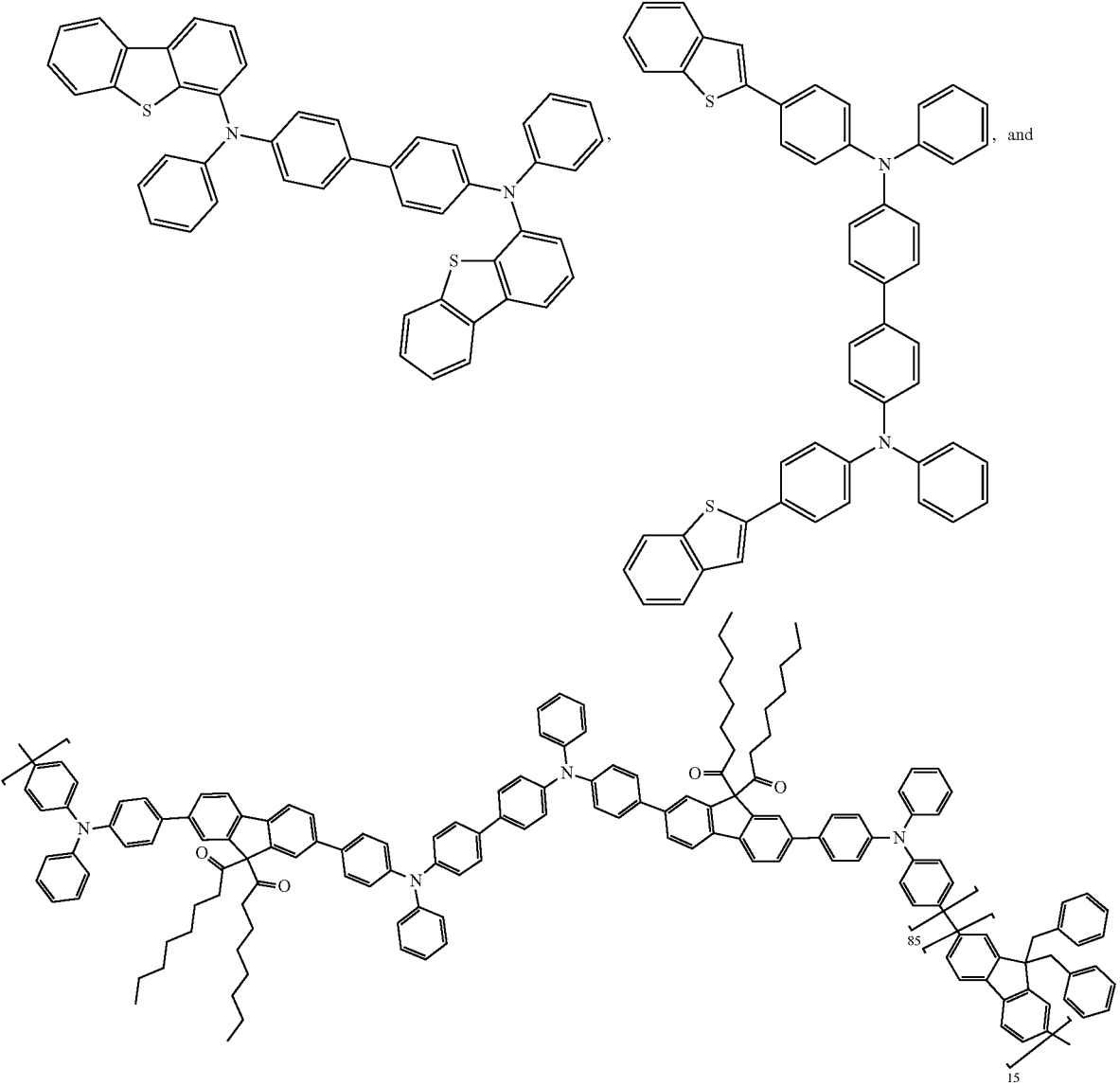

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

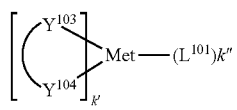

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

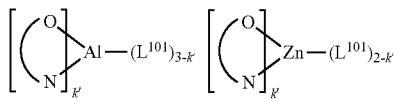

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

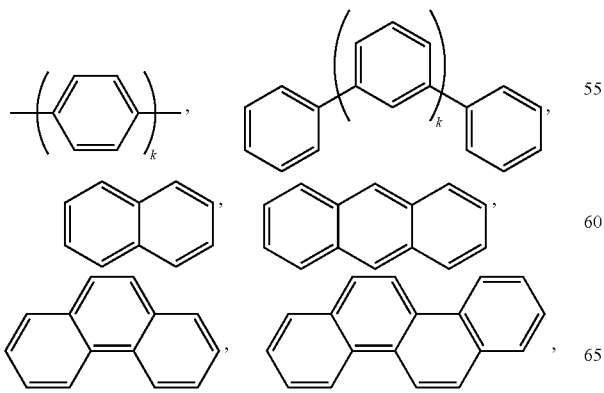

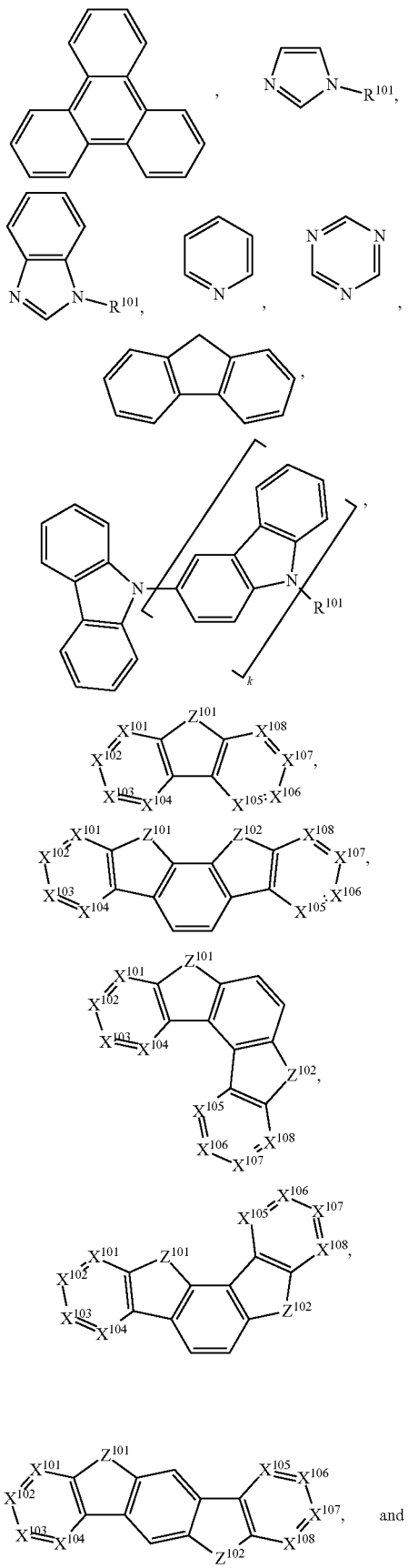

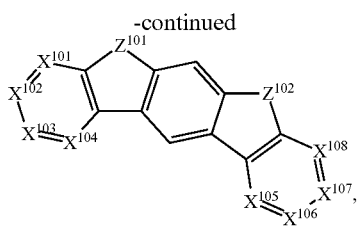

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

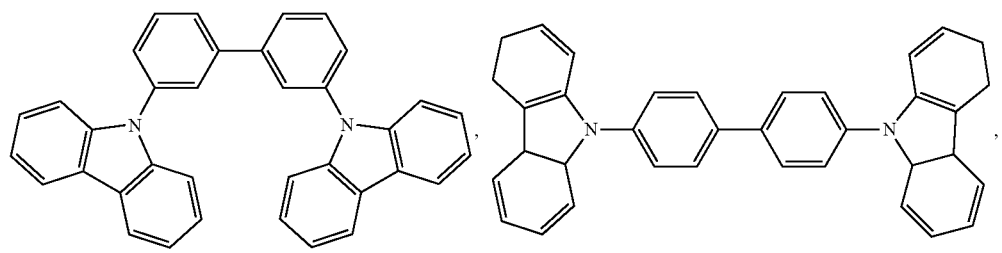

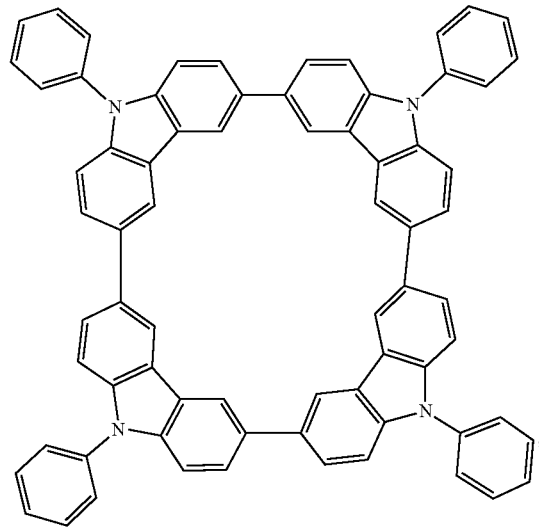

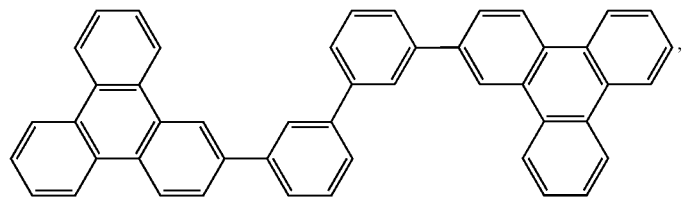

221 222
-continued
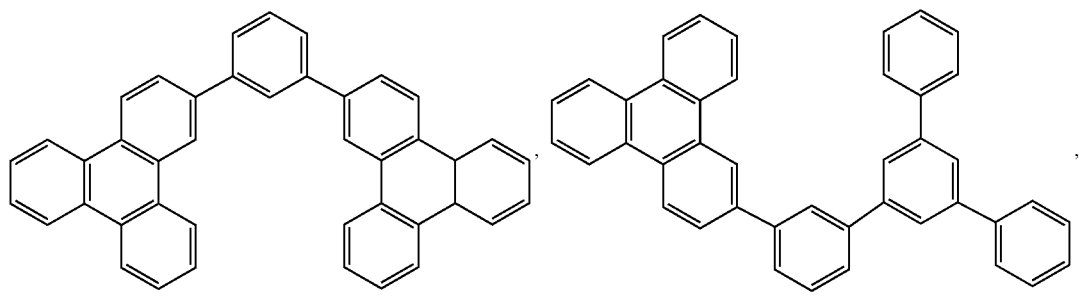
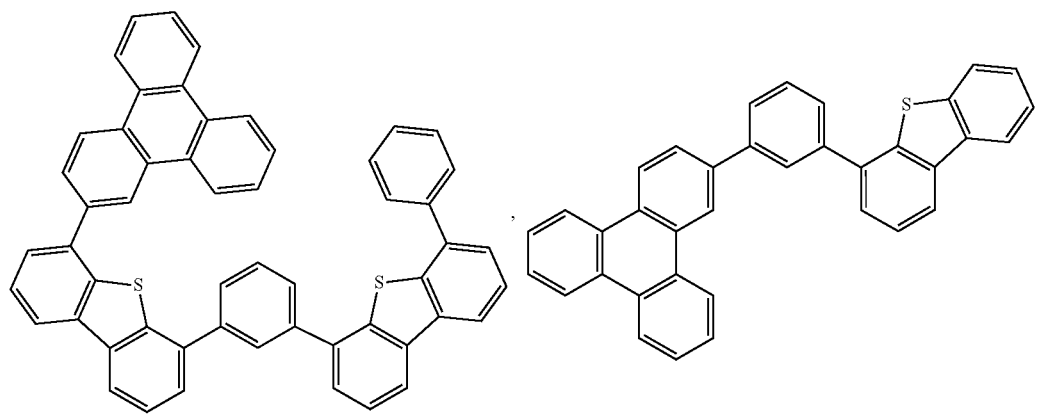
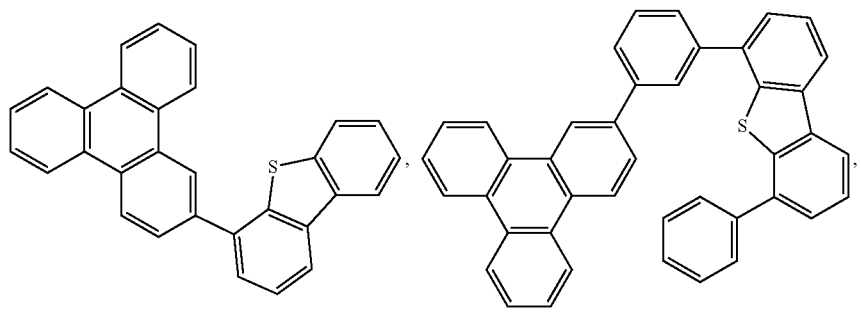
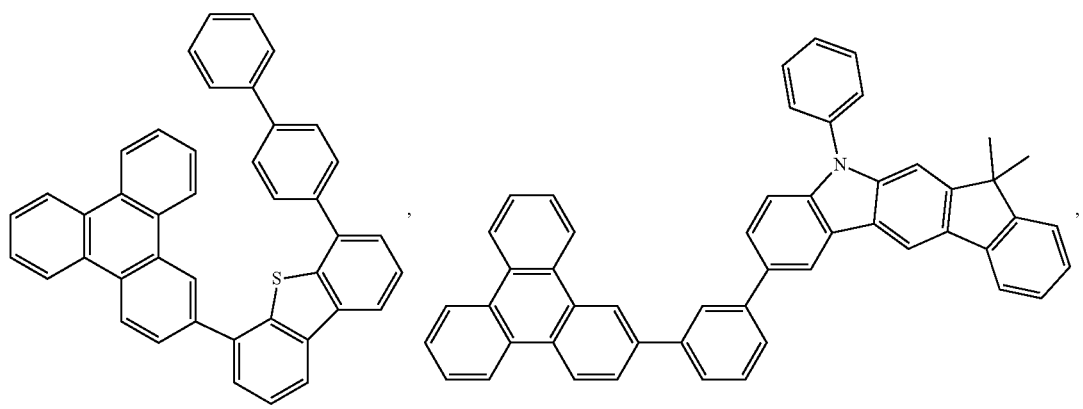

-continued
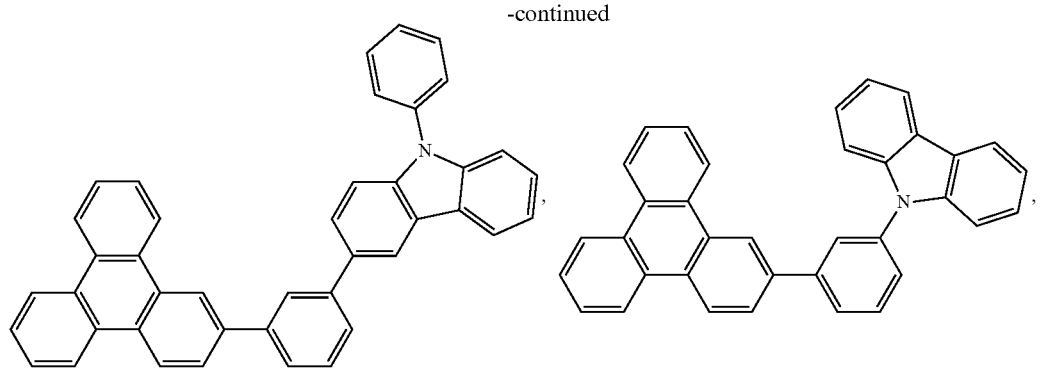
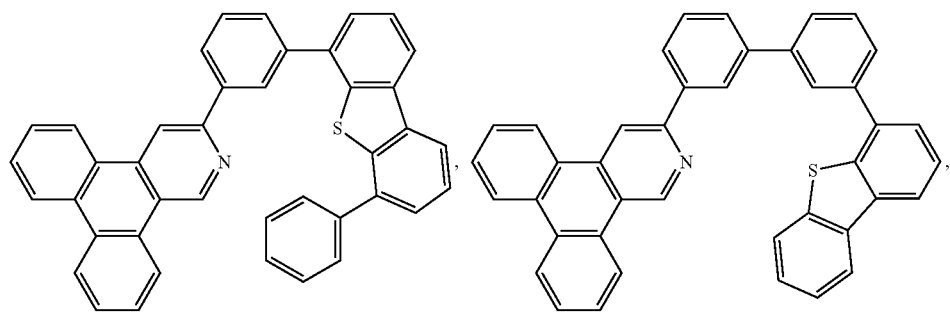
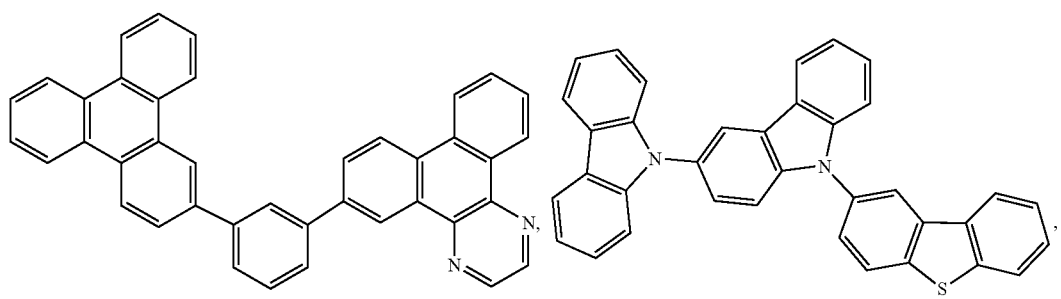
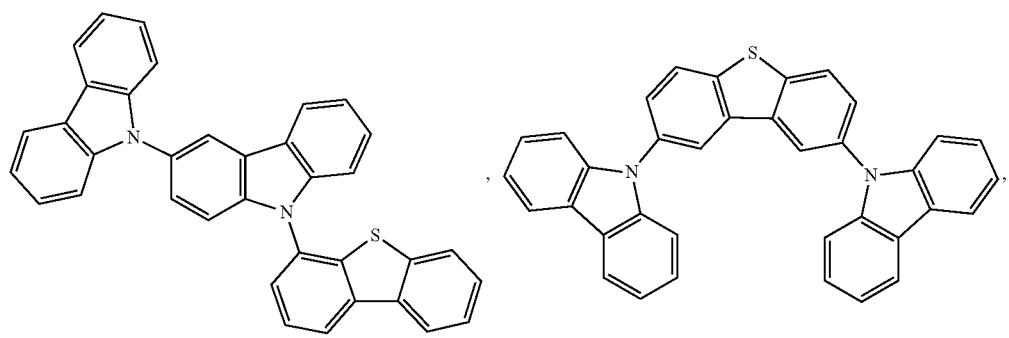
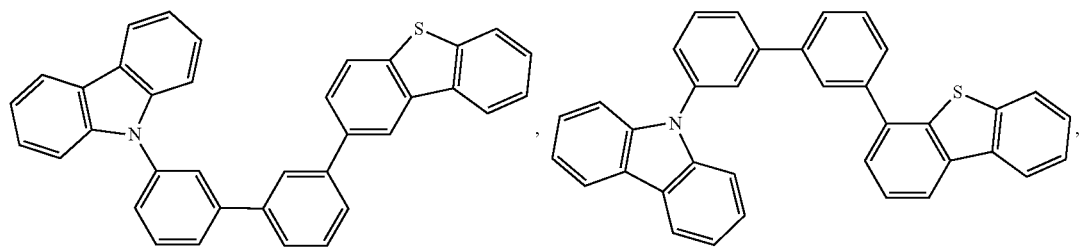

-continued
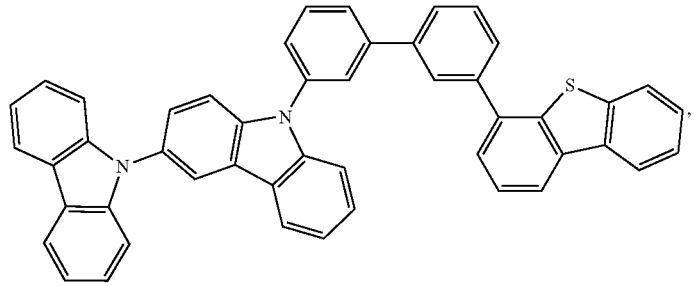
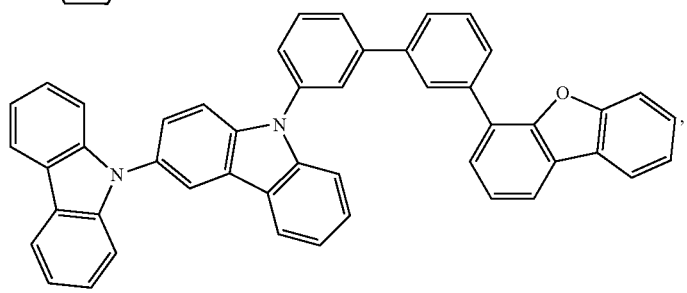
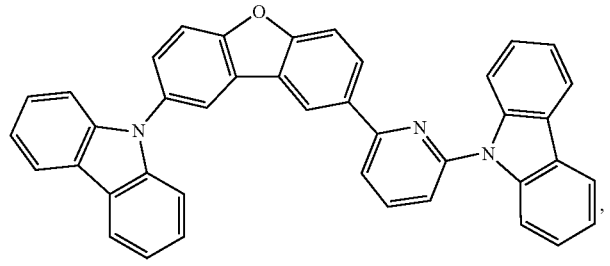
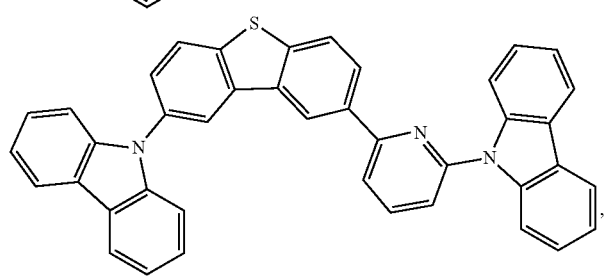
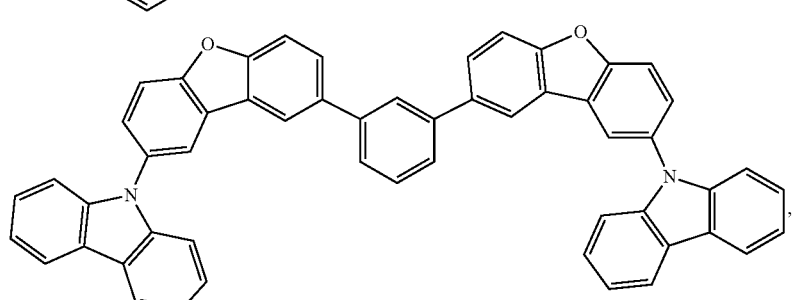
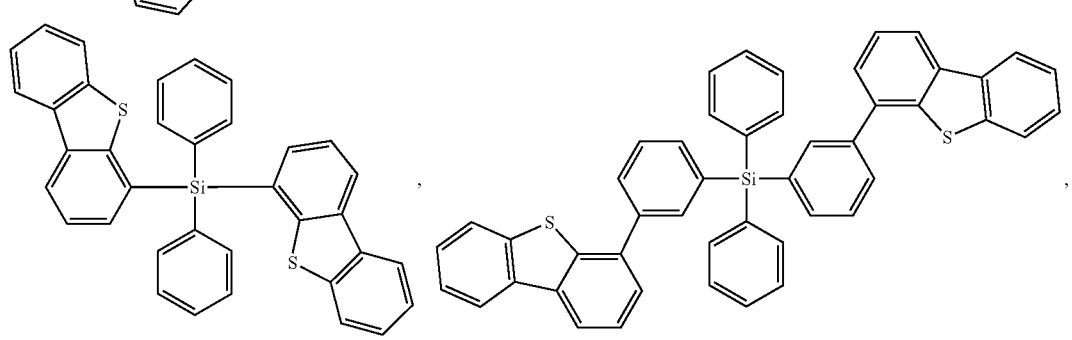

-continued
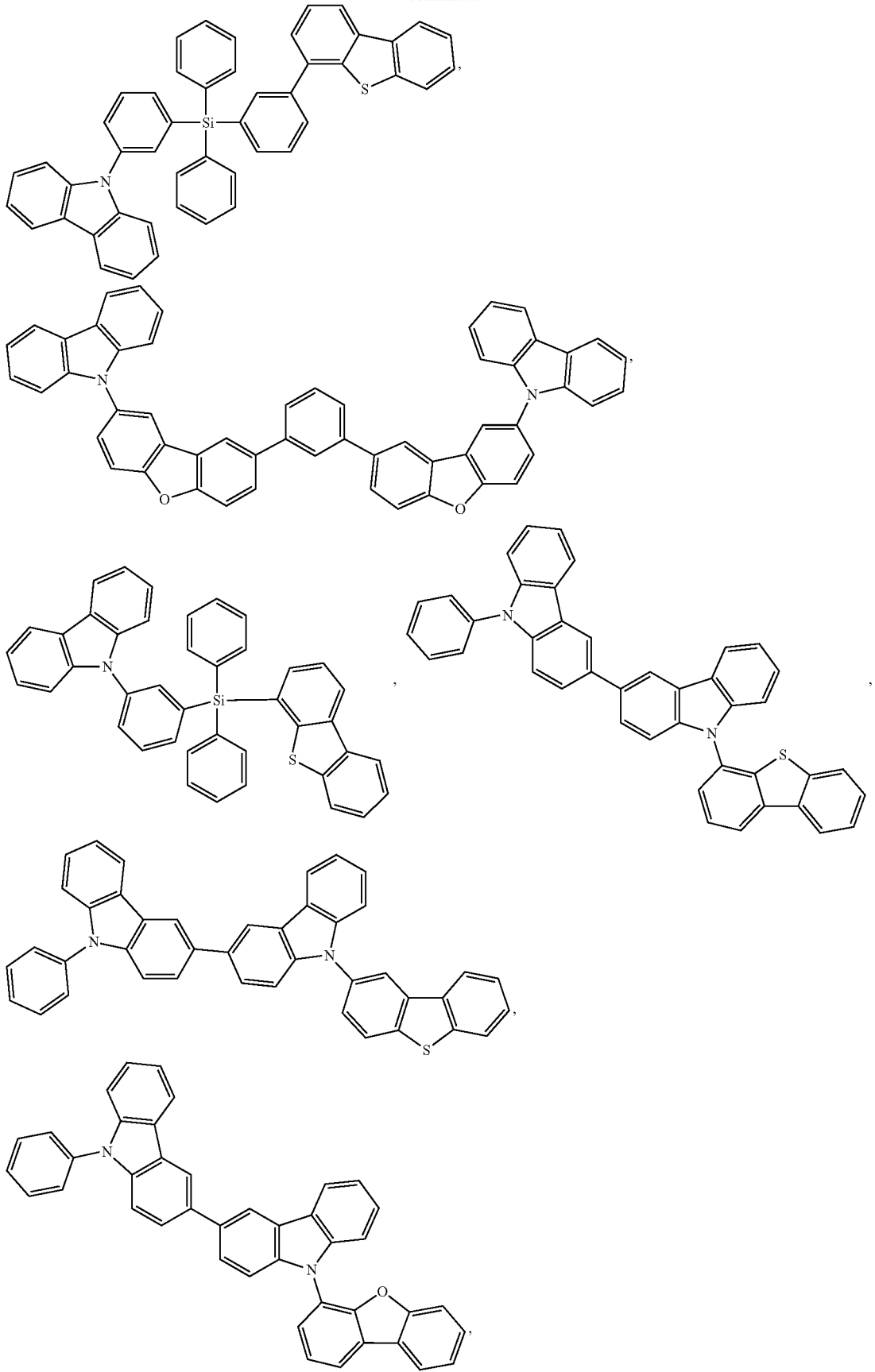

229
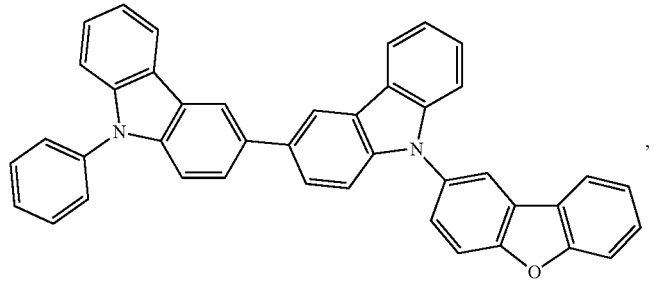
230
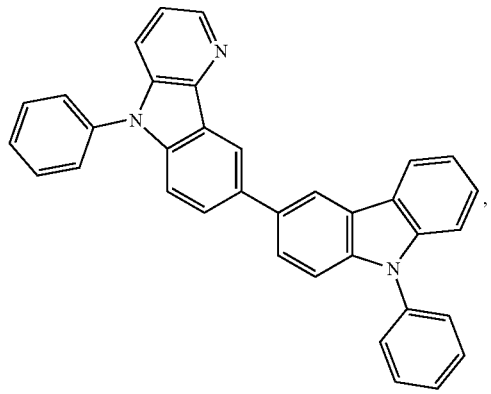
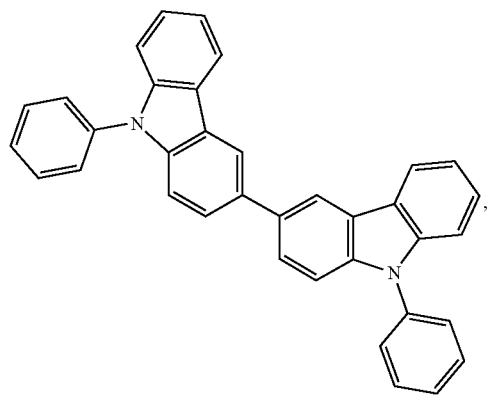
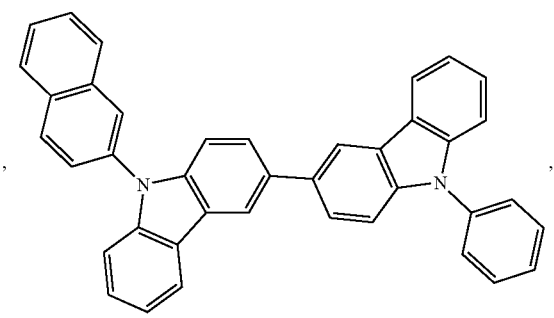
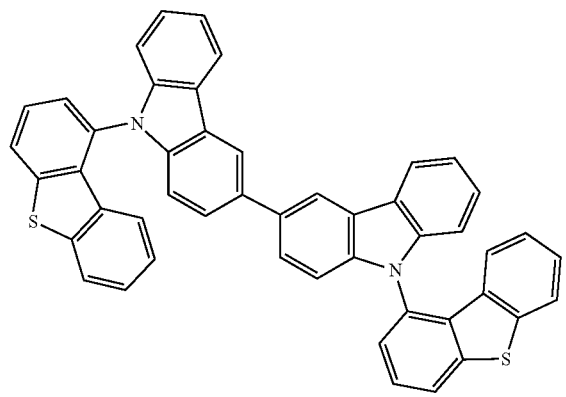
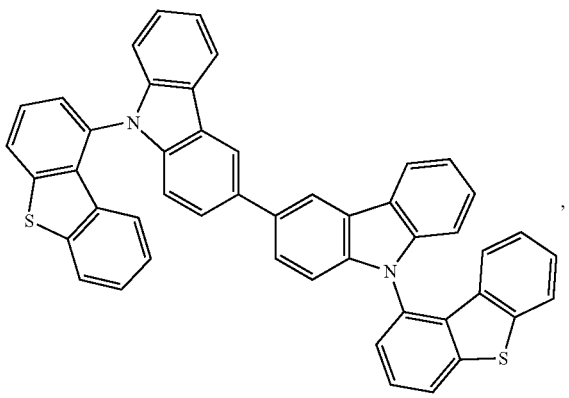
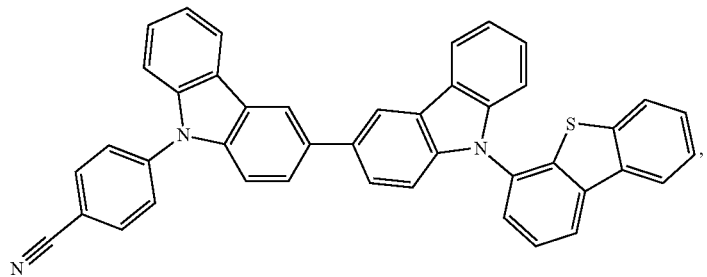

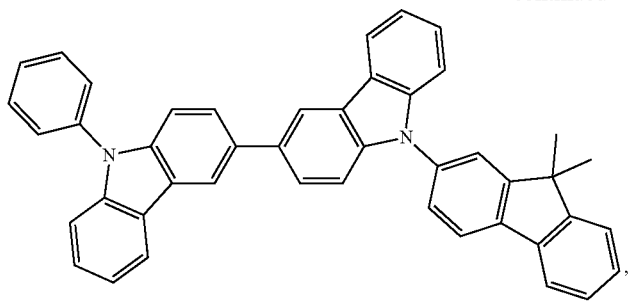
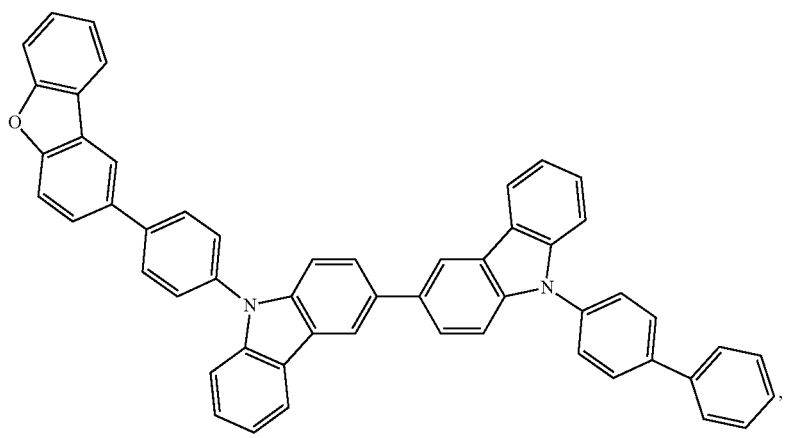
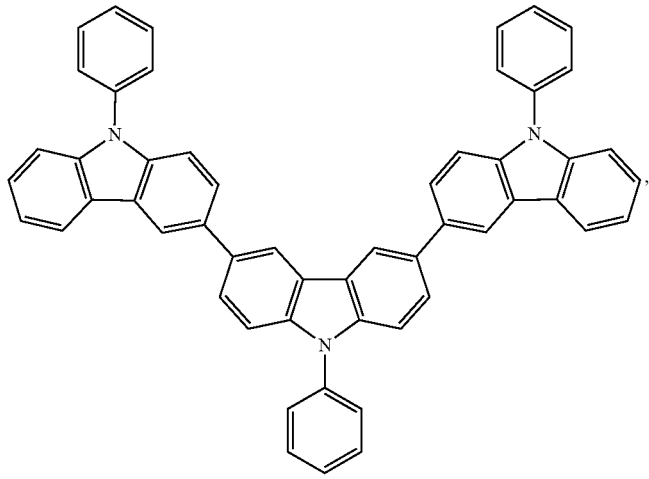
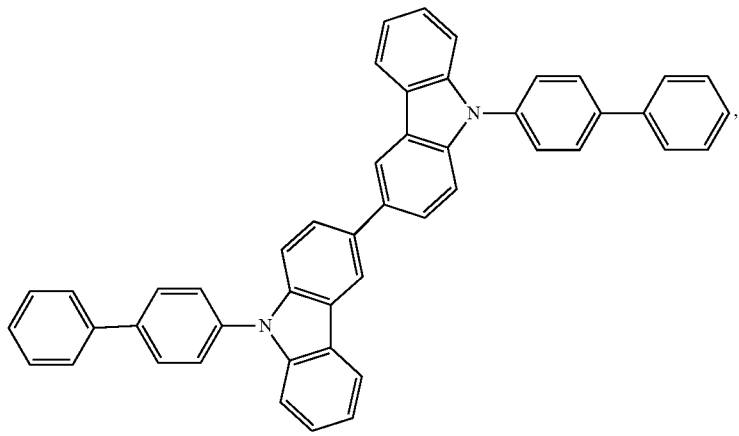

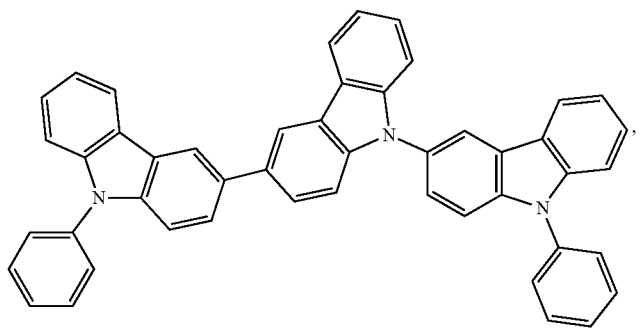
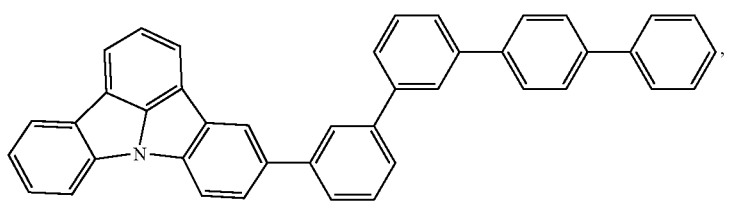
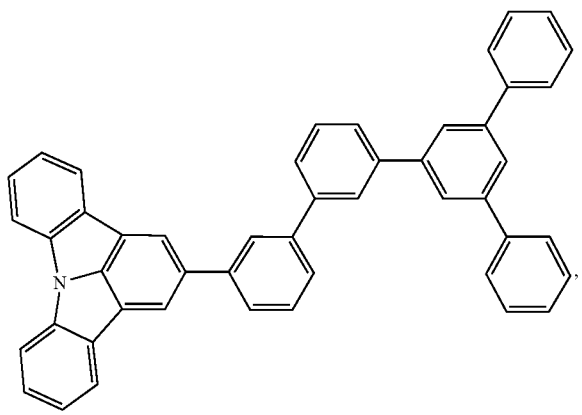
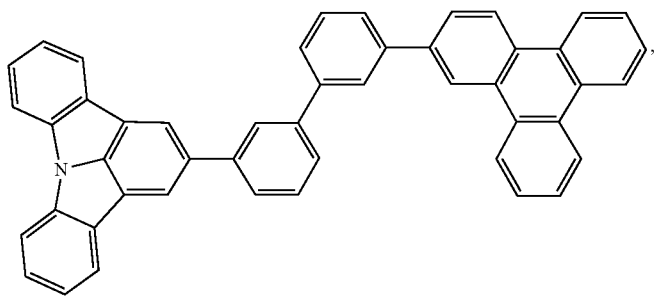
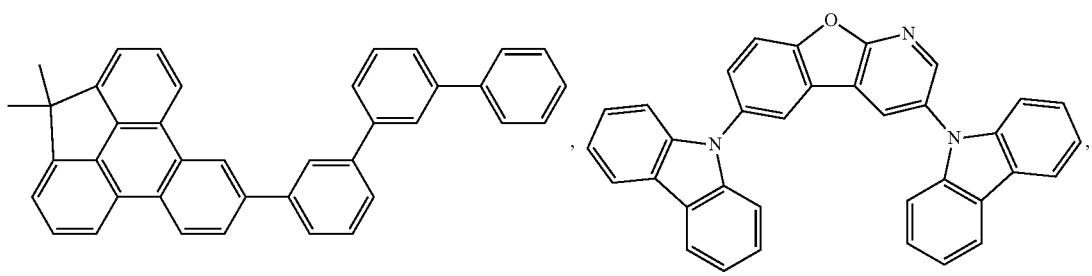

-continued
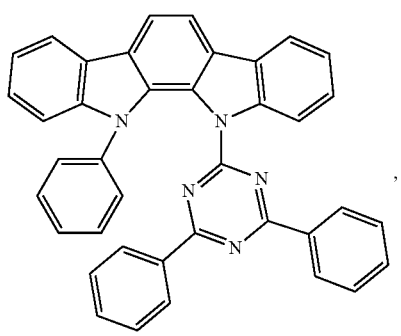 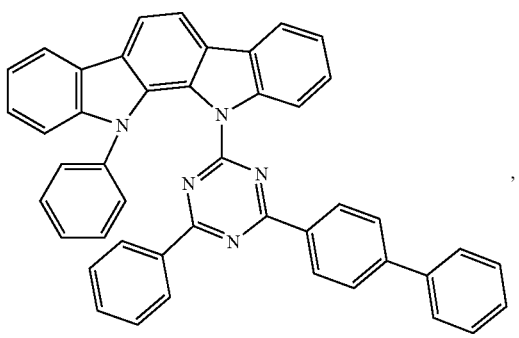
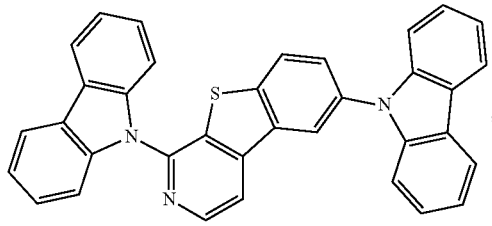 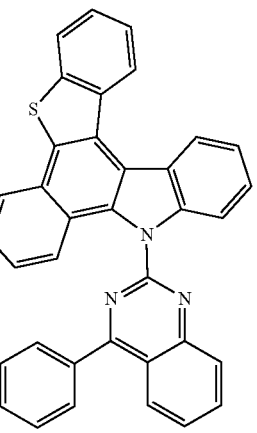 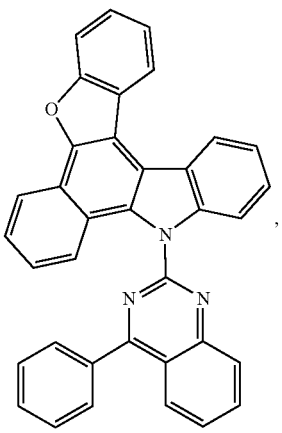
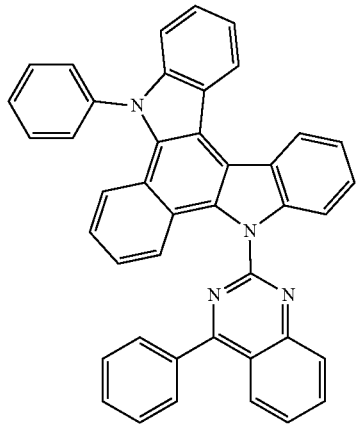 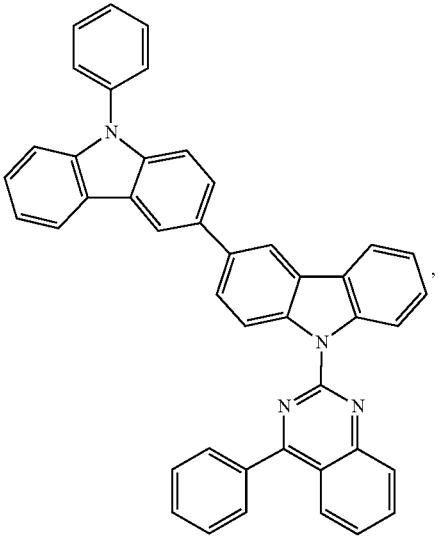
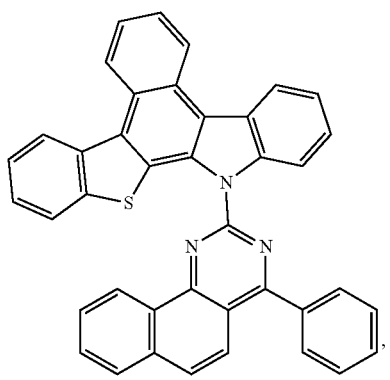 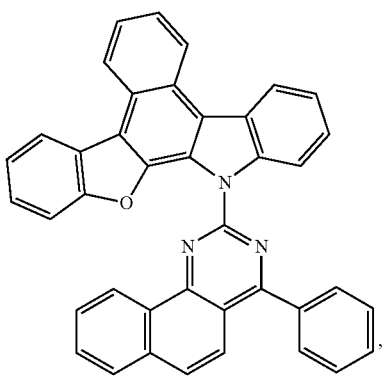

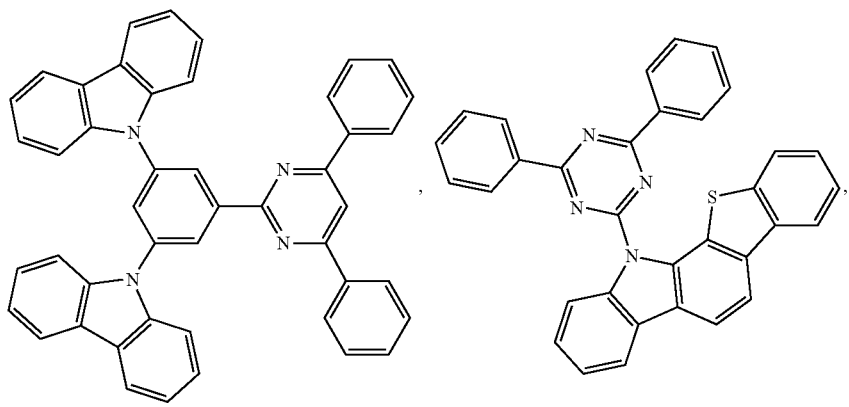
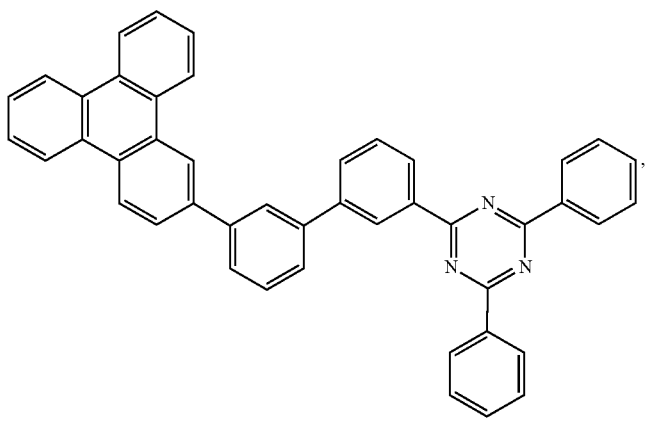
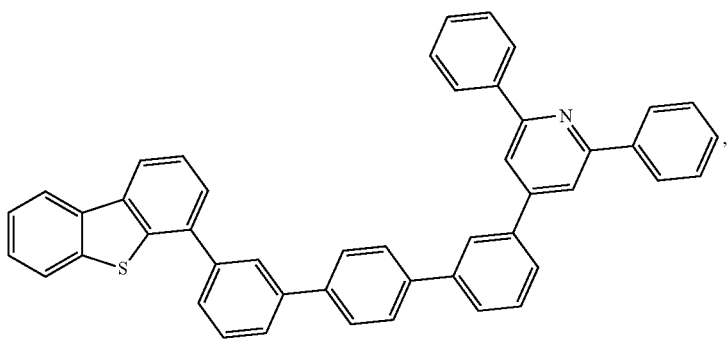
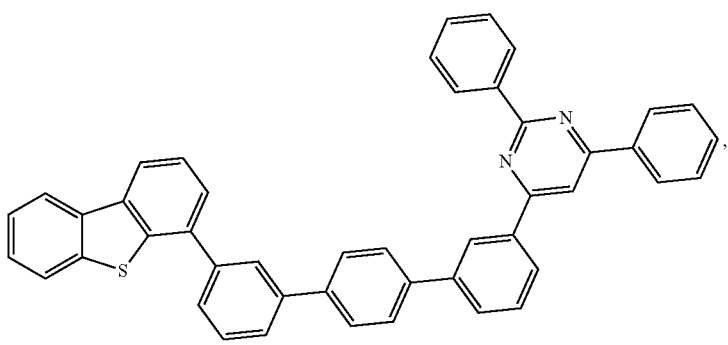

-continued
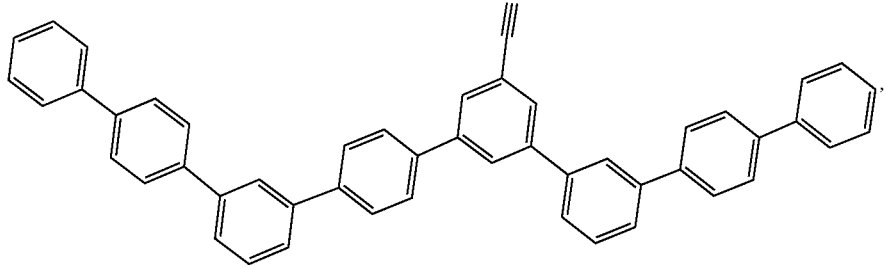
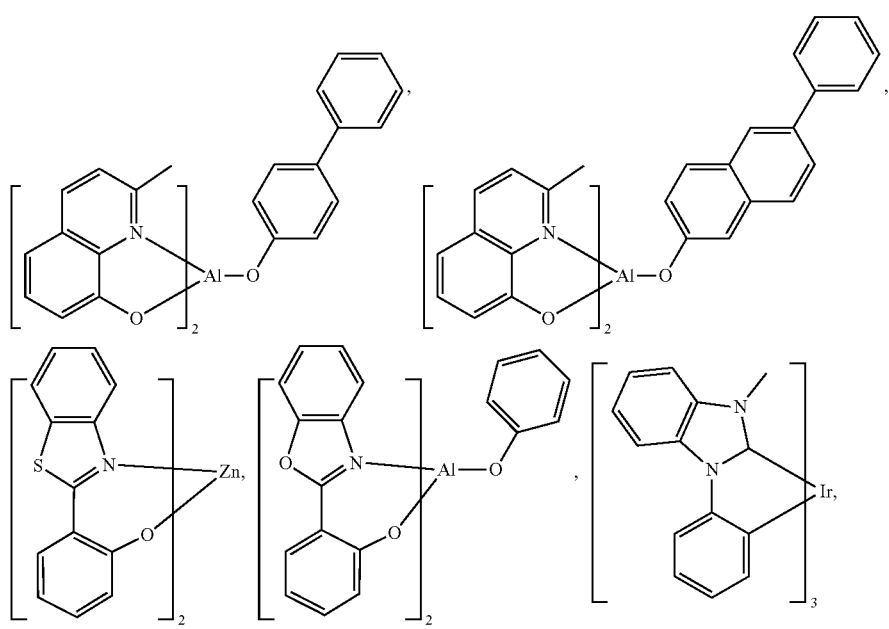
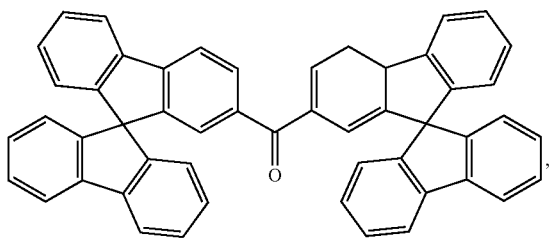
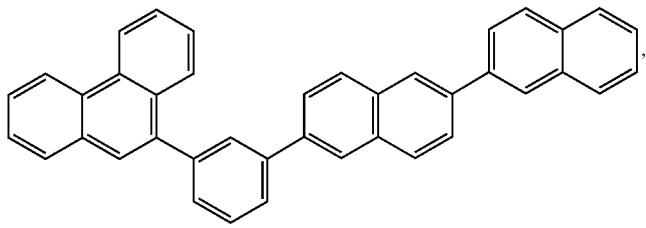
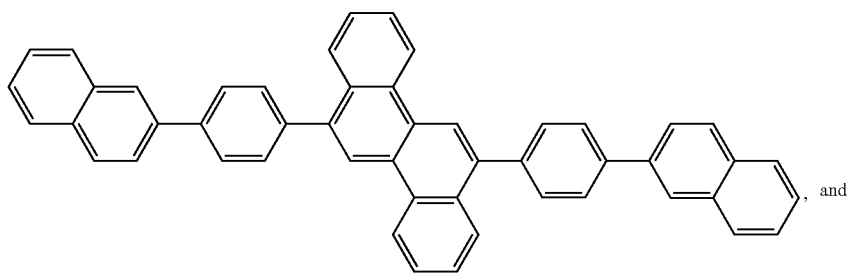, and

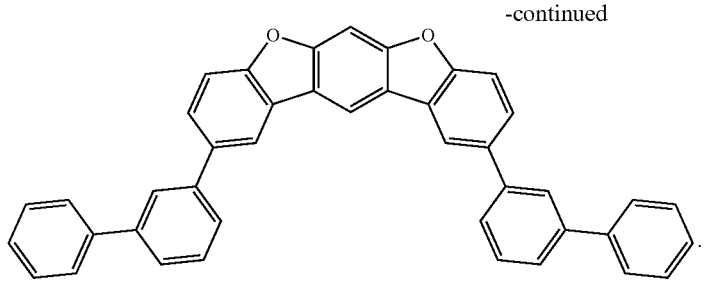

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Pat. Nos. 6,699,599, 6,916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

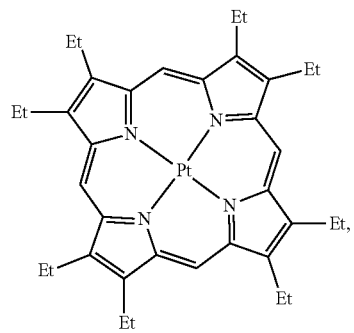

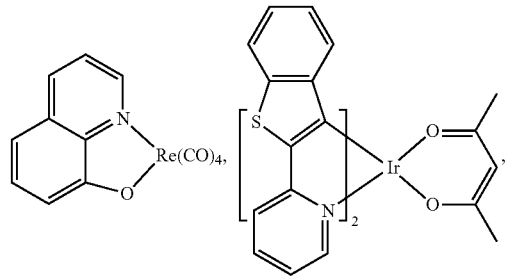

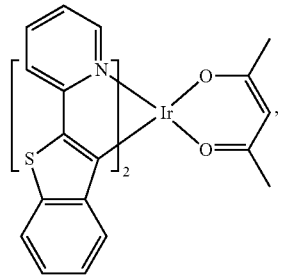

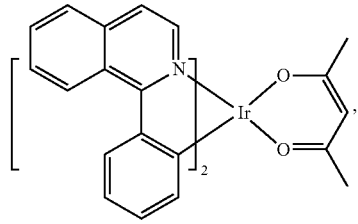

243
-continued
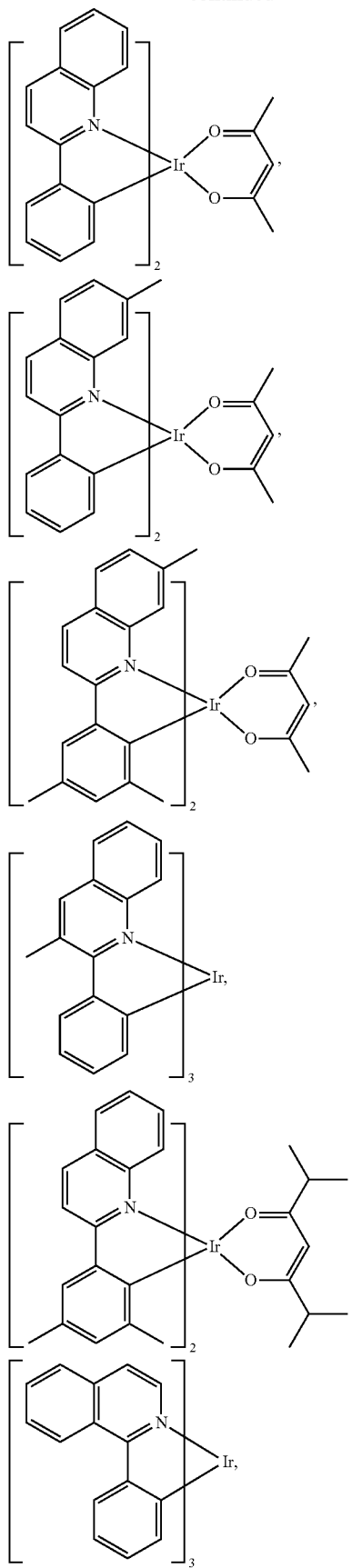
244
-continued
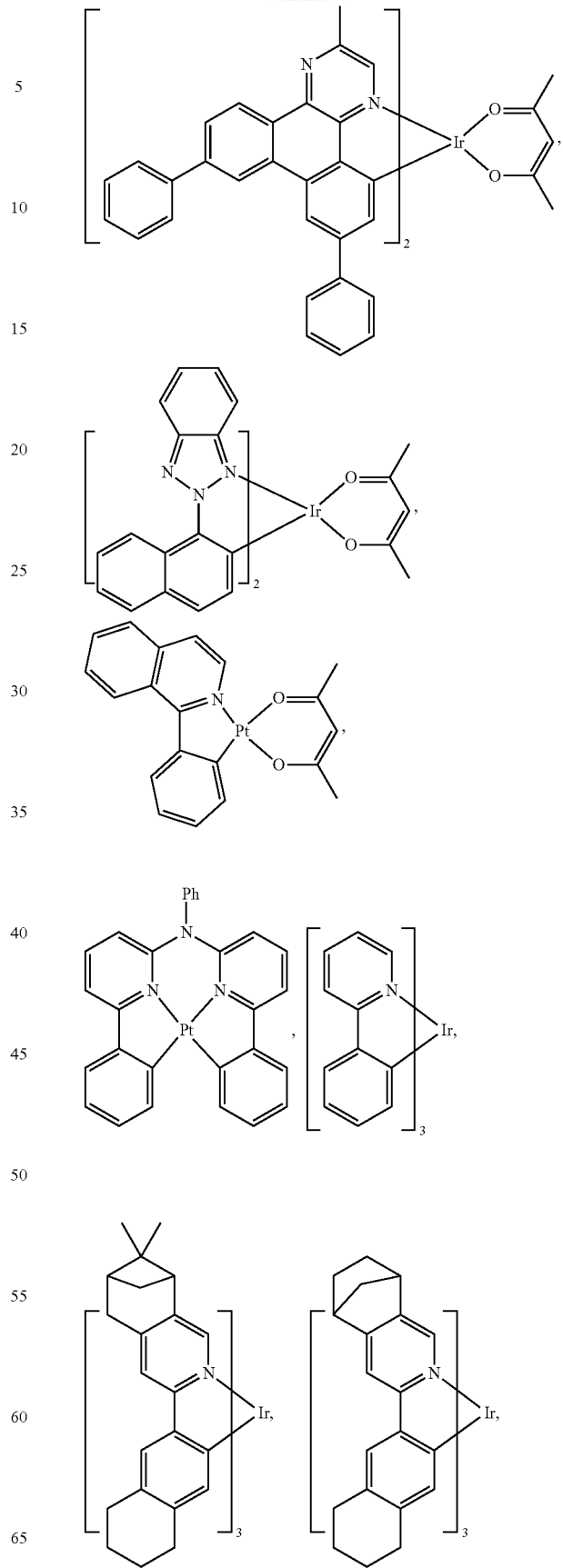

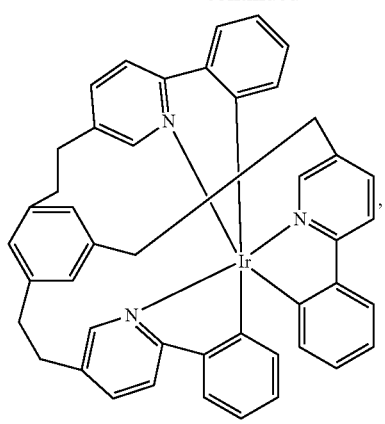
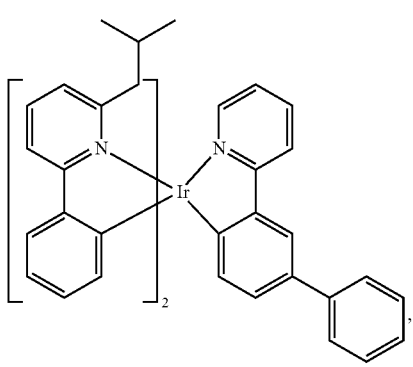
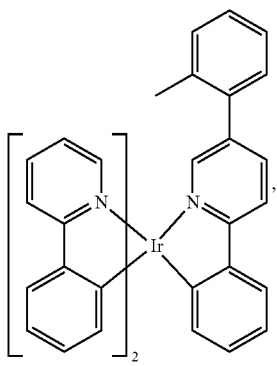
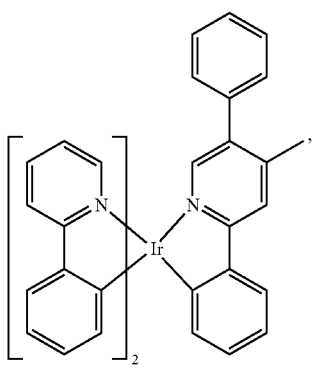
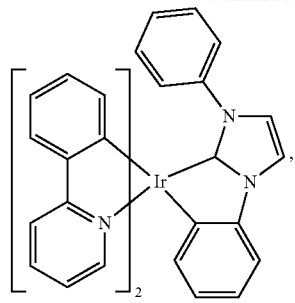
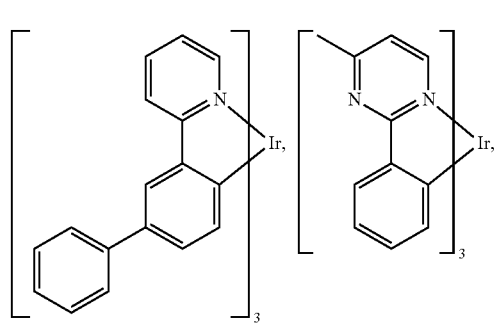
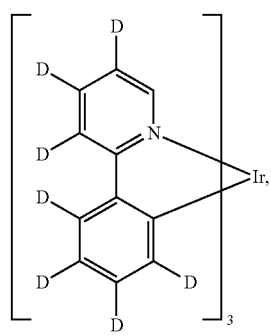
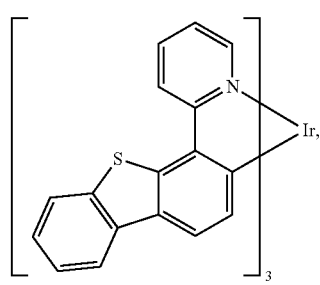
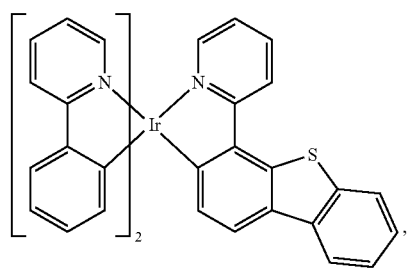

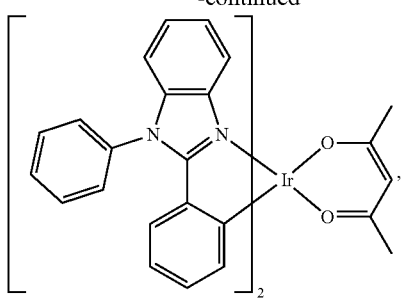
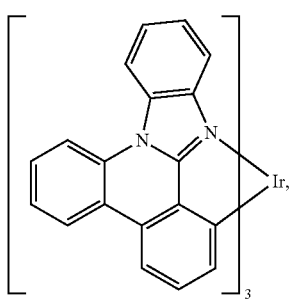
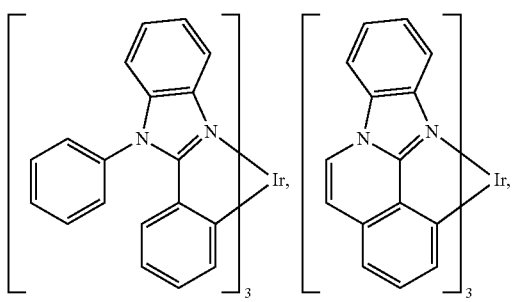
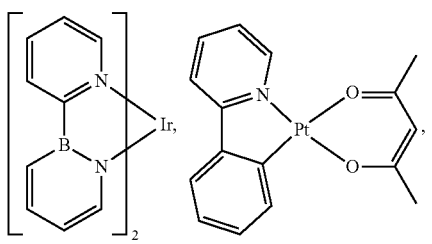
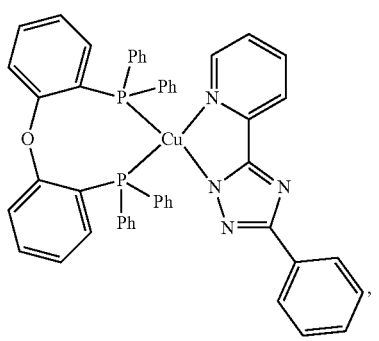
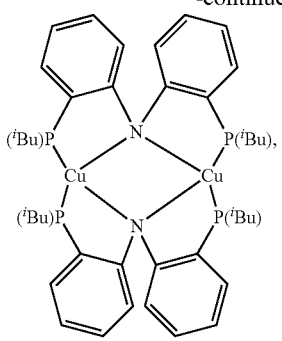
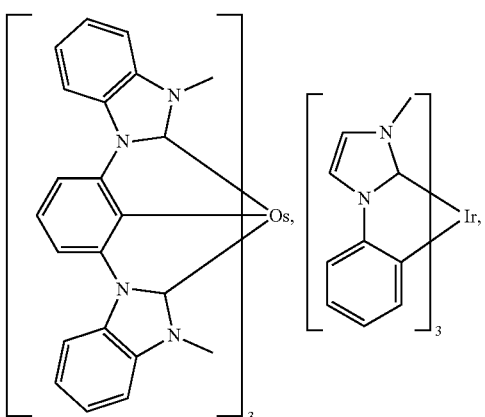
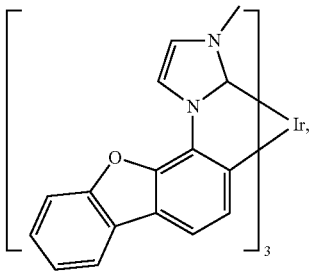
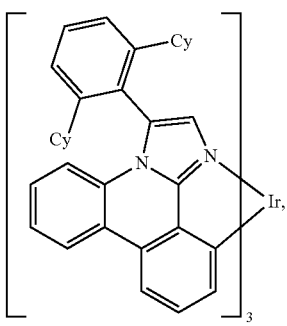
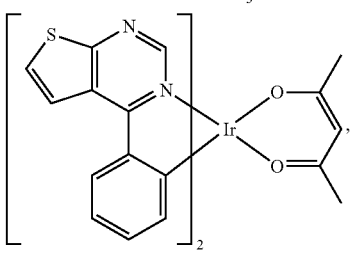

249
-continued
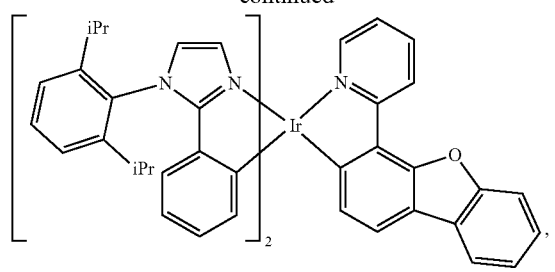
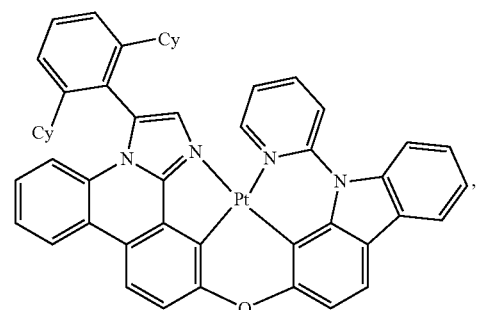
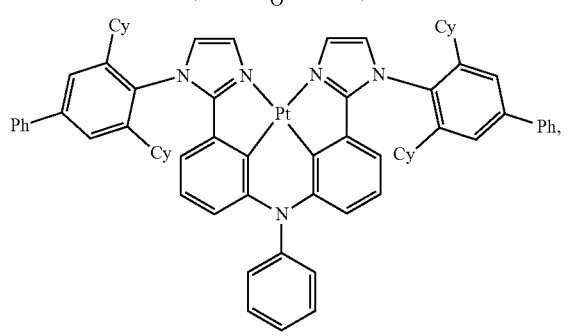
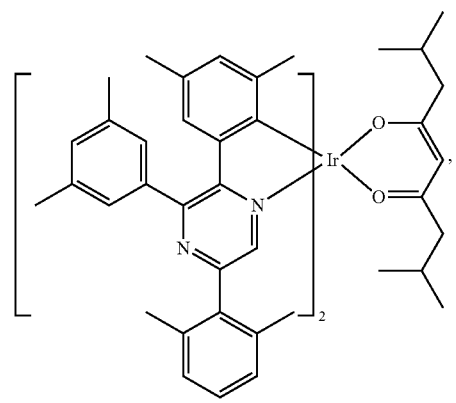
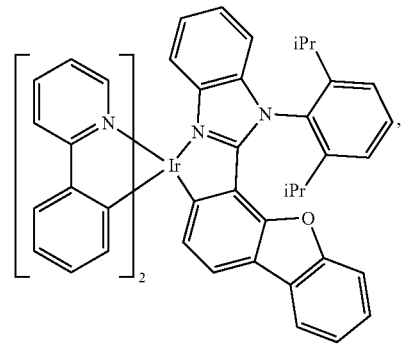
250
-continued
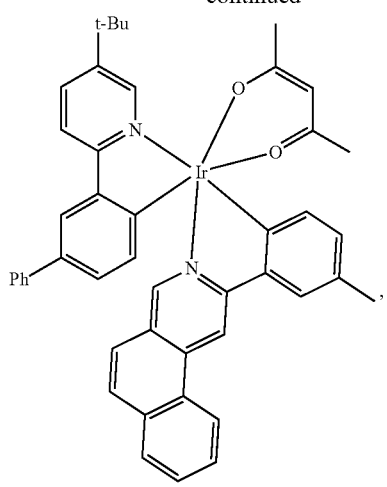
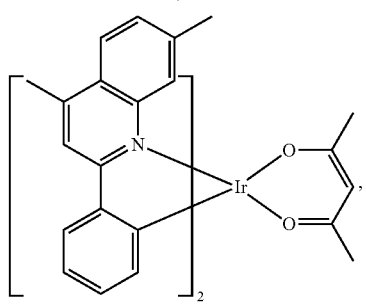
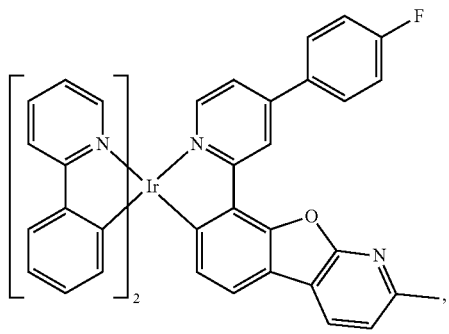
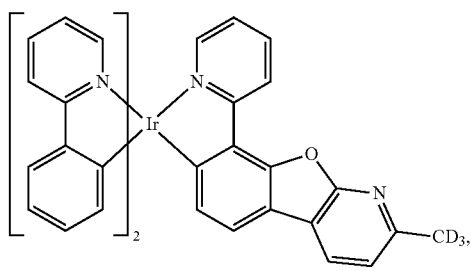
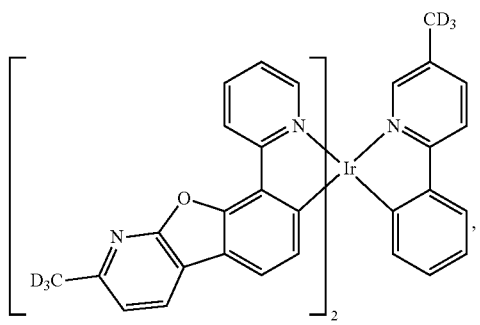

251
-continued
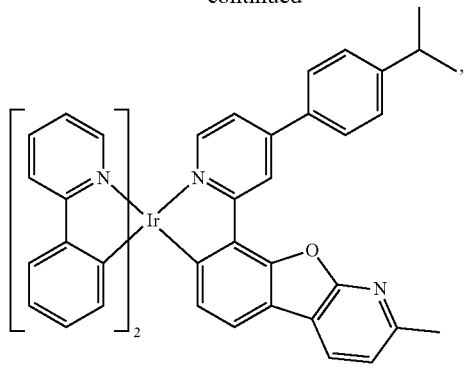
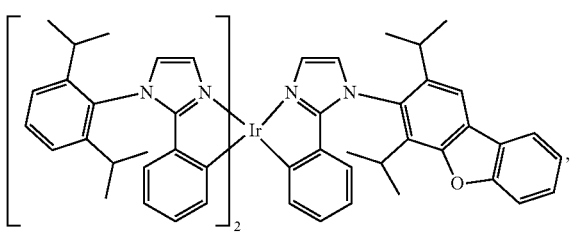
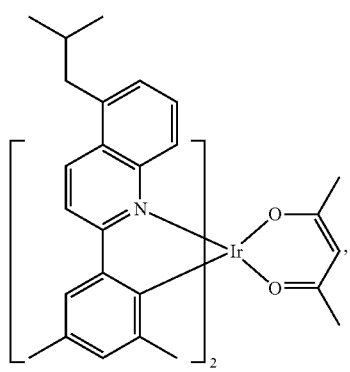
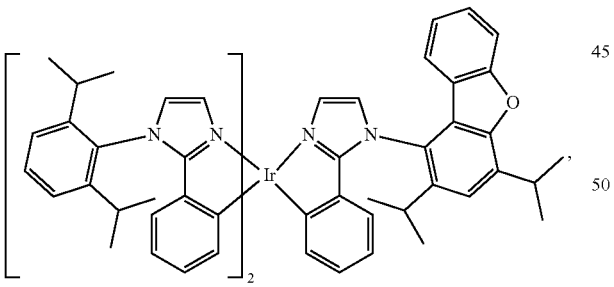
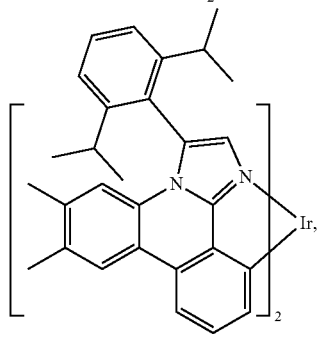
252
-continued
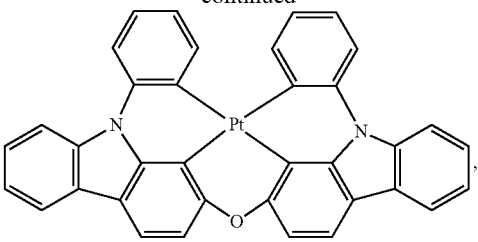
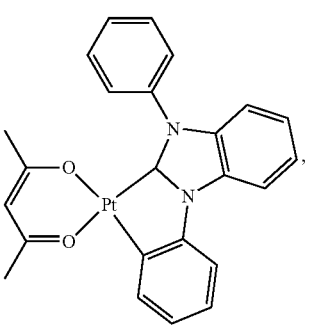
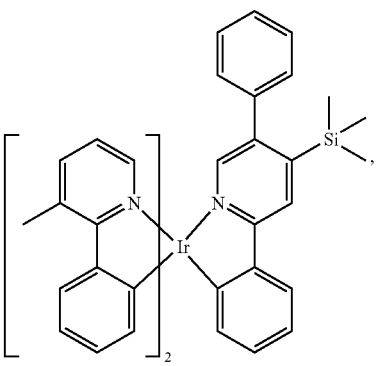
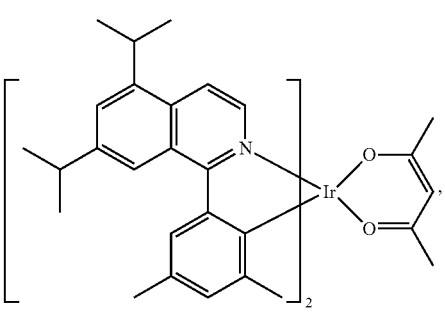
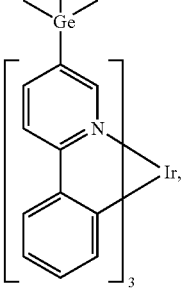

253
-continued
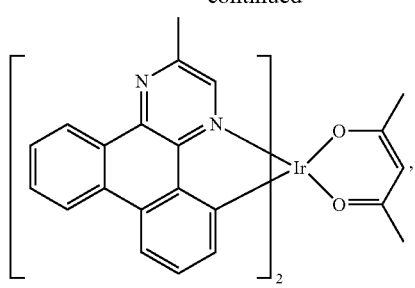
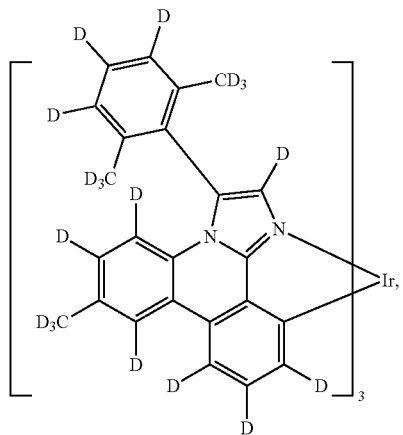
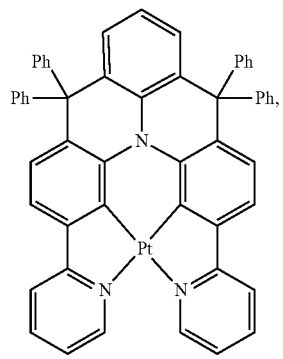
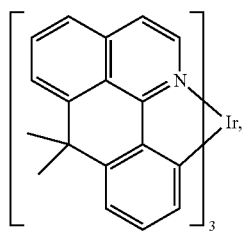
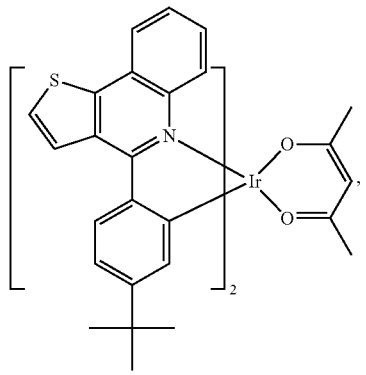
254
-continued
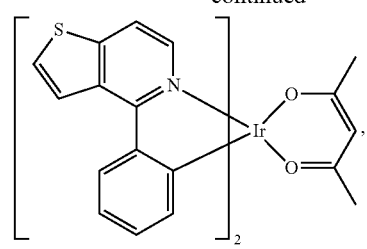
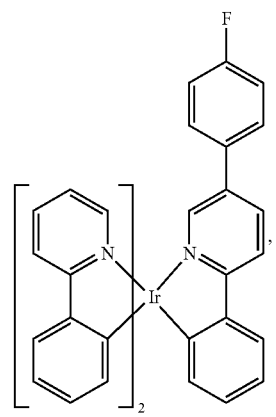
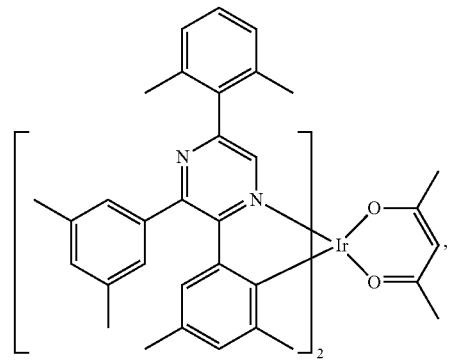
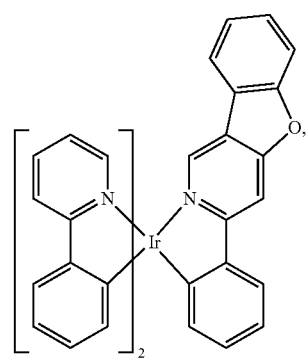

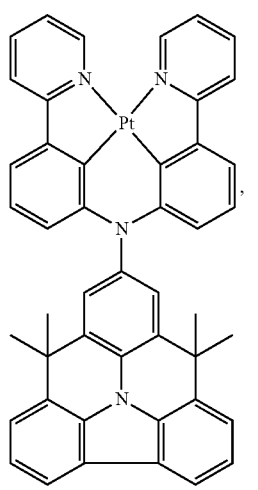
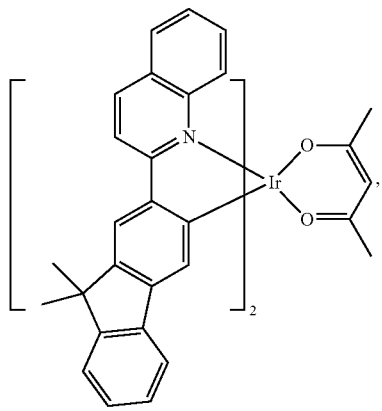
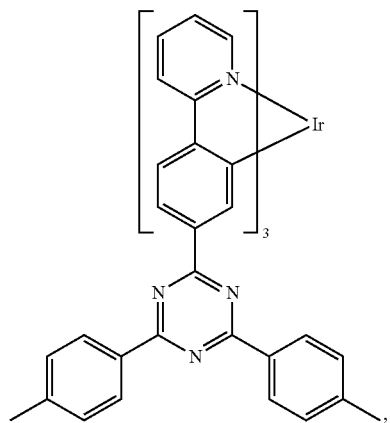
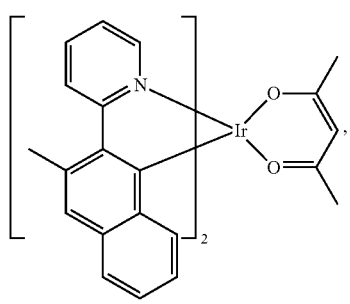
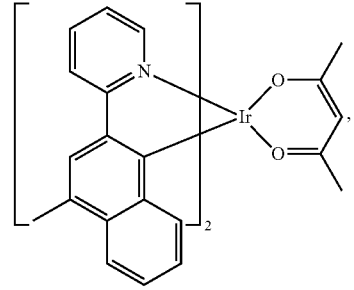
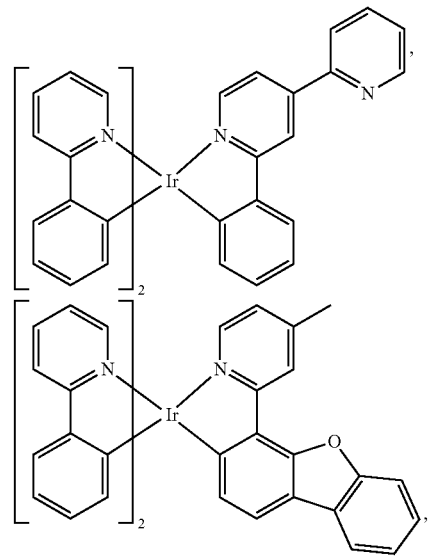
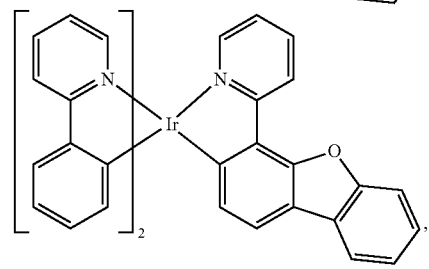
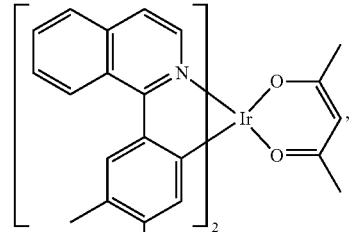
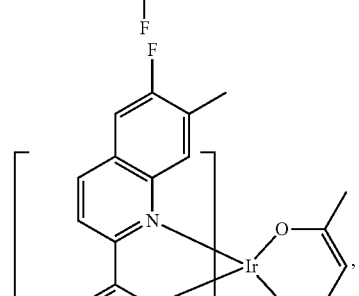
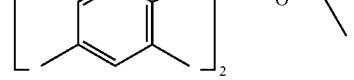

-continued
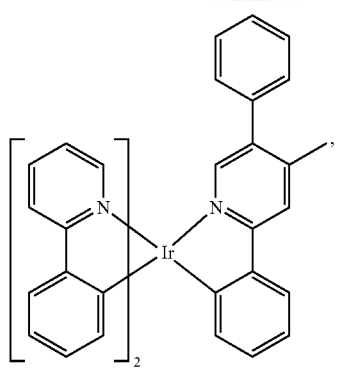
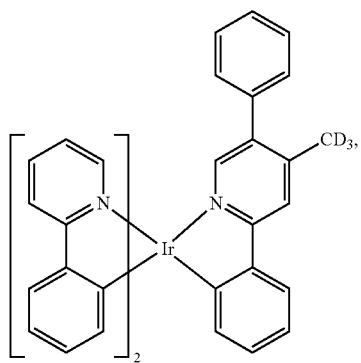
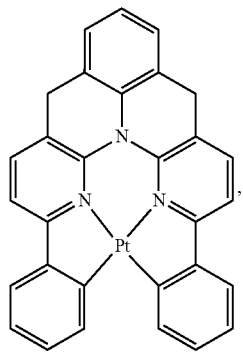
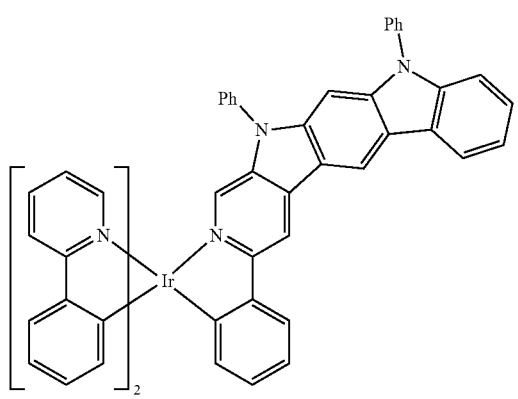
-continued
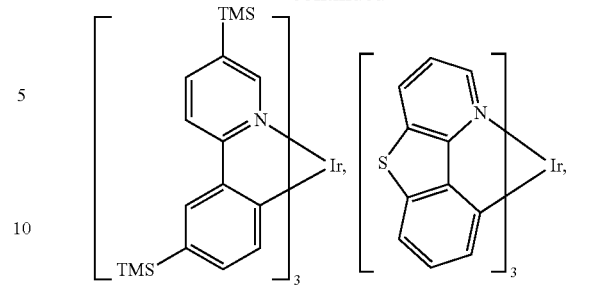
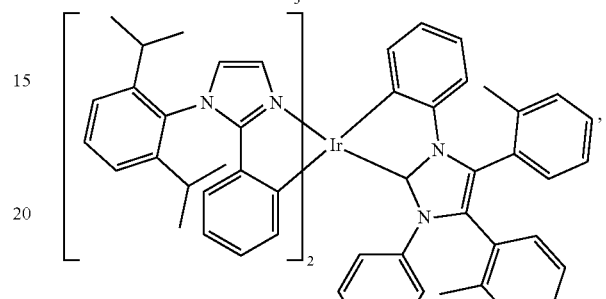
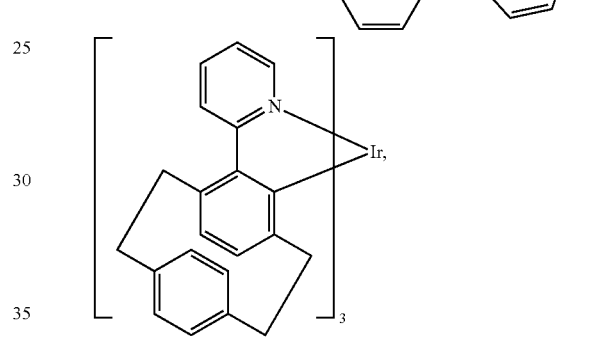
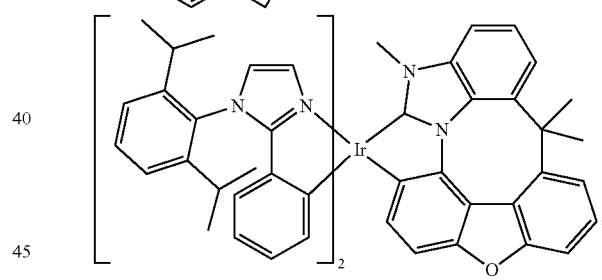
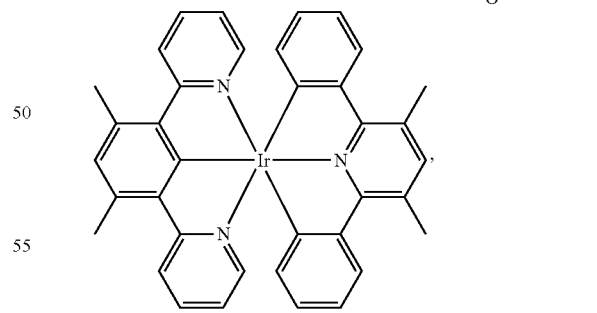
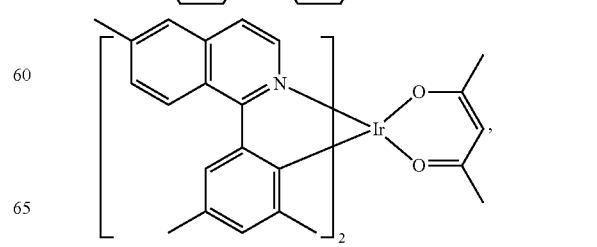

-continued
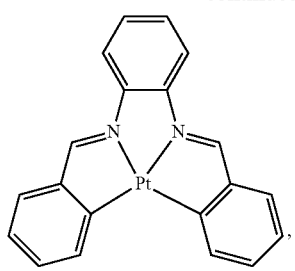
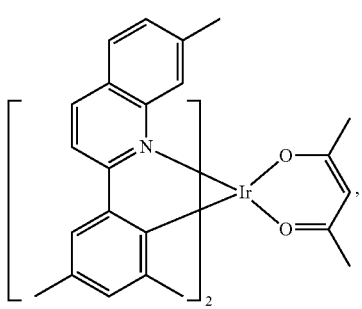
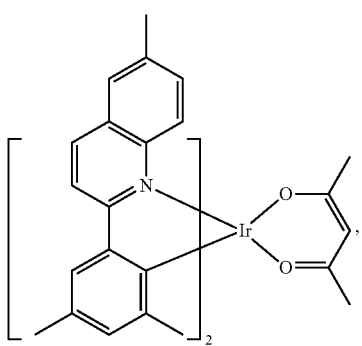
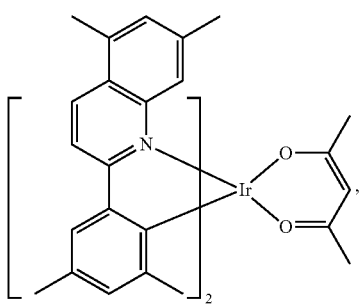
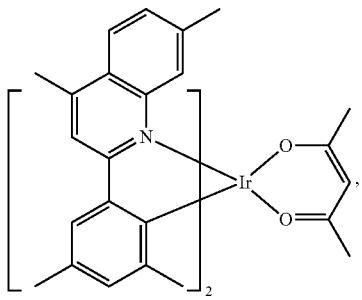
-continued
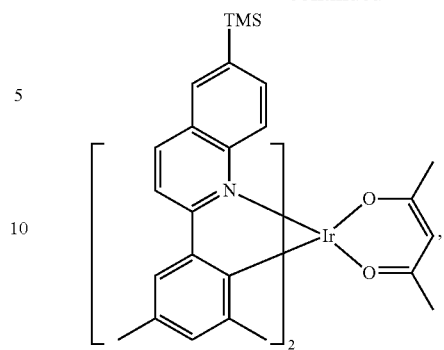
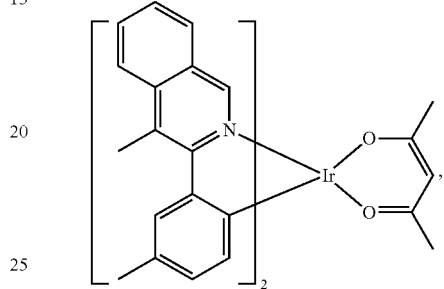
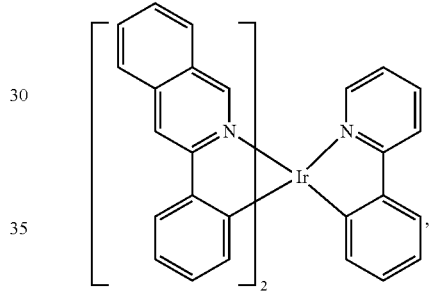
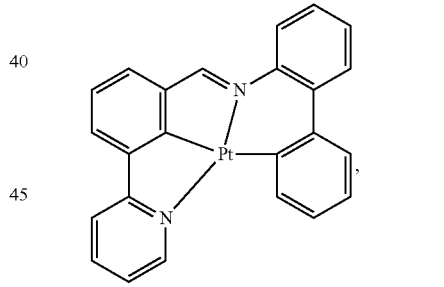
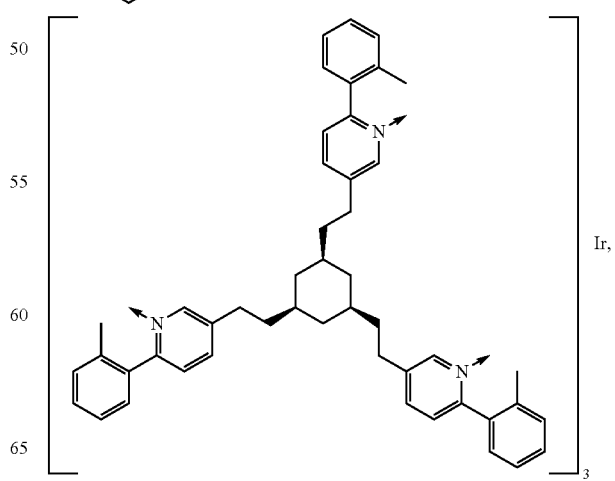

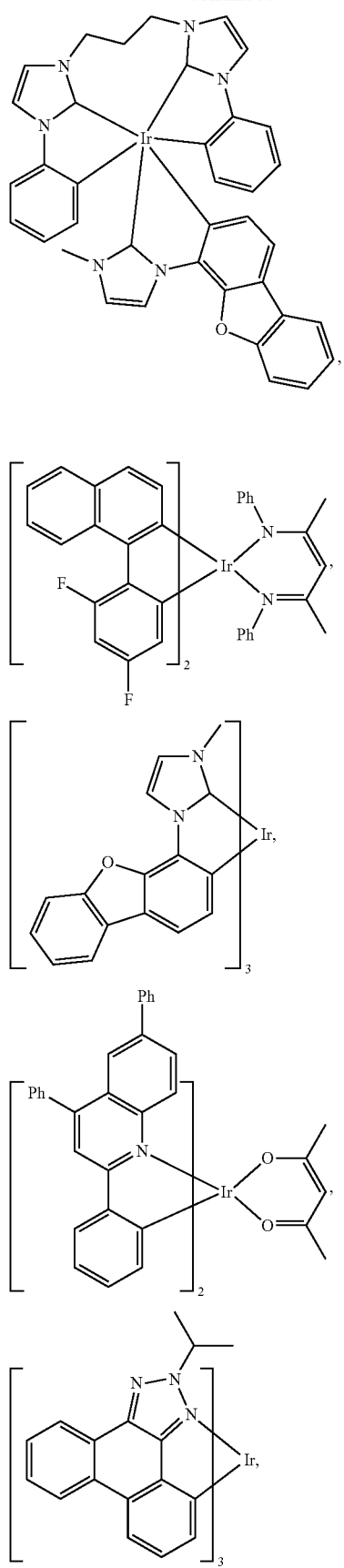
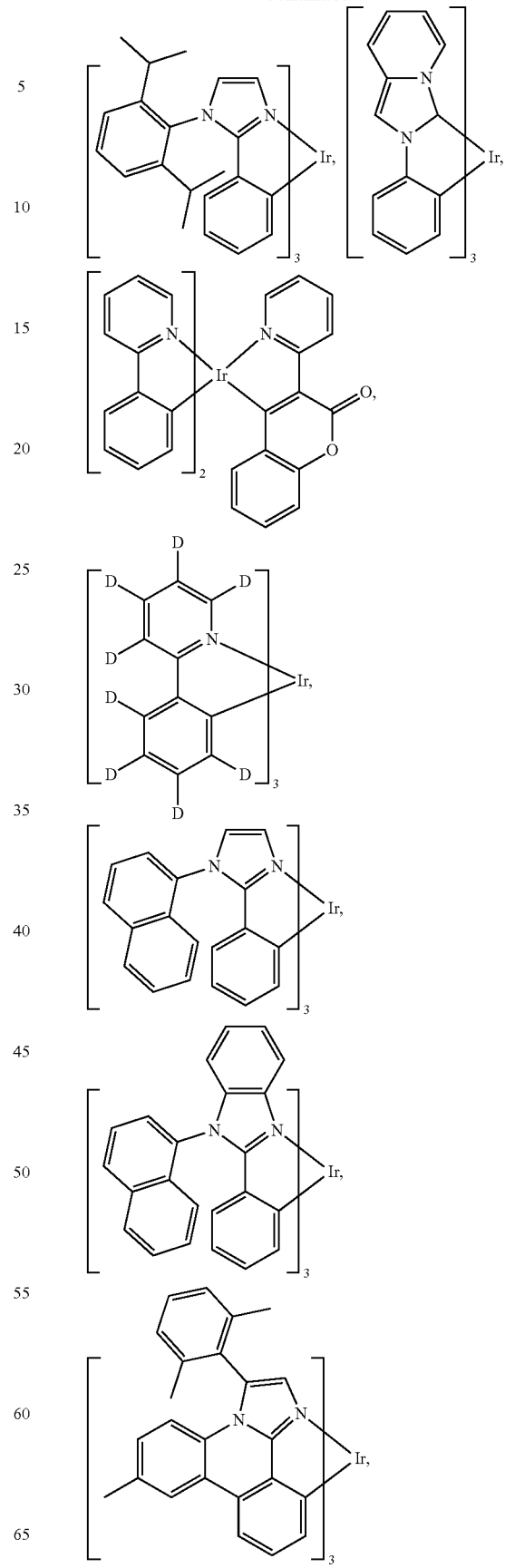

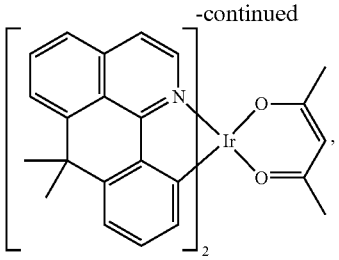

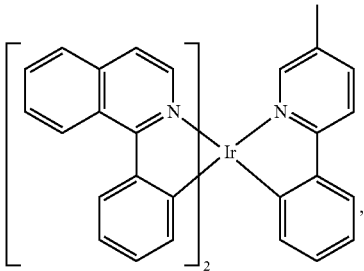

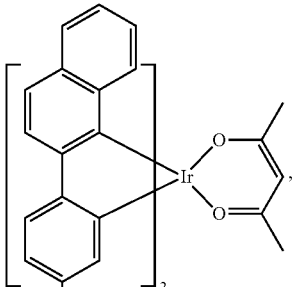

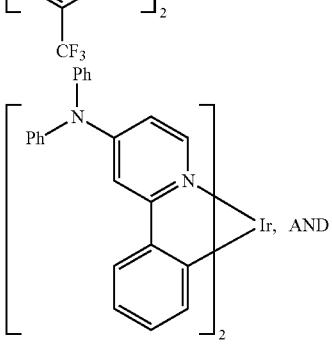

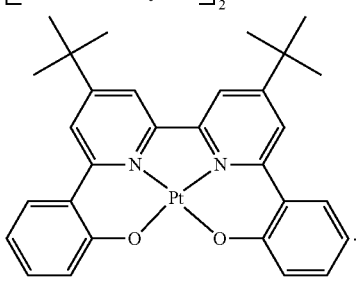

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

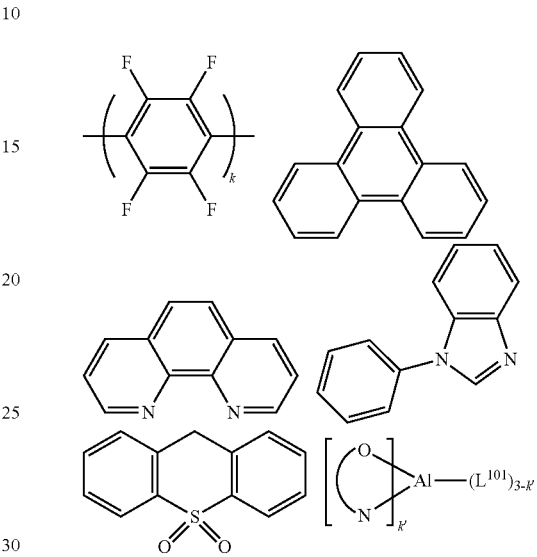

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

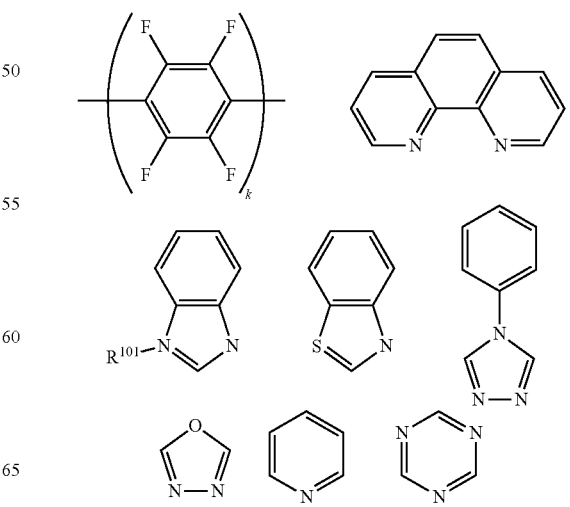

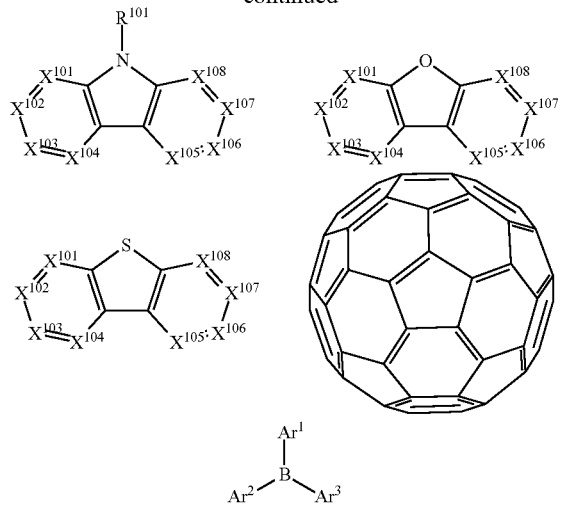

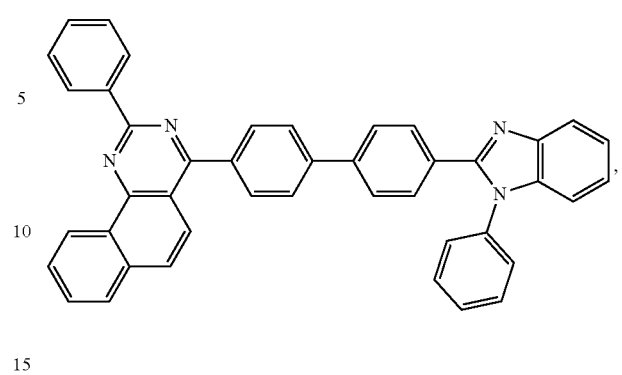

wherein R$^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. Ar$^1$ to Ar$^3$ has the similar definition as Ar's mentioned above. k is an integer from 1 to 20. X$^{101}$ to X$^{108}$ is selected from C (including CH) or N.

In another aspect, the metal complexes used in ETL contains, but not limit to the following general formula:

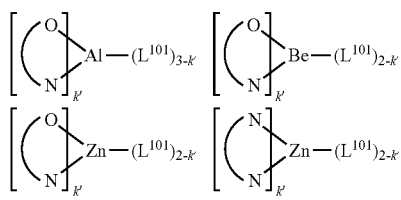

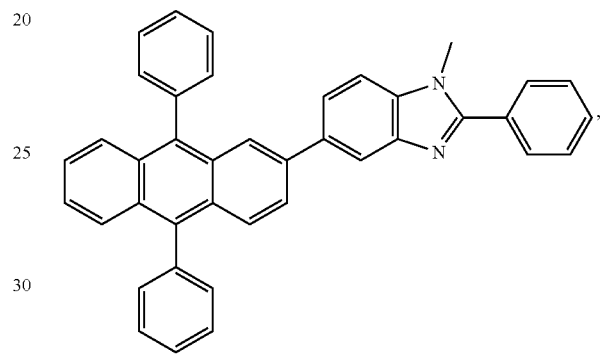

wherein (O—N) or (N—N) is a bidentate ligand, having metal coordinated to atoms O, N or N, N; L$^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

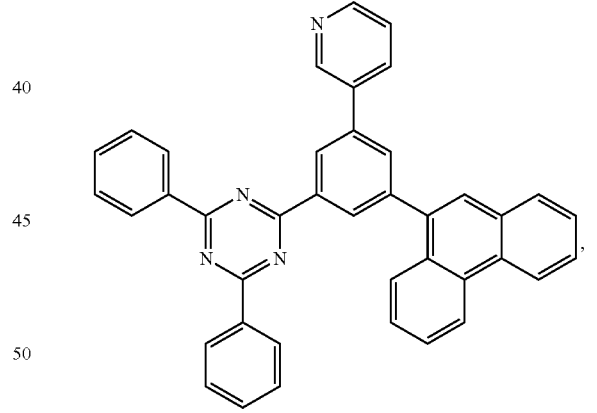

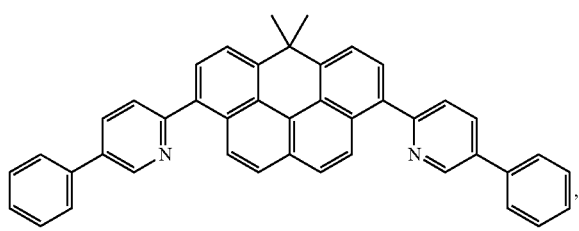

267
-continued
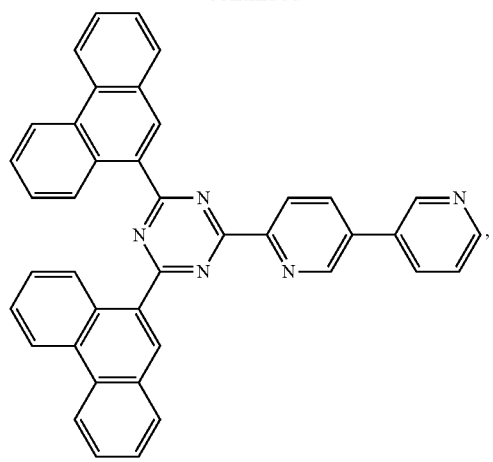
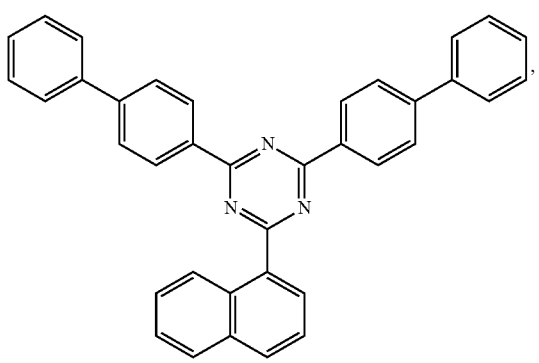
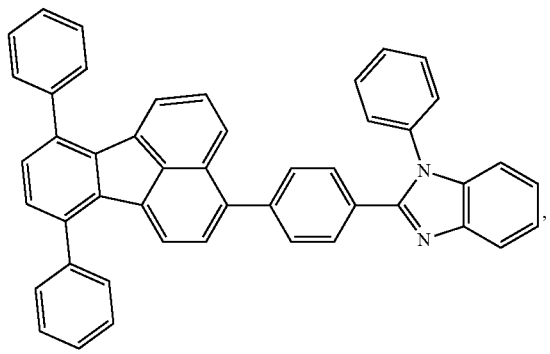
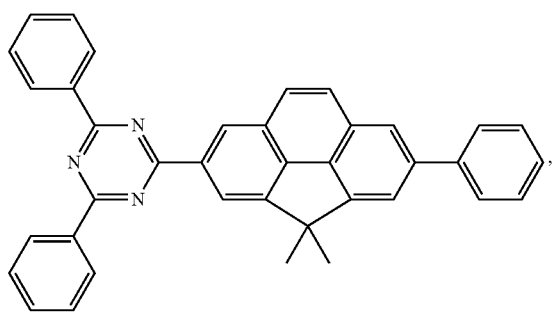
268
-continued
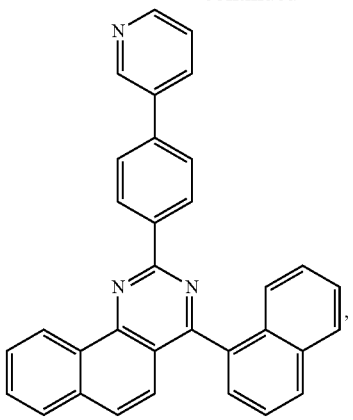
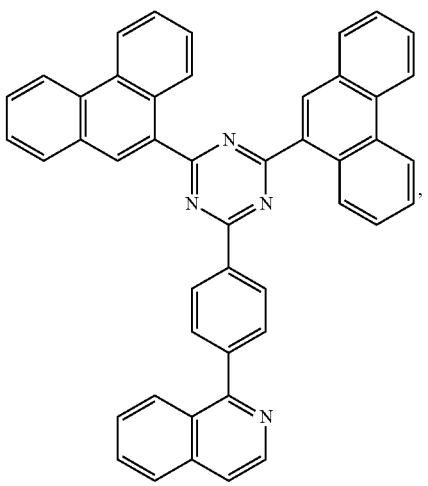
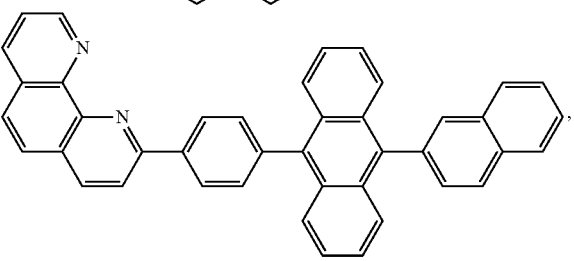
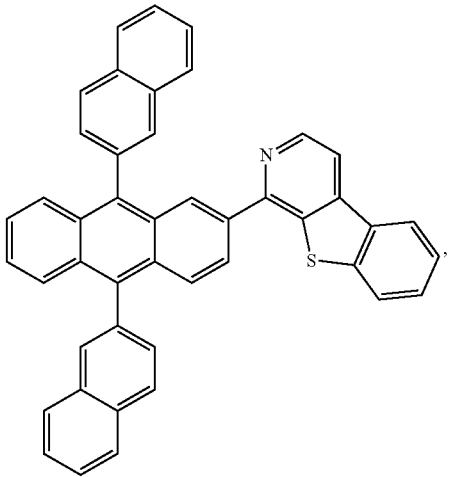

269
-continued
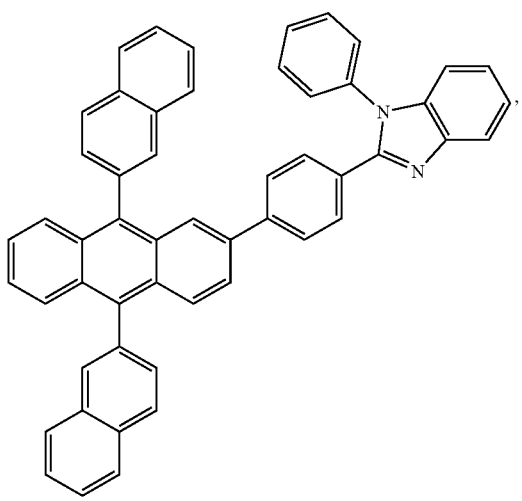
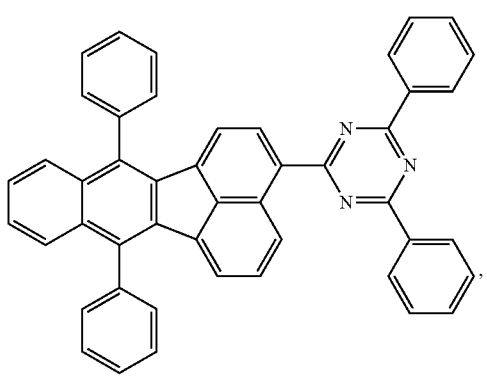
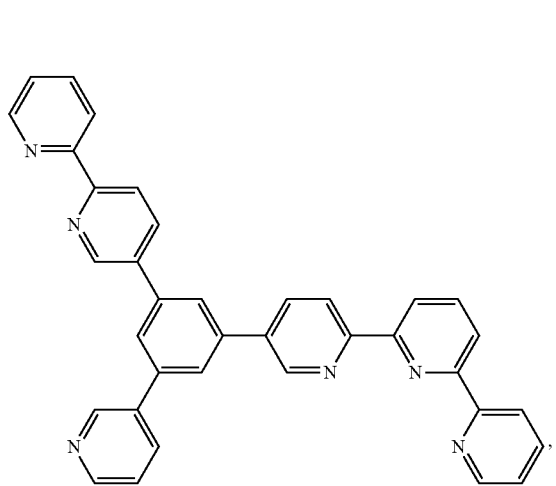
270
-continued
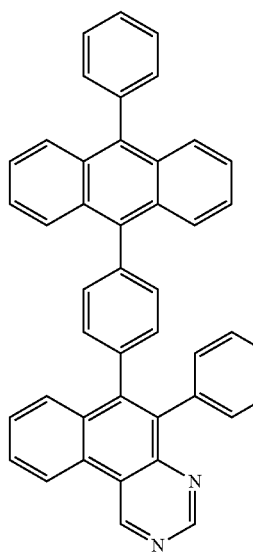
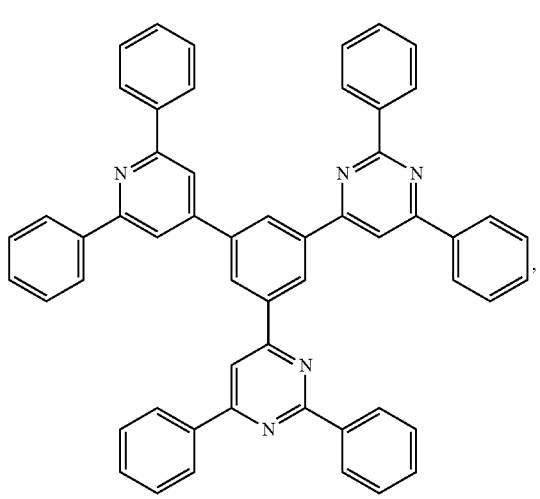

271
-continued
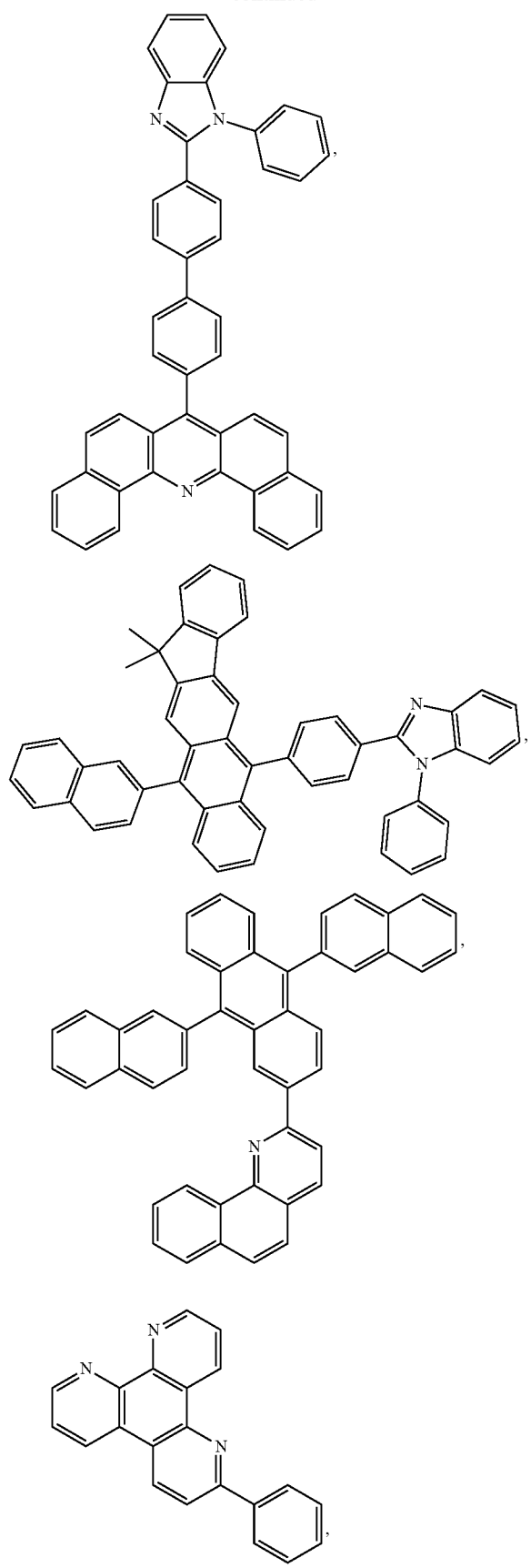
272
-continued
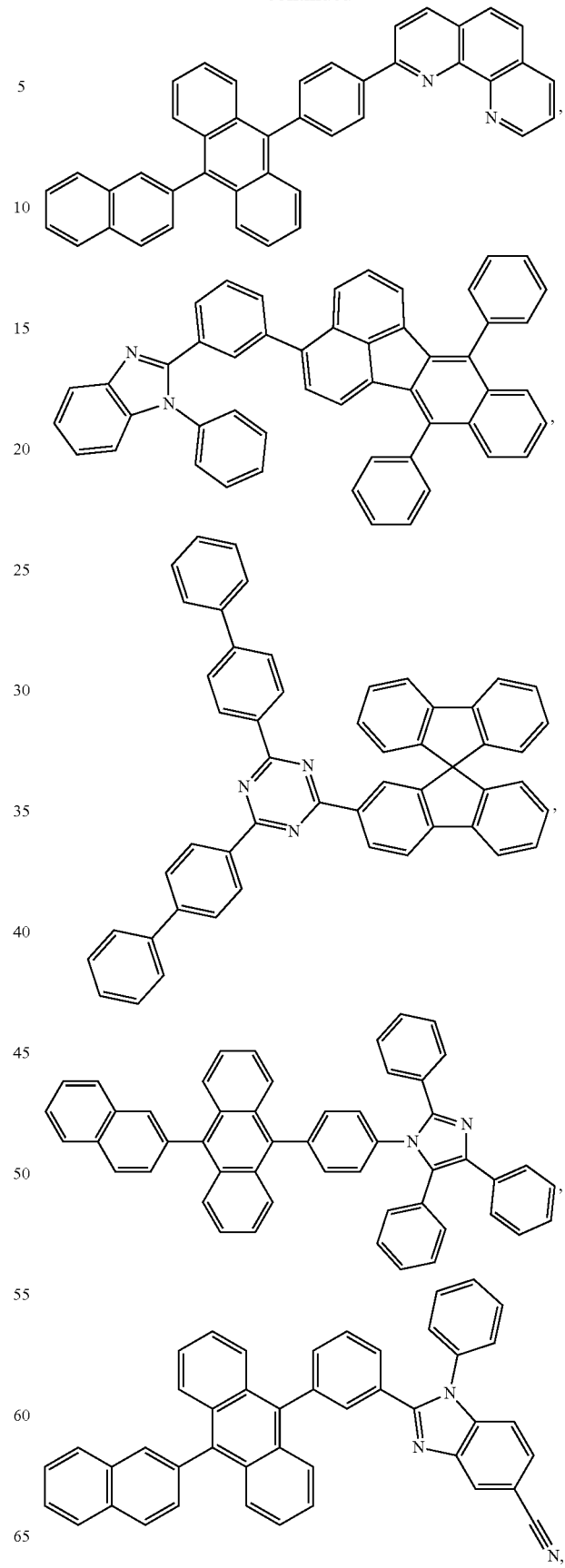

273
-continued

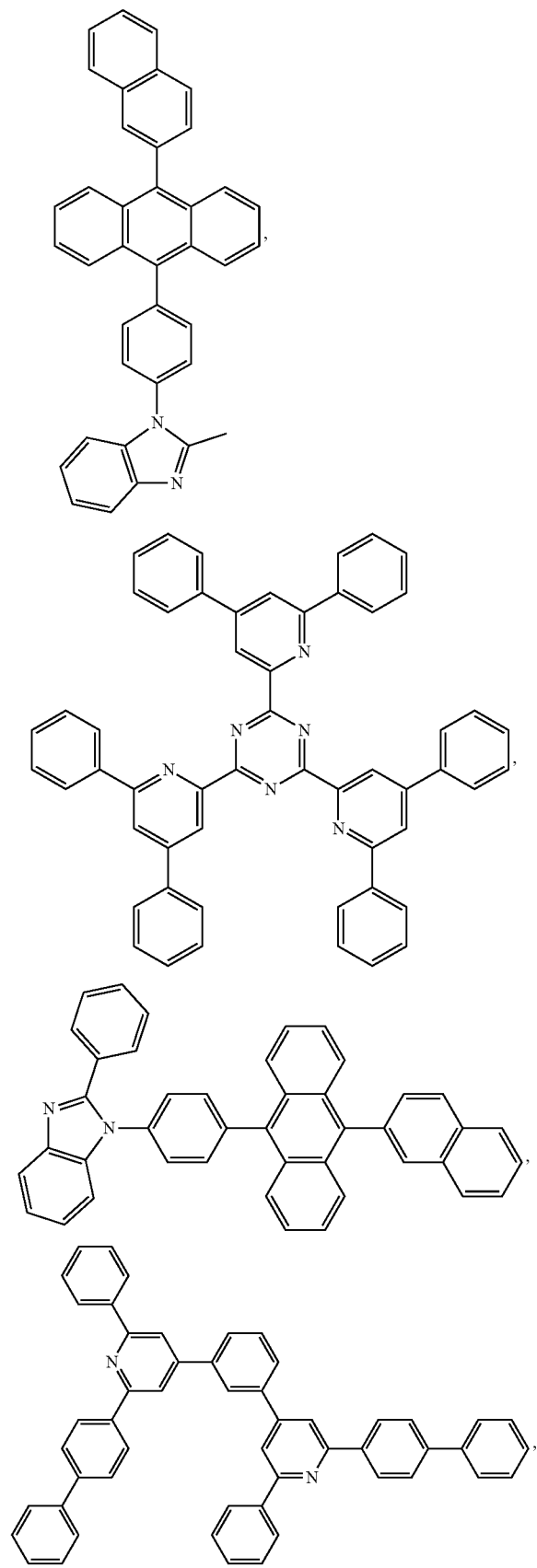

274
-continued

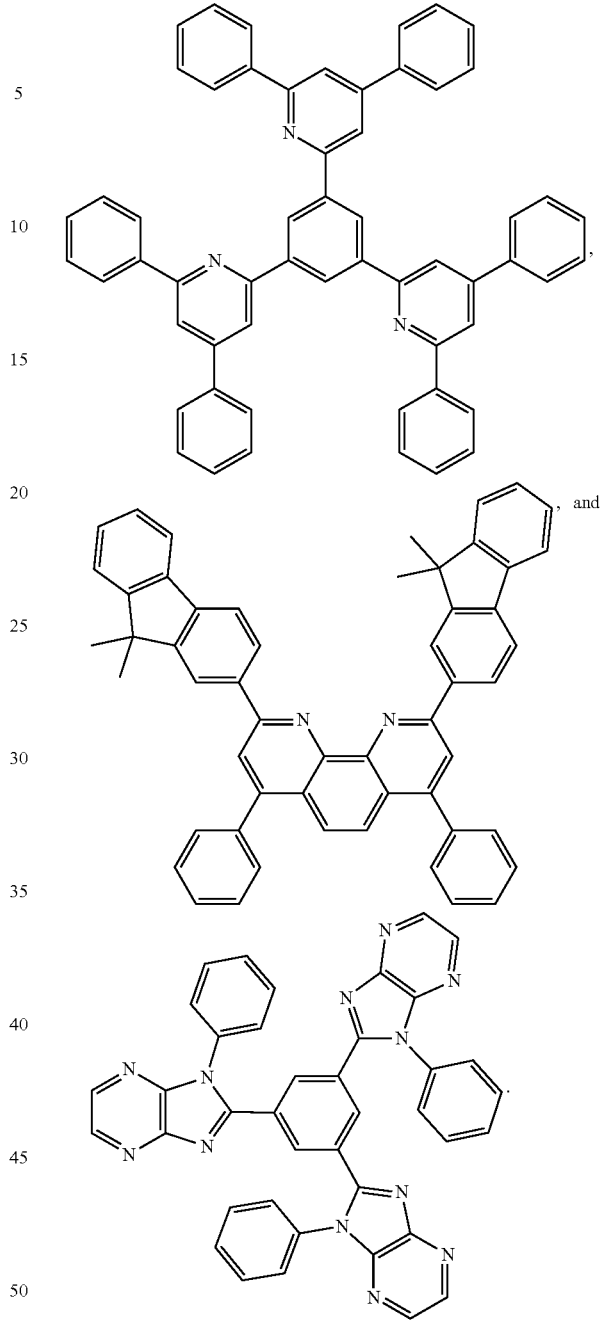

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. An organic light emitting device (OLED) having an emission spectrum, the OLED comprising:
   an anode;
   a cathode; and
   an organic emissive layer, disposed between the anode and the cathode, comprising:
      a first host material having a highest occupied molecular orbital (HOMO) energy and a lowest unoccupied molecular orbital (LUMO) energy; and
      an emitter material having a HOMO energy and a LUMO energy;
   wherein,
      all materials in the organic emissive layer are mixed together;
      the emitter material is a phosphorescent metal complex;
      High HOMO energy is the highest HOMO energy among all materials in the organic emissive layer;
      Low LUMO energy is the lowest LUMO energy among all materials in the organic emissive layer;
      a≤$E_T$−ΔE≤b, wherein $E_T$ is triplet energy $T_1$ of the emitter material, which is the lowest $T_1$ energy among all materials in the organic emissive layer, ΔE is the energy gap between the High HOMO energy and the Low LUMO energy, a is 0.00 up to 0.15 eV, and b is 0.05 up to 0.45 eV; and
   wherein root mean squared function (RMSD) value for the emission spectrum of the OLED and an emission spectrum of a reference OLED, whose organic emissive layer consists of the emitter material and an inert host, is not greater than 0.05,
      wherein RMSD value is a single value that represents the average difference between the emission spectrum of the OLED and the emission spectrum of the reference OLED at all wavelengths obtained by the following equation:

$$RMSD = \sqrt{\frac{1}{n}\sum_1^n (I_1(\lambda) - I_2(\lambda))^2},$$

wherein n is the number of points on the two emission spectrums being compared, and $I_1$ and $I_2$ are the normalized intensity spectrums as a function of wavelength, λ.

2. The OLED of claim 1, wherein $E_T$ is at least 2.60 eV.

3. The OLED of claim 1, wherein the High HOMO energy is the HOMO energy of the emitter material, and the Low LUMO energy is the LUMO energy of the first host.

4. The OLED of claim 1, wherein the High HOMO energy is the HOMO energy of the first host, and the Low LUMO energy is the LUMO energy of the emitter material.

5. The OLED of claim 1, wherein the OLED further comprises a second host, wherein the High HOMO energy is the HOMO energy of the first host, and the Low LUMO energy is the LUMO energy of the second host.

6. The OLED of claim 1, wherein the OLED further comprises a second host, wherein the High HOMO energy is the HOMO energy of the second host, and the Low LUMO energy is the LUMO energy of the first host.

7. The OLED of claim 1, wherein the first host comprises at least one chemical moiety selected from the group consisting of triphenylene, carbazole, indolocarbazole, benzothiophene, benzofuran, dibenzothiophene, dibenzofuran, pyridine, pyridazine, pyrimidine, pyrazine, triazine, imidazole, boryl, 5,9-dioxa-13b-boranaphtho[3,2,1-de]anthracene, and aza-variants thereof.

8. The OLED of claim 1, wherein the emitter material has the formula of $M(L^1)_x(L^2)_y(L^3)_z$;
   wherein,
   $L^1$, $L^2$ and $L^3$ can be the same or different;
   x is 1, 2, or 3;
   y is 0, 1, or 2;
   z is 0, 1, or 2;
   x+y+z is the oxidation state of the metal M;
   $L^1$, $L^2$, and $L^3$ are each independently selected from the group consisting of:

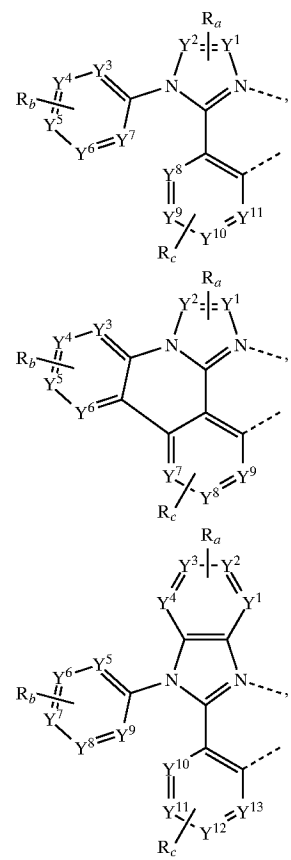

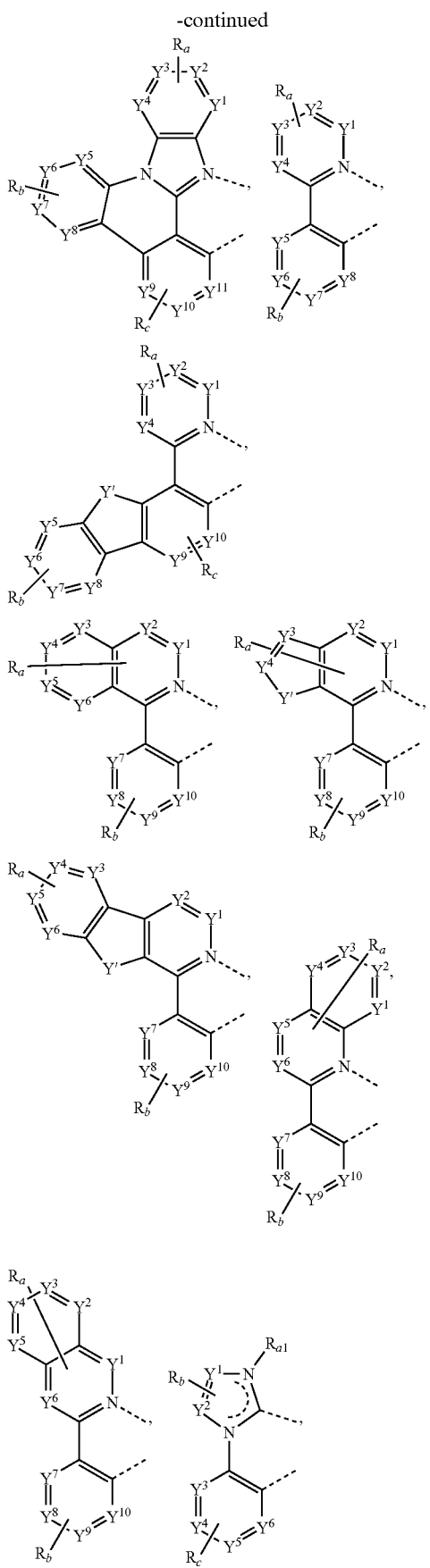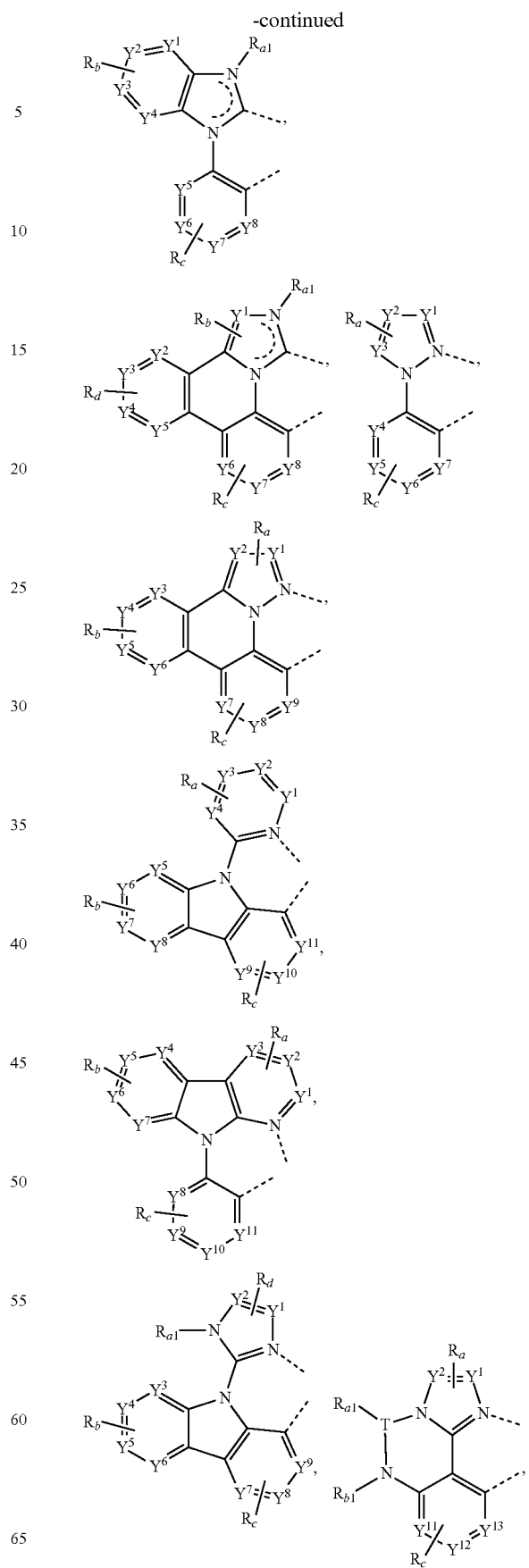

-continued

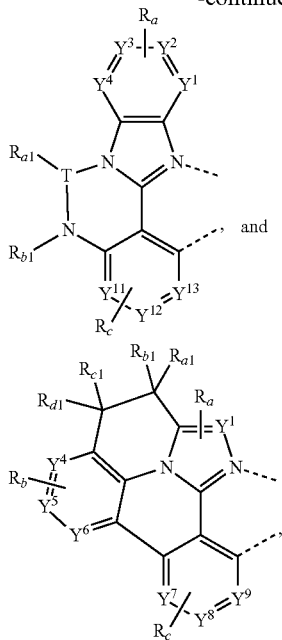

wherein;
T is selected from the group consisting of B, Al, Ga, and In;
each $Y^1$ to $Y^{13}$ are independently selected from the group consisting of carbon and nitrogen;
Y' is selected from the group consisting of $BR_e$, $NR_e$, $PR_e$, O, S, Se, C=O, S=O, $SO_2$, $CR_eR_f$, $SiR_eR_f$, and $GeR_eR_f$;
$R_e$ and $R_f$ can be fused or joined to form a ring;
each $R_a$, $R_b$, $R_c$, and $R_d$ may represent from mono substitution to the possible maximum number of substitution, or no substitution;
each of the $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, boryl, selenyl, and combinations thereof; and
any two $R_{a1}$, $R_{b1}$, $R_{c1}$, $R_{d1}$, $R_a$, $R_b$, $R_c$, $R_d$, $R_e$ and $R_f$ can be fused or joined to form a ring or form a multidentate ligand.

9. The OLED of claim 8, wherein at least one of $R_{a1}$, $R_{b1}$, $R_{c1}$, $R_{d1}$, $R_a$, $R_b$, $R_c$, $R_d$, $R_e$ and $R_f$ comprises a chemical group containing at least three 6-membered aromatic rings that are not fused next to each other.

10. The OLED of claim 8, wherein the emitter material has the formula selected from the group consisting of $Pt(L^1)_2$, $Pt(L^1)(L^2)$, $Pd(L^1)_2$, and $Pd(L^1)(L^2)$; wherein $L^1$ and $L^2$ are each a different bidentate ligand; and wherein $L^1$ can be connected to the other $L^1$ or $L^2$ to form a tetradentate ligand.

11. The OLED of claim 8, wherein the emitter material comprises at least one metal-carbene bond.

12. The OLED of claim 8, wherein the minimum amount of the hydrogen of the emitter material being deuterated is selected from the group consisting of 25%, 30%, 35%, 40%, 50%, 60%, 70%, 80%, 90%, and 100%.

13. The OLED of claim 10, wherein the emitter material is selected from the group consisting of:

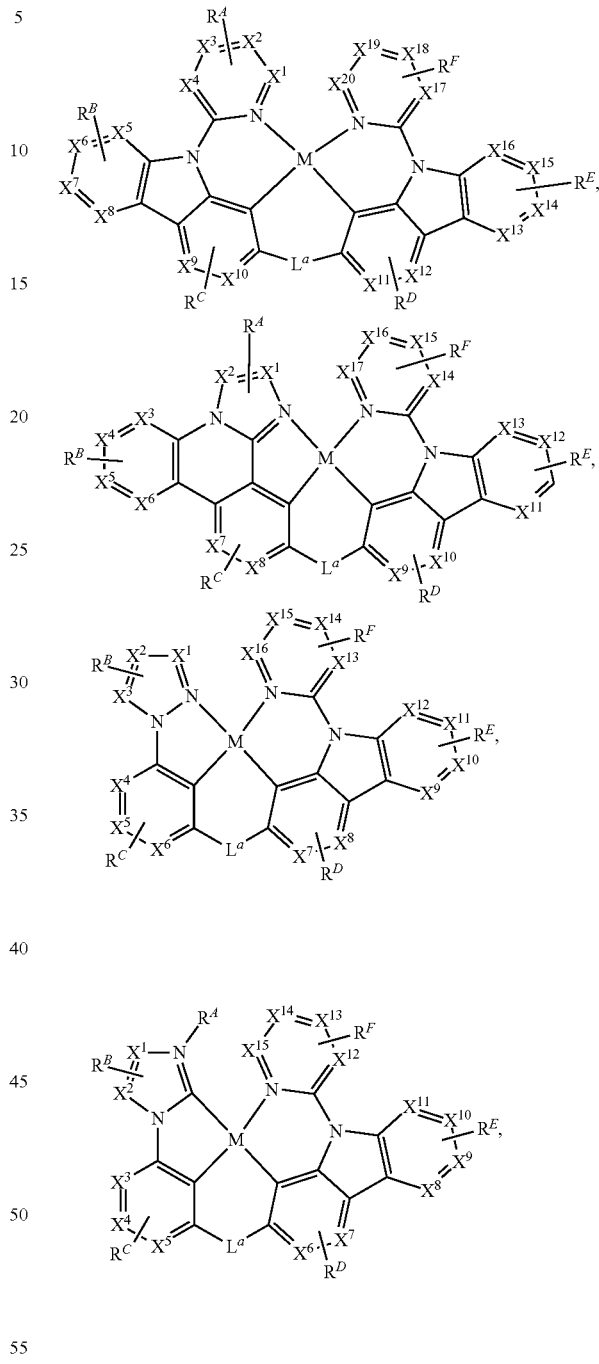

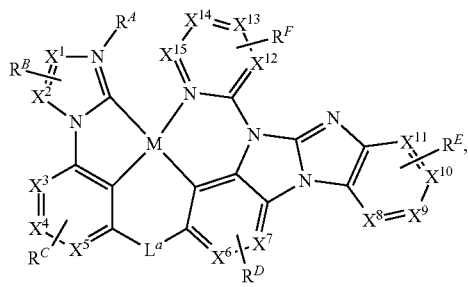

-continued

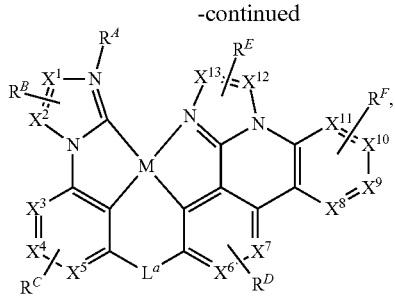

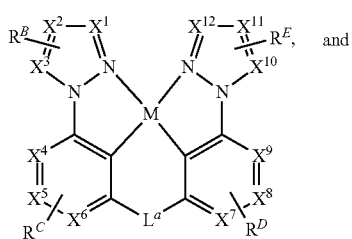

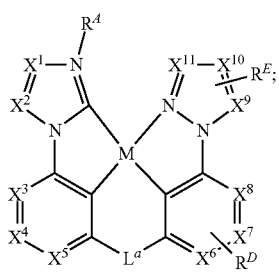

wherein,

X¹ to X²⁰ is C or N;

$L^a$ is selected from the group consisting of O, S, Se, NR, PR, BR, BRR', CRR', SiRR', GeRR', and C=X, wherein X is O, S, NR", or CR'R";

each R, R', R", $R^A$ to $R^F$ represents from mono substitution to the possible maximum number of substitutions, or no substitution;

each R, R', R", $R^A$ to $R^F$ is independently a hydrogen or a substitution selected from the group consisting of deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, boryl, selenyl, and combinations thereof; and any two R, R', R", $R^A$ to $R^F$ are optionally fused or joined to form a ring or form a multidentate ligand.

14. The OLED of claim 13, wherein at least one of $R^A$ to $R^F$ comprises a chemical group containing at least three 6-membered aromatic rings that are not fused next to each other.

15. The OLED of claim 13, wherein $R^A$ comprises a chemical group containing at least three 6-membered aromatic rings that are not fused next to each other.

16. The OLED of claim 13, wherein the emitter material is selected from the group consisting of:

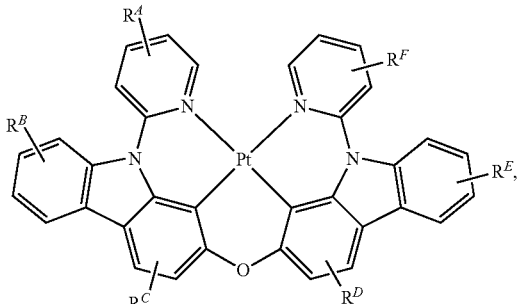

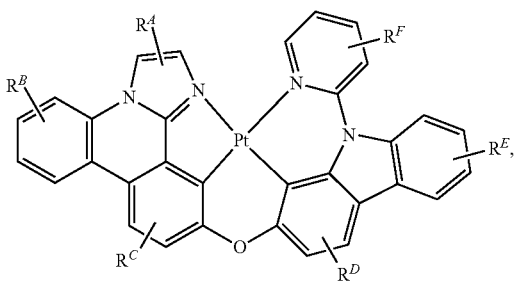

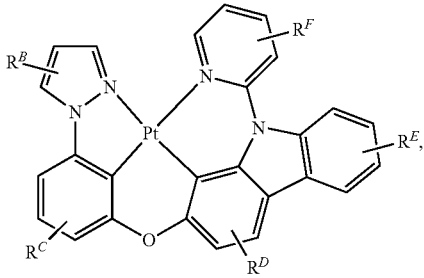

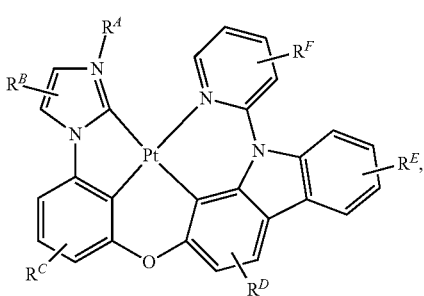

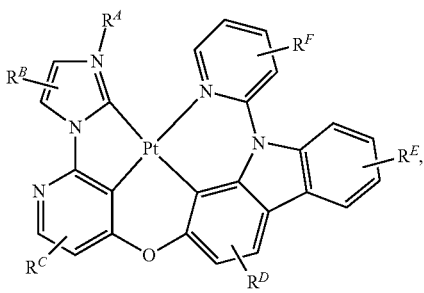

283
-continued
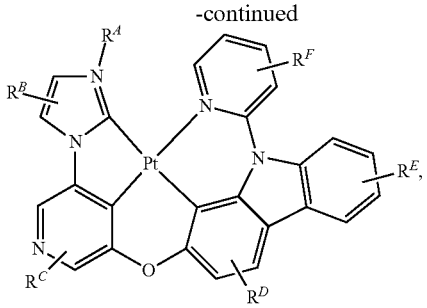
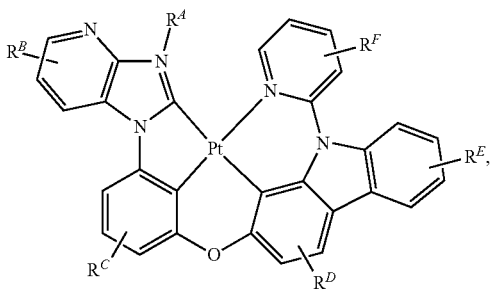
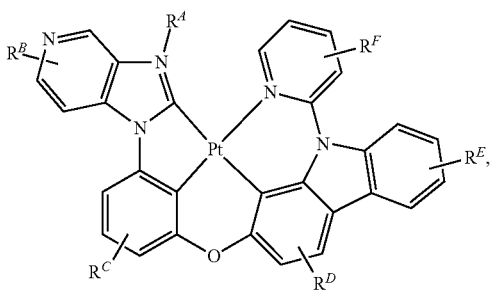
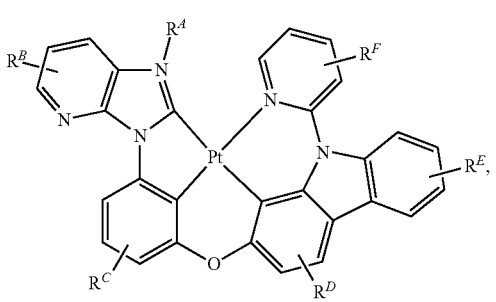
284
-continued
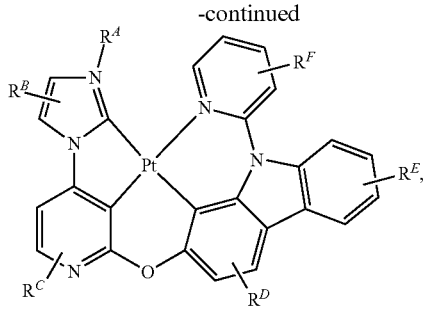
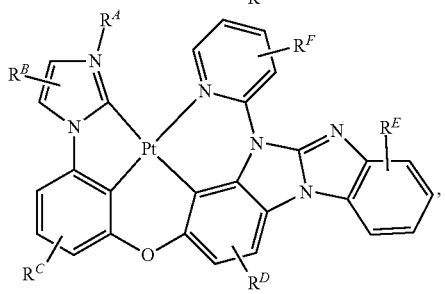
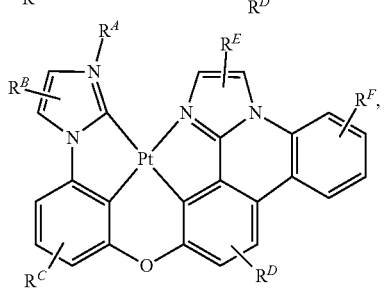
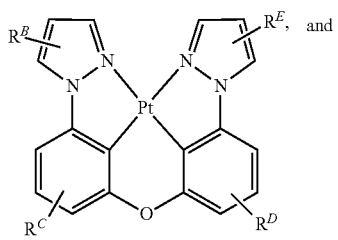, and
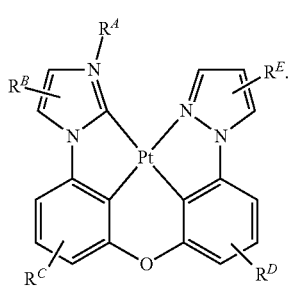.
17. The OLED of claim 13, wherein the emitter material is selected from the group consisting of the structures defined by β-(Ri)(Rj)(Rk)(Rl)(Rm)(Rn), where β is an integer from 1 to 15, and β'-(Ri)(Rj)(Rk)(Rl)(Rm)(Rn)(Xo), where β' is an integer from 16 to 27, where i is an integer from 1 to 292, j, k, l, m, and n are integers independently from 1 to 307, and o is an integer from 1 to 21:

| Emitter Material | Structure of emitter material |
|---|---|
| wherein when β is 1,<br>1-(R1)(R1)(R1)(R1)(R1)(R1) to<br>1-(R292)(R307)(R307)(R307)(R307)(R307), having the structure | 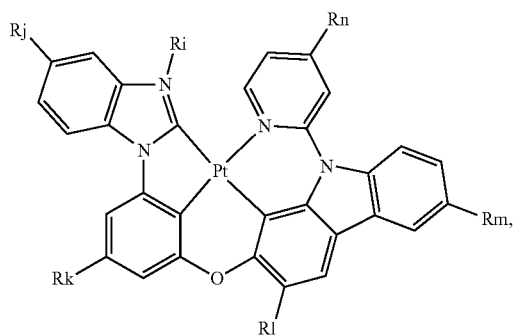 |
| wherein when β is 2,<br>2-(R1)(R1)(R1)(R1)(R1)(R1) to<br>2-(R292)(R307)(R307)(R307)(R307)(R307), having the structure | 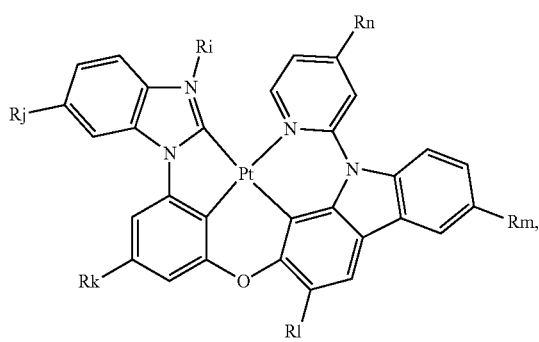 |
| wherein when β is 3,<br>3-(R1)(R1)(R1)(R1)(R1)(R1) to<br>3-(R292)(R307)(R307)(R307)(R307)(R307), having the structure | 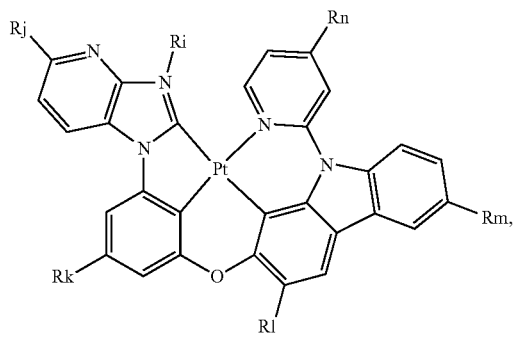 |
| wherein when β is 4,<br>4-(R1)(R1)(R1)(R1)(R1)(R1) to<br>4-(R292)(R307)(R307)(R307)(R307)(R307), having the structure | 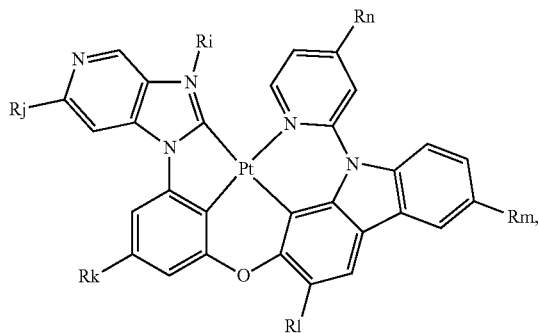 |

| Emitter Material | Structure of emitter material |
|---|---|
| wherein when β is 5,<br>5-(R1)(R1)(R1)(R1)(R1) to<br>5-(R292)(R307)(R307)(R307)(R307)(R307), having the structure | 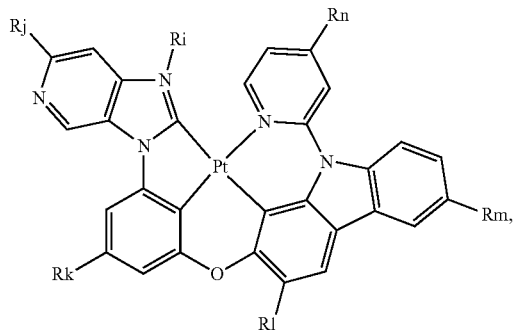 |
| wherein when β is 6,<br>6-(R1)(R1)(R1)(R1)(R1) to<br>6-(R292)(R307)(R307)(R307)(R307)(R307), having the structure | 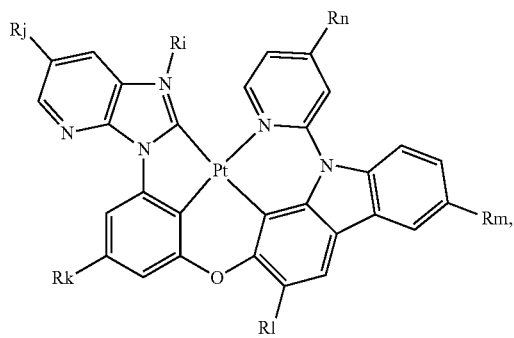 |
| wherein when β is 7,<br>7-(R1)(R1)(R1)(R1)(R1)(R1) to<br>7-(R292)(R307)(R307)(R307)(R307)(R307), having the structure | 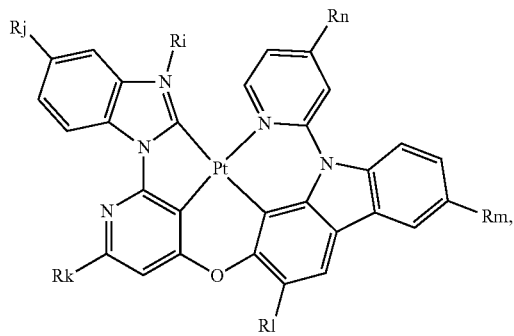 |
| wherein when β is 8,<br>8-(R1)(R1)(R1)(R1)(R1)(R1) to<br>8-(R292)(R307)(R307)(R307)(R307)(R307), having the structure | 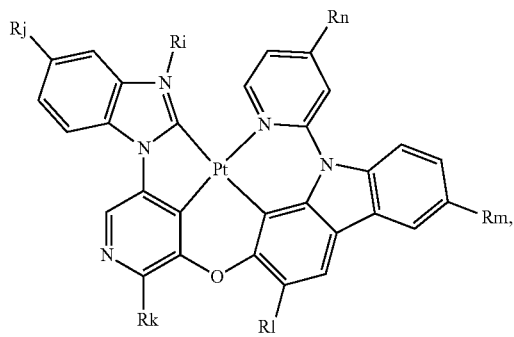 |

| Emitter Material | Structure of emitter material |
|---|---|
| wherein when β is 9,<br>9-(R1)(R1)(R1)(R1)(R1) to<br>9-(R292)(R307)(R307)(R307)(R307), having the structure | 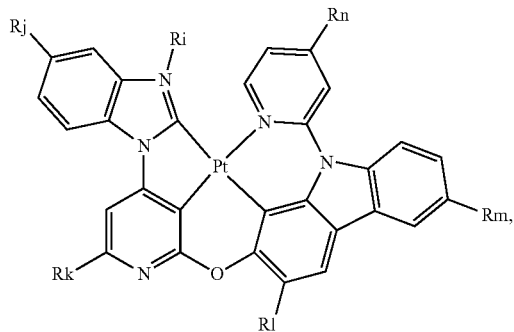 |
| wherein when β is 10,<br>10-(R1)(R1)(R1)(R1)(R1) to<br>10-(R292)(R307)(R307)(R307)(R307), having the structure | 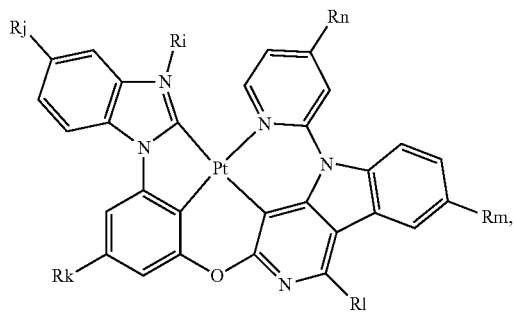 |
| wherein when β is 11,<br>11-(R1)(R1)(R1)(R1)(R1) to<br>11-(R292)(R307)(R307)(R307)(R307), having the structure | 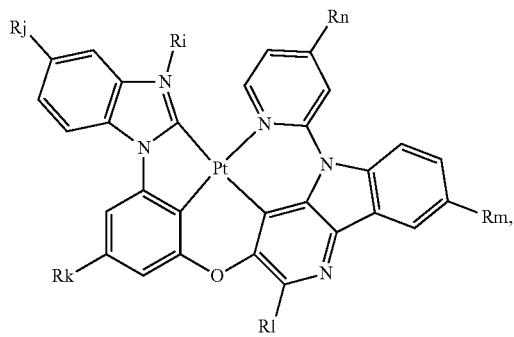 |
| wherein when β is 12,<br>12-(R1)(R1)(R1)(R1)(R1) to<br>12-(R292)(R307)(R307)(R307)(R307), having the structure | 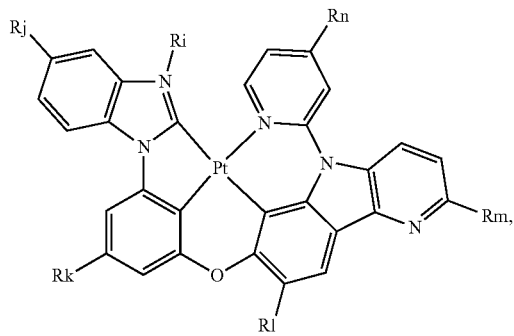 |

| Emitter Material | Structure of emitter material |
|---|---|
| wherein when β is 13, 13-(R1)(R1)(R1)(R1)(R1) to 13-(R292)(R307)(R307)(R307)(R307)(R307), having the structure | 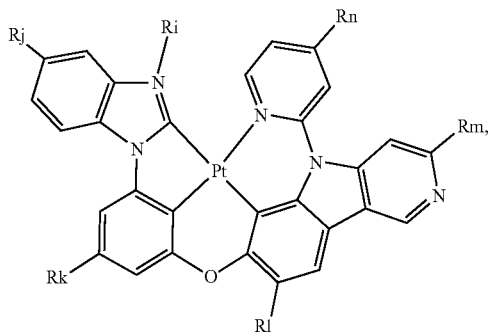 |
| wherein when β is 14, 14-(R1)(R1)(R1)(R1)(R1) to 14-(R292)(R307)(R307)(R307)(R307)(R307), having the structure | 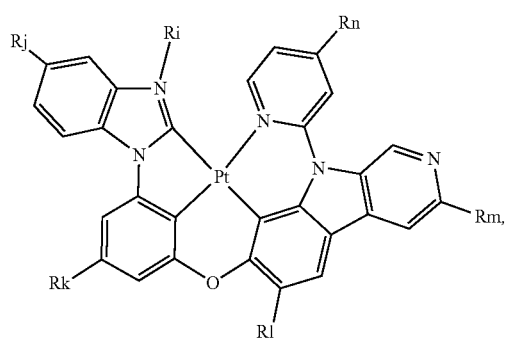 |
| wherein when β is 15, 15-(R1)(R1)(R1)(R1)(R1) to 15-(R292)(R307)(R307)(R307)(R307)(R307), having the structure | 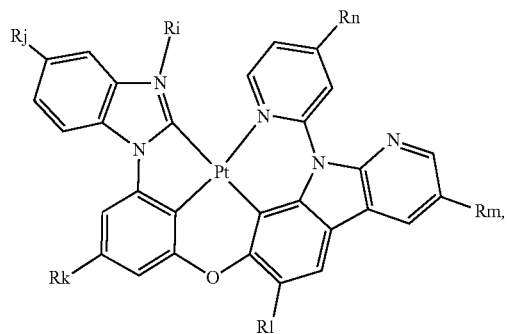 |
| wherein when β' is 16, 16-(R1)(R1)(R1)(R1)(R1)(X1) to 16-(R292)(R307)(R307)(R307)(R307)(R307)(X21), having the structure | 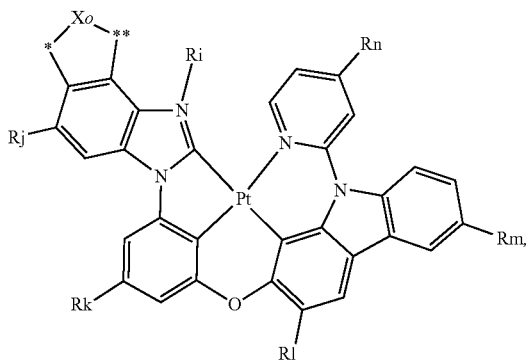 |

| Emitter Material | Structure of emitter material |
|---|---|
| wherein when β' is 17,<br>17-(R1)(R1)(R1)(R1)(R1)(R1)(X1) to<br>17-(R292)(R307)(R307)(R307)(R307)(R307)(X21),<br>having the structure | 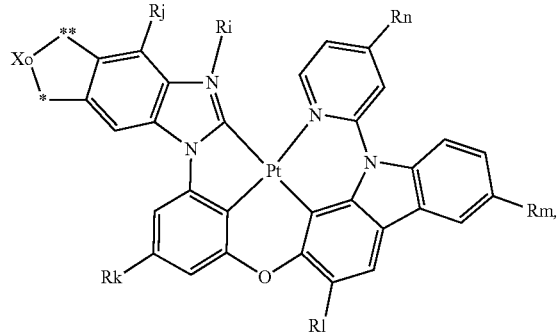 |
| wherein when β' is 18,<br>18-(R1)(R1)(R1)(R1)(R1)(R1)(X1) to<br>18-(R292)(R307)(R307)(R307)(R307)(R307)(X21),<br>having the structure | 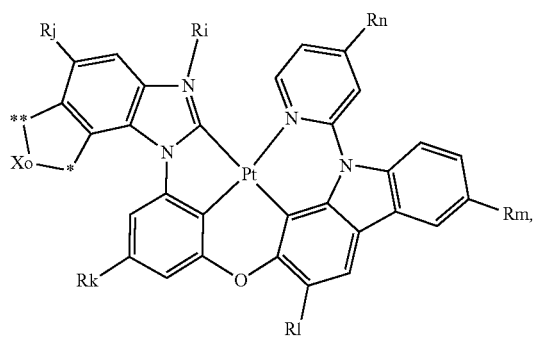 |
| wherein when β' is 16,<br>19-(R1)(R1)(R1)(R1)(R1)(R1)(X1) to<br>19-(R292)(R307)(R307)(R307)(R307)(R307)(X21),<br>having the structure | 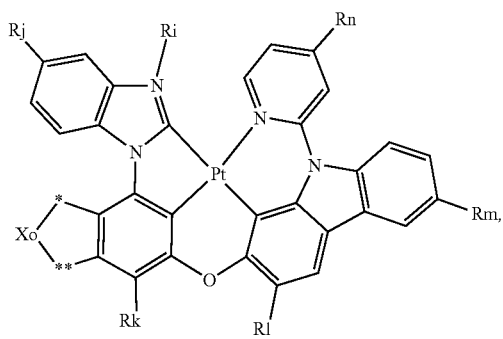 |
| wherein when β' is 20,<br>20-(R1)(R1)(R1)(R1)(R1)(R1)(X1) to<br>20-(R292)(R307)(R307)(R307)(R307)(R307)(X21),<br>having the structure | 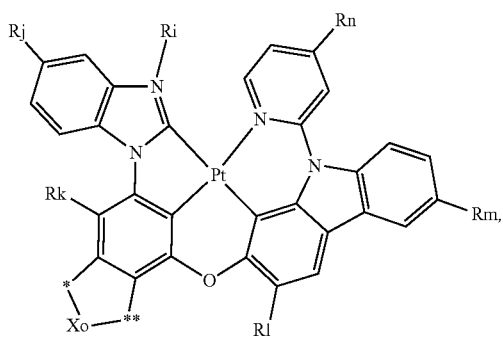 |

| Emitter Material | Structure of emitter material |
|---|---|
| wherein when β' is 21,<br>21-(R1)(R1)(R1)(R1)(R1)(R1)(X1) to<br>21-(R292)(R307)(R307)(R307)(R307)(R307)(X21),<br>having the structure | 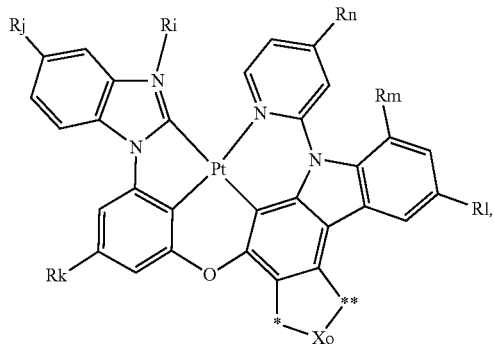 |
| wherein when β' is 22,<br>22-(R1)(R1)(R1)(R1)(R1)(R1)(X1) to<br>22-(R292)(R307)(R307)(R307)(R307)(R307)(X21),<br>having the structure | 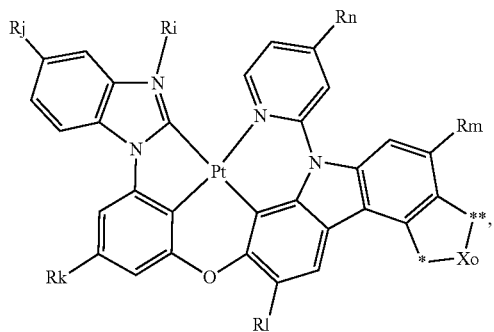 |
| wherein when β' is 23,<br>23-(R1)(R1)(R1)(R1)(R1)(R1)(X1) to<br>23-(R292)(R307)(R307)(R307)(R307)(R307)(X21),<br>having the structure | 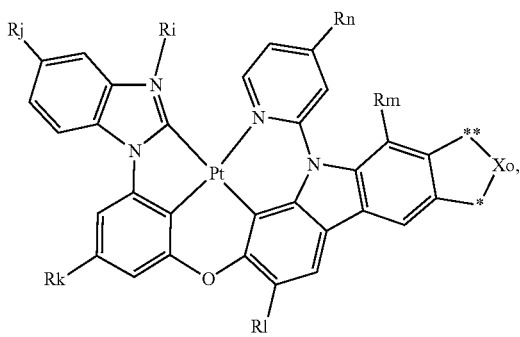 |
| wherein when β' is 24,<br>24-(R1)(R1)(R1)(R1)(R1)(R1)(X1) to<br>24-(R292)(R307)(R307)(R307)(R307)(R307)(X21),<br>having the structure | 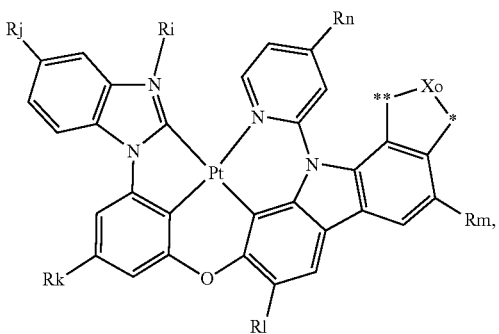 |

| Emitter Material | Structure of emitter material |
|---|---|
| wherein when β' is 25,<br>25-(R1)(R1)(R1)(R1)(R1)(R1)(X1) to<br>25-(R292)(R307)(R307)(R307)(R307)(R307)(X21),<br>having the structure | 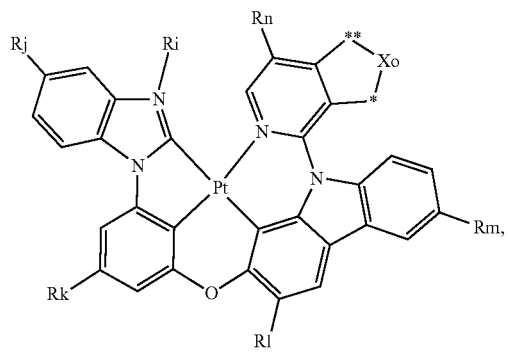 |
| wherein when β' is 26,<br>26-(R1)(R1)(R1)(R1)(R1)(R1)(X1) to<br>26-(R292)(R307)(R307)(R307)(R307)(R307)(X21),<br>having the structure | 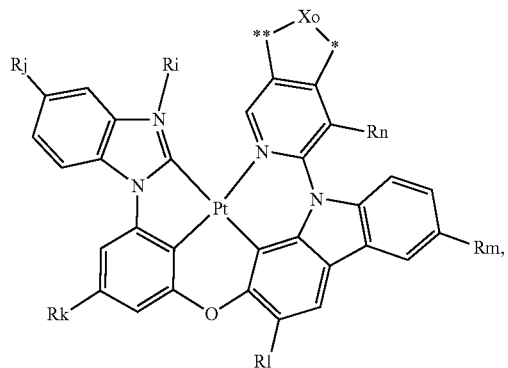 |
| wherein when β' is 27,<br>27-(R1)(R1)(R1)(R1)(R1)(R1)(X1) to<br>27-(R292)(R307)(R307)(R307)(R307)(R307)(X21),<br>having the structure | 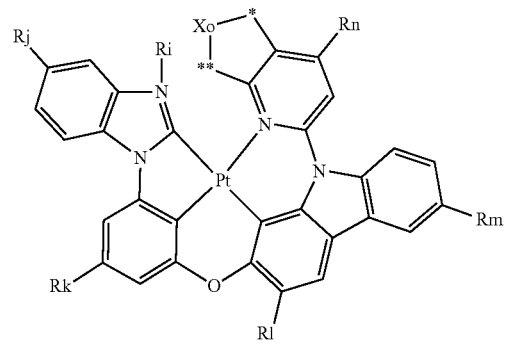 |
wherein R1 to R307 have the following structures:
R1  Me,
R2  iPr,
R3  tBu,
R4  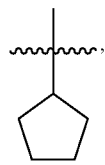

-continued
R5
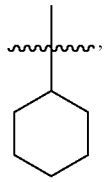
R6
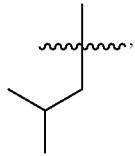
R7
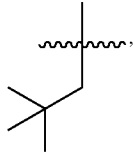
R8
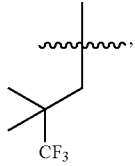
R9
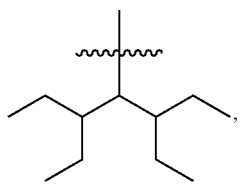
R10
CD₃,
R11
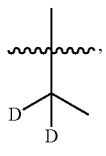
R12
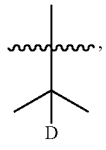
R13
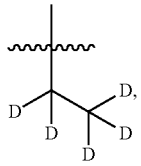
R14
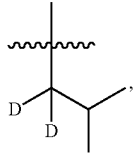

-continued
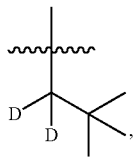 R15
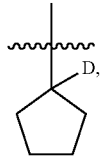 R16
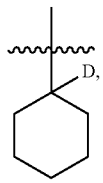 R17
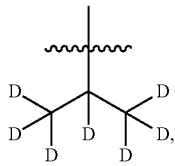 R18
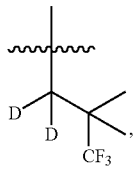 R19
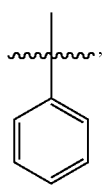 R20
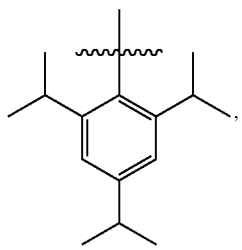 R21
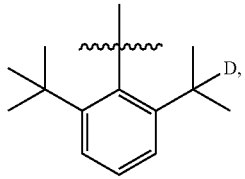 R22

-continued
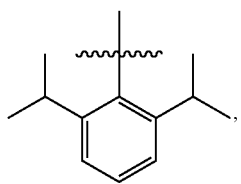 R23
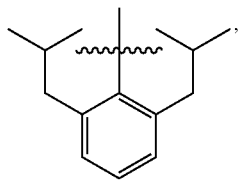 R24
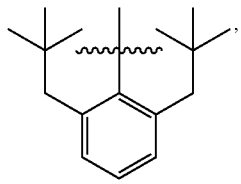 R25
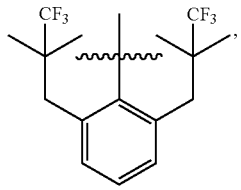 R26
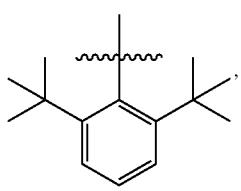 R27
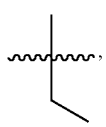 R28
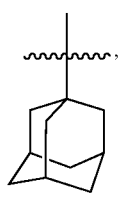 R29
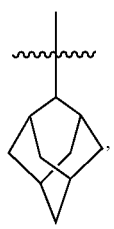 R30

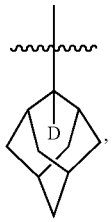
R31
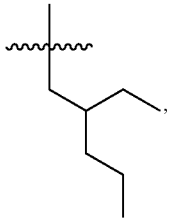
R32
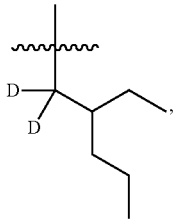
R33
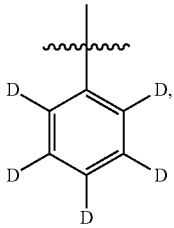
R34
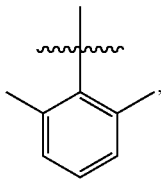
R35
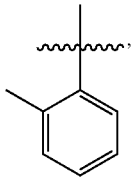
R36
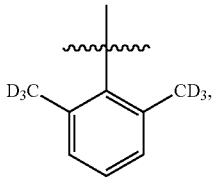
R37

-continued
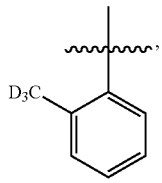
R38
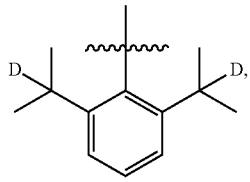
R39
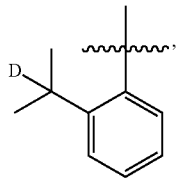
R40
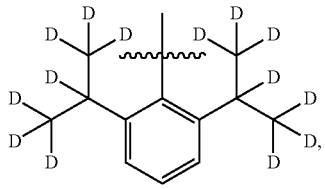
R41
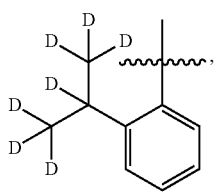
R42
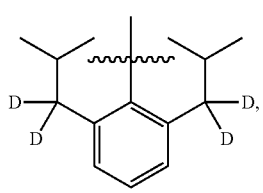
R43
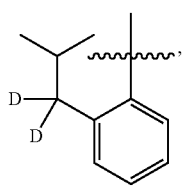
R44
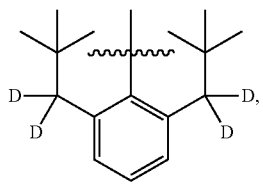
R45

-continued
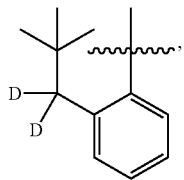
R46
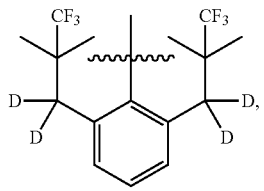
R47
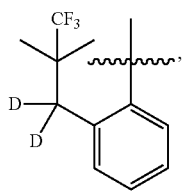
R48
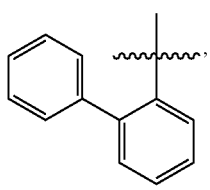
R49
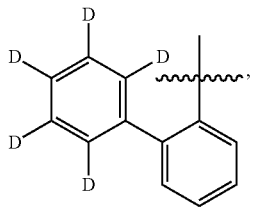
R50
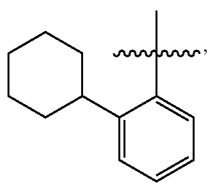
R51
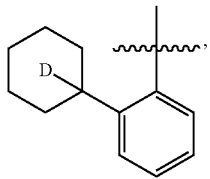
R52
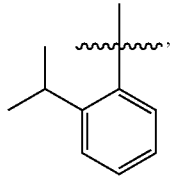
R53

-continued
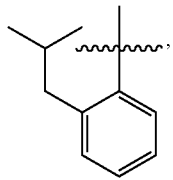
R54
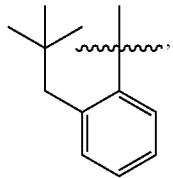
R55
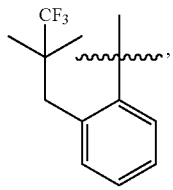
R56
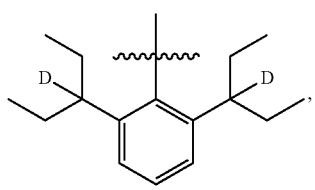
R57
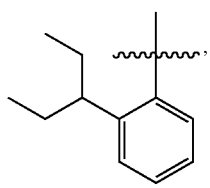
R58
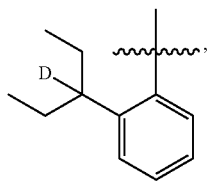
R59
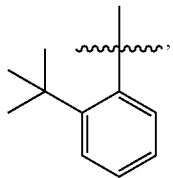
R60
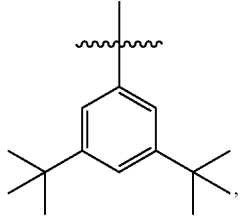
R61

-continued
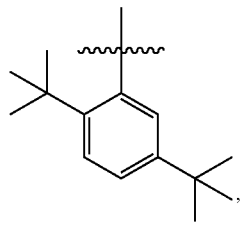
R62
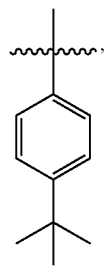
R63
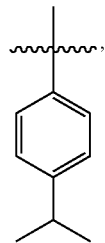
R64
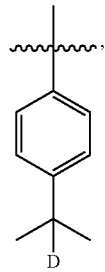
R65
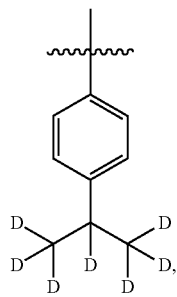
R66
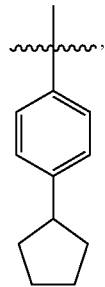
R67

-continued
R68
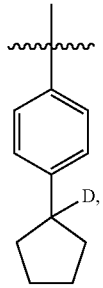
R69
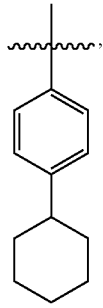
R70
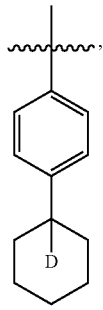
R71
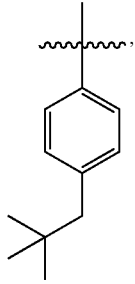
R72
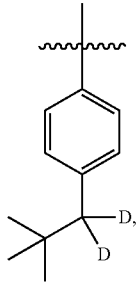

-continued
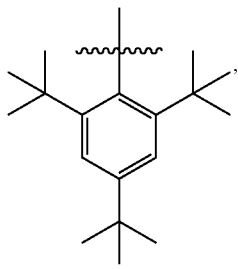
R73
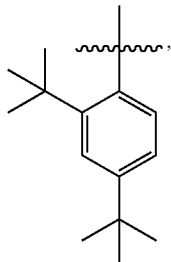
R74
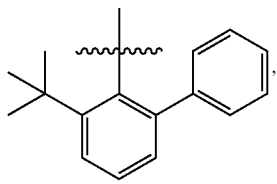
R75
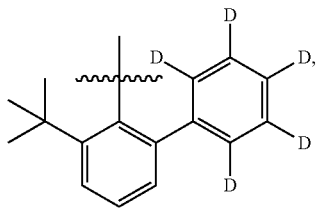
R76
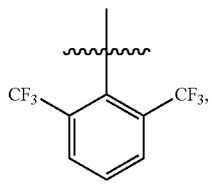
R77
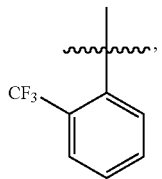
R78
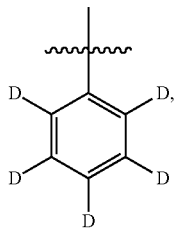
R79

-continued
R80
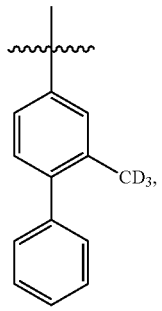
R81
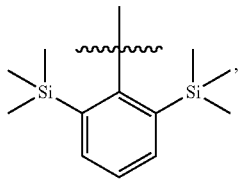
R82
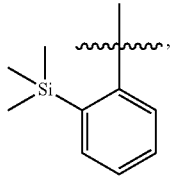
R83
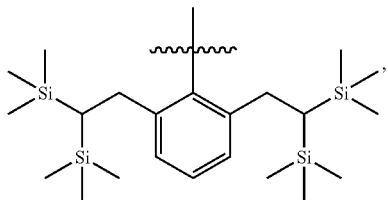
R84
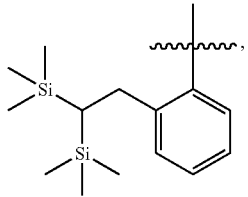
R85
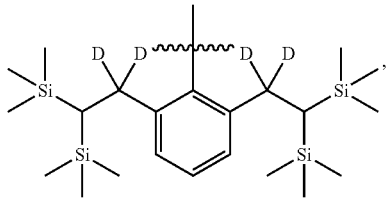
R86
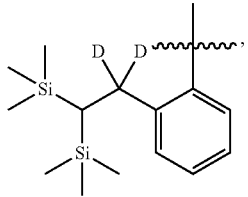

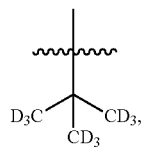
R87
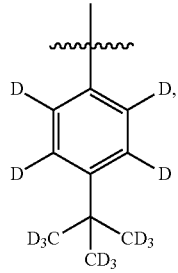
R88
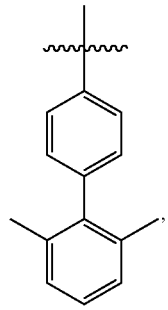
R89
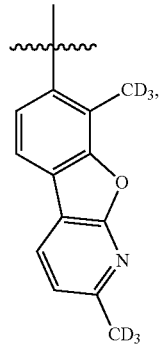
R90
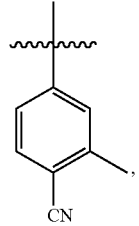
R91
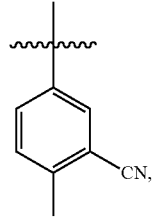
R92

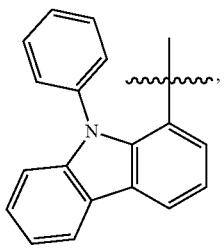 R93
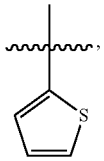 R94
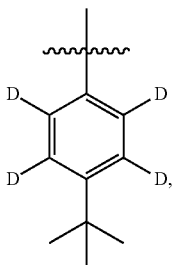 R95
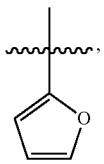 R96
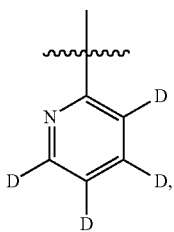 R97
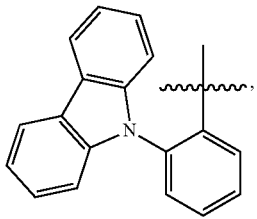 R98
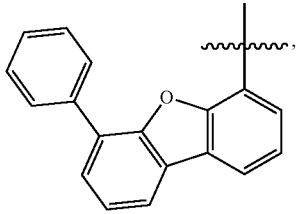 R99

-continued
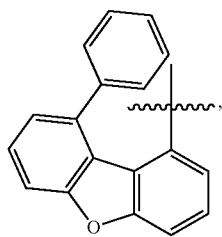 R100
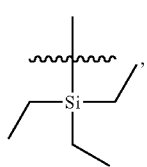 R101
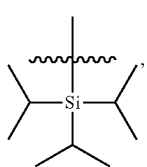 R102
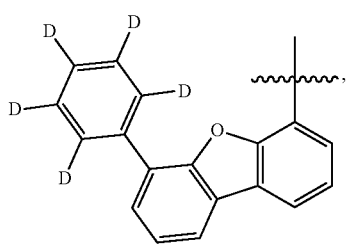 R103
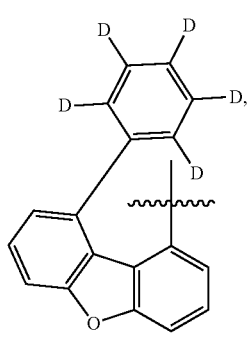 R104
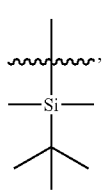 R105
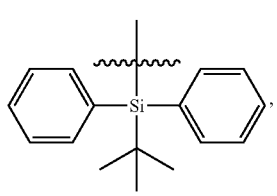 R106

-continued
R107
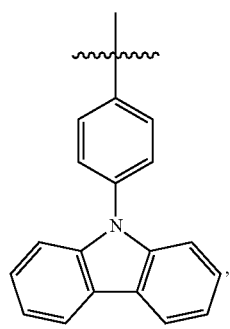
R108
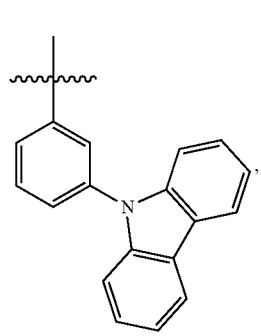
R109
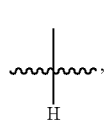
R110
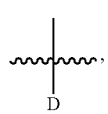
R111
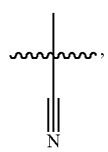
R112
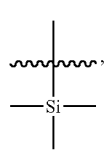
R113
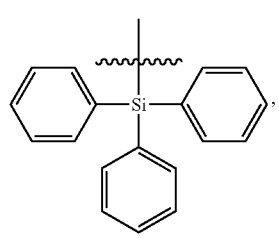

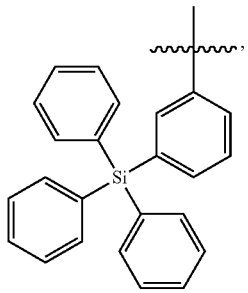 R114
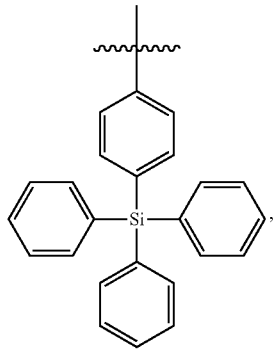 R115
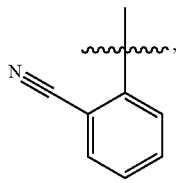 R116
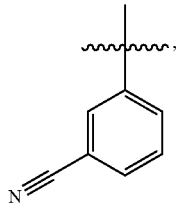 R117
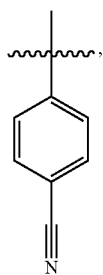 R118
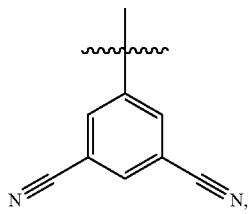 R119

-continued
R120
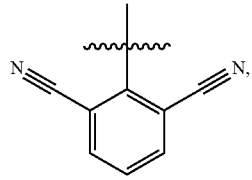
R121
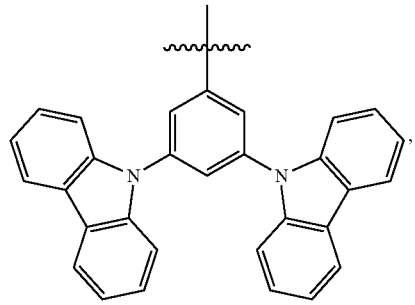
R122
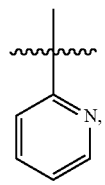
R123
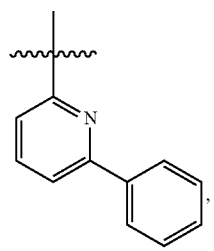
R124
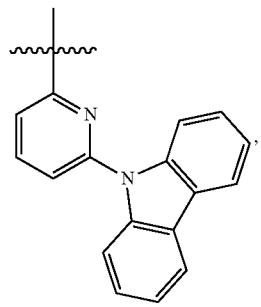
R125
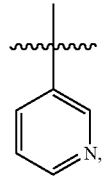

R126
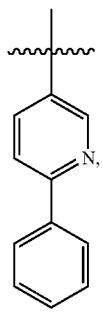
R127
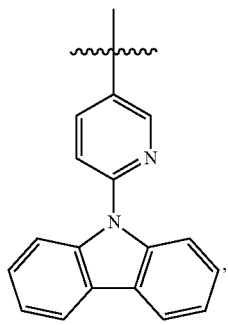
R128
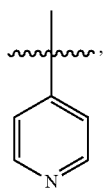
R129
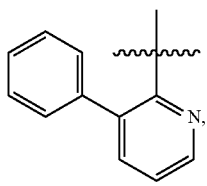
R130
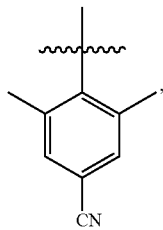
R131
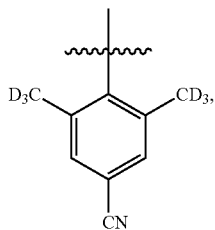

-continued
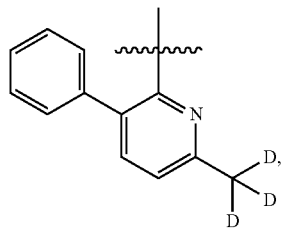
R132
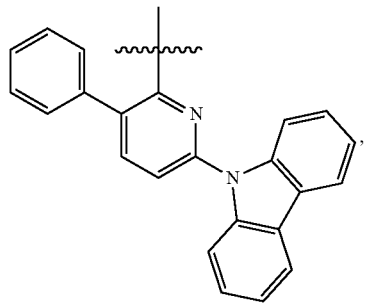
R133
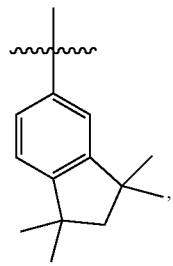
R134
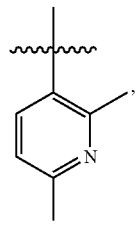
R135
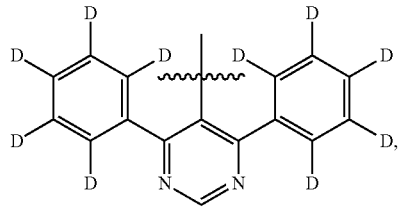
R136
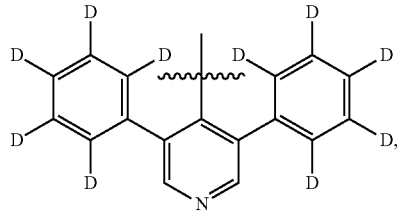
R137

-continued
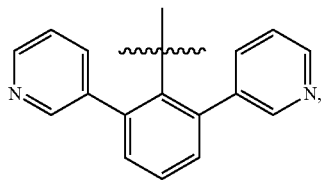
R138
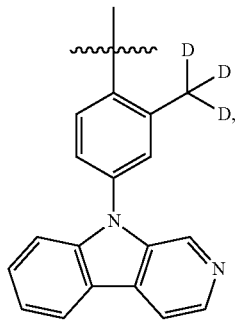
R139
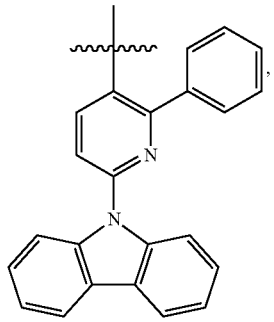
R140
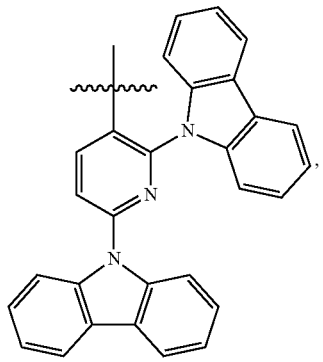
R141
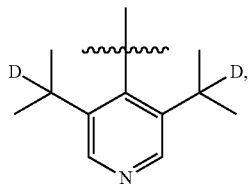
R142
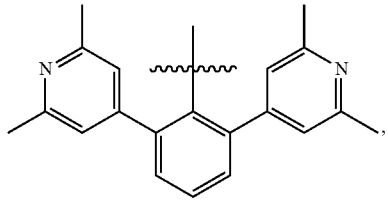
R143

-continued
R144
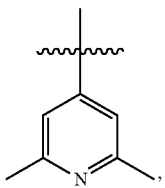
R145
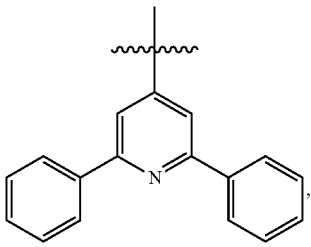
R146
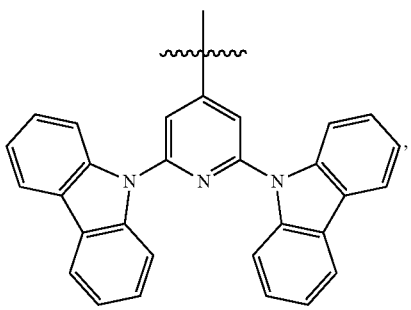
R147
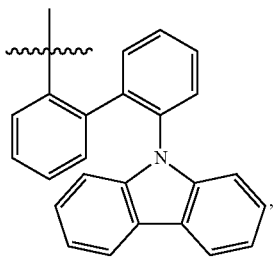
R148
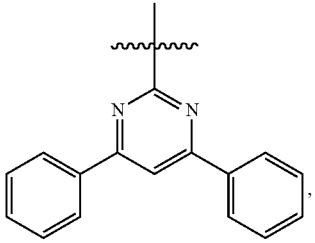
R149
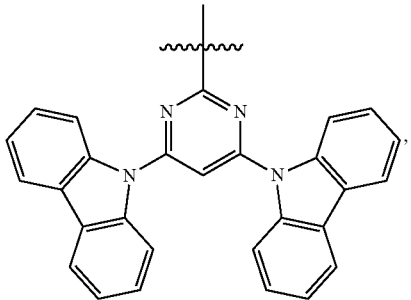

-continued
R150
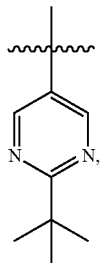
R151
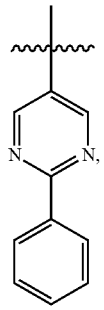
R152
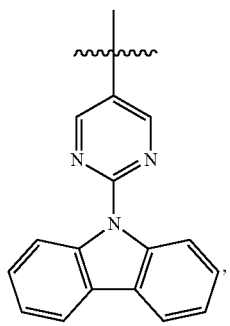
R153
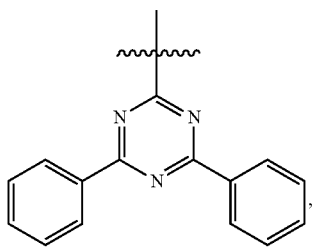
R154
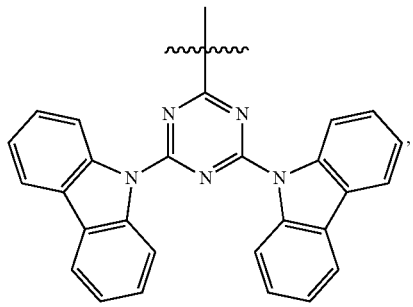

-continued
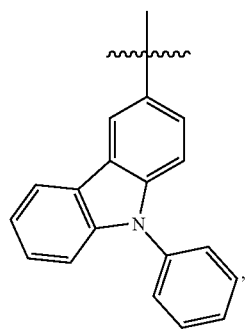
R155
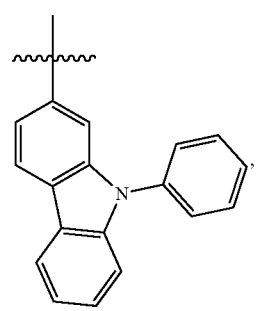
R156
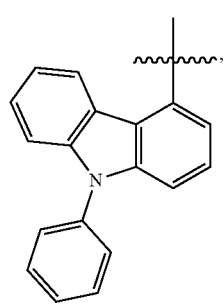
R157
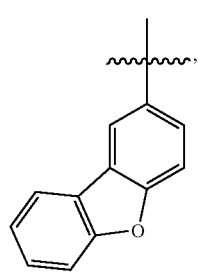
R158
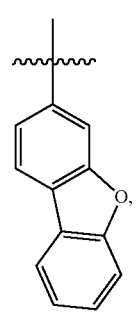
R159

-continued
R160
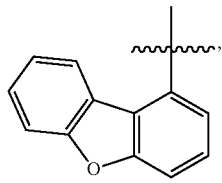
R161
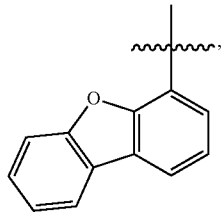
R162
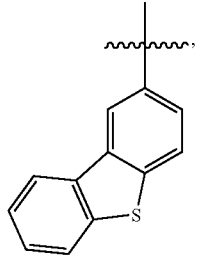
R163
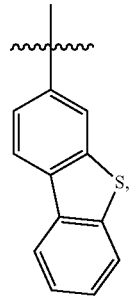
R164
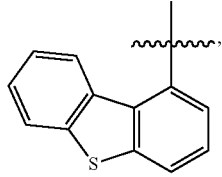
R165
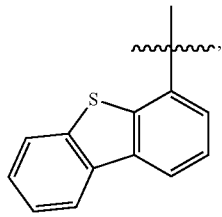

R166
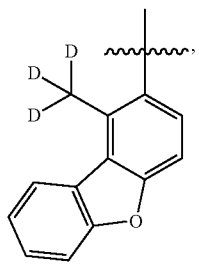
R167
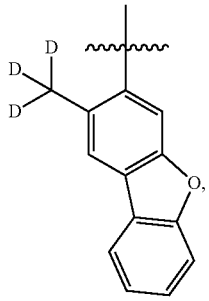
R168
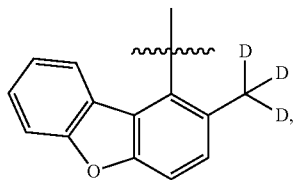
R169
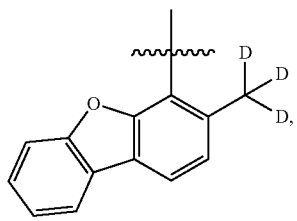
R170
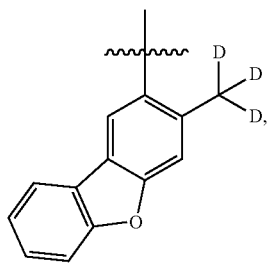
R171
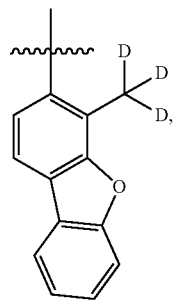

-continued
R172
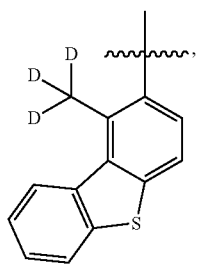
R173
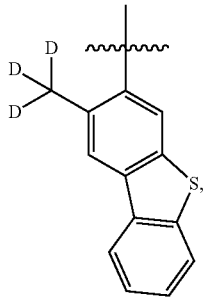
R174
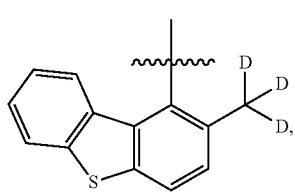
R175
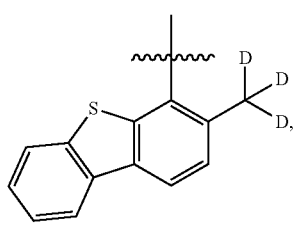
R176
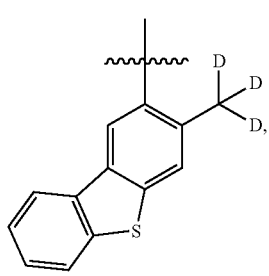
R177
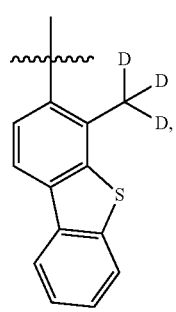

-continued
R178
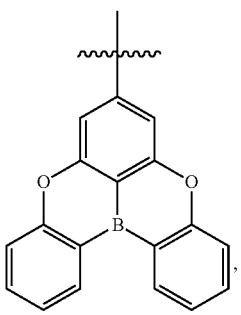
R179
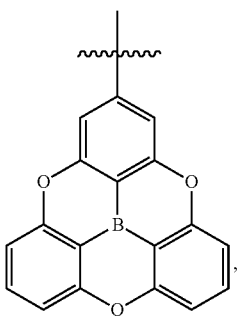
R180
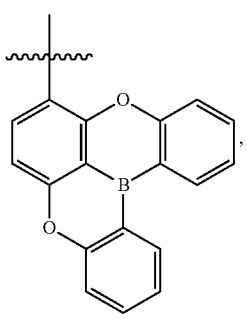
R181
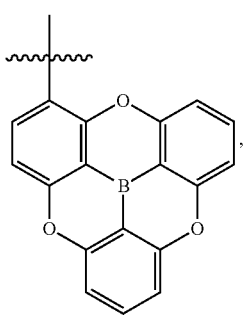
R182
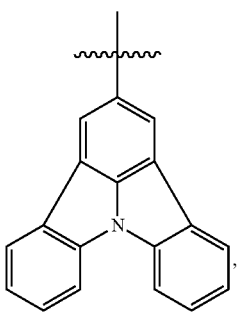

-continued
R183
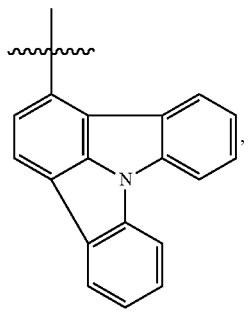
R184
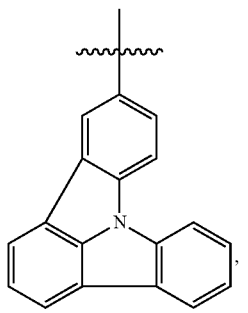
R185
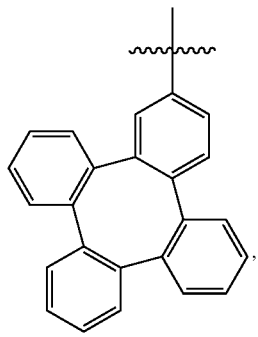
R186
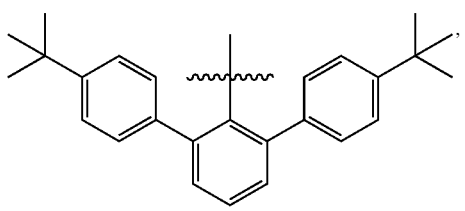
R187
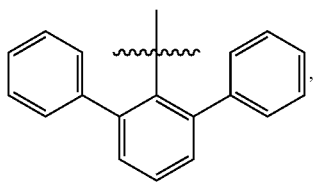
R188
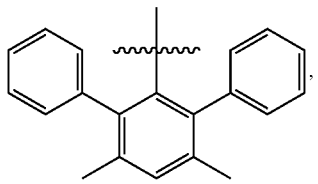

R189
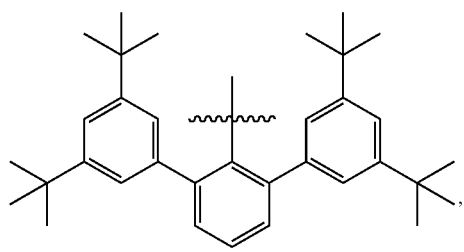
R190
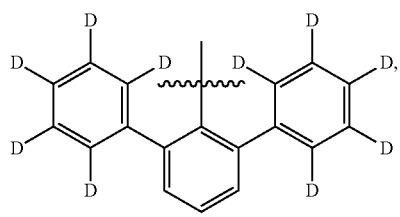
R191
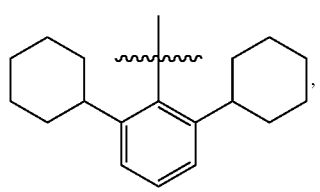
R192
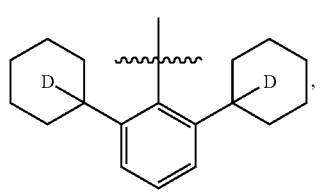
R193
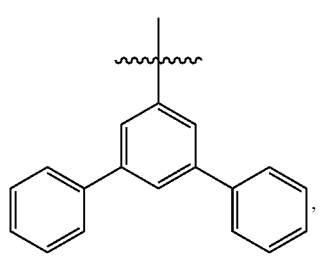
R194
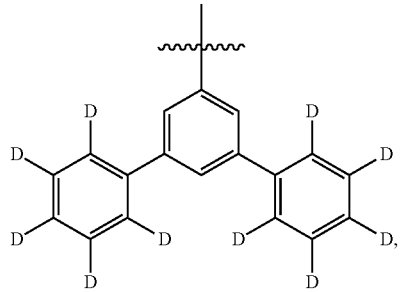

R195
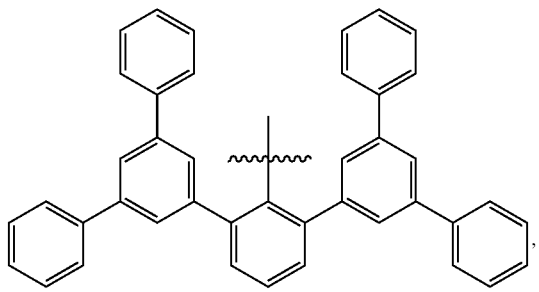
R196
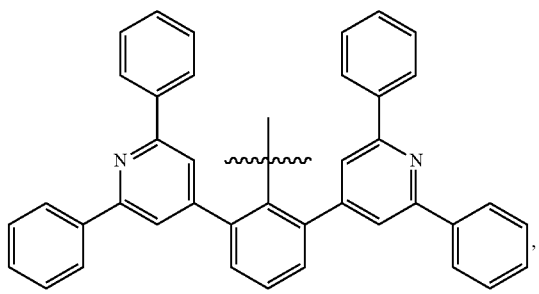
R197
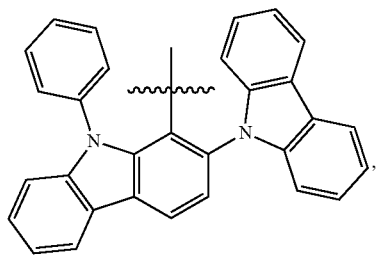
R198
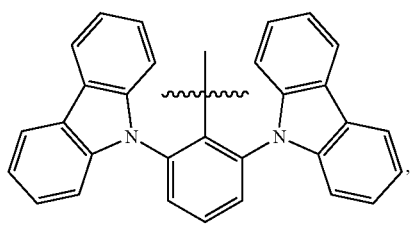
R199

R200
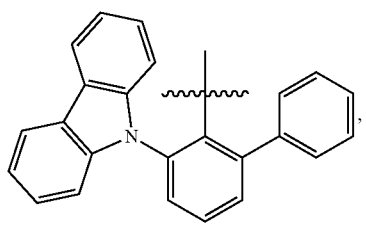
R201
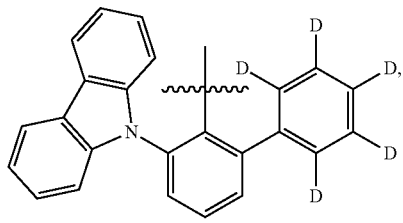
R202
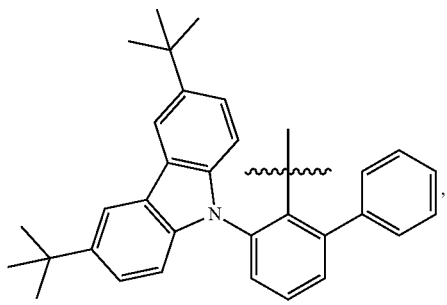
R203
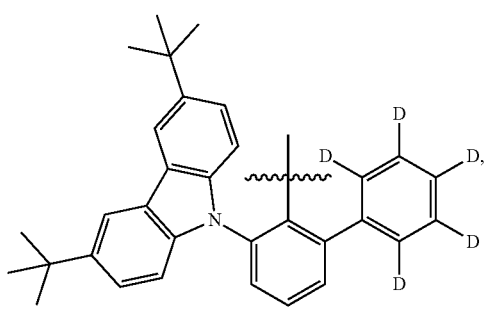
R204
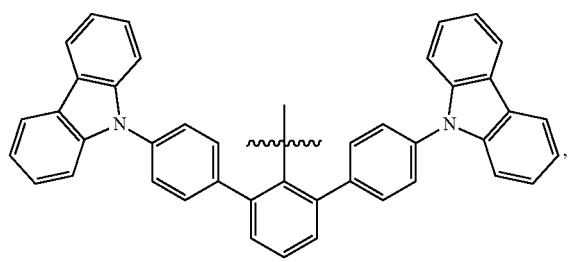

-continued
R205
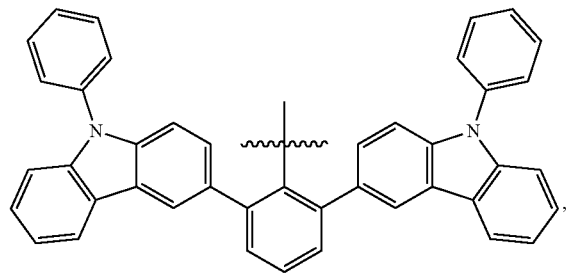
R206
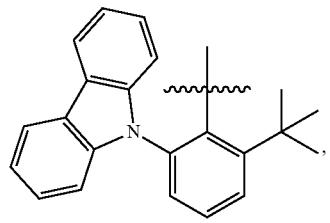
R207
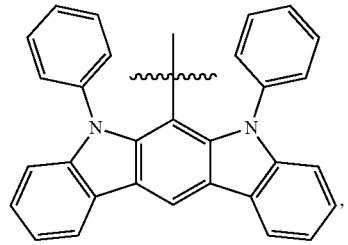
R208
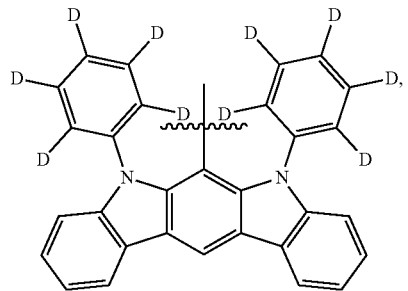
R209
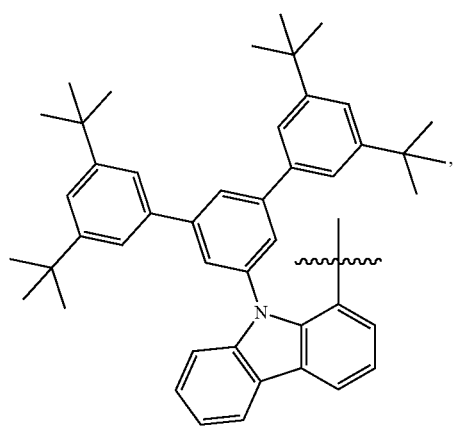

R210
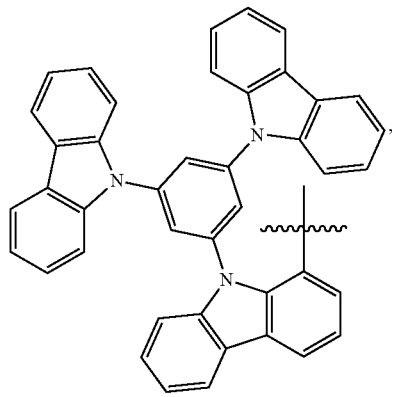
R211
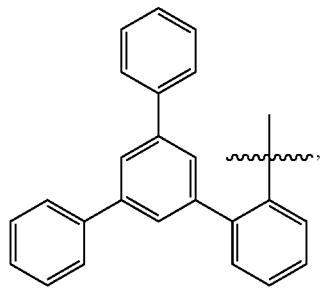
R212
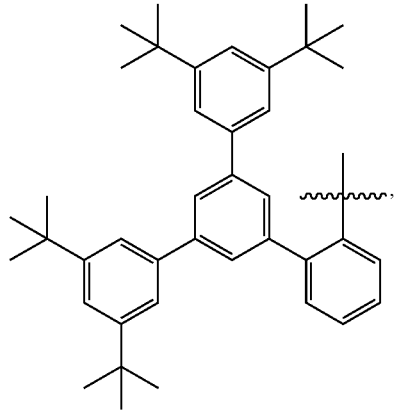
R213
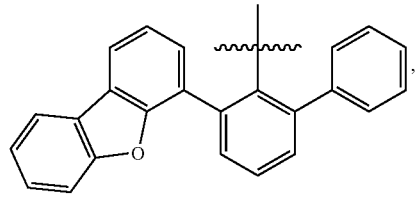
R214
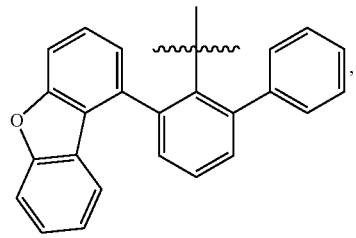

R215
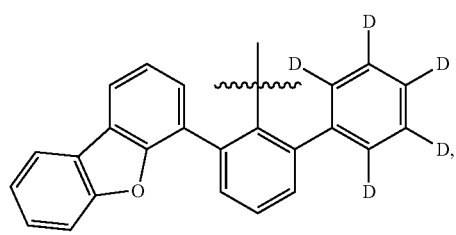
R216
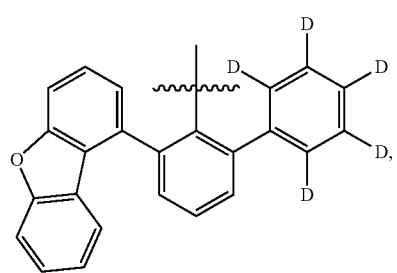
R217
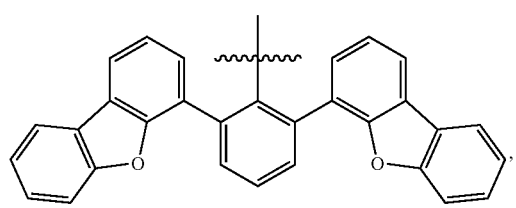
R218
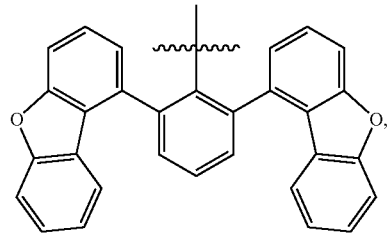
R219
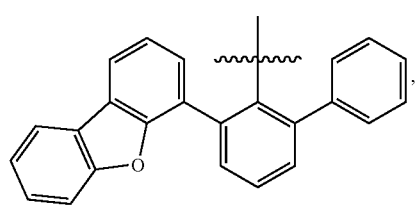
R220
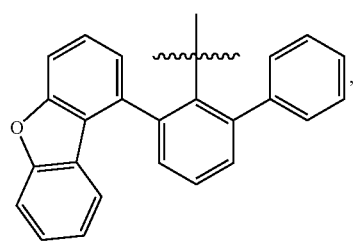

R221
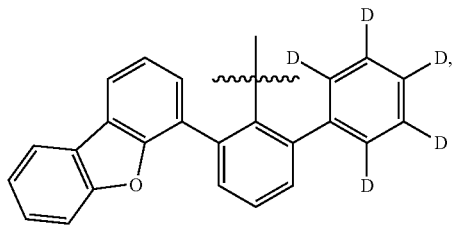
R222
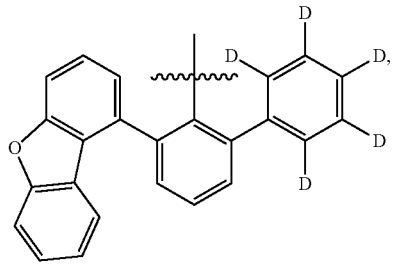
R223
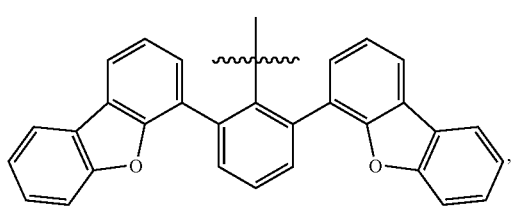
R224
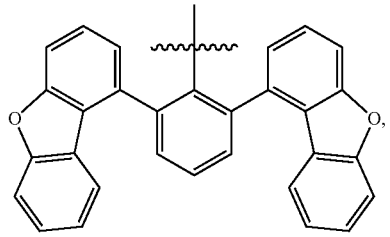
R225
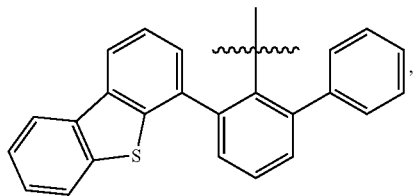
R226
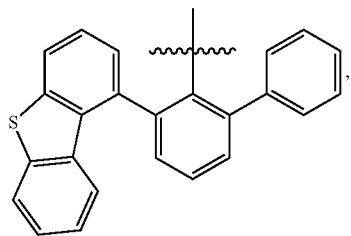

-continued
R227
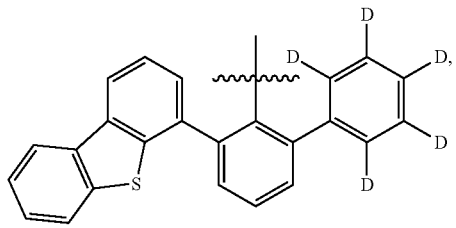
R228
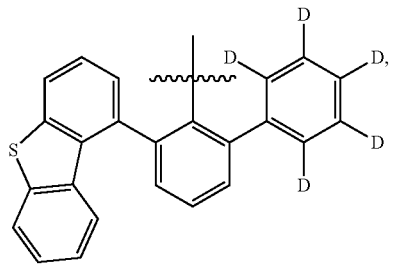
R229
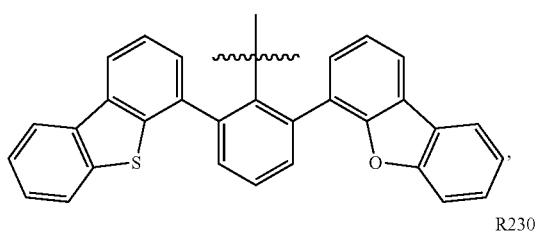
R230
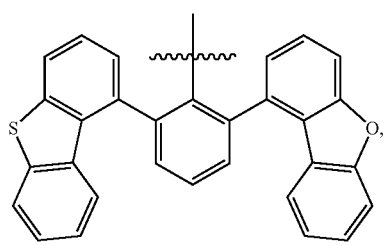
R231
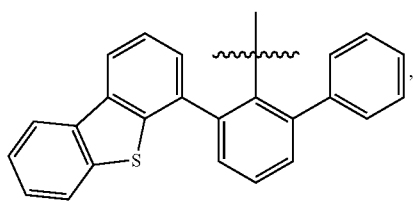
R232
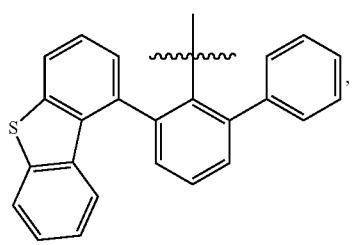

-continued
R233
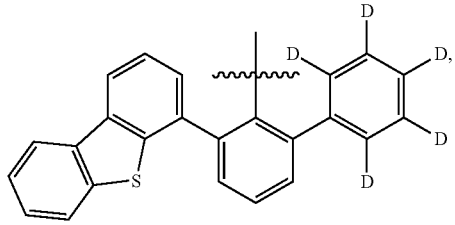
R234
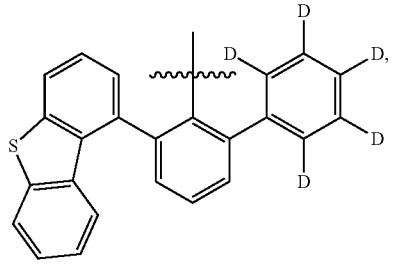
R235
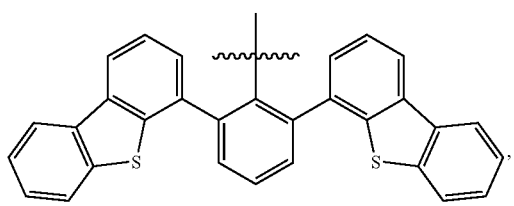
R236
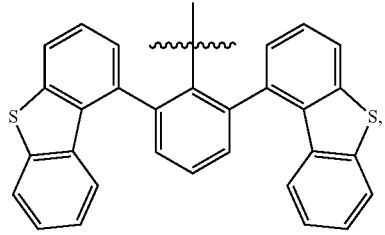
R237
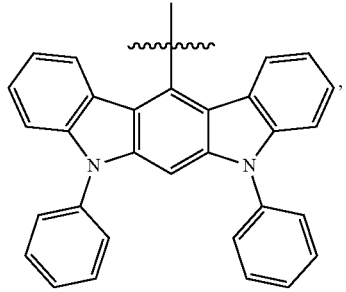
R238
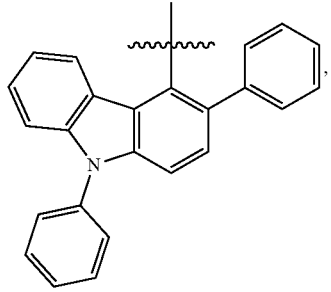

-continued
R239
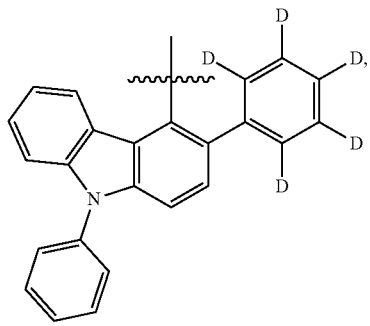
R240
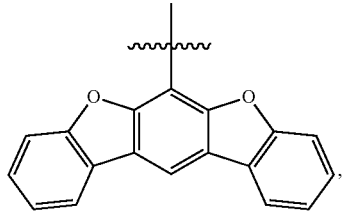
R241
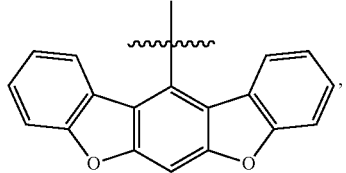
R242
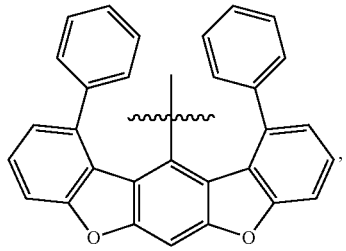
R243
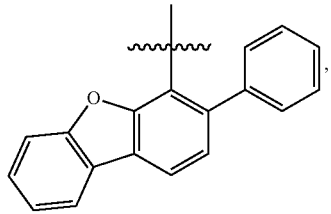
R244
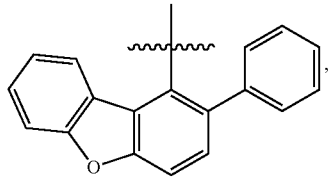
R245
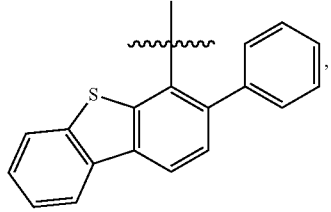

-continued
R246
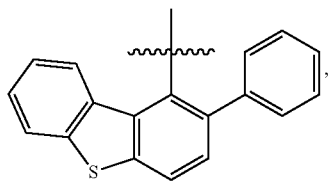
R247
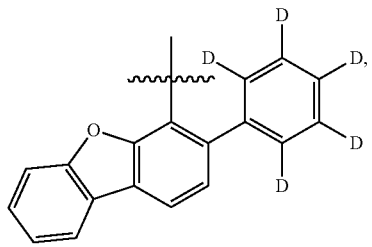
R248
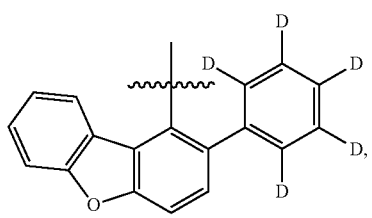
R249
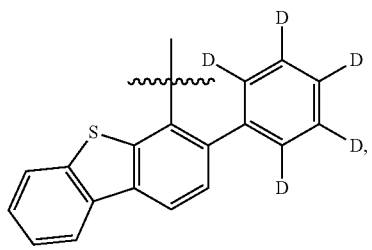
R250
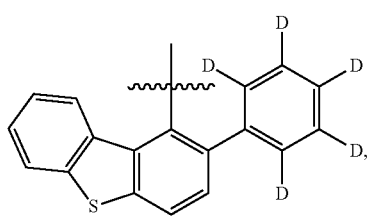
R251
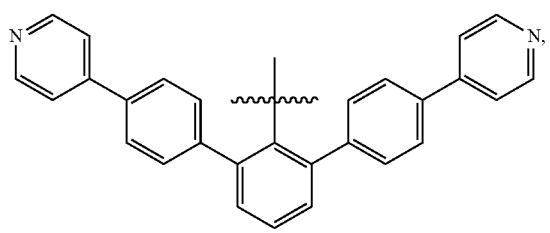
R252
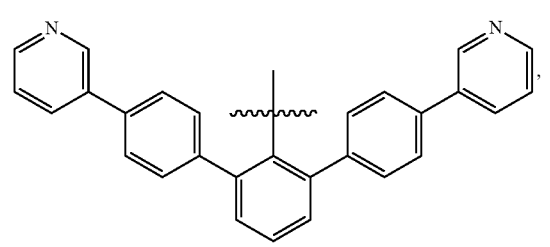

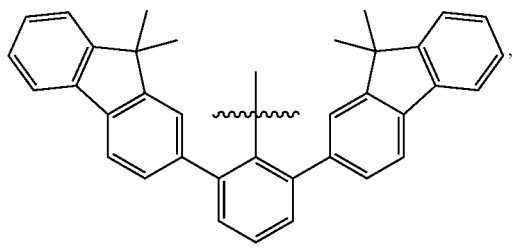
R253
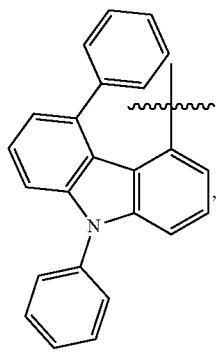
R254
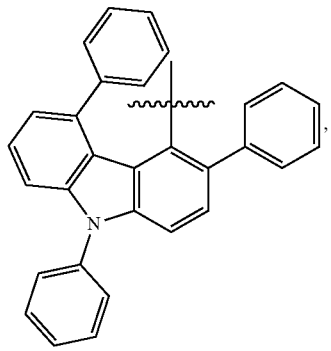
R255
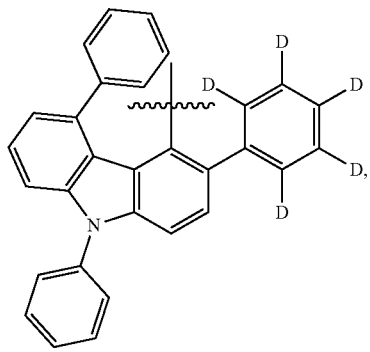
R256

-continued
R257
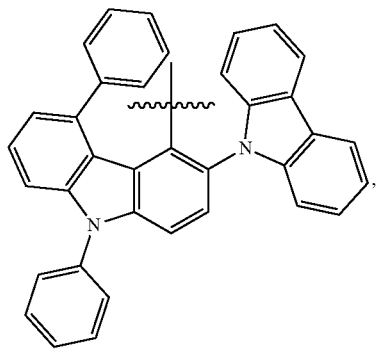
R258
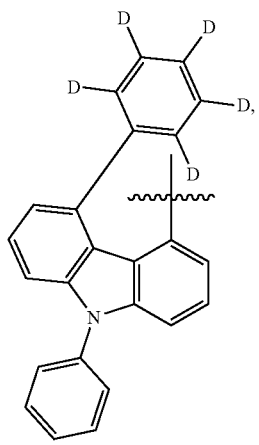
R259
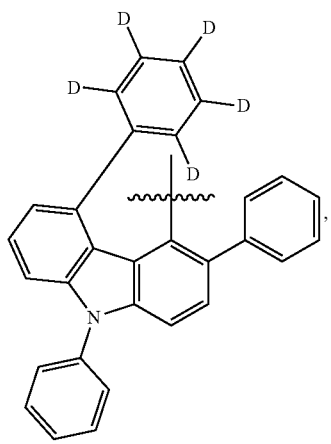

R260
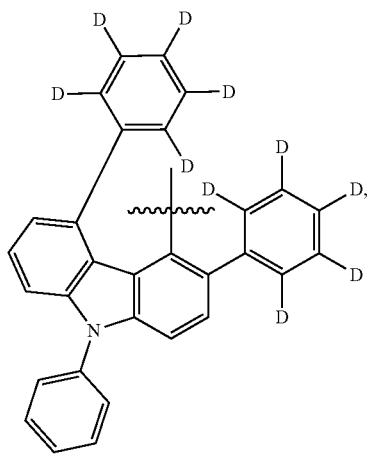
R261
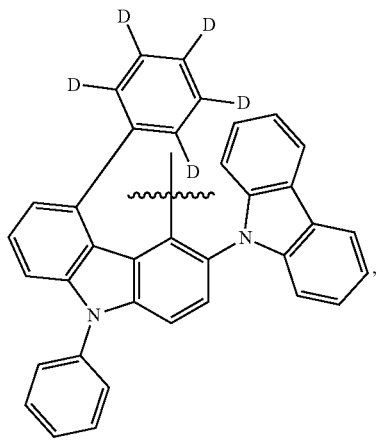
R262
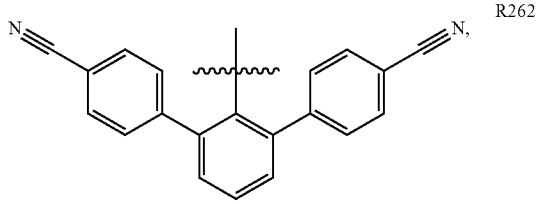
R263
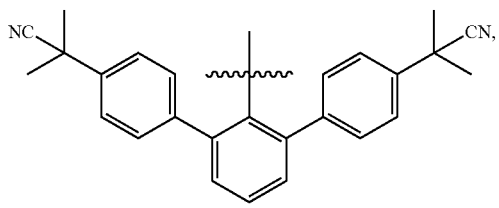
R264
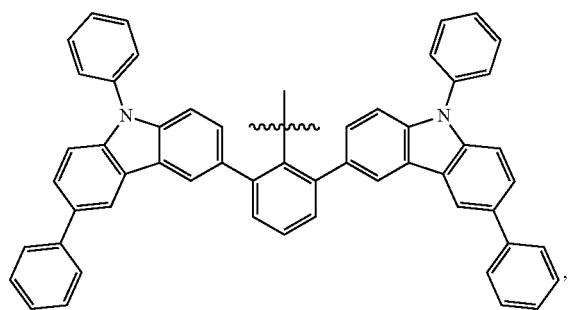

-continued
R265
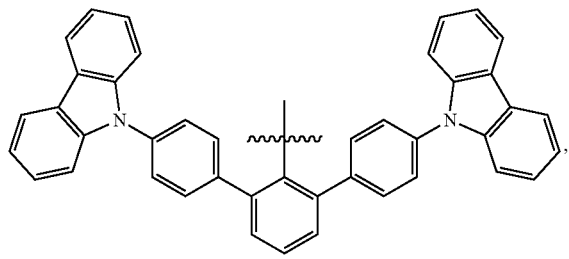
R266
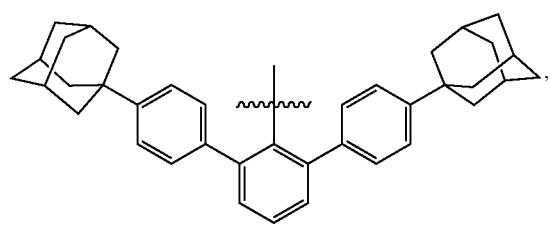
R267
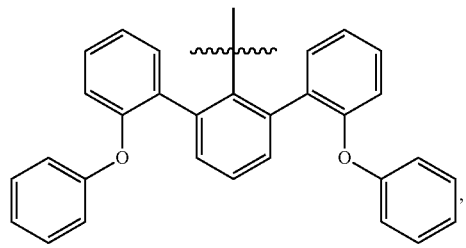
R268
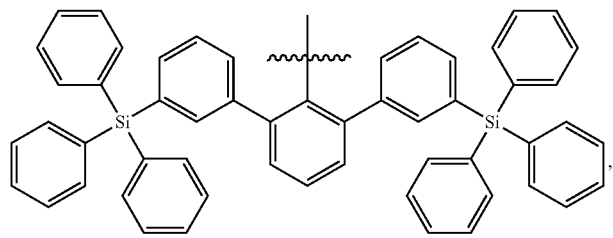
R269
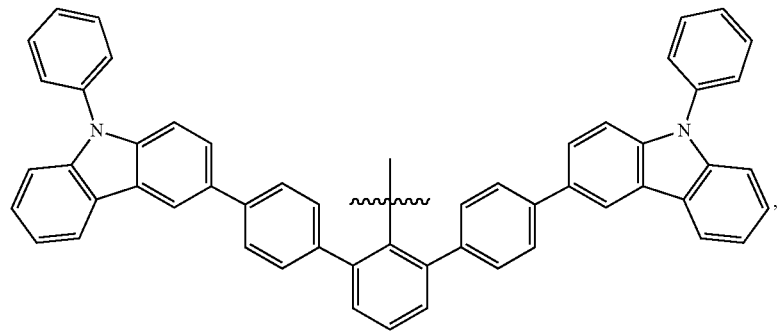
R270
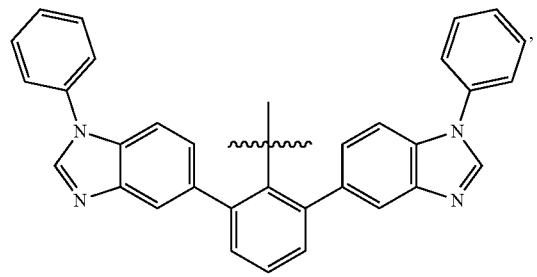

-continued
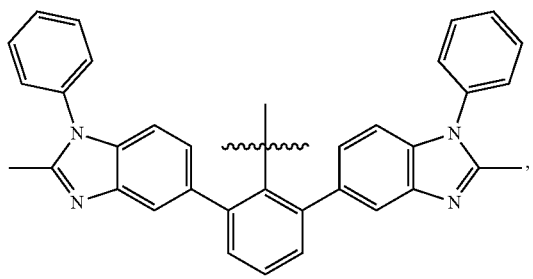
R271
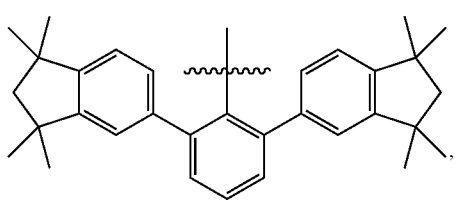
R272
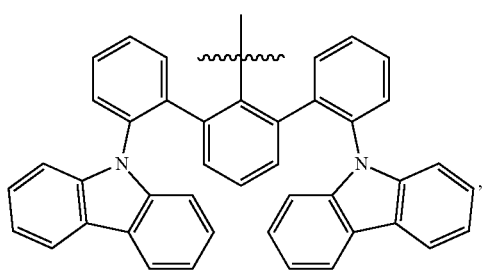
R273
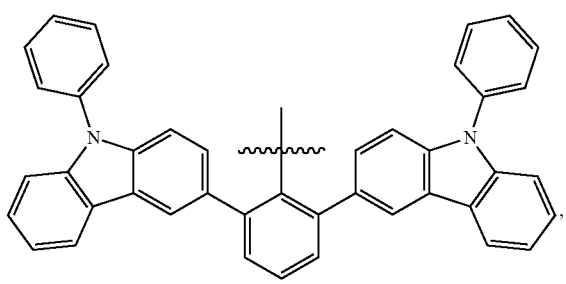
R274
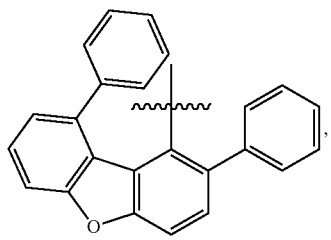
R275
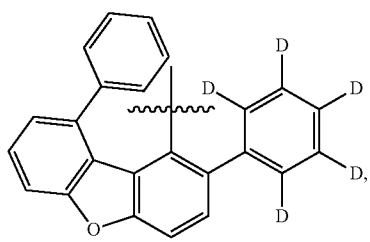
R276

-continued
R277
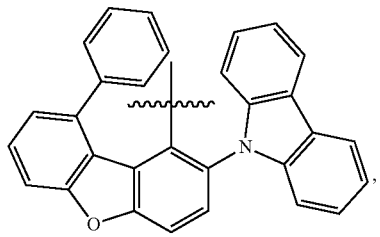
R278
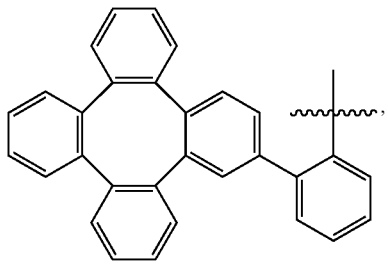
R279
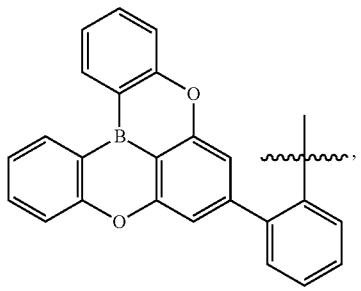
R280
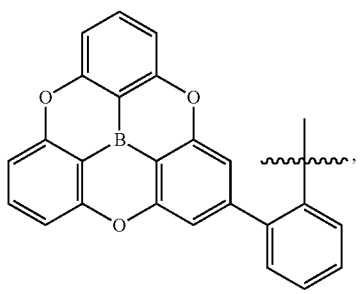
R281
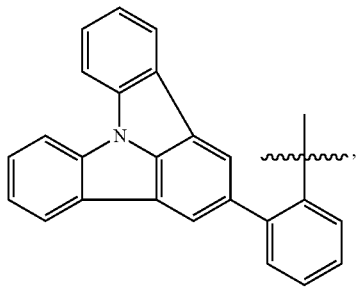

-continued
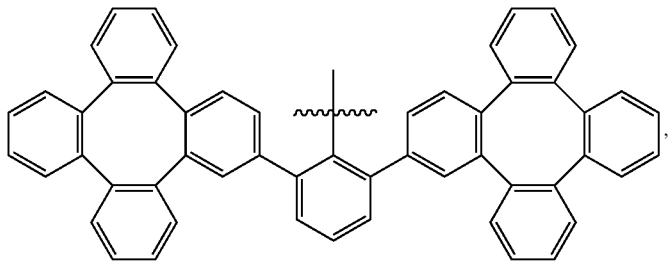
R282
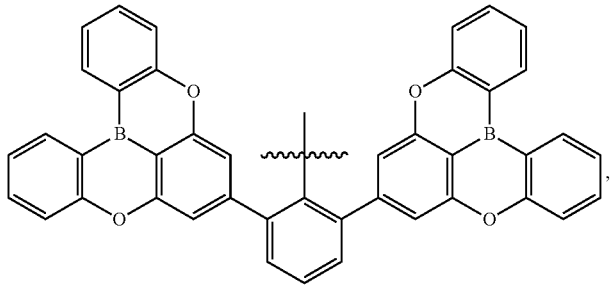
R283
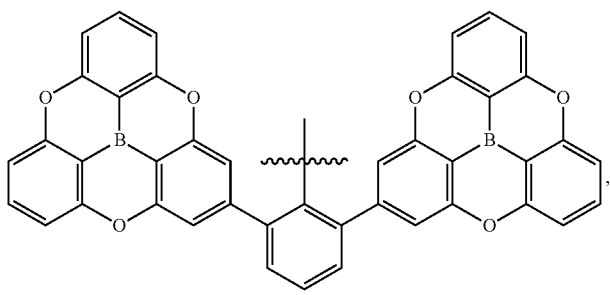
R284
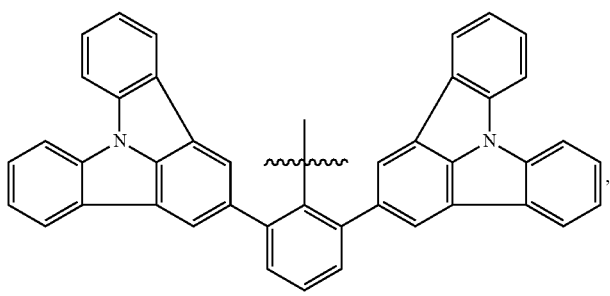
R285
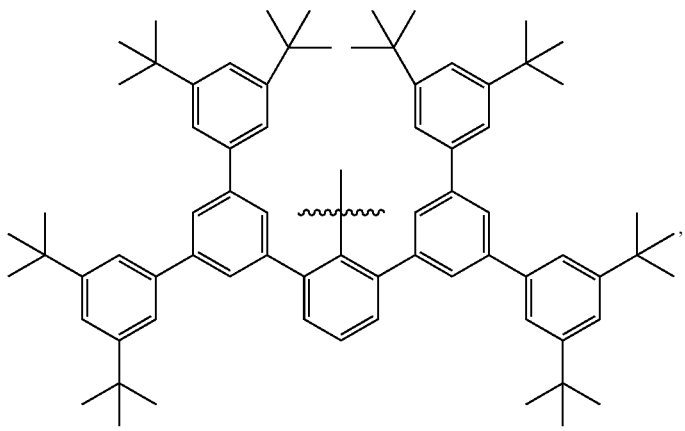
R286

R287
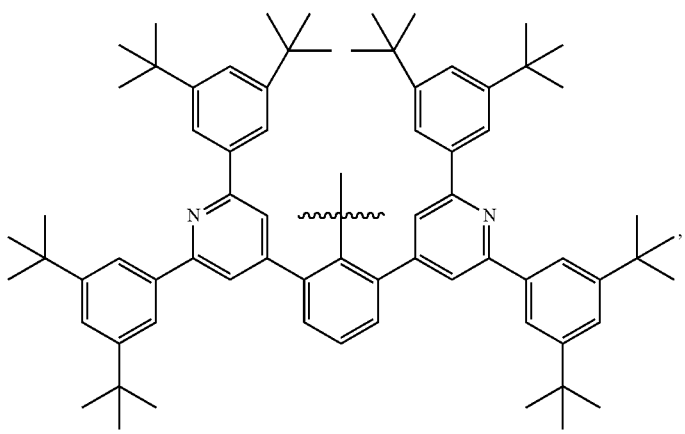
R288
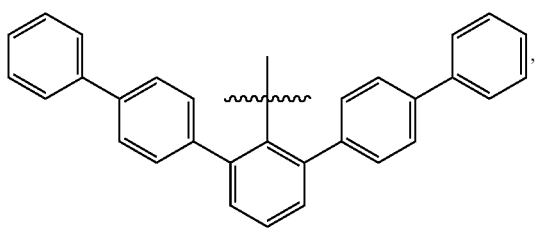
R289
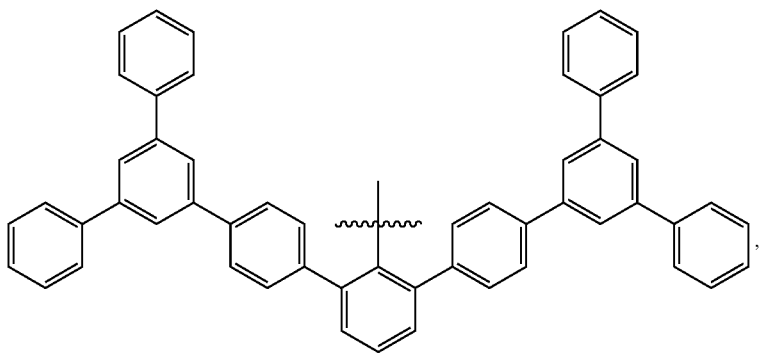
R290
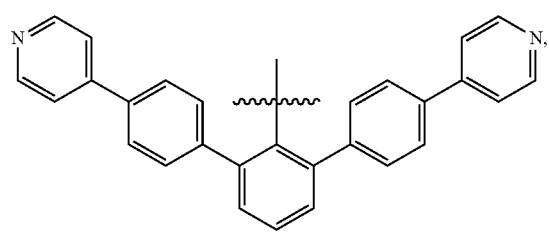
R291
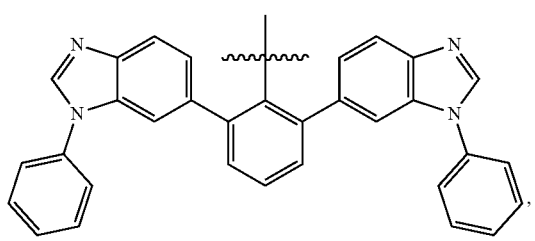

-continued
R292
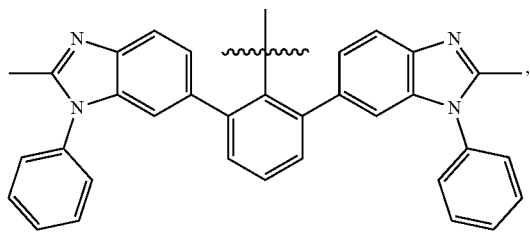
R293
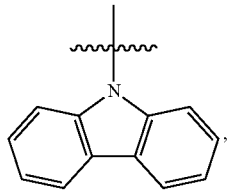
R294
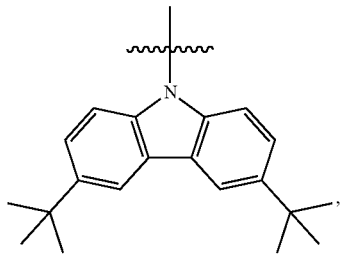
R295
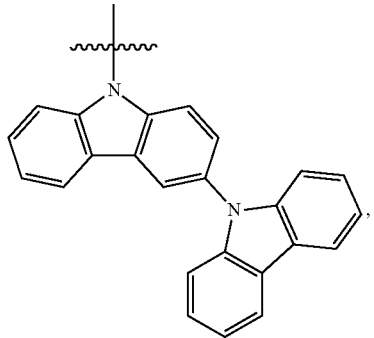
R296
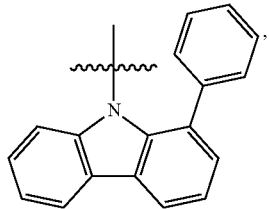
R297
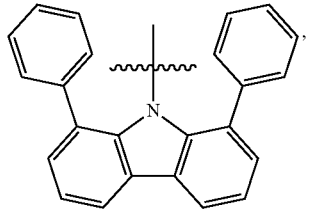

-continued
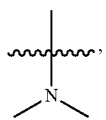
R298
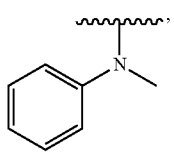
R299
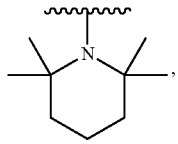
R300
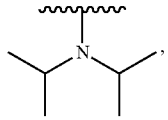
R301
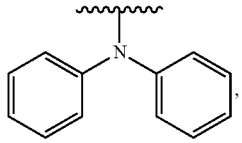
R302
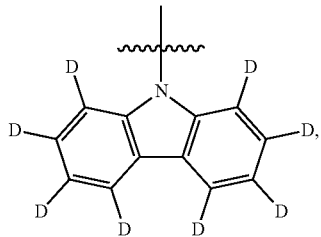
R303
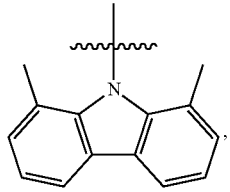
R304
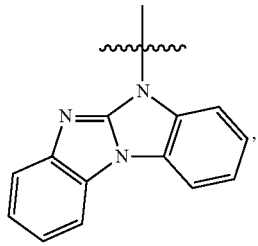
R305

R306
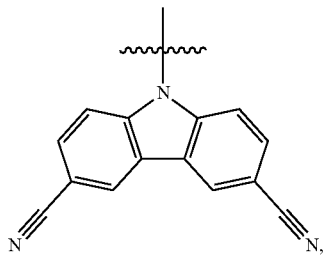
R307
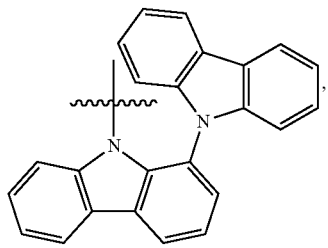
wherein X1 to X21 have the following structures:
X1
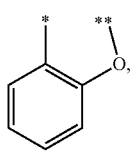
X2
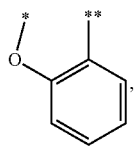
X3
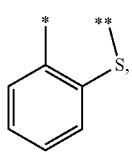
X4
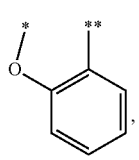
X5
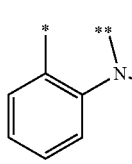
X6
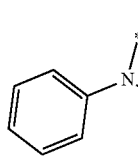
X7
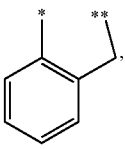
X8
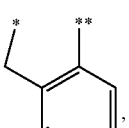
X9
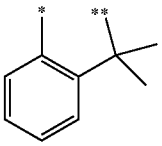
X10
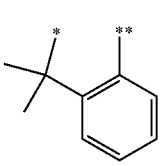
X11
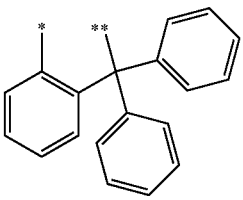
X12
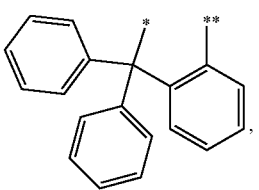

399
-continued
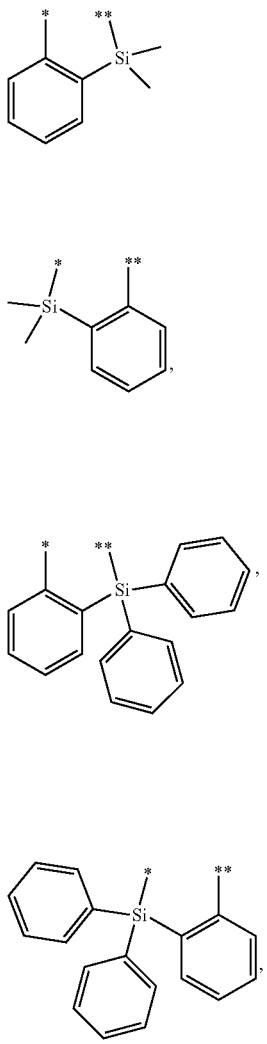
400
-continued
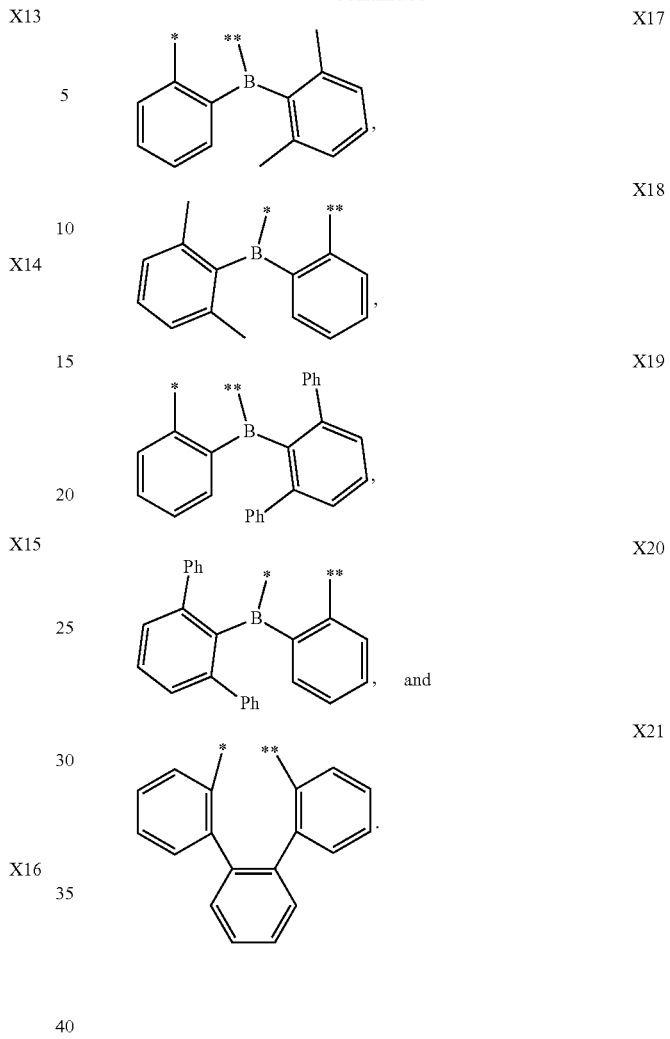
18. The OLED of claim 13, wherein the emitter material is selected from the group consisting of:
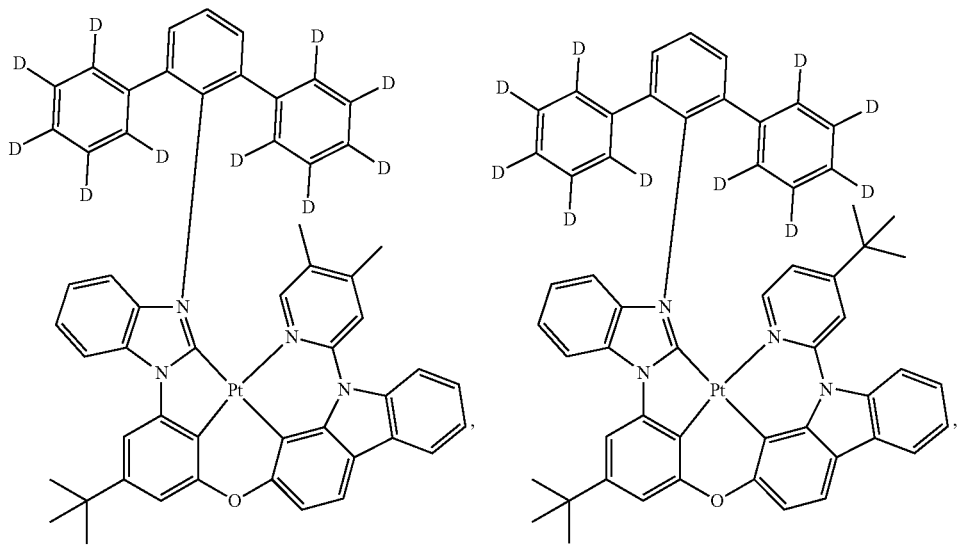

-continued
401
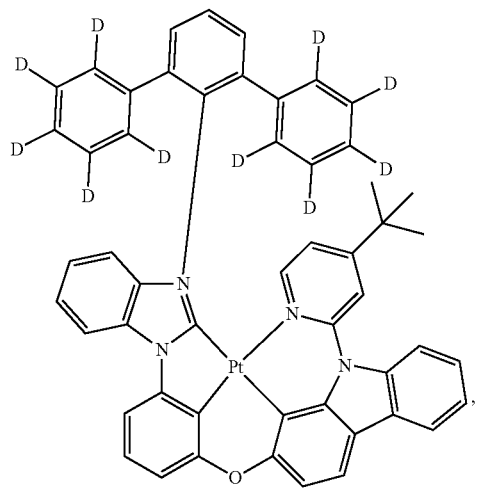
402
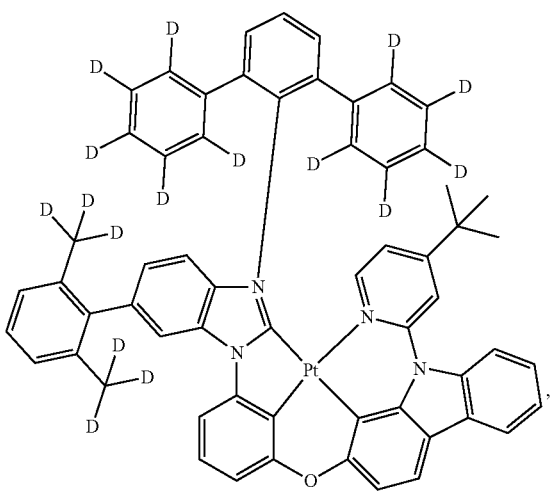
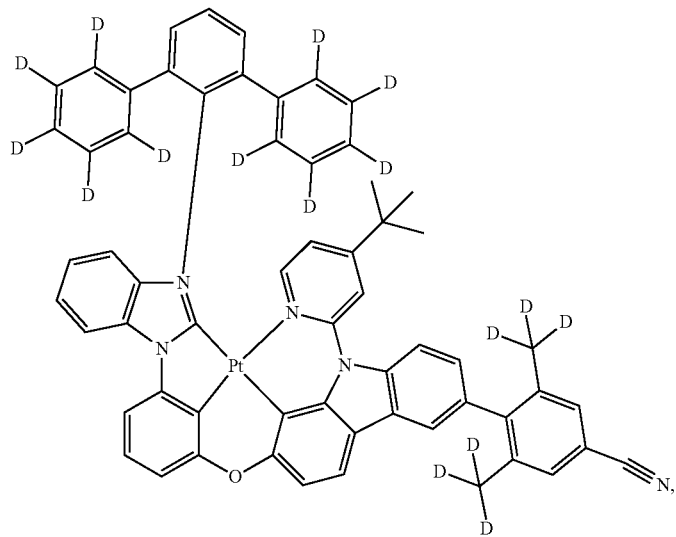
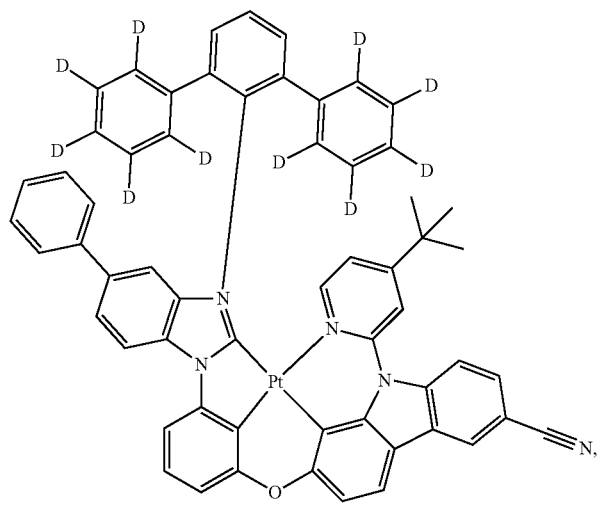

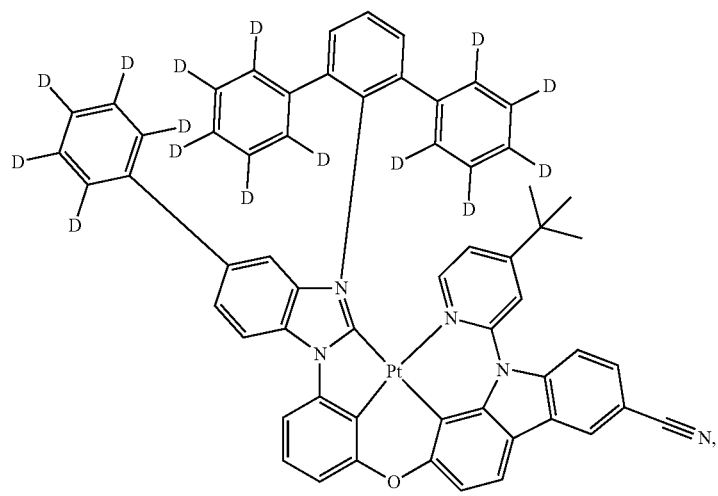
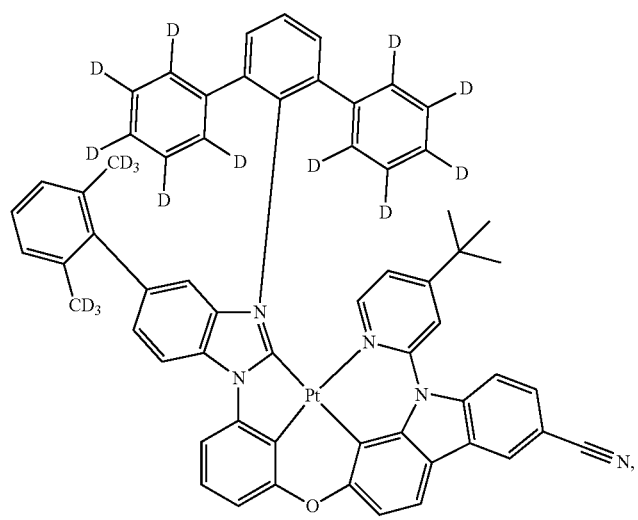
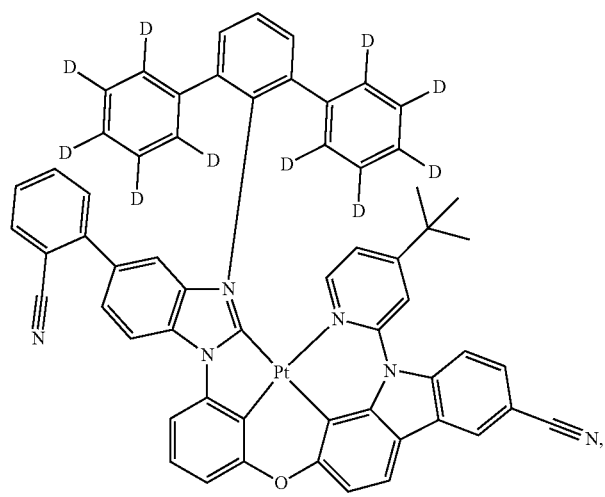

405 406
-continued
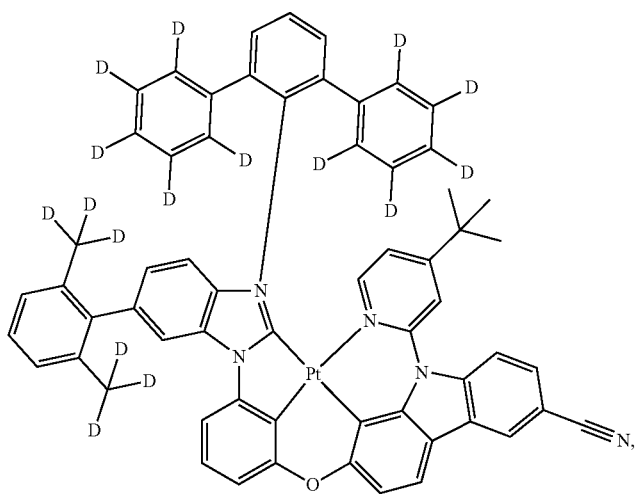
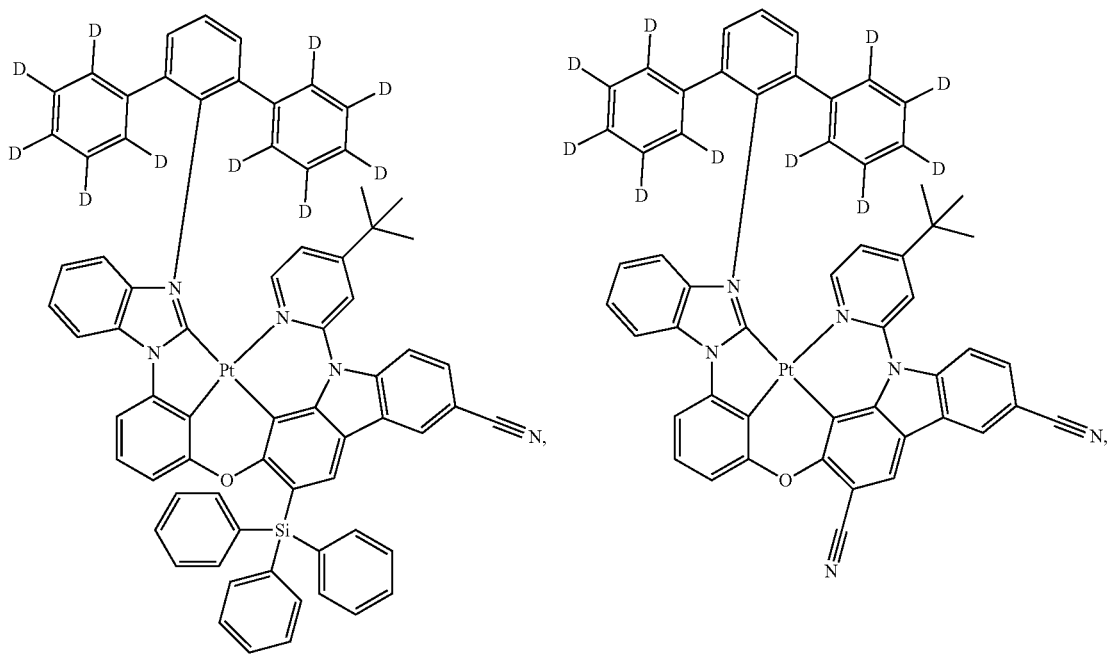

-continued
407
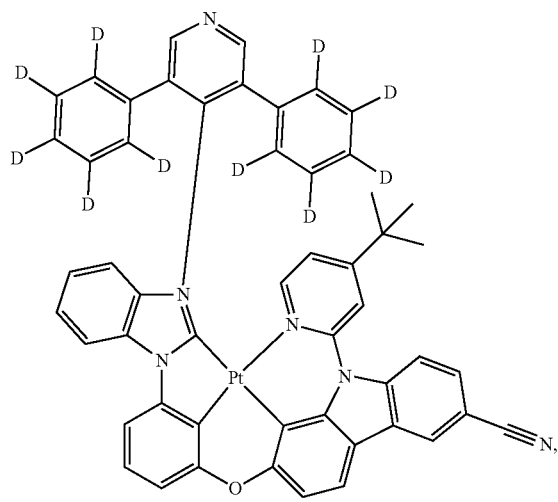
408
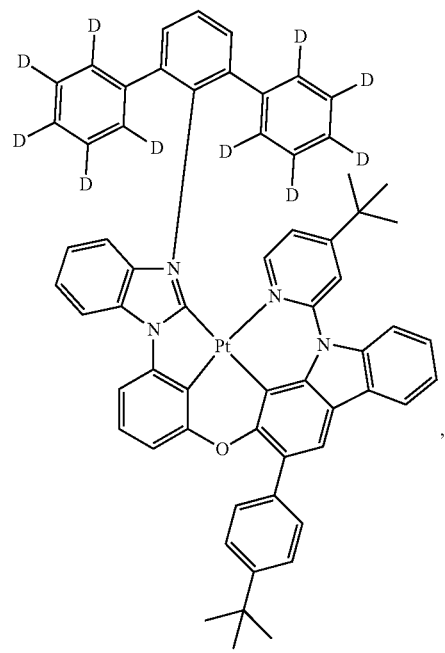
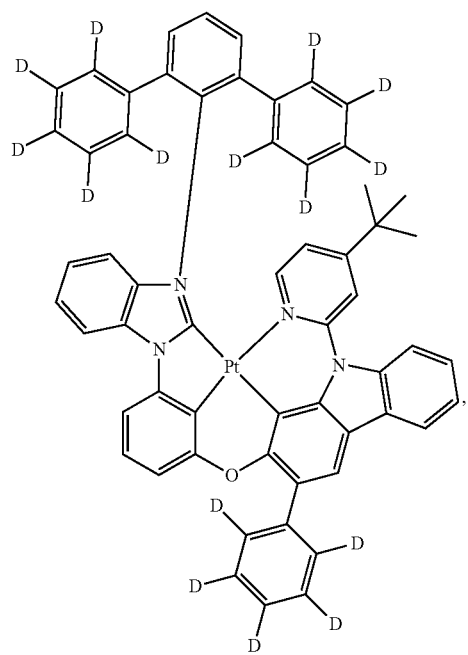
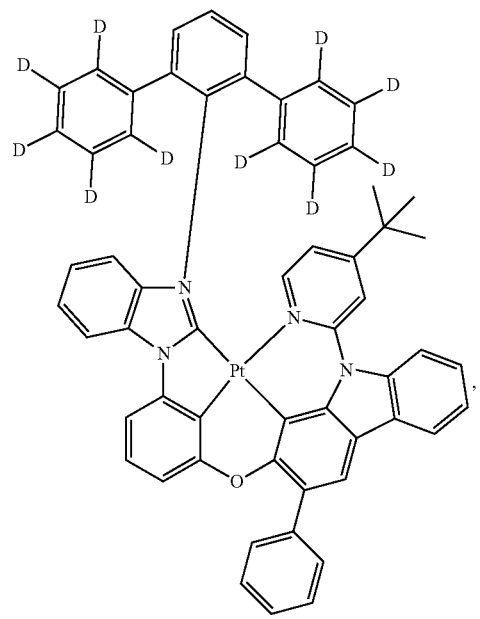

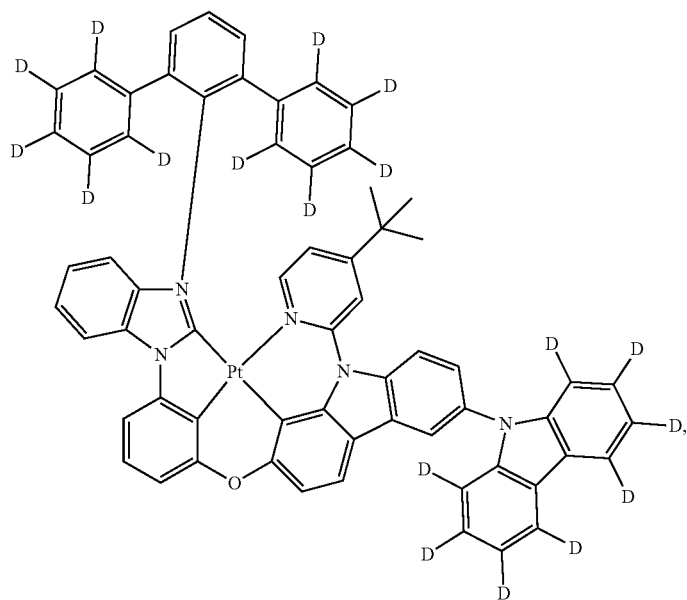
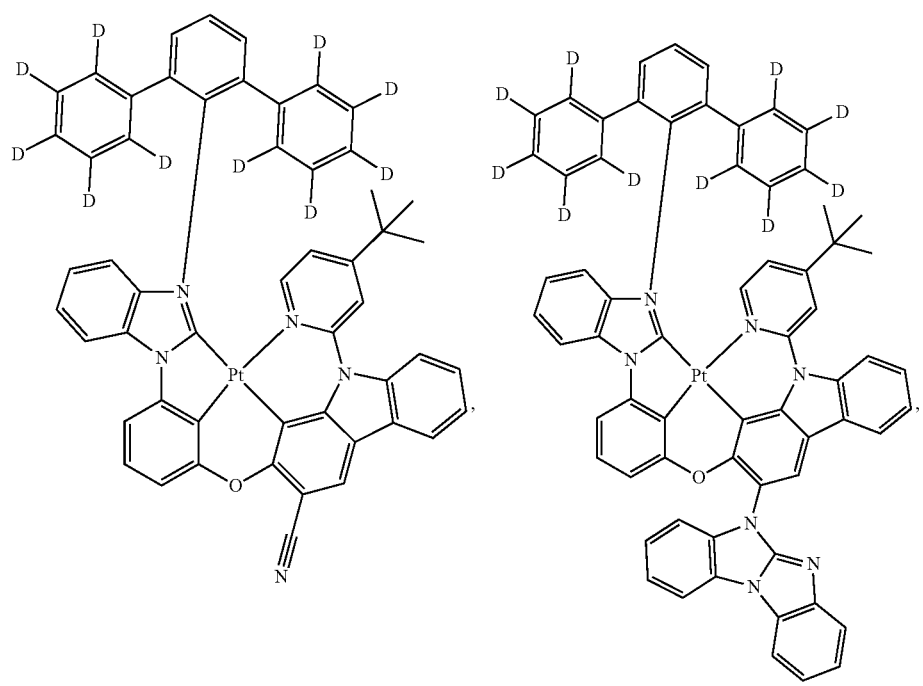

411
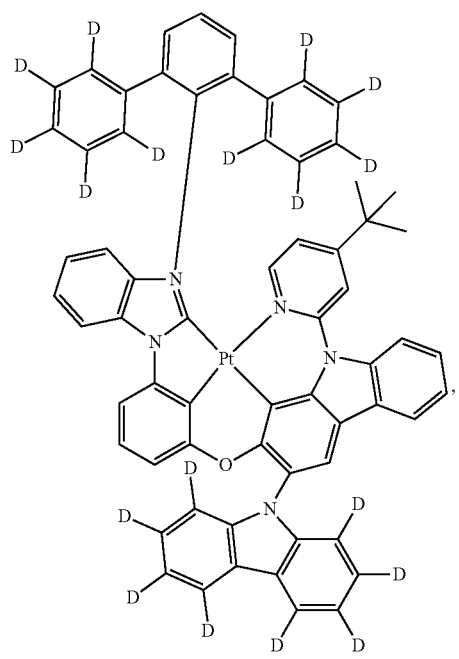
412
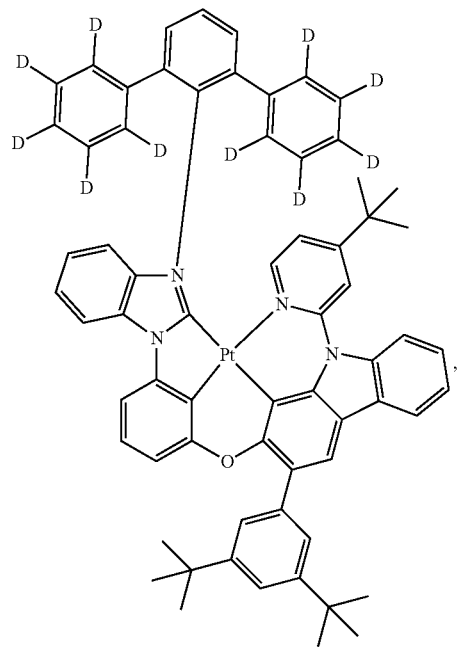
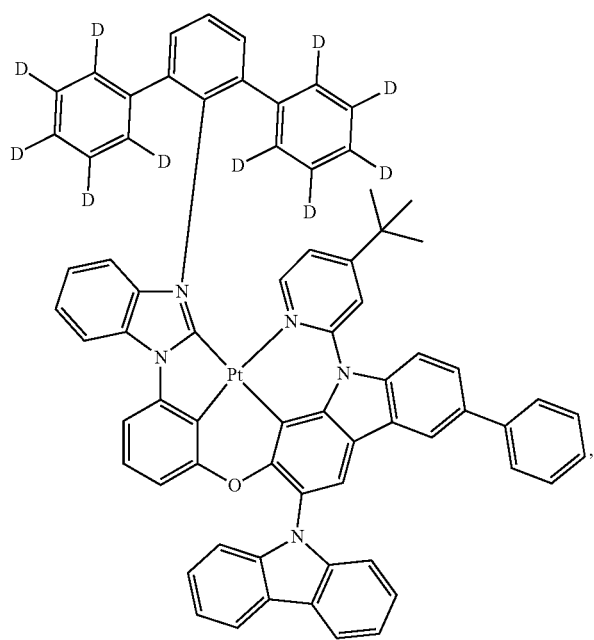

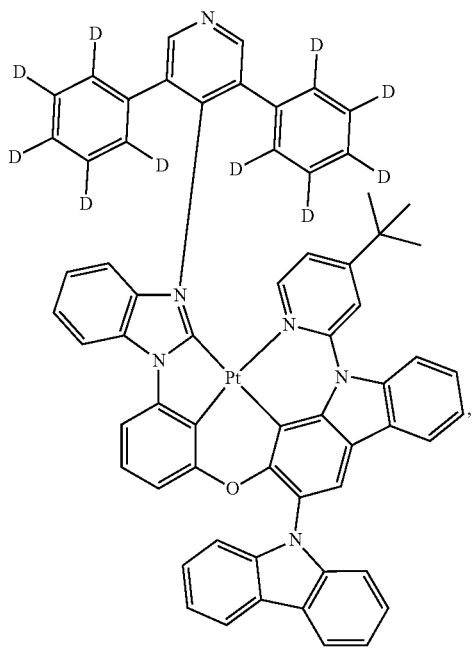
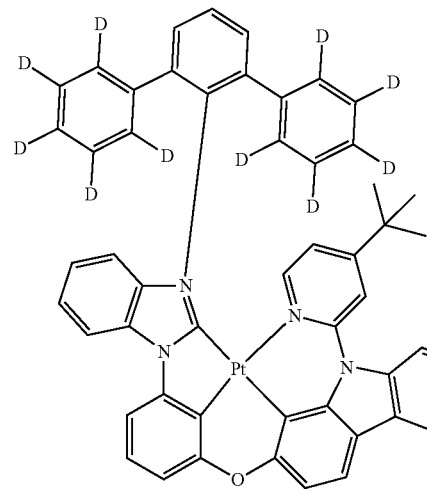
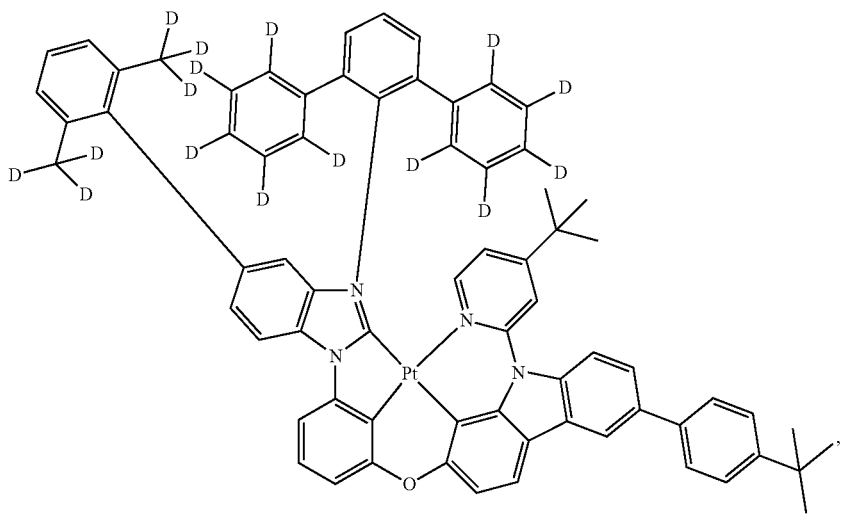
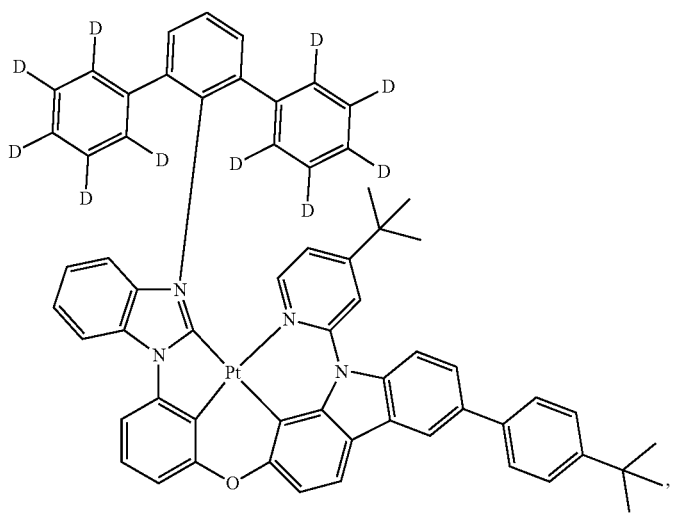

-continued
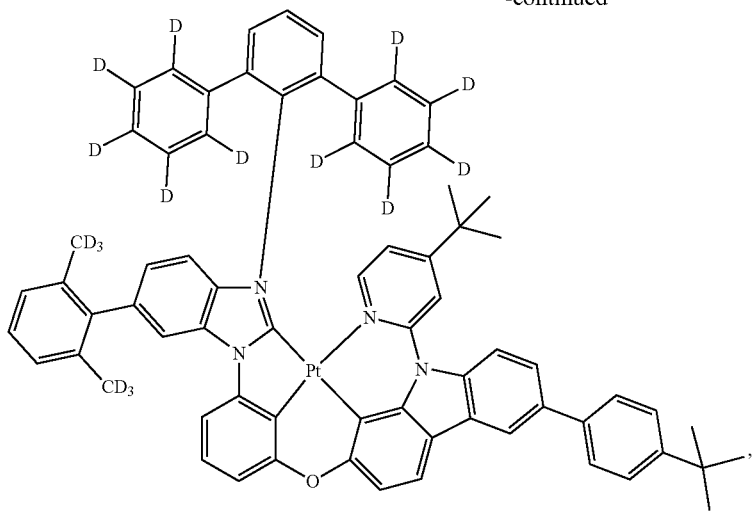
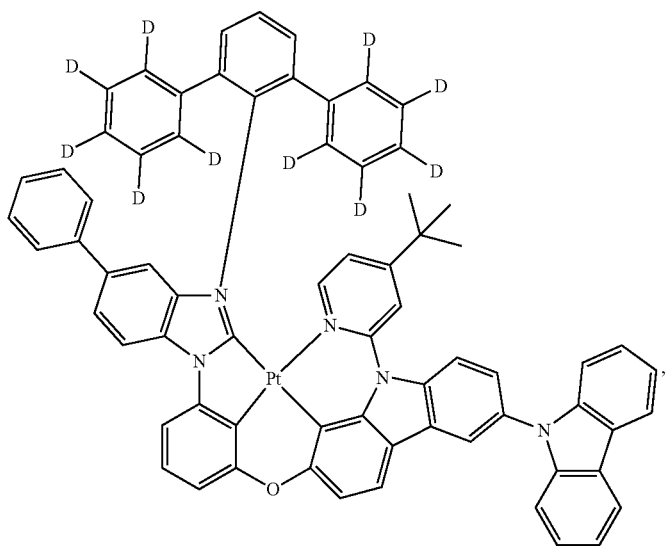
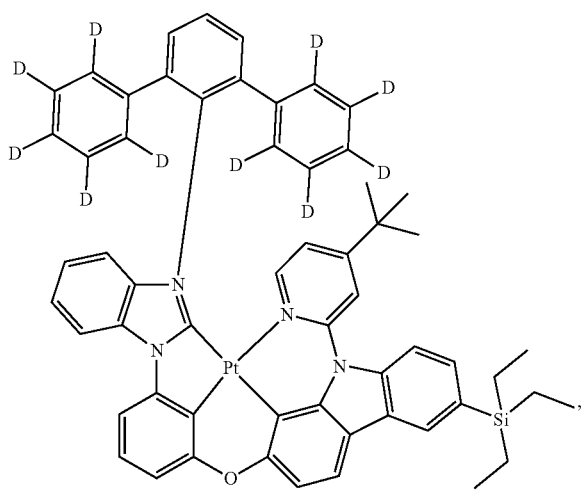

-continued
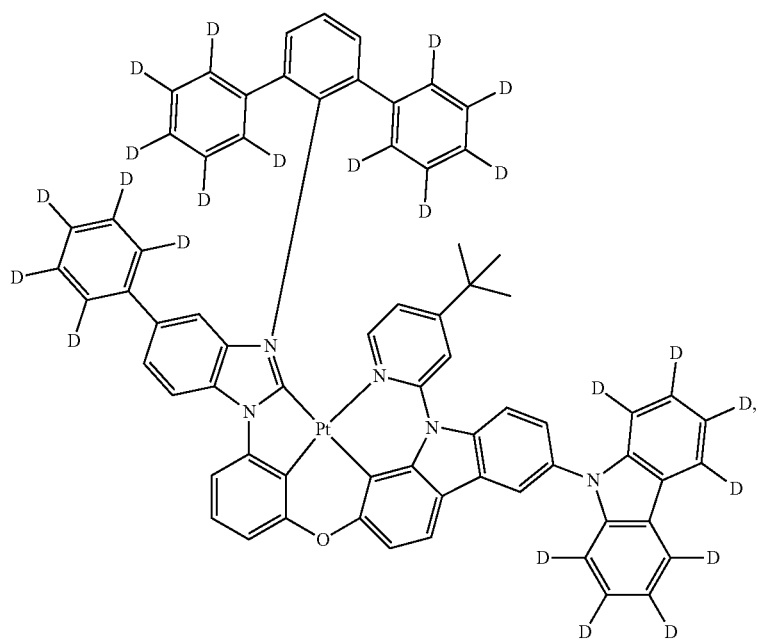
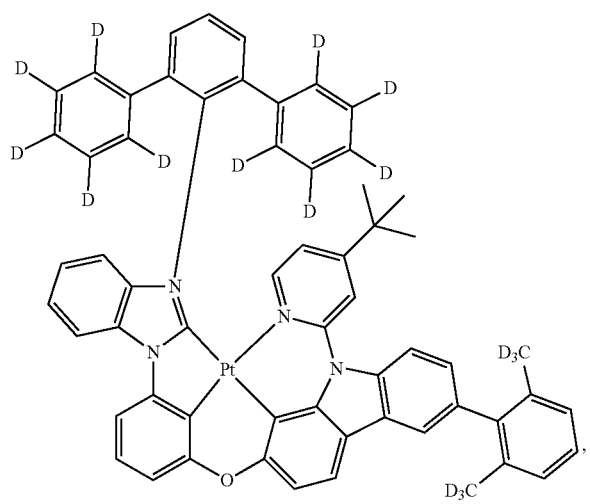
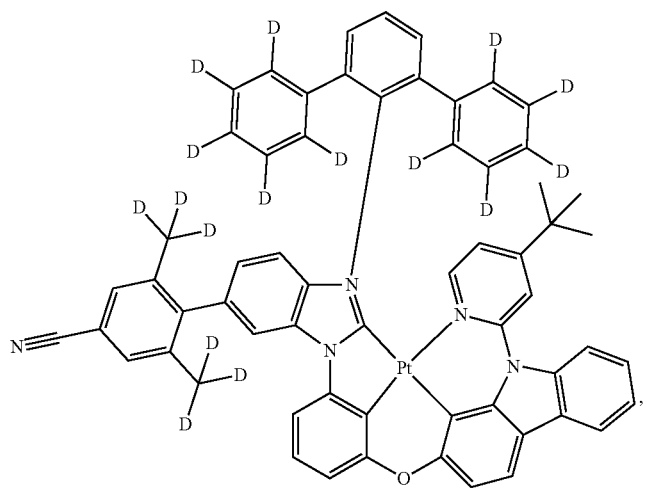

419
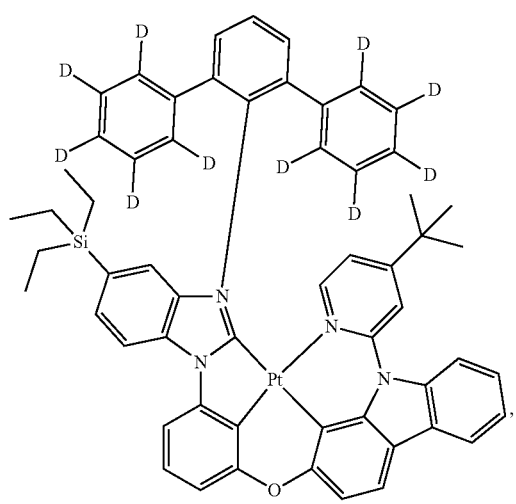
420
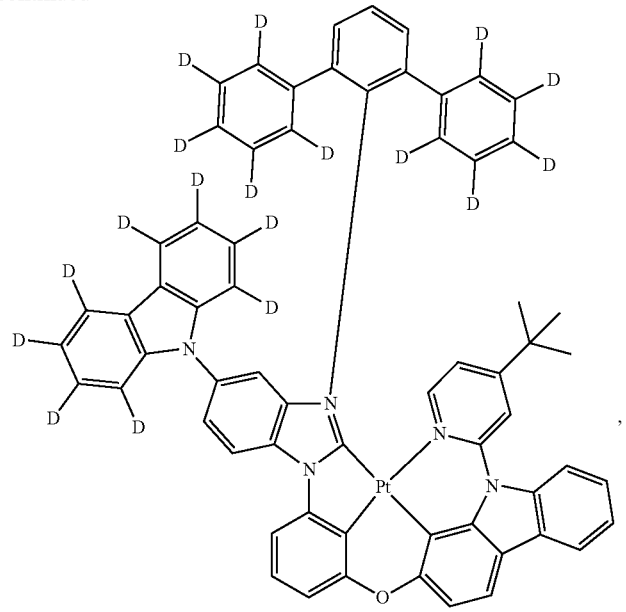
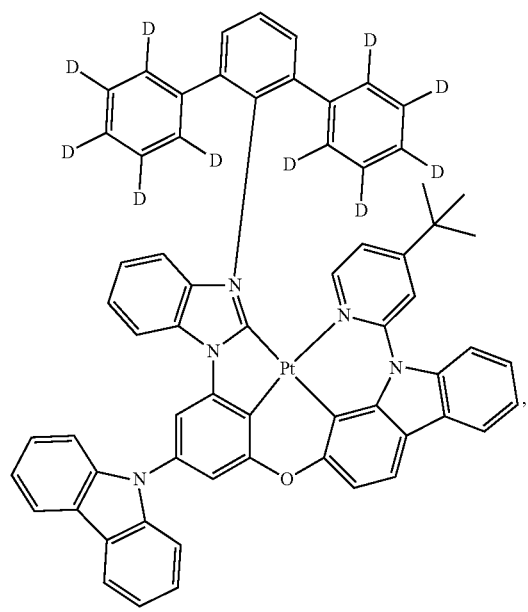
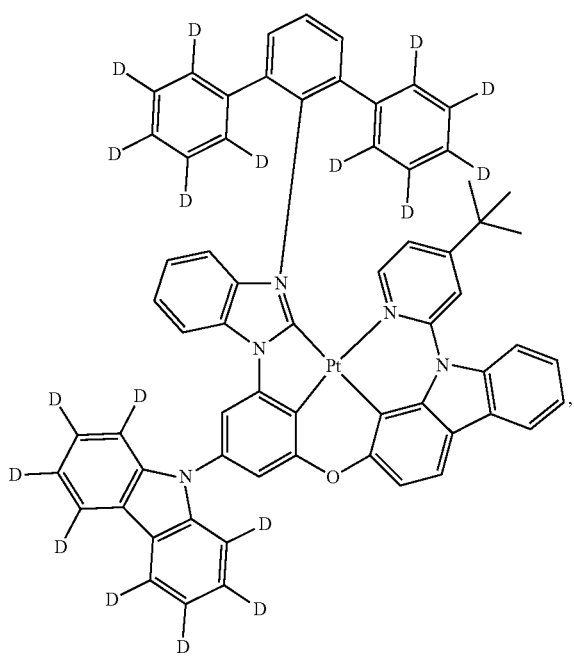

421
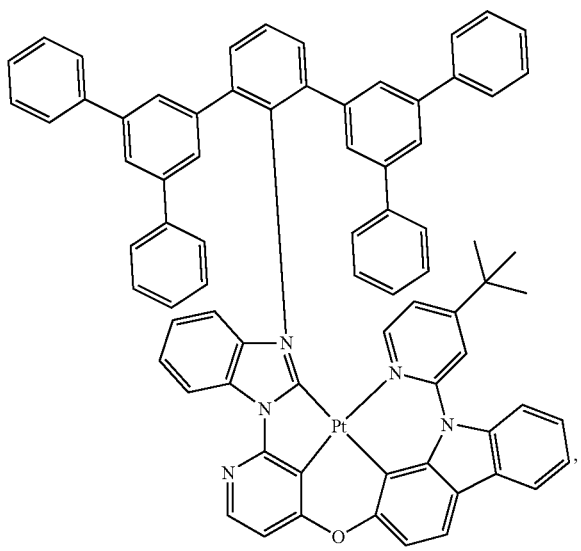
422
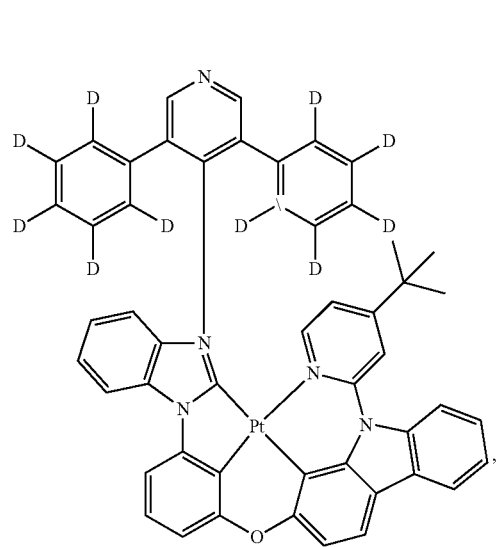
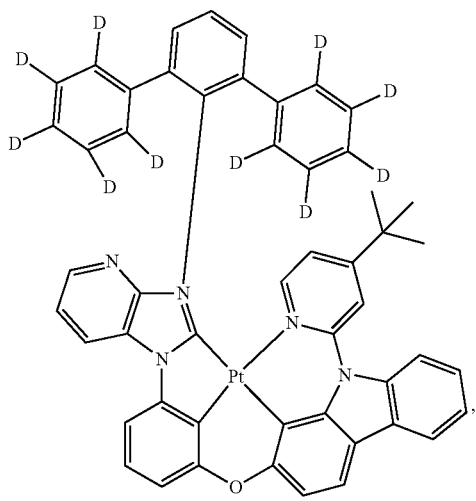
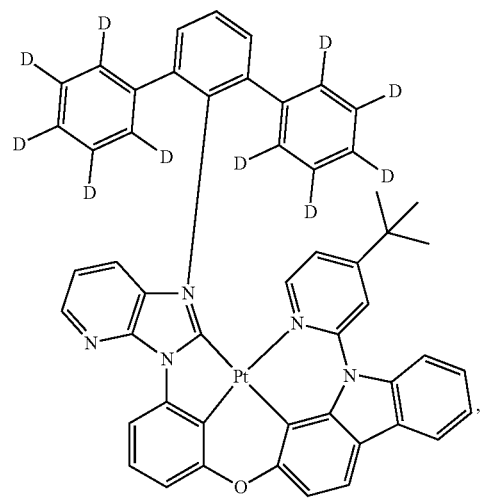
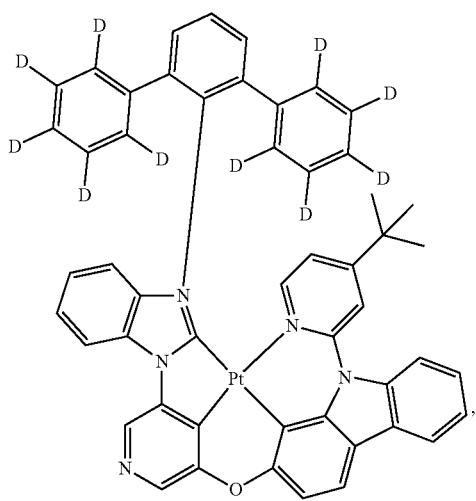
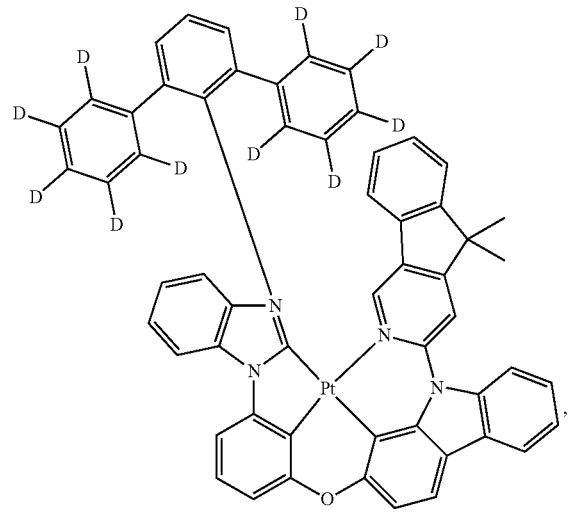

423    424
-continued
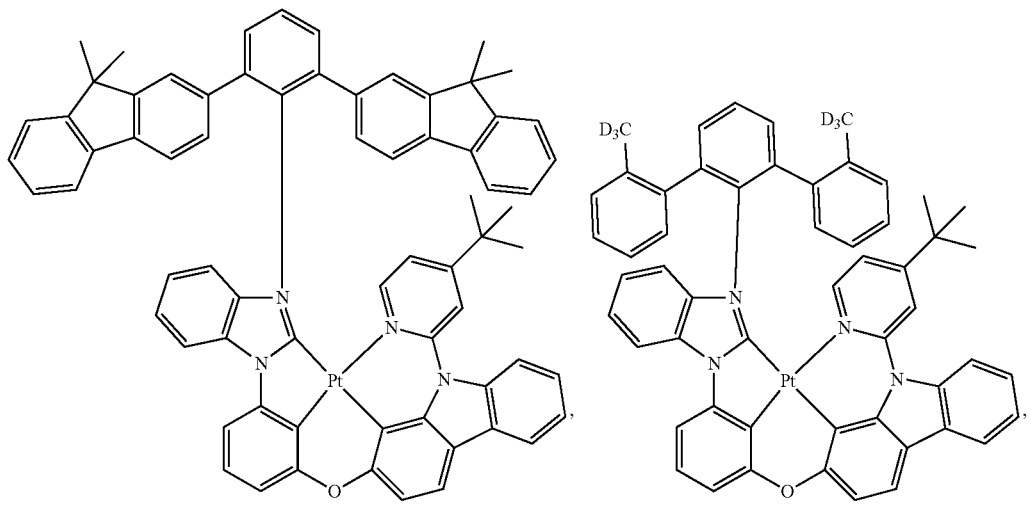
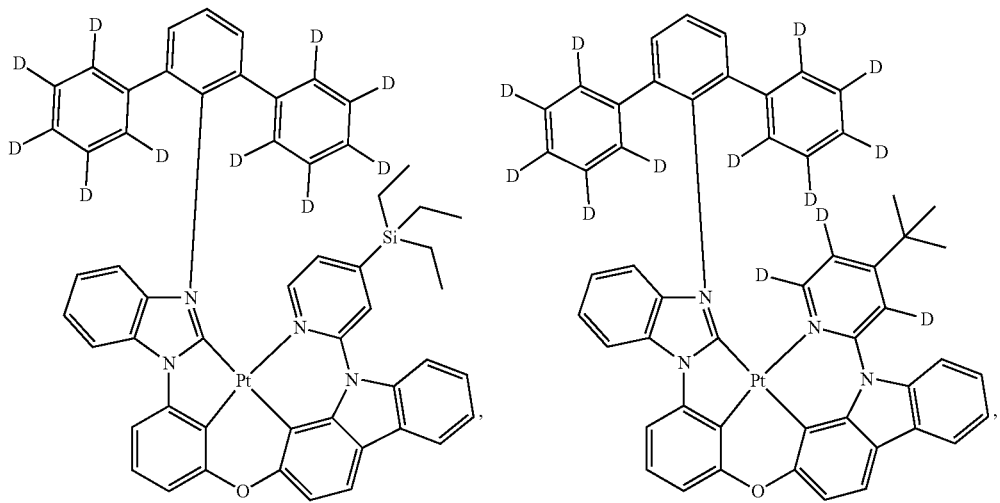
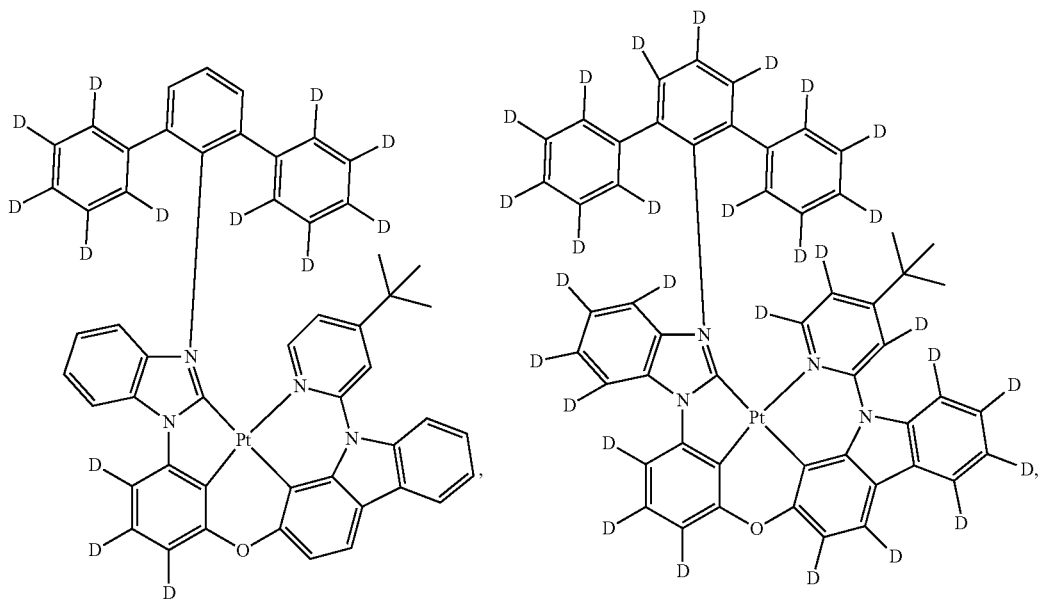

425
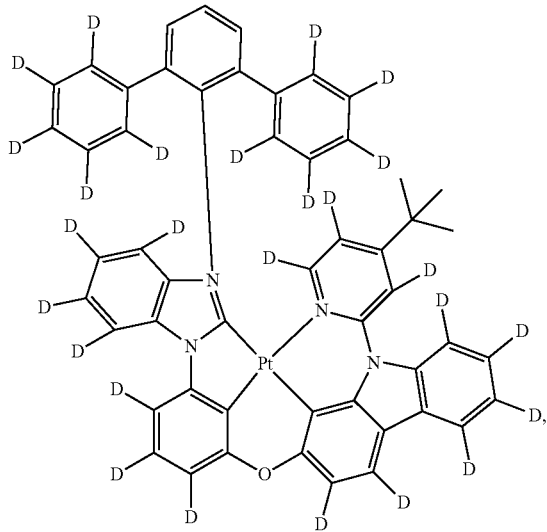
426
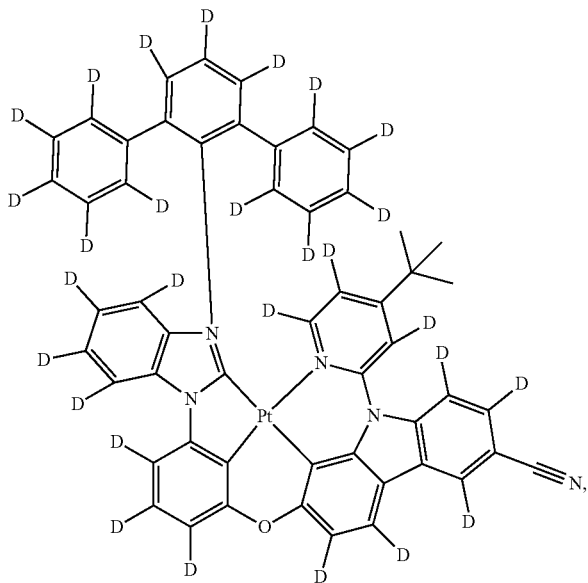
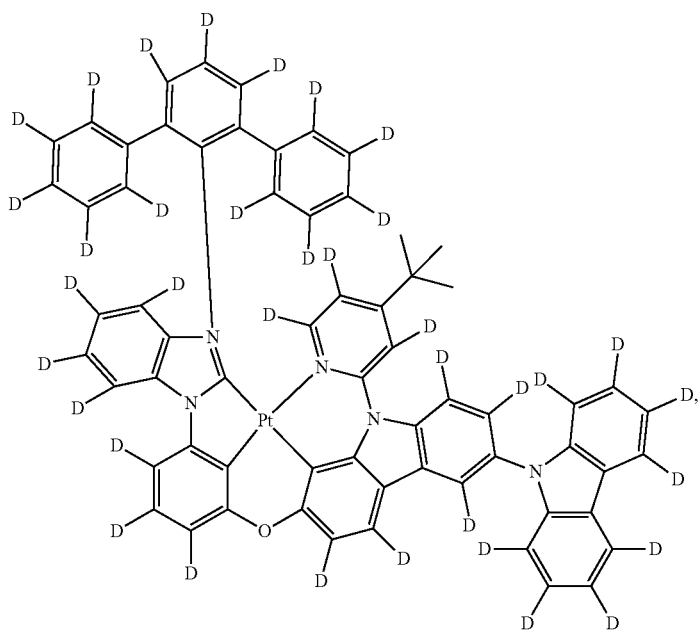

-continued
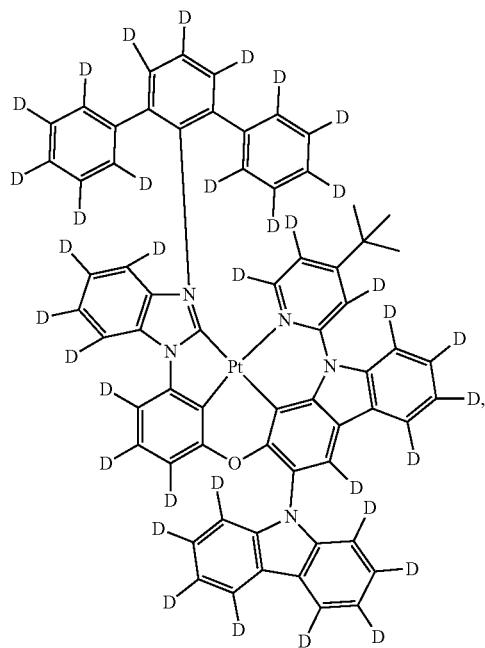
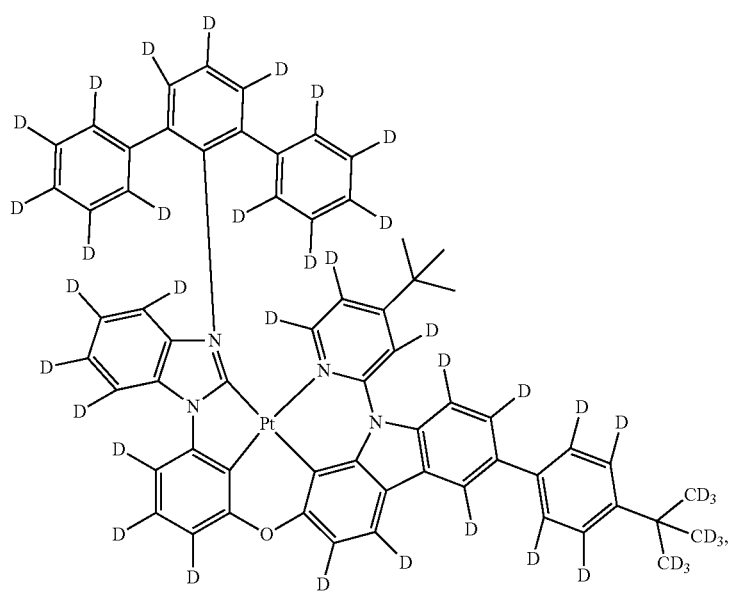

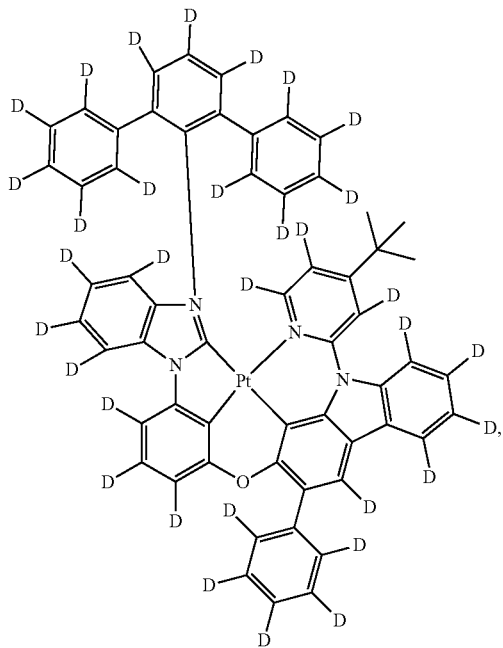
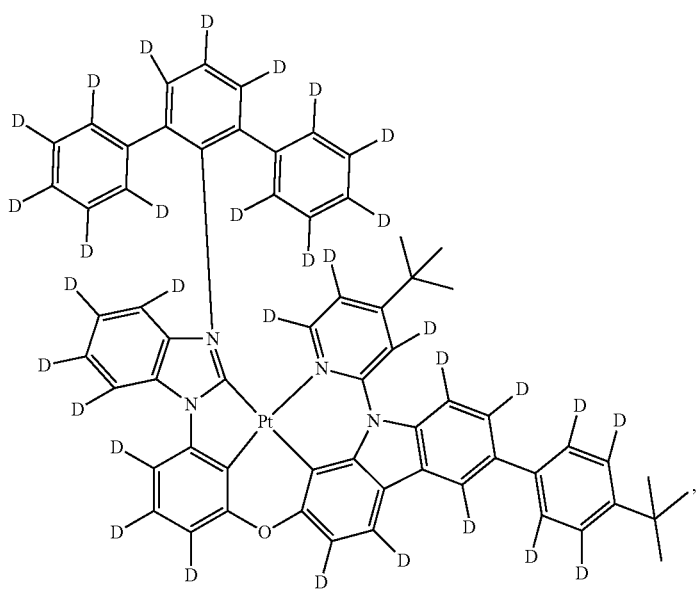

431
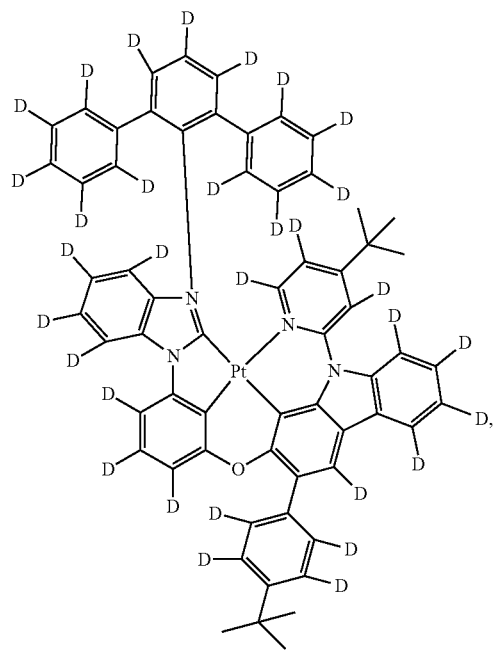
-continued
432
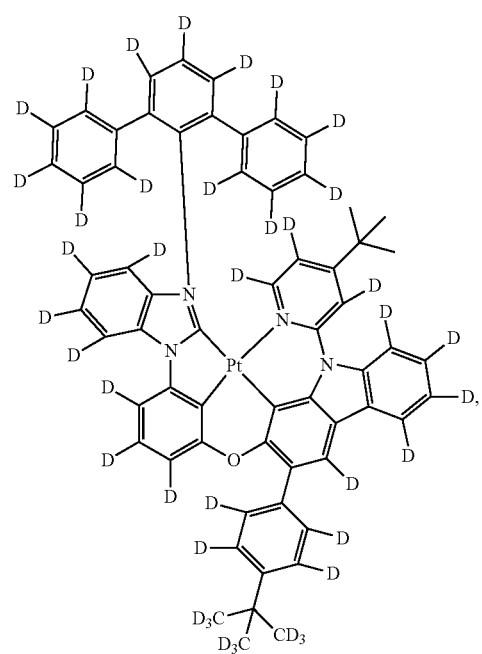
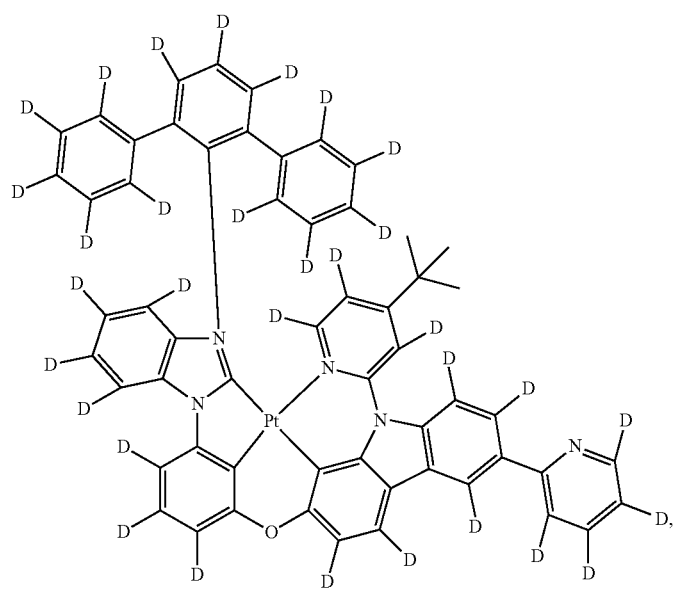

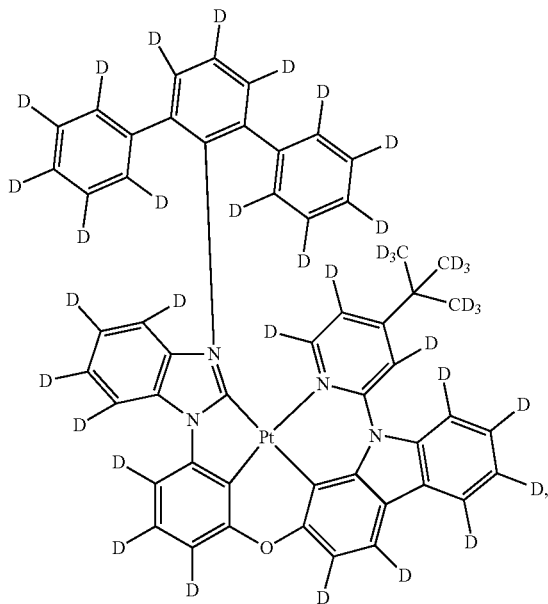
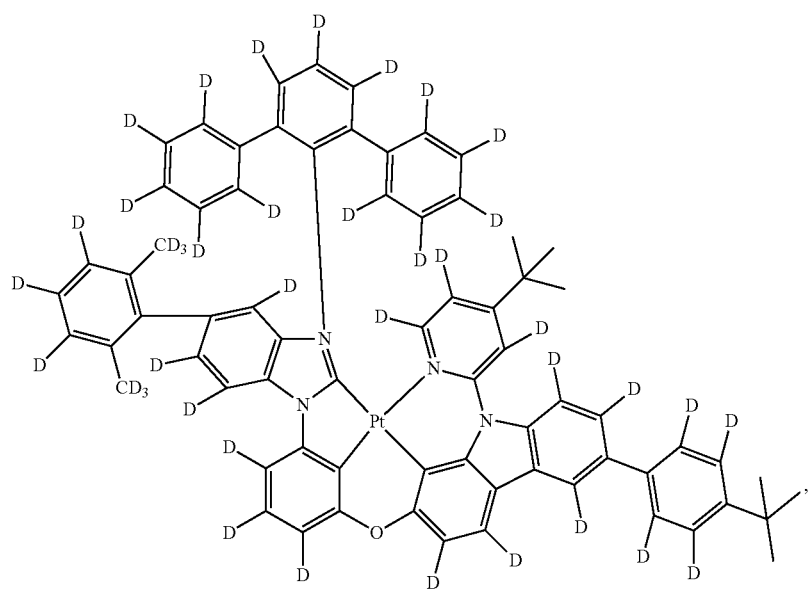

-continued
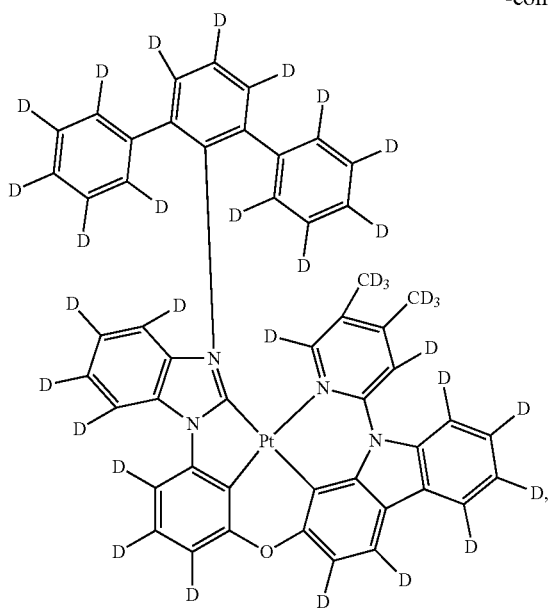
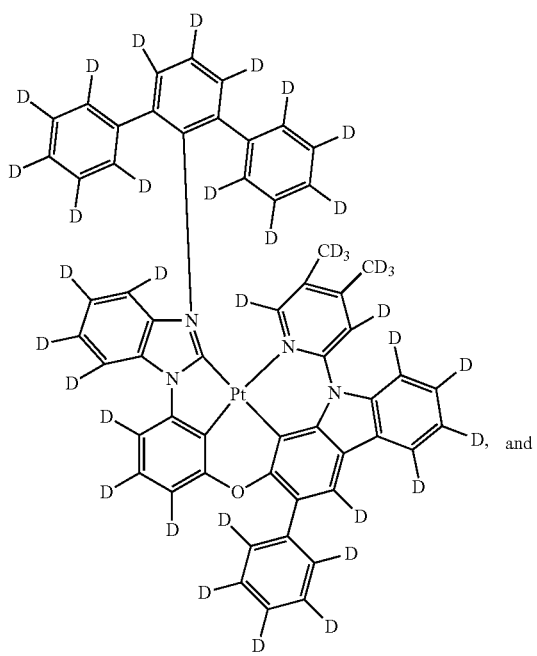
and

-continued

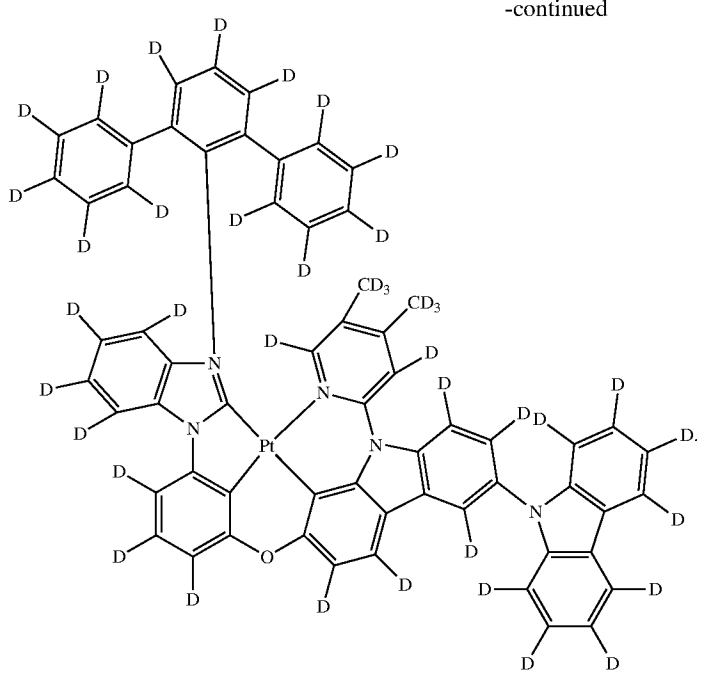

19. A consumer product comprising an organic light-emitting device (OLED) having an emission spectrum, the OLED comprising:
   an anode;
   a cathode; and
   an organic emissive layer, disposed between the anode and the cathode, comprising:
      a first host material having a highest occupied molecular orbital (HOMO) energy and a lowest unoccupied molecular orbital (LUMO) energy; and
      an emitter material having a HOMO energy and a LUMO energy;
   wherein,
      all materials in the organic emissive layer are mixed together;
      the emitter material is a phosphorescent metal complex;
      High HOMO energy is the highest HOMO energy among all materials in the organic emissive layer;
      Low LUMO energy is the lowest LUMO energy among all materials in the organic emissive layer;
      $a \leq E_T - \Delta E \leq b$, wherein $E_T$ is triplet energy $T_1$ of the emitter material, which is the lowest $T_1$ energy among all materials in the organic emissive layer, $\Delta E$ is the energy gap between the High HOMO energy and the Low LUMO energy, a is 0.00 up to 0.15 eV, and b is 0.05 up to 0.45 eV; and
   wherein root mean squared function (RMSD) value for the emission spectrum of the OLED and an emission spectrum of a reference OLED, whose organic emissive layer consists of the emitter material and an inert host, is not greater than 0.05,
   wherein RMSD value is a single value that represents the average difference between the emission spectrum of the OLED and the emission spectrum of the reference OLED at all wavelengths obtained by the following equation:

$$RMSD = \sqrt{\frac{1}{n}\sum_{1}^{n}(I_1(\lambda) - I_2(\lambda))^2},$$

wherein n is the number of points on the two emission spectrums being compared, and $I_1$ and $I_2$ are the normalized intensity spectrums as a function of wavelength, $\lambda$.

20. The consumer product of claim 19, wherein the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a microdisplay that is less than 2 inches diagonal, a 3-D display, a virtual reality or augmented reality display, a vehicle, a video walls comprising multiple displays tiled together, a theater or stadium screen, and a sign.

* * * * *

UNITED STATES PATENT AND TRADEMARK OFFICE
CERTIFICATE OF CORRECTION

PATENT NO. : 11,690,285 B2  
APPLICATION NO. : 17/328403  
DATED : June 27, 2023  
INVENTOR(S) : Nicholas J. Thompson, Chun Lin and Hsiao-Fan Chen Page 1 of 1

It is certified that error appears in the above-identified patent and that said Letters Patent is hereby corrected as shown below:

In the Claims

In Claim 17, Column 397, Lines 47-53, please delete compound " 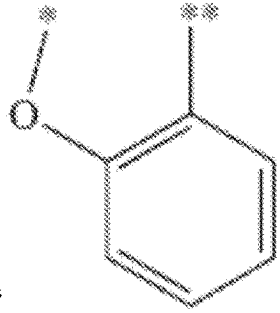 " and insert -- 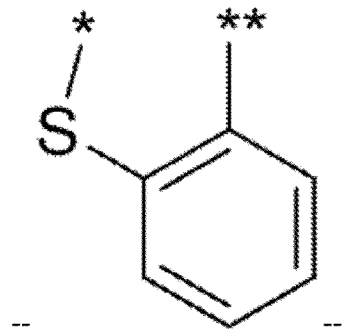 --

Signed and Sealed this  
Seventh Day of November, 2023

Katherine Kelly Vidal  
*Director of the United States Patent and Trademark Office*